United States Patent [19]
Hodge et al.

[11] Patent Number: 5,877,170
[45] Date of Patent: Mar. 2, 1999

[54] SUBSTITUTE CAPROLACTAMS AND DERIVATIVES THEREOF USEFUL FOR TREATMENT OF HIV DISEASE

[75] Inventors: Carl Nicholas Hodge, Wilmington; Christina Howard Fernandez, Bear; Prabhakar Kondaji Jadhav, Wilmington, all of Del.; Patrick Yuk-Sun Lam, Chadds Ford, Pa.

[73] Assignee: DuPont Pharmaceuticals Company, Wilmington, Del.

[21] Appl. No.: 862,560

[22] Filed: May 23, 1997

Related U.S. Application Data

[60] Division of Ser. No. 040,324, Mar. 30, 1993, Pat. No. 5,663,333, which is a continuation-in-part of Ser. No. 965,061, Oct. 22, 1992, abandoned.

[51] Int. Cl.[6] .......................... A61K 31/33; C07D 255/02
[52] U.S. Cl. ........................... 514/183; 540/492; 540/554
[58] Field of Search ...................................... 540/554, 492; 514/183

[56] References Cited

U.S. PATENT DOCUMENTS

| 5,663,333 | 9/1997 | Hodge et al. | 540/492 |
| 5,670,497 | 9/1997 | Bold et al. | 514/183 |

*Primary Examiner*—Mukund J. Shah
*Assistant Examiner*—Pavanaram K. Sripada
*Attorney, Agent, or Firm*—Scott K. Larsen

[57] ABSTRACT

This invention relates to novel substituted caprolactams, including 4-azacaprolactams, and derivatives thereof which inhibit HIV protease and are useful for treatment of HIV disease. Also included in this invention are pharmaceutical compositions containing such caprolactams, and to methods of using such caprolactams for the treatment of HIV disease.

18 Claims, No Drawings

SUBSTITUTE CAPROLACTAMS AND DERIVATIVES THEREOF USEFUL FOR TREATMENT OF HIV DISEASE

CROSS-REFERENCE TO EARLIER FILED APPLICATION

This application is a divisional of U.S. patent application Ser. No. 08/040,324 filed Mar. 30, 1993 allowed U.S. Pat. No. 5,663,333, which is a continuation-in-part of U.S. patent application Ser. No. 07/965,061 filed Oct. 22, 1992 now abandoned.

FIELD OF THE INVENTION

This invention relates to novel substituted caprolactams, including 4-azacaprolactams, and derivatives thereof which inhibit HIV protease and are useful for treatment of HIV disease. Also included in this invention are pharmaceutical compositions containing such caprolactams, and to methods of using such caprolactams for the treatment of HIV disease.

BACKGROUND OF THE INVENTION

Current treatments for viral diseases usually involve administration of compounds that inhibit viral DNA synthesis. Current treatments for AIDS (Dagani, Chem. Eng. News, Nov. 23, 1987 pp. 41–49) involve administration of agents such as 2',3'-dideoxycytidine, trisodium phosphonoformate, ammonium 21-tungsto-9-antimoniate, 1-b-D-ribofuranoxyl-1,2,4-triazole-3-carboxamide, 3'-azido-3'-deoxythymidine (AZT), and adriamycin that inhibit viral DNA synthesis; compounds such as AL-721 and polymannoacetate which may prevent HIV from penetrating the host cell; and compounds which treat the opportunistic infections caused by the immunosupression resulting from HIV infection. None of the current AIDS treatments have proven to be totally effective in treating and/or reversing the disease. In addition, many of the compounds currently used to treat AIDS cause adverse side effects including low platelet count, renal toxicity, and bone marrow cytopenia.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. However, no therapeutically useful renin protease inhibitors have been developed, due to problems of oral availability and in vivo stability.

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into the core proteins, and also process the pol precursor into reverse transcriptase and retroviral protease.

The correct processing of the precursor polyproteins by the retroviral protease is necessary for the assembly of the infectious virions. It has been shown that in vitro mutagenesis that produces protease-defective virus leads to the production of immature core forms which lack infectivity. See Crawford et al., J. Virol. 53 899 (1985); Katoh et al., Virology 145 280 (1985). Therefore, retroviral protease inhibition provides an attractive target for antiviral therapy. See Mitsuya, Nature 325 775 (1987).

Moore, Biochem. Biophys. Res. Commun., 159 420 (1989) discloses peptidyl inhibitors of HIV protease. Erickson, European Patent Application No. WO 89/10752 discloses derivatives of peptides which are inhibitors of HIV protease.

U.S. Pat. No. 4,652,552 discloses methyl ketone derivatives of tetrapeptides as inhibitors of viral proteases. U.S. Pat. No. 4,644,055 discloses halomethyl derivatives of peptides as inhibitors of viral proteases. European Patent Application No. WO 87/07836 discloses L-glutamic acid gamma-monohydroxamate as an antiviral agent.

Japanese Patent Number 02306992 and Kimura, Agric. Biol. Chem., 53, 1811 (1989) describe compounds of the formula:

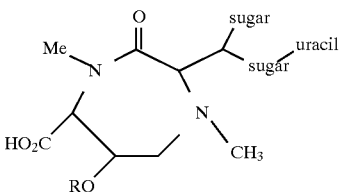

wherein R is a fatty acid. These compounds were isolated from streptomyces and shown to be useful as peptidoglycan inhibitors.

French Patent Number 2396002 describes quaternary amines, of the formula shown below, which are useful as vasodilators:

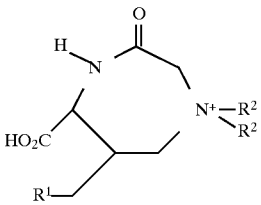

wherein $R^1$ is hydrogen or ester and $R^2$ is $C_1$–$C_2$ alkyl.

The ability to inhibit a viral protease provides a method for blocking viral replication and therefore a treatment for viral diseases, such as AIDS, that may have fewer side effects, be more efficacious, and be less prone to drug resistance when compared to current treatments.

The topic of the present invention is substituted caprolactams and derivatives thereof, which compounds are capable of inhibiting HIV protease and are, therefore, useful for combating HIV diseases, such as AIDS. The caprolactams and derivatives thereof of this invention provide significant improvements over protease inhibitors that are known in the art. A large number of compounds have been reported to be inhibitors of proteases, such as renin, but these have suffered from lack of adequate bioavailability and are thus not useful as therapeutic agents, particularly if oral administration is desired. This poor activity has been ascribed to the relatively high molecular weight of most protease inhibitors, to inadequate solubility properties, and to the presence of a number of peptide bonds, which are vulnerable to cleavage by mammalian proteases in vivo and which generally cause the molecules to be extensively bound in human serum. The substituted caprolactams and derivatives thereof of the present invention and described herein have a distinct advantage in this regard, in that they do not contain peptide bonds, are of low molecular weight, and can be hydrophilic yet still inhibit the viral protease enzyme.

The structures disclosed also have a particular advantage in the presence of a basic amine in the ring; which provides good in vitro potency and aids in formulation, in vivo absorption and CNS penetration of the compound.

The substituted caprolactams of the present invention are particularly useful as inhibitors of HIV protease and similar retroviral proteases.

The compounds of the invention are of low molecular weight and may, therefore, have good oral absorption properties in mammals.

DETAILED DESCRIPTION OF THE INVENTION

[1] There is provided by this invention compound of the formula (I):

or a pharmaceutically acceptable salt or prodrug form thereof wherein:

X is S, O, N—$R^7$;

$X^1$ is $C(R^4)(R^{4a})$ or N—$R^4$;

$R^4$ and $R^7$ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
$C_3$–$C_8$ cycloalkyl substituted with 0–3 $R^{11}$;
$C_6$–$C_{10}$ bicycloalkyl substituted with 0–3 $R^{11}$;
aryl substituted with 0–3 $R^{12}$;
a $C_6$–$C_{14}$ carbocyclic ring system substituted with 0–3 $R^{12}$;
a 5- to 10-membered heterocyclic ring system containing 1 to 4 heteroatoms independently selected from oxygen, nitrogen or sulfur, said heterocyclic ring system being substituted with 0–3 $R^{12}$;

$R^{4a}$ is selected from the following groups:
hydrogen;
$C_1$–$C_4$ alkyl substituted with 1–4 groups selected independently from: halogen or $C_1$–$C_2$ alkoxy;
benzyl substituted with 1–4 groups selected independently from: halogen or $C_1$–$C_2$ alkoxy;
—$OR^{20}$;
$SR^{20}$;

$R^4$ and $R^{4a}$ can alternatively join to form a 5–7 membered carbocyclic ring substituted with 0–2 $R^{12}$;

n is 0, 1, or 2;

$R^5$ is selected from H; halogen; —$N(R^{20})_2$; —$SR^{20}$; —$OR^{20}$; or $C_1$–$C_6$ alkyl substituted with 0–3 —$N(R^{20})_2$, —$SR^{20}$, or —$OR^{20}$;

$R^{5a}$ is selected from H, halogen, $C_1$–$C_6$ alkyl, —$N(R^{20})_2$, —$SR^{20}$, or —$OR^{20}$;

$R^5$ and $R^{5a}$ can alternatively join to form =O, =S, or a ketal ring;

$R^{20}$ and $R^{21}$ are independently selected from:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$;
$C_1$–$C_6$ alkylsulfenyl substituted with 0–3 $R^{11}$;
$C_1$–$C_6$ alkylsulfonyl substituted with 0–3 $R^{11}$; or
any group that, when administered to a mammalian subject, cleaves to form a free hydroxyl, amino or sulfhydryl;

$R^{11}$ is selected from one or more of the following:
keto, halogen, cyano, —$CH_2NR^{13}R^{14}$, —$NR^{13}R^{14}$, —$CO_2R^{13}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, or —$C(R^{14})=N(OR^{14})$;

$C_1$–$C_4$ alkyl substituted with 0–2 $R^{12}$,

1–3 amino acids, linked together via amide bonds and linked to $R^4$ or $R^7$, $R^{20}$, or $R^{21}$ via the amine or carboxy terminus;

—($C_1$–$C_3$ alkyl)aryl substituted with 0–2 $R^{12}$;

a $C_3$–$C_{14}$ carbocyclic residue substituted with 0–3 $R^{12}$;

aryl substituted with 0–3 $R^{12}$; or a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy; or a 5- or 6-membered heterocyclic ring containing from 1 to 4 heteroatoms independently selected from oxygen, nitrogen or sulfur;

when $R^{12}$ is attached to a saturated carbon atom, it may be carbonyl or thiocarbonyl;

or $R^{12}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$;

$R^{12}$, when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3-C_6$ cycloalkylmethyl, —$CH_2NR^{13}R^{14}$, —$NR^{13}R^{14}$, $C_2-C_6$ alkoxyalkyl, $C_1-C_4$ haloalkyl, $C_1-C_4$ alkoxycarbonyl, —$CO_2H$, $C_1-C_4$ alkylcarbonyloxy, $C_1-C_4$ alkylcarbonyl, —$C(R^{14})=N(OR^{14})$;

$R^{13}$ is selected from:
  H;
  phenyl substituted with 0–3 $R^{11A}$;
  benzyl substituted with 0–3 $R^{11A}$;
  $C_1-C_6$ alkyl substituted with 0–3 $R^{11A}$;
  $C_2-C_4$ alkenyl substituted with 0–3 $R^{11A}$;
  $C_1-C_6$ alkylcarbonyl substituted with 0–3 $R^{11A}$;
  $C_1-C_6$ alkoxycarbonyl substituted with 0–3 $R^{11A}$;
  $C_1-C_6$ alkylaminocarbonyl substituted with 0–3 $R^{11A}$;
  $C_3-C_6$ alkoxyalkyl substituted with 0–3 $R^{11A}$;
  an amine protecting group when $R^{13}$ is bonded to N;
  a hydroxy protecting group when $R^{13}$ is bonded to O;

$R^{14}$ is OH; H; $CF_3$; $C_1-C_4$ alkyl substituted with 0–3 groups selected from OH, $C_1-C_4$ alkoxy, halogen, $NH_2$; $C_1-C_6$ alkoxy; $NH_2$; $C_2-C_6$ alkenyl; benzyl; an amine protecting group when $R^{14}$ is bonded to N; a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;
m is 0, 1 or 2;

W is selected from:
  —$N(R^{22})C(=Z)N(R^{23})$—;
  —$OC(=Z)O$—;
  —$N(R^{22})C(=Z)O$—;
  —$C(R^{25})(R^{26})C(=Z)C(R^{27})(R^{28})$—;
  —$N(R^{22})C(=Z)C(R^{27})(R^{28})$—;
  —$C(R^{25})(R^{26})C(=Z)O$—;
  —$N(R^{22})C(=O)C(=O)N(R^{23})$—;
  —$N(R^{22})C(=S)C(=S)N(R^{23})$—;
  —$C(R^{25})(R^{26})C(F_2)C(R^{27})(R^{28})$—;
  —$C(R^{25})(R^{26})N(CH_3)(O)C(R^{27})(R^{28})$—;
  —$C(R^{25})(R^{26})N(OR^{29})C(R^{27})(R^{28})$—;
  —$C(R^{25})(R^{26})C(=Z)S$—;
  —$N(R^{22})S(=Z')N(R^{23})$—;
  —$N(R^{22})S(=Z')_2N(R^{23})$—;
  —$N(R^{22})P(=O)(R^{24a})(N(R^{23}))$—;
  —$C(R^{25})(R^{26})S(=Z')C(R^{27})(R^{28})$—;
  —$C(R^{25})(R^{26})S(=Z')_2C(R^{27})(R^{28})$—;
  —$C(R^{25})(R^{26})P(=O)(R^{24a})C(R^{27})(R^{28})$—;
  —$C(R^{25})(R^{26})S(=Z')N(R^{23})$—;
  —$C(R^{25})(R^{26})S(=Z')_2N(R^{23})$—;
  —$C(R^{25})(R^{26})S(=O)_2O$—;
  —$C(R^{25})(R^{26})P(=O)(R^{24a})N(R^{23})$—;
  —$C(R^{25})(R^{26})P(=O)(R^{24a})O$—;
  —$C(R^{25})(R^{26})C(F_2)C(=O)N(R^{23})$—;
  —$C(R^{25})(R^{26})C(F_2)S(=O)_2N(R^{23})$—;
  —$SC(=Z)$—;
  —$C(R^{25})(R^{26})C(R^{34})(R^{35})C(R^{27})(R^{28})$—;
  —$N(R^{22})C(R^{34})(R^{35})N(R^{23})$—;
  —$N=C(R^{36})N(R^{23})$—;
  —$N(R^{22})P(R^{24a})N(R^{23})$—;
  —$C(=Z)$—;
  —$P(=O)(R^{24a})$—;
  —$S(=Z)$—;
  —$S(=Z')_2$—;

Z is O, S, or $NR^{24}$;
Z' is O or $NR^{24}$;
$R^{22}$ is independently selected from the following:
  hydrogen;
  $C_1-C_8$ alkyl substituted with 0–3 $R^{31}$;
  $C_2-C_8$ alkenyl substituted with 0–3 $R^{31}$;
  $C_2-C_8$ alkynyl substituted with 0–3 $R^{31}$;
  a $C_3-C_{14}$ carbocyclic ring system substituted with 0–5 $R^{31}$ or $R^{32}$;
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{23}$ is independently selected from the following:
  hydrogen;
  $C_1-C_8$ alkyl substituted with 0–3 $R^{31}$;
  $C_2-C_8$ alkenyl substituted with 0–3 $R^{31}$;
  $C_2-C_8$ alkynyl substituted with 0–3 $R^{31}$;
  a $C_3-C_{14}$ carbocyclic ring system substituted with 0–5 $R^{31}$ or $R^{32}$;
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{24}$ is selected from: hydrogen; hydroxy; amino; $C_1-C_4$ alkyl; $C_1-C_4$ alkoxy; mono- or di-($C_1-C_6$ alkyl)amino; cyano; nitro; benzyloxy; —$NHSO_2$aryl, aryl being optionally substituted with ($C_1-C_6$)alkyl;

$R^{24a}$ is selected from: hydroxy; amino; $C_1-C_4$ alkyl; $C_1-C_4$ alkoxy; mono- or di-($C_1-C_6$ alkyl)amino; cyano; nitro; benzyloxy; or phenoxy;

$R^{25}$ is independently selected from the following:
  hydrogen;
  $C_1-C_8$ alkyl substituted with 0–3 $R^{31}$;
  $C_2-C_8$ alkenyl substituted with 0–3 $R^{31}$;
  $C_2-C_8$ alkynyl substituted with 0–3 $R^{31}$;
  a $C_3-C_{14}$ carbocyclic ring system substituted with 0–3 $R^{31}$ or $R^{32}$;
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{27}$ is selected from the following:
  hydrogen;
  $C_1-C_8$ alkyl substituted with 0–3 $R^{31}$;
  $C_2-C_8$ alkenyl substituted with 0–3 $R^{31}$;
  $C_2-C_8$ alkynyl substituted with 0–3 $R^{31}$;
  $C_3-C_8$ cycloalkyl substituted with 0–3 $R^{31}$;
  a $C_3-C_{14}$ carbocyclic ring system substituted with 0–3 $R^{31}$ or $R^{32}$;
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{26}$ is independently selected from:
  hydrogen;
  halogen;
  $C_1-C_4$ alkyl substituted with 0–3 halogen or $C_1-C_2$ alkoxy;
  benzyl substituted with 0–3 halogen or $C_1-C_2$ alkoxy;

$R^{28}$ is independently selected from:
  hydrogen;
  halogen;
  $C_1-C_4$ alkyl substituted with 0–3 halogen or $C_1-C_2$ alkoxy;
  benzyl substituted with 0–3 halogen or $C_1-C_2$ alkoxy;

$R^{29}$ is selected from:
  hydrogen;
  $C_1-C_4$ alkyl substituted with 0–3 halogen or $C_1-C_2$ alkoxy;

benzyl substituted with 0–3 halogen or $C_1$–$C_2$ alkoxy;

alternatively, $R^{22}$, $R^{25}$, or $R^{26}$, independently, can join with $R^4$ or $R^{4A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$, $R^{27}$, or $R^{28}$, independently, can join with $R^7$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$, $R^{25}$, $R^{26}$, $R^{23}$, $R^{27}$, $R^{28}$, $R^{34}$, or $R^{35}$ can join with $R^5$ or $R^6$ to form a 0- to 7-membered bridge to form a carbocyclic or heterocyclic ring, said bridge being substituted with 0–2 $R^{12}$ and said bridge containing 0–3 heteroatoms independently selected from N, S, or O (i.e., a 0-membered bridge is formed when $R^{22}$, $R^{25}$, $R^{26}$, $R^{23}$, $R^{27}$, $R^{28}$, $R^{34}$, or $R^{35}$ are taken together with $R^5$ or $R^6$ to form a direct bond);

$R^{31}$ is selected from one or more of the following:
  keto, halogen, cyano, —$CH_2NR^{13}R^{14}$, —$NR^{13}R^{14}$, —$CO_2R^{13}$, —$C(=O)R^{11}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})=N(OR^{14})$; or 1–3 amino acids, linked together via amide bonds and linked to $R^{22}$, $R^{23}$, $R^{25}$, $R^{27}$, $R^4$ or $R^7$ via the amine or carboxy terminus;

a $C_3$–$C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
  phenyl, benzyl, phenethyl, phenoxy, benzyloxy, halogen, hydroxy, nitro, cyano, $C_1$–$C_4$ alkyl, $C_3$–$C_{10}$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, —$CONR^{13}NR^{13}R^{14}$, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy, —$C(R^{14})=N(OR^{14})$; $NO_2$, —$OR^{13}$, —$NR^{40}OR^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—($C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or
—$C(=O)$ $NR^{13}C(R^{11})_2NR^{13}R^{14}$; —$C(=O)NR^{13}C(R^{11})_2NR^{13}NR^{14}$;
—$C(=O)NR^{13}C(R^{11})_2NR^{13}CO_2R^{13}$;
—$C(=O)NR^{13}$—($C_1$–$C_4$ alkyl)-$NR^{13}CO_2R^{13}$; or
—$C(=O)C(R^{11})_2NR^{13}R^{14}$; —$C(=O)C(R^{11})_2NR^{13}NR^{14}$;
—$C(=O)C(R^{11})_2NR^{13}CO_2R^{13}$; —$C(=O)$—($C_1$–$C_4$ alkyl)—$NR^{13}R^{14}$;
—$C(=O)$—($C_1$–$C_4$ alkyl)—$NR^{13}CO_2R^{13}$; or
$C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or OH;
$C_1$–$C_4$ alkyl substituted with 0–4 groups selected from: $R^{11}$, =$NR^{14}$, =$NNR^{13}C(=O)NR^{13}R^{14}$ or —$NR^{13}R^{14}$;
$C_2$–$C_4$ alkenyl substituted with 0–4 $R^{11}$;
$C_2$–$C_4$ alkynyl substituted with 0–4 $R^{11}$;
a 5- or 6-membered heterocyclic ring containing from 1 to 4 heteroatoms selected from oxygen, nitrogen or sulfur;
when $R^{32}$ is attached to a saturated carbon atom, it may be =O or =S;
$R^{32}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$;

$R^{32}$, when a substituent on nitrogen, is selected from one or more of the following:
  phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{33}$ is selected from:
  H;
  $C_1$–$C_3$ alkyl substituted at the $C_2$ or $C_3$ carbon with —$N(R^{20})_2$, —$SR^{20}$, or —$OR^{21}$;
  or when taken together with $R^{33a}$, form =O, =S, or a ketal group;

$R^{33a}$ is selected from:
  H;
  $C_1$–$C_3$ alkyl substituted at the $C_2$ or $C_3$ carbon with —$N(R^{20})_2$, —$SR^{20}$, or —$OR^{21}$;
  or, when taken together with $R^{33}$, form =O;
alternatively, $R^{33}$ or $R^{33a}$ can join with $R^7$ to form a fused 5- or 6-membered carbocyclic ring;

$R^{34}$ is selected from:
  hydrogen;
  $OR^{13}$;
  $SR^{13}$;
  halogen;
  $N(R^{38})(R^{39})$
  $C_1$–$C_6$ alkyl substituted with 0–3 $R^{11}$;
  $C_1$–$C_6$ alkoxy substituted with 0–3 $R^{11}$;
  $C_1$–$C_6$ thioalkyl substituted with 0–3 $R^{11}$;

$R^{35}$ is selected from:
  hydrogen;

OR$^{13}$;
SR$^{13}$;
halogen;
N(R$^{38}$)(R$^{39}$)
C$_1$–C$_6$ alkyl substituted with 0–3 R$^{11}$;
C$_1$–C$_6$ alkoxy substituted with 0–3 R$^{11}$;
C$_1$–C$_6$ thioalkyl substituted with 0–3 R$^{11}$;
R$^{34}$ and R$^{35}$ can be taken together to form a ketal ring, a 3- to 8-membered carbocyclic ring, or a 5- or 6-membered heterocyclic ring containing 1–3 heteroatoms independently selected from the group O, N, or S, said ring substituted with 0–5 R$^{11}$;
R$^{36}$ is selected from:
   C$_1$–C$_6$ alkyl substituted with 0–3 R$^{11}$;
   —COR$^{37}$;
   —NR$^{38}$R$^{39}$;
   —CN;
R$^{37}$ is selected from:
   hydrogen;
   C$_1$–C$_6$ alkyl substituted with 0–3 R$^{11}$;
   hydroxyl;
   C$_1$–C$_6$ alkoxy substituted with 0–3 R$^{11}$;
   —NR$^{38}$R$^{39}$;
R$^{38}$ and R$^{39}$ are independently selected from:
   hydrogen;
   C$_1$–C$_6$ alkyl substituted with 0–3 R$^{11}$; or
   an amine protecting group;
R$^{40}$ is selected from: H, C$_1$–C$_3$ alkyl;
R$^{41}$ is selected from:
   —C(=O) NR$^{13}$R$^{14}$;
   —C(=O) NR$^{13}$NR$^{14}$;
   —C(=O)C(R$^{11}$)$_2$NR$^{13}$R$^{14}$;
   —C(=O)C(R$^{11}$)$_2$NR$^{13}$NR$^{14}$;
   —C(=O)C(R$^{11}$)$_2$NR$^{13}$CO$_2$R$^{13}$;
   —C(=O)H;
   —C(=O)R$^{11}$;
   —C(=O)—(C$_1$–C$_4$ alkyl)-NR$^{13}$R$^{14}$;
   —C(=O)—(C$_1$–C$_4$ alkyl)-NR$^{13}$CO$_2$R$^{13}$;
   1–3 amino acids linked together via amide bonds, and linked to the N atom via the carboxy terminus;
provided that:
   when R$^4$ and R$^{4a}$ are hydrogen and X is N—R$^7$, at least one of the following is not hydrogen: R$^7$, R$^{22}$, R$^{27}$ or R$^{28}$;
   when R$^4$ and R$^{4a}$ are hydrogen and X is S or O, at least two of the following are not hydrogen: R$^{22}$, R$^{27}$ or R$^{28}$.

[2] Preferred compounds of Formula (I) are compounds described above, wherein:
W is selected from:
   —N(R$^{22}$)C(=Z)N(R$^{23}$)—;
   —OC(=Z)O—;
   —N(R$^{22}$)C(=Z)O—;
   —C(R$^{25}$) (R$^{26}$)C(=Z)C(R$^{27}$) (R$^{28}$)—;
   —N(R$^{22}$)C(=Z)C(R$^{27}$)(R$^{28}$)—;
   —C(R$^{25}$) (R$^{26}$)C(=Z)O—;
   —N(R$^{22}$)C(=O)C(=O)N(R$^{23}$)—;
   —N(R$^{22}$)C(=S)C(=S)N(R$^{23}$)—;
   —C(R$^{25}$) (R$^{26}$)C(F$_2$)C(R$^{27}$) (R$^{28}$)—;
   —C(R$^{25}$)(R$^{26}$)N(CH$_3$)(O)C(R$^{27}$)(R$^{28}$)—;
   —C(R$^{25}$) (R$^{26}$)N(OR$^{29}$)C(R$^{27}$) (R$^{28}$)—;
   —N(R$^{22}$)S(=Z')N(R$^{23}$)—;
   —N(R$^{22}$)S(=Z')$_2$N (R$^{23}$)—;
   —N(R$^{22}$)P(=O)(R$^{24a}$)(N(R$^{23}$)—;
   —C(R$^{25}$)(R$^{26}$)S(=Z')C(R$^{27}$)(R$^{28}$)—;
   —C(R$^{25}$) (R$^{26}$)S(=Z')$_2$C(R$^{27}$) (R$^{28}$)—;
   —C(R$^{25}$) (R$^{26}$)P(=O) (R$^{24a}$)C(R$^{27}$) (R$^{28}$)—;
   —C(R$^{25}$) (R$^{26}$)S(=Z')N(R$^{23}$)—;
   —C(R$^{25}$)(R$^{26}$)S(=Z')$_2$N(R$^{23}$)—;
   —C(R$^{25}$) (R$^{26}$)S(=O)$_2$O—;
   —C(R$^{25}$) (R$^{26}$)P(=O) (R$^{24a}$)N(R$^{23}$)—;
   —C(R$^{25}$)(R$^{26}$)C(F$_2$)C(=O)N(R$^{23}$)—;
   —C(R$^{25}$) (R$^{26}$)C(F$_2$)S(=O)$_2$N(R$^{23}$)—;
   —C(R$^{25}$) (R$^{26}$)C(R$^{34}$) (R$^{35}$)C(R$^{27}$) (R$^{28}$)—;
   —N(R$^{22}$)C(R$^{34}$) (R$^{35}$)N(R$^{23}$)—;
   —N(R$^{22}$)=C(R$^{36}$)N(R$^{23}$)—;
   —N(R$^{22}$)P(R$^{24a}$)N(R$^{23}$)—;

[3] The present invention includes compounds of Formula (I) described above of the Formula (Ia):

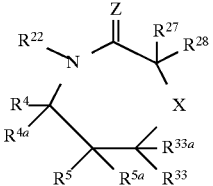

(Ia)

wherein the groups and substituents are as defined above.

[4] The present invention includes compounds of Formula (I) described above of the Formula (Ia):

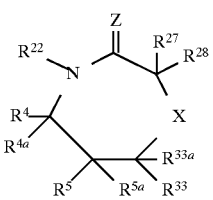

(Ia)

wherein:
   X is S, O or N—R$^7$;
   R$^4$ and R$^7$ are independently selected from the following groups:
      hydrogen;
      C$_1$–C$_4$ alkyl substituted with 0–3 R$^{11}$;
      C$_3$–C$_4$ alkenyl substituted with 0–3 R$^{11}$;
      C$_3$–C$_4$ alkynyl substituted with 0–3 R$^{11}$;
   R$^{4a}$ is hydrogen;
   R$^5$ is selected from H; halogen; —N(R$^{20}$)$_2$; —SR$^{20}$; —OR$^{20}$; or C$_1$–C$_3$ alkyl substituted with 0–3 —N(R$^{20}$)$_2$, —SR$^{20}$, or —OR$^{20}$;
   R$^{5a}$ is selected from hydrogen or fluoro;
   R$^5$ and R$^{5a}$ can alternatively join to form =O, =S, or a ketal ring;
   R$^{20}$ and R$^{21}$ are independently selected from:
      hydrogen;
      C$_1$–C$_6$ alkylcarbonyl;
      C$_1$–C$_6$ alkoxycarbonyl;
      benzoyl; or
      any group that, when administered to a mammalian subject, cleaves to form a free hydroxyl, amine or sulfhydryl;
   R$^{11}$ is selected from one or more of the following:
      keto; halogen; cyano; —CH$_2$NR$^{13}$R$^{14}$; —NR$^{13}$R$^{14}$; —CO$_2$R$^{13}$; —OC(=O)R$^{13}$; —OR$^{13}$; C$_2$–C$_6$ alkoxyalkyl;
      —S(O)$_m$R$^{13}$; C$_2$–C$_4$ alkenyl;
      C$_1$–C$_4$ alkyl substituted with 0–2 R$^{12}$,
      a C$_3$–C$_{14}$ carbocyclic residue substituted with 0–3 R$^{12}$;
      aryl(C$_1$–C$_3$ alkyl) substituted with 0–2 R$^{12}$;
      aryl substituted with 0–3 R$^{12}$; or a 5- to 10-membered heterocyclic ring system containing 1 to 4 heteroatoms independently selected from oxygen, nitrogen or sulfur, said heterocyclic ring system being substituted with 0–2 $R^{12}$;

$R^{12}$, when a substituent on carbon, is selected from one or more of the following:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy; or a 5- or 6-membered heterocyclic ring containing from 1 to 4 heteroatoms independently selected from oxygen, nitrogen or sulfur;

when $R^{12}$ is attached to a saturated carbon atom, it may be carbonyl or thiocarbonyl;

or $R^{12}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$;

$R^{12}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl;

$R^{13}$ is H, $C_1$–$C_6$ alkyl, or $C_3$–$C_6$ alkoxyalkyl; $C_2$–$C_4$ alkenyl, phenyl, or benzyl;

$R^{14}$ is OH, H, $CF_3$, $C_1$–$C_4$ alkyl, $C_1$–$C_4$ alkoxy, $NH_2$, $C_2$–$C_4$ alkenyl, phenyl or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

Z is O, S, N—CN, N—OH, N—$OCH_3$;

$R^{22}$ is independently selected from the following:
hydrogen;
$C_1$–$C_8$ alkyl substituted with 0–3 $R^{31}$;
$C_3$–$C_8$ alkenyl substituted with 0–3 $R^{31}$;
$C_3$–$C_8$ alkynyl substituted with 0–3 $R^{31}$;
$C_3$–$C_6$ cycloalkyl substituted with 0–3 $R^{31}$;

$R^{27}$ is selected from the following:
hydrogen;
$C_1$–$C_8$ alkyl substituted with 0–3 $R^{31}$;
$C_2$–$C_8$ alkenyl substituted with 0–3 $R^{31}$;
$C_3$–$C_8$ alkynyl substituted with 0–3 $R^{31}$;

$R^{28}$ is hydrogen;

$R^{31}$ is selected from one or more of the following:
keto, halogen, cyano, —$CH_2NR^{13}R^{14}$, —$NR^{13}R^{14}$, —$CO_2R^{13}$, —$OC(=O)R^{13}$, —$OR^{13}$, $C_2$–$C_6$ alkoxyalkyl, —$S(O)_mR^{13}$, $C_1$–$C_4$ alkyl, $C_2$–$C_4$ alkenyl, $C_3$–$C_6$ cycloalkyl, $C_3$–$C_{10}$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, —$C(R^{14})=N(OR^{14})$; or;

a $C_3$–$C_{14}$ saturated or partially unsaturated carbocyclic residue substituted with 0–5 $R^{32}$;

aryl substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenethyl, phenoxy, $C_3$–$C_{10}$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, boronic acid, sulfonamide, —CHO, $C_3$–$C_6$ cycloalkoxy, —$NR^{13}R^{14}$, —$C(R^{14})=N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—$(C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or —$C(=O)NR^{13}C(R^{11})_2NR^{13}R^{14}$; —$C(=O)NR^{13}C(R^{11})_2NR^{13}R^{14}$;

—$C(=O)NR^{13}C(R^{11})_2NR^{13}CO_2R^{13}$;

—$C(=O)NR^{13}$—$(C_1$–$C_4$ alkyl)-$NR^{13}CO_2R^{13}$; or

—$C(=O)C(R^{11})_2NR^{13}R^{14}$; —$C(=O)C(R^{11})_2NR^{13}NR^{14}$;

—$C(=O)C(R^{11})_2NR^{13}CO_2R^{13}$; —$C(=O)$—$(C_1$–$C_4$ alkyl)-$NR^{13}R^{14}$;

—$C(=O)$—$(C_1$–$C_4$ alkyl)-$NR^{13}CO_2R^{13}$; or $C_1$–$C_4$ alkoxy substituted with 0–3 groups selected from: $R^{11}$, $C_3$–$C_6$ cycloalkyl, —$CO_2R^{13}$, —$C(=O)NR^{13}R^{14}$, —$NR^{13}R^{14}$ or OH;

$C_1$–$C_4$ alkyl substituted with 0–3 groups selected from: $R^{11}$, =$NR^{14}$, =$NNR^{13}C(=O)NR^{13}R^{14}$ or —$NR^{13}R^{14}$;

$C_2$–$C_4$ alkenyl substituted with 0–3 $R^{11}$;

$C_2$–$C_4$ alkynyl substituted with 0–3 $R^{11}$;

a 5- or 6-membered heterocyclic ring containing from 1 to 4 heteroatoms independently selected from oxygen, nitrogen or sulfur;

when $R^{32}$ is attached to a saturated carbon atom, it may be =O or =S;

$R^{32}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$;

$R^{32}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{33}$ is selected from:
  H;
  $C_1$–$C_3$ alkyl substituted at the $C_2$ or $C_3$ carbon with halogen, —$N(R^{20})_2$, —$SR^{20}$, or —$OR^{21}$;
  or, when taken together with $R^{33a}$, form a =O group;

$R^5$ and the —$OR^{21}$ group of $R^{33}$ can alternatively join to form: —$OS(=O)O$—; —$OC(=O)O$—; —$OCH_2O$—; —$OC(=S)O$—; —$OC(CH_3)_2O$—; —$OC(OCH_3)(CH_2CH_2CH_3)O$—; or any group that, when administered to a mammalian subject, cleaves to form a free dihydroxyl;

$R^{33a}$ is H or may be taken together with $R^{33}$ form =O;

$R^{40}$ is selected from: H, $C_1$–$C_3$ alkyl;

$R^{41}$ is selected from:
  —$C(=O)NR^{13}R^{14}$;
  —$C(=O)NR^{13}NR^{14}$;
  —$C(=O)C(R^{11})_2NR^{13}R^{14}$;
  —$C(=O)C(R^{11})_2NR^{13}NR^{14}$;
  —$C(=O)C(R^{11})_2NR^{13}CO_2R^{13}$;
  —$C(=O)H$;
  —$C(=O)R^{11}$;
  —$C(=O)$—$(C_1$–$C_4$ alkyl)-$NR^{13}R^{14}$;
  —$C(=O)$—$(C_1$–$C_4$ alkyl)-$NR^{13}CO_2R^{13}$;
  1–3 amino acids linked together via amide bonds, and linked to the N atom via the carboxy terminus of the amino acid;
  provided that:
    when $R^4$ and $R^{4a}$ are hydrogen and X is N—$R^7$, at least one of the following is not hydrogen: $R^7$, $R^{22}$, $R^{27}$ or $R^{28}$;
    when $R^4$ and $R^{4a}$ are hydrogen and X is S or O, at least two of the following are not hydrogen: $R^{22}$, $R^{27}$ or $R^{28}$.

[5] Preferred compounds of Formula (Ia) described above, wherein:

$R^4$ and $R^7$ are independently selected from the following groups:
  hydrogen;
  $C_1$–$C_4$ alkyl substituted with 0–3 $R^{11}$;
  $C_3$–$C_4$ alkenyl substituted with 0–3 $R^{11}$;

$R^5$ is —$OR^{20}$;

$R^{5a}$ is H;

$R^{20}$ is H or any group that, when administered to a mammalian subject, cleaves to form a free hydroxyl;

$R^{11}$ is selected from one or more of the following:
  keto; halogen; —$CH_2NR^{13}R^{14}$; —$NR^{13}R^{14}$; —$OR^{13}$; $C_2$–$C_4$ alkoxyalkyl; $C_2$–$C_4$ alkenyl;
  $C_3$–$C_{10}$ cycloalkyl substituted with 0–2 $R^{12}$; $C_1$–$C_4$ alkyl substituted with 0–2 $R^{12}$,
  aryl($C_1$–$C_3$ alkyl) substituted with 0–2 $R^{12}$; aryl substituted with 0–3 $R^{12}$; or
  a 5- to 10-membered heterocyclic ring system containing 1 to 4 heteroatoms independently selected from oxygen, nitrogen or sulfur, said heterocyclic ring system being substituted with 0–2 $R^{12}$;

$R^{12}$, when a substituent on carbon, is selected from one or more of the following:
  phenyl, benzyl, phenethyl, phenoxy, benzyloxy, halogen, $C_1$–$C_4$ alkyl, $C_7$–$C_{10}$ arylalkyl, $C_1$–$C_4$ alkoxy, —$CO_2H$, hydroxamic acid, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, methylenedioxy, $C_1$–$C_4$ haloalkyl, $C_1$–$C_4$ alkylcarbonyl, $C_1$–$C_4$ alkylcarbonylamino, —OH, hydroxymethyl; or
  a 5- or 6-membered heterocyclic ring containing from 1 to 4 heteroatoms selected from oxygen, nitrogen or sulfur;

$R^{12}$, when a substituent on nitrogen, is benzyl or methyl;

$R^{13}$ is H, $C_1$–$C_4$ alkyl, or $C_3$–$C_6$ alkoxyalkyl, $C_2$–$C_4$ alkenyl, or benzyl;

$R^{14}$ is OH, H, $CF_3$, $C_1$–$C_4$ alkyl, $C_1$–$C_4$ alkoxy, $NH_2$, $C_2$–$C_4$ alkenyl, or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

Z is O, S, or N—CN;

$R^{22}$ is independently selected from the following:
  hydrogen;
  $C_1$–$C_8$ alkyl substituted with 0–3 $R^{31}$;
  $C_2$–$C_6$ alkenyl substituted with 0–3 $R^{31}$;
  $C_2$–$C_4$ alkynyl substituted with 0–3 $R^{31}$;

$R^{27}$ is selected from the following:
  hydrogen;
  $C_1$–$C_4$ alkyl substituted with 0–3 $R^{31}$;
  $C_2$–$C_4$ alkenyl substituted with 0–3 $R^{31}$;

$R^{31}$ is selected from one or more of the following:
  keto, halogen, —$CH_2NR^{13}R^{14}$, —$NR^{13}R^{14}$, —$OR^{13}$, $C_2$–$C_4$ alkoxyalkyl, $C_1$–$C_4$ alkyl, $C_2$–$C_4$ alkenyl, $C_3$–$C_{10}$ cycloalkyl, —$C(R^{14})=N(OR^{14})$, —$CO_2R^{13}$, —$S(O)_mR^{13}$;
  aryl substituted with 0–5 $R^{32}$; or
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
  phenethyl, phenoxy, $C_3$–$C_{10}$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, boronic acid, sulfonamide, —CHO, $C_3$–$C_6$ cycloalkoxy, —$NR^{13}R^{14}$, —$C(R^{14})=N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—$(C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or
  $C_1$–$C_4$ alkoxy substituted with 0–3 groups selected from: $R^{11}$, $C_3$–$C_6$ cycloalkyl, —$CO_2R^{13}$, —$C(=O)NR^{13}R^{14}$, —$NR^{13}R^{14}$ or OH;
  $C_1$–$C_4$ alkyl substituted with 0–3 groups selected from: $R^{11}$, =$NR^{14}$, =$NNR^{13}C(=O)NR^{13}R^{14}$ or —$NR^{13}R^{14}$;
  $C_2$–$C_4$ alkenyl substituted with 0–3 $R^{11}$;
  $C_2$–$C_4$ alkynyl substituted with 0–3 $R^{11}$;
  a 5- or 6-membered heterocyclic ring containing from 1 to 4 heteroatoms independently selected from oxygen, nitrogen or sulfur;

$R^{32}$, when a substituent on nitrogen, is benzyl or methyl;

$R^{33}$ is hydrogen or, when taken together with $R^{33}$, form a =O group;

provided that:
when $R^4$ is hydrogen and X is N—$R^7$, at least one of the following is not hydrogen: $R^7$, $R^{22}$, or $R^{27}$;
when $R^4$ is hydrogen and X is S or O, at least two of the following are not hydrogen: $R^{22}$ or $R^{27}$.

[6] More preferred are compounds of Formula (Ia) described above, wherein:

$R^4$ and $R^7$ are independently selected from the following groups:
hydrogen;
$C_1$–$C_3$ alkyl substituted with 0–3 $R^{11}$;

$R^{11}$ is selected from one or more of the following:
halogen, —$OR^{13}$;
$C_3$–$C_{10}$ cycloalkyl substituted with 0–2 $R^{12}$;
$C_1$–$C_4$ alkyl substituted with 0–2 $R^{12}$, aryl($C_1$–$C_3$ alkyl) substituted with 0–2 $R^{12}$;
aryl substituted with 0–2 $R^{12}$; or
a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{12}$, when a substituent on carbon, is selected from one or more of the following:
benzyloxy, halogen, methyl, $C_1$–$C_4$ alkoxy, $CF_3$, 2-(1-morpholino)ethoxy, —$CO_2H$, hydroxamic acid, hydrazide, oxime, cyano, boronic acid, sulfonamide, formyl, $C_3$–$C_6$ cycloalkoxy, $C_1$–$C_4$ alkyl substituted with —$NR^{13}R^{14}$, —$NR^{13}R^{14}$, —OH, hydroxymethyl; or $R^{12}$, when a substituent on nitrogen, is methyl;

$R^{13}$ is H, $C_1$–$C_4$ alkyl, $C_2$–$C_4$ alkenyl, or benzyl;

Z is O or N—CN;

$R^{27}$ is selected from the following:
hydrogen;
$C_1$–$C_4$ alkyl substituted with 0–3 $R^{31}$;
$C_3$–$C_4$ alkenyl substituted with 0–3 $R^{31}$;

$R^{31}$ is selected from one or more of the following:
halogen, —$OR^{13}$, $C_1$–$C_4$ alkyl, $C_3$–$C_{10}$ cycloalkyl, —$C(R^{14})=N(OR^{14})$, —$CO_2R^{13}$, —$S(O)_mR^{13}$;
aryl substituted with 0–5 $R^{32}$; or
a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring being substituted with 0–2 $R^{32}$;

$R^{32}$, when a substituent on carbon, is selected from one or more of the following:
benzyloxy, halogen, 2-(1-morpholino)ethoxy, —$CO_2R^{13}$, hydroxamic acid, —$CONR^{13}NR^{13}R^{14}$, cyano, boronic acid, sulfonamide, formyl, $C_3$–$C_{10}$ cycloalkoxy, —$NR^{13}R^{14}$, —$C(R^{14})=N(OR^{14})$, $NO_2$, —$OR^{13}$, $NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$–($C_1$–$C_3$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, —$C(=O)NR^{13}R^{14}$; —$C(=O)C(R^{11})_2NR^{13}R^{14}$; —$C(=O)C(R^{11})_2NR^{13}NR^{14}$; —$C(=O)C(R^{11})_2NR^{13}CO_2R^{13}$; —$C(=O)$—$(C_1$–$C_4$ alkyl)-$NR^{13}R^{14}$; —$C(=O)$—$(C_1$–$C_4$ alkyl)-$NR^{13}CO_2R^{13}$; or $C_1$–$C_4$ alkoxy substituted with 0–3 groups selected from: $R^{11}$, $C_3$–$C_6$ cycloalkyl, —$C(=O)NR^{13}R^{14}$, —$NR^{13}R^{14}$ or OH;
$C_1$–$C_4$ alkyl substituted with 0–3 groups selected from: $R^{11}$, =$NR^{14}$, =$NNR^{13}C(=O)NR^{13}R^{14}$ or —$NR^{13}R^{14}$;
$C_2$–$C_4$ alkenyl substituted with 0–3 $R^{11}$;
$C_2$–$C_4$ alkynyl substituted with 0–3 $R^{11}$;
a 5- or 6-membered heterocyclic ring containing from 1 to 4 heteroatoms independently selected from oxygen, nitrogen or sulfur;

$R^{32}$, when a substituent on nitrogen, is methyl.

[7] Further preferred compounds of the present invention are compounds of Formula (Ia) described above, wherein:

$R^4$ and $R^7$ are selected from benzyl, fluorobenzyl, pyrrolylmethyl, methoxybenzyl, isobutyl, nitrobenzyl or aminobenzyl;

$R^5$ is —OH;

$R^{13}$ is H, $C_1$–$C_4$ alkyl, $C_2$–$C_4$ alkenyl, or benzyl;

$R^{14}$ is OH, H, $CF_3$, $C_1$–$C_4$ alkyl, $C_1$–$C_4$ alkoxy, $NH_2$, $C_2$–$C_4$ alkenyl, or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{22}$ is independently selected from the following:
hydrogen;
$C_1$–$C_8$ alkyl substituted with 0–2 $R^{31}$;
$C_2$–$C_6$ alkenyl substituted with 0–2 $R^{31}$;
$C_2$–$C_4$ alkynyl substituted with 0–2 $R^{31}$;

$R^{27}$ is H or $C_1$–$C_4$ alkyl substituted with 0–3 $R^{31}$;

$R^{32}$, when a substituent on carbon, is selected from one or more of the following:
—$CONH_2$, —$CO_2H$, —CHO, —$CH_2NHOH$, —$CH_2NR^{13}R^{14}$, —$NR^{13}R^{14}$, hydroxy, hydroxymethyl, —$C(R^{14})=N(OR^{14})$, halogen, methoxy, methyl, nitro, cyano, allyloxy, —$CO_2CH_3$, —NHCHO, —$NHCOCH_3$, —$OCO_2CH_3$, —CH=$NCH_2CH_2OH$, —$OCONHCH_2C_6H_5$, —$OCONHCH_3$, oxazolidinyl, —C≡C—$CH_2OH$, —$COCH_3$, hydroxyethyl, $C_1$–$C_3$ alkyl (said alkyl substituted with 0–4 halogen, or OH), tetrazolyl, —$OCH_2CONH_2$, —$CONHNH_2$, —CH=$NNHCONH_2$, —$CONHOCH_3$, —$CH_2CH(OH)CH_2OH$, adamantamido, hydroxyethoxy, dihydroxyethyl, —$C(NH_2)$=NH, —$CONHCH_3$, —$B(OH)_2$, benzyloxy, —$CONHCH_2CH_3$, —$CON(CH_2CH_3)_2$, methylthio, —$SO_2CH_3$, —$NHCONH_2$, —$NHCONHCH_3$, —$NHCOCH_2N(CH_3)_2$, —$NHCOCH_2NHCH_3$, —$NHCOCH_2NHCO_2CH_2C_6H_5$, —$NHCOCH_2NH_2$, —$NHCOCH(CH_3)NHCO_2CH_2C_6H_5$, —$NHCOCH(CH_2C_6H_5)NHCO_2CH_2C_6H_5$, —$NHCOCH(CH_3)NH_2$, —$NHCOCH(CH_2C_6H_5)NH_2$, —$CO_2CH_2CH_3$, —$CONHCH_2CH_2CH_3$, —$CONHCH(CH_3)_2$, —$CH_2$-imidazole, —$COC(CH_3)_3$, —$CH(OH)CF_3$, —CO-imidazole, —$COCF_3$, —$COCH_2CH_3$, —$COCH_2CH_2CH_3$, pyrazolyl, —$SO_2NH_2$, —$C(CH_2CH_3)$=N(OH) or —$C(CF_3)$=N(OH), phenyl, acetoxy, hydroxyamino, —N($CH_3$) (CHO), cyclopropylmethoxy, —$CONR^{13}R^{14}$, —CONHOH, (diethylaminoethyl)aminocarbonyl, (N-ethyl,N-methylaminoethyl)aminocarbonyl, (4-methylpiperazinylethyl)aminocarbonyl, pyrrolidinylethyl)aminocarbonyl, (piperidinylethyl) aminocarbonyl, —$NHCOCH_2NHCH_3$, N-(2-(4-morpholino)ethyl)aminocarbonyl, N-(2-(N,N-dimethylamino)ethyl)aminocarbonyl.

[8] More further preferred compounds of Formula (Ia) described above, wherein:

X is N—R$^7$;

R$^4$ and R$^7$ are benzyl;

R$^{4a}$ is hydrogen;

R$^5$ is —OH;

Z is O or N—CN;

R$^{28}$ is hydrogen;

R$^{22}$ and R$^{27}$ are independently selected from the group consisting of:

hydrogen, allyl, methyl, ethyl, propyl, cyclopropylmethyl, n-butyl, i-butyl, CH$_2$CH=C(CH$_3$)$_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, (H$_2$NC(=O))-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, (CH$_3$C(=NOH))-benzyl, (H$_2$NNHC(=O))-benzyl, (H$_2$NC(=O)NHN=CH)-benzyl, (CH$_3$ONHC(=O))-benzyl, (HONHC(=O))-benzyl, (CH$_3$NHC(=O))-benzyl, N,N-dimethylaminocarbonylbenzyl, (HOCH$_2$CH(OH)CH$_2$O)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N, N-di-n-propylaminocarbonylbenzyl, (hydroxypropynyl)benzyl, (imidazolyl-C(=O))-benzyl, trifluoroacetylbenzyl, (pyrazolyl)benzyl, (H$_2$NSO$_2$)-benzyl, dihydroxyethylbenzyl, (MeHNC(=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butylbenzoyl, (CH$_3$CH$_2$C(=NOH))-benzyl, (trifluorohydroxyethyl)benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C—C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl.

[9] Preferred compounds of the invention of Formula (Ia) are compounds of Formula (Ib):

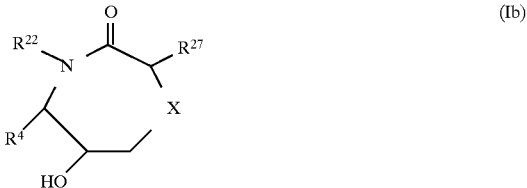

(Ib)

or a pharmaceutically acceptable salt or prodrug form thereof wherein:

X is S, O or N—R$^7$;

R$^4$ and R$^7$ are independently selected from the following groups:
hydrogen;
C$_1$–C$_4$ alkyl substituted with 0–3 R$^{11}$;
C$_3$–C$_4$ alkenyl substituted with 0–3 R$^{11}$;

R$^{11}$ is selected from one or more of the following:
keto; halogen; cyano; —CH$_2$NR$^{13}$R$^{14}$; —NR$^{13}$R$^{14}$; —CO$_2$R$^{13}$; —OC(=O)R$^{13}$; —OR$^{13}$; C$_2$–C$_6$ alkoxyalkyl;
—S(O)$_m$R$^{13}$; C$_2$–C$_4$ alkenyl;
a C$_5$–C$_{14}$ carbocyclic residue substituted with 0–3 R$^{12}$;
aryl(C$_1$–C$_3$ alkyl) substituted with 0–2 R$^{12}$;
aryl substituted with 0–3 R$^{12}$; or
a 5- to 10-membered heterocyclic ring system containing 1 to 4 heteroatoms independently selected from oxygen, nitrogen or sulfur, said heterocyclic ring system being substituted with 0–2 R$^{12}$;

R$^{12}$, when a substituent on carbon, is selected from one or more of the following:
phenyl, benzyl, phenethyl, phenoxy, benzyloxy, halogen, C$_1$–C$_4$ alkyl, C$_7$–C$_{10}$ arylalkyl, C$_1$–C$_4$ alkoxy, —CO$_2$H, hydroxamic acid, hydrazide, oxime, boronic acid, sulfonamide, formyl, C$_3$–C$_6$ cycloalkoxy, —OR$^{13}$, C$_1$–C$_4$ alkyl substituted with —NR$^{13}$R$^{14}$, —NR$^{13}$R$^{14}$, methylenedioxy, C$_1$–C$_4$ haloalkyl, C$_1$–C$_4$ alkylcarbonyl, C$_1$–C$_4$ alkylcarbonylamino, —OH, hydroxymethyl; or
a 5- or 6-membered heterocyclic ring containing from 1 to 4 heteroatoms selected from oxygen, nitrogen or sulfur;

R$^{12}$, when a substituent on nitrogen, is benzyl or methyl;

R$^{13}$ is H, C$_1$–C$_4$ alkyl, or C$_3$–C$_6$ alkoxyalkyl, C$_2$–C$_4$ alkenyl, or benzyl;

R$^{14}$ is OH, H, CF$_3$, or C$_1$–C$_4$ alkyl, C$_1$–C$_4$ alkoxy, NH$_2$, C$_2$–C$_4$ alkenyl, or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{22}$ is independently selected from the following:
hydrogen;
$C_1$–$C_8$ alkyl substituted with 0–3 $R^{31}$;
$C_2$–$C_6$ alkenyl substituted with 0–3 $R^{31}$;
$C_2$–$C_4$ alkynyl substituted with 0–1 $R^{31}$;

$R^{27}$ is selected from the following:
hydrogen;
$C_1$–$C_4$ alkyl substituted with 0–3 $R^{31}$;
$C_2$–$C_4$ alkenyl substituted with 0–3 $R^{31}$;

$R^{31}$ is selected from one or more of the following:
keto, halogen, —$CH_2NR^{13}R^{14}$, —$NR^{13}R^{14}$, —$OR^{13}$, $C_2$–$C_4$
alkoxyalkyl, $C_1$–$C_4$ alkyl, $C_2$–$C_4$ alkenyl, $C_3$–$C_{10}$ cycloalkyl, —$C(R^{14})=N(OR^{14})$, —$CO_2R^{13}$, —$S(O)_m R^{13}$;
aryl substituted with 0–5 $R^{32}$; or
a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
phenethyl, phenoxy, $C_3$–$C_6$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, boronic acid, sulfonamide, —CHO, $C_3$–$C_6$ cycloalkoxy, —$NR^{13}R^{14}$, —$C(R^{14})=N(OR^{14})$, $NO_2$, —$OR^{13}$, —$NR^{40}R^{41}$, —$SO_m R^{13}$, —$SO_m NR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—$(C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or
$C_1$–$C_4$ alkoxy substituted with 0–3 groups selected from: $R^{11}$, $C_3$–$C_6$ cycloalkyl, —$CO_2R^{13}$, —$C(=O)NR^{13}R^{14}$, —$NR^{13}R^{14}$ or OH;
$C_1$–$C_4$ alkyl substituted with 0–3 groups selected from: $R^{11}$, $=NR^{14}$, $=NNR^{13}C(=O)NR^{13}R^{14}$ or —$NR^{13}R^{14}$;
$C_2$–$C_4$ alkenyl substituted with 0–3 $R^{11}$;
$C_2$–$C_4$ alkynyl substituted with 0–3 $R^{11}$;
a 5- or 6-membered heterocyclic ring containing from 1 to 4 heteroatoms independently selected from oxygen, nitrogen or sulfur;

$R^{32}$, when a substituent on nitrogen, is benzyl or methyl;

m is 0, 1, or 2;

$R^{33}$ is hydrogen or, when taken together with $R^{33}$, form a =O group;

$R^{40}$ is selected from: H, $C_1$–$C_3$ alkyl;

$R^{41}$ is selected from:
—$C(=O)NR^{13}R^{14}$;
—$C(=O)NR^{13}NR^{14}$;
—$C(=O)C(R^{11})_2NR^{13}R^{14}$;
—$C(=O)C(R^{11})_2NR^{13}NR^{14}$;
—$C(=O)C(R^{11})_2NR^{13}CO_2R^{13}$;
—$C(=O)H$;
—$C(=O)R^{11}$;
—$C(=O)$—$(C_1$–$C_4$ alkyl)-$NR^{13}R^{14}$;
—$C(=O)$—$(C_1$–$C_4$ alkyl)-$NR^{13}CO_2R^{13}$;
1–3 amino acids linked together via amide bonds, and linked to the N atom via the carboxy terminus;
provided that:
when $R^4$ is hydrogen and X is N—$R^7$, at least one of the following is not hydrogen: $R^7$, $R^{22}$, or $R^{27}$;
when $R^4$ is hydrogen and X is S or O, at least two of the following are not hydrogen: $R^{22}$ or $R^{27}$.

[10] Preferred compounds of the invention of Formula (Ib) are compounds of Formula (Ic):

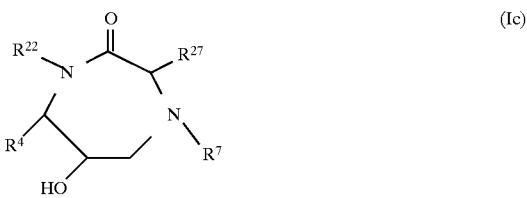

(Ic)

wherein:

$R^4$ and $R^7$ are independently selected from the following groups:
hydrogen;
$C_1$–$C_4$ alkyl substituted with 0–3 $R^{11}$;
$C_3$–$C_4$ alkenyl substituted with 0–3 $R^{11}$;

$R^{11}$ is selected from one or more of the following:
keto, halogen, —$CH_2NR^{13}R^{14}$, —$NR^{13}R^{14}$, —$OR^{13}$, $C_2$–$C_4$ alkoxyalkyl, $C_1$–$C_4$ alkyl, $C_2$–$C_4$ alkenyl, $C_3$–$C_6$ cycloalkyl;
aryl($C_1$–$C_3$ alkyl) substituted with 0–2 $R^{12}$;
aryl substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–2 $R^{12}$;

$R^{12}$, when a substituent on carbon, is selected from one or more of the following: phenyl, benzyl, phenethyl, phenoxy, benzyloxy, halogen, $C_1$–$C_4$ alkyl, $C_7$–$C_{10}$ arylalkyl, $C_1$–$C_4$ alkoxy, —$CO_2H$, hydroxamic acid, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, methylenedioxy, $C_1$–$C_4$ haloalkyl, $C_1$–$C_4$ alkylcarbonyl, $C_1$–$C_4$ alkylcarbonylamino, —OH, hydroxymethyl; or
a 5- or 6-membered heterocyclic ring containing from 1 to 4 heteroatoms selected from oxygen, nitrogen or sulfur;

$R^{12}$, when a substituent on nitrogen, is benzyl or methyl;

$R^{13}$ is H, $C_1$–$C_4$ alkyl, or $C_3$–$C_6$ alkoxyalkyl, $C_2$–$C_4$ alkenyl, or benzyl;

$R^{14}$ is OH, H, $CF_3$, or $C_1$–$C_4$ alkyl, $C_1$–$C_4$ alkoxy, $NH_2$, $C_2$–$C_4$ alkenyl, or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{22}$ is independently selected from the following:
hydrogen;
$C_1$–$C_8$ alkyl substituted with 0–3 $R^{31}$;
$C_2$–$C_6$ alkenyl substituted with 0–3 $R^{31}$;
$C_2$–$C_4$ alkynyl substituted with 0–1 $R^{31}$;

$R^{27}$ is selected from the following:
hydrogen;

21

$C_1$–$C_4$ alkyl substituted with 0–3 $R^{31}$;
$C_2$–$C_4$ alkenyl substituted with 0–3 $R^{31}$;

$R^{31}$ is selected from one or more of the following:
keto, halogen, —$CH_2NR^{13}R^{14}$, —$NR^{13}R^{14}$, —$OR^{13}$, $C_2$–$C_4$ alkoxyalkyl, $C_1$–$C_4$ alkyl, $C_2$–$C_4$ alkenyl, $C_3$–$C_{10}$ cycloalkyl, —$C(R^{14})=N(OR^{14})$, —$CO_2R^{13}$, —$S(O)_mR^{13}$;
aryl substituted with 0–5 $R^{32}$; or
a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
phenethyl, phenoxy, $C_3$–$C_6$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, boronic acid, sulfonamide, —CHO, $C_3$–$C_6$ cycloalkoxy, —$NR^{13}R^{14}$, —$C(R^{14})=N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—($C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl; or
$C_1$–$C_4$ alkoxy substituted with 0–3 groups selected from: $R^{11}$, $C_3$–$C_6$ cycloalkyl, —$CO_2R^{13}$, —$C(=O)NR^{13}R^{14}$, —$NR^{13}R^{14}$ or OH;
$C_1$–$C_4$ alkyl substituted with 0–3 groups selected from: $R^{11}$, =$NR^{14}$, =$NNR^{13}C(=O)NR^{13}R^{14}$ or —$NR^{13}R^{14}$;
$C_2$–$C_4$ alkenyl substituted with 0–3 $R^{11}$;
$C_2$–$C_4$ alkynyl substituted with 0–3 $R^{11}$;
a 5- or 6-membered heterocyclic ring containing from 1 to 4 heteroatoms independently selected from oxygen, nitrogen or sulfur;

$R^{32}$, when a substituent on nitrogen, is benzyl or methyl;
m is 0, 1, or 2;
$R^{33}$ is hydrogen or, when taken together with $R^{33}$, form a =O group;
$R^{40}$ is selected from: H, $C_1$–$C_3$ alkyl;
$R^{41}$ is selected from:
—$C(=O)NR^{13}R^{14}$;
—$C(=O)NR^{13}NR^{14}$;
—$C(=O)C(R^{11})_2NR^{13}R^{14}$;
—$C(=O)C(R^{11})_2NR^{13}NR^{14}$;
—$C(=O)C(R^{11})_2NR^{13}CO_2R^{13}$;
—$C(=O)H$;
—$C(=O)R^{11}$;
—$C(=O)$—($C_1$–$C_4$ alkyl)-$NR^{13}R^{14}$;
—$C(=O)$—($C_1$–$C_4$ alkyl)-$NR^{13}CO_2R^{13}$;
1–3 amino acids linked together via amide bonds, and linked to the N atom via the carboxy terminus;
provided that:
when $R^4$ is hydrogen at least one of the following is not hydrogen: $R^7$, $R^{22}$, or $R^{27}$.

[11] More preferred compounds of Formula (Ic) are described above, wherein:
$R^4$ and $R^7$ are selected from benzyl, fluorobenzyl, pyrrolylmethyl, methoxybenzyl, isobutyl, nitrobenzyl or aminobenzyl;

22

$R^{13}$ is H, $C_1$–$C_4$ alkyl, $C_2$–$C_4$ alkenyl, or benzyl;
$R^{14}$ is OH, H, $CF_3$, $C_1$–$C_4$ alkyl, $C_1$–$C_4$ alkoxy, $NH_2$, $C_2$–$C_4$ alkenyl, or benzyl;
$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{22}$ and $R^{27}$ are independently selected from the following:
hydrogen;
$C_1$–$C_8$ alkyl substituted with 0–2 $R^{31}$;
$C_2$–$C_6$ alkenyl substituted with 0–2 $R^{31}$;
$C_2$–$C_4$ alkynyl substituted with 0–2 $R^{31}$;

$R^{31}$ is selected from one or more of the following:
halogen, —$OR^{13}$, $C_1$–$C_4$ alkyl, $C_3$–$C_{10}$ cycloalkyl, —$C(R^{14})=N(OR^{14})$, —$CO_2R^{13}$, —$S(O)_mR^{13}$;
aryl substituted with 0–5 $R^{32}$; or
a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring being substituted with 0–2 $R^{32}$;

$R^{32}$, when a substituent on carbon, is selected from one or more of the following:
—$CONH_2$, —$CO_2H$, —CHO, —$CH_2NHOH$, —$CH_2NR^{13}R^{14}$, —$NR^{13}R^{14}$, hydroxy, hydroxymethyl, —$C(R^{14})=N(OR^{14})$, halogen, methoxy, methyl, nitro, cyano, allyloxy, —$CO_2CH_3$, —NHCHO, —$NHCOCH_3$, —$OCO_2CH_3$, —CH=$NCH_2CH_2OH$, —$OCONHCH_2C_6H_5$, —$OCONHCH_3$, oxazolidinyl, —C≡C—$CH_2OH$, —$COCH_3$, hydroxyethyl, $C_1$–$C_3$ alkyl (said alkyl substituted with 0–4 halogen, or OH), tetrazolyl, —$OCH_2CONH_2$, -$CONHNH_2$, —CH=$NNHCONH_2$, —$CONHOCH_3$, —$CH_2CH(OH)CH_2OH$, adamantamido, hydroxyethoxy, dihydroxyethyl, —$C(NH_2)=NH$, —$CONHCH_3$, —$B(OH)_2$, benzyloxy, —$CONHCH_2CH_3$, —CON$(CH_2CH_3)_2$, methylthio, —$SO_2CH_3$, —$NHCONH_2$, —$NHCONHCH_3$, —$NHCOCH_2N(CH_3)_2$, —NHCOCH$_2$NHCH$_3$, —$NHCOCH_2NHCO_2CH_2C_6H_5$, —$NHCOCH_2NH_2$, —NHCOCH($CH_3$)NHCO$_2CH_2C_6H_5$, —NHCOCH($CH_2C_6H_5$)NHCO$_2CH_2C_6H_5$, —NHCOCH($CH_3$)NH$_2$, —NHCOCH($CH_2C_6H_5$)NH$_2$, —$CO_2CH_2CH_3$, —$CONHCH_2CH_2CH_3$, —$CONHCH(CH_3)_2$, —$CH_2$-imidazole, —$COC(CH_3)_3$, —$CH(OH)CF_3$, —CO-imidazole, —$COCF_3$, —$COCH_2CH_3$, —$COCH_2CH_2CH_3$, pyrazolyl, —$SO_2NH_2$, —$C(CH_2CH_3)=N(OH)$ or —$C(CF_3)=N(OH)$, phenyl, acetoxy, hydroxyamino, —$N(CH_3)(CHO)$, cyclopropylmethoxy, —$CONR^{13}R^{14}$, —CONHOH, (diethylaminoethyl)aminocarbonyl, (N-ethyl,N-methylaminoethyl)aminocarbonyl, (4-methylpiperazinylethyl)aminocarbonyl, pyrrolidinylethyl)aminocarbonyl, (piperidinylethyl)aminocarbonyl, —NHCOCH$_2$NHCH$_3$, N-(2-(4-morpholino)ethyl)aminocarbonyl, N-(2-(N,N-dimethylamino)ethyl)aminocarbonyl;

$R^{32}$, when a substituent on nitrogen, is methyl.

[12] Specifically preferred compounds of Formula (Ic) are described above, wherein:
$R^4$ and $R^7$ are selected from benzyl, fluorobenzyl, pyrrolylmethyl, methoxybenzyl, isobutyl, nitrobenzyl or aminobenzyl;
$R^{22}$ and $R^{27}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=O))$-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, $(CH_3O_2CO)$-benzyl, $(HOCH_2CH_2N=CH)$-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, $(CH_3NHC(=O))$-benzyl, N,N-dimethylaminocarbonylbenzyl, $(HOCH_2CH(OH)CH_2O)$-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, $(CH_3CH_2NHC(=O))$-benzyl, N,N-diethylaminocarbonylbenzyl, N-ethylaminocarbonylbenzyl, N-propylaminocarbonylbenzyl, N,N-diisopropylaminocarbonylbenzyl, N, N-di-n-propylaminocarbonylbenzyl, (hydroxypropynyl)benzyl, (imidazolyl-C(=O))-benzyl, trifluoroacetylbenzyl, (pyrazolyl)benzyl, $(H_2NSO_2)$-benzyl, dihydroxyethylbenzyl, $(MeHNC(=O)NH)$-benzyl, $(H_2NC(=O)NH)$-benzyl, $(HC(=O)NH)$-benzyl, methanesulfonylpentyl, methoxypentyl, N-formyl-N-methylaminobenzyl, acetylaminobenzyl, propionylbenzyl, butyrylbenzyl, $(CH_3CH_2C(=NOH))$-benzyl, (trifluorohydroxyethyl)benzyl, $(CF_3C(=NOH))$-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, $(CH_3NHC(=O)O)$benzyl, $(NH_2C(=O)CH_2O)$benzyl, $(NH_2C(=NH))$benzyl, ((N-phenylmethoxycarbonyl)glycylamino)benzyl, (imidazolylmethyl)benzyl, $((CH_3)_3C(=O))$benzyl, (N-methyl-N-ethylaminoethyl)aminocarbonylbenzyl, (pyrrolidinylethyl)aminocarbonylbenzyl, (piperidinylethyl)aminocarbonylbenzyl.

[13] Still more specifically preferred compounds of Formula (Ic) are described above, wherein:

$R^4$ and $R^7$ are benzyl;

$R^{22}$ and $R^{27}$ are imdependently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=O))$-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, $(CH_3O_2CO)$-benzyl, $(HOCH_2CH_2N=CH)$-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, $(CH_3NHC(=O))$-benzyl, N,N-dimethylaminocarbonylbenzyl, $(HOCH_2CH(OH)CH_2O)$-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, $(CH_3CH_2NHC(=O))$-benzyl, N,N-diethylaminocarbonylbenzyl, N-ethylaminocarbonylbenzyl, N-propylaminocarbonylbenzyl, N,N-diisopropylaminocarbonylbenzyl, N, N-di-n-propylaminocarbonylbenzyl, (hydroxypropynyl)benzyl, (imidazolyl-C(=O))-benzyl, trifluoroacetylbenzyl, (pyrazolyl)benzyl, $(H_2NSO_2)$-benzyl, dihydroxyethylbenzyl, $(MeHNC(=O)NH)$-benzyl, $(H_2NC(=O)NH)$-benzyl, $(HC(=O)NH)$-benzyl, methanesulfonylpentyl, methoxypentyl, N-formyl-N-methylaminobenzyl, acetylaminobenzyl, propionylbenzyl, butyrylbenzyl, (CH₃CH₂C(═NOH))-benzyl, (trifluorohydroxyethyl)benzyl, (CF₃C(═NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(═O)O)benzyl, (CH₃NHC(═O)O) benzyl, (NH₂C(═O)CH₂O)benzyl, (NH₂C(═NH)) benzyl, ((N-phenylmethoxycarbonyl)glycylamino) benzyl, (imidazolylmethyl)benzyl, ((CH₃)₃C—C(═O))benzyl, (N-methyl-N-ethylaminoethyl) aminocarbonylbenzyl, (pyrrolidinylethyl) aminocarbonylbenzyl, (piperidinylethyl) aminocarbonylbenzyl.

[14] Most specifically preferred compounds of Formula (Ic) are compounds of Formula (Id):

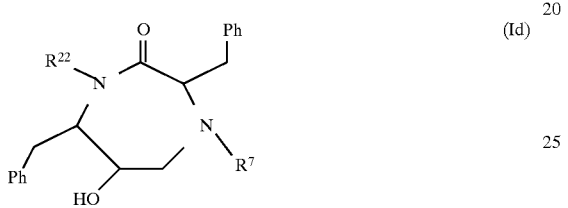

selected from the group consisting of:
the compound of the Formula (Id) wherein $R^{22}$ is hydrogen and $R^7$ is hydrogen;
the compound of the Formula (Id) wherein $R^{22}$ is hydrogen and $R^7$ is benzyl;
the compound of the Formula (Id) wherein $R^{22}$ is cyclopropylmethyl and $R^7$ is hydrogen;

[11] Another embodiment of the present invention are compounds of Formula (I) of the Formula (IIa):

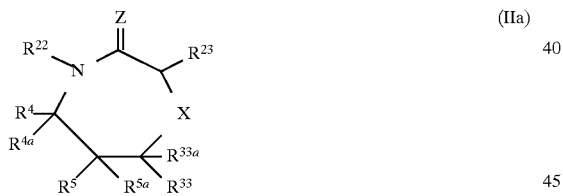

or a pharmaceutically acceptable salt or prodrug form thereof, wherein:
X is S, O, N—$R^7$;
$R^4$ and $R^7$ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
$C_3$–$C_8$ cycloalkyl substituted with 0–3 $R^{11}$;
$C_6$–$C_{10}$ bicycloalkyl substituted with 0–3 $R^{11}$;
aryl substituted with 0–3 $R^{12}$;
a $C_6$–$C_{14}$ carbocyclic residue substituted with 0–3 $R^{12}$;
a heterocyclic ring system substituted with 0–2 $R^{12}$ composed of 5 to 10 atoms including at least one, preferably 1–4, nitrogen, oxygen or sulfur atom;
$R^{4a}$ is selected from the following groups:
hydrogen;
$C_1$–$C_4$ alkyl substituted with halogen or $C_1$–$C_2$ alkoxy;
benzyl substituted with halogen or $C_1$–$C_2$ alkoxy;
—$OR^{20}$; or $SR^{20}$;

$R^4$ and $R^{4a}$ can alternatively join to form a 5–7 membered carbocyclic ring substituted with 0–2 $R^{12}$;
$R^5$ is selected from ═O; H; halogen; $C_1$–$C_6$ alkyl substituted with 0–3 —OH; —N($R^{20}$)₂; —$SR^{20}$; or —$OR^{20}$;
$R^{5a}$ is selected from hydrogen, halogen, $C_1$–$C_6$ alkyl, —N($R^{20}$)₂, —$SR^{20}$, or —$OR^{20}$;
$R^5$ and $R^{5a}$ can alternatively join to form ═O, ═S, or a ketal ring;
$R^{20}$ and $R^{21}$ are independently selected from:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$;
$C_1$–$C_6$ alkylsulfenyl substituted with 0–3 $R^{11}$;
$C_1$–$C_6$ alkylsulfonyl substituted with 0–3 $R^{11}$; or
any group that, when administered to a mammalian subject, cleaves to form a free hydroxyl, amino or sulfhydryl;
$R^{11}$ is selected from one or more of the following:
keto, halogen, cyano, —CH₂N$R^{13}R^{14}$, —N$R^{13}R^{14}$, —CO₂$R^{13}$, —OC(═O)$R^{13}$, —O$R^{13}$, $C_2$–$C_6$ alkoxyalkyl, —S(O)$_m R^{13}$, —NHC(═NH)NH$R^{13}$, —C(═NH)NH$R^{13}$, —C(═O)N$R^{13}R^{14}$, —N$R^{14}$C(═O)$R^{13}$, ═NO$R^{14}$, —N$R^{14}$C(═)O$R^{14}$, —OC(═O)N$R^{13}R^{14}$, —N$R^{13}$C(═O)N$R^{13}R^{14}$ —N$R^{14}$SO₂N$R^{13}R^{14}$, —N$R^{14}$SO₂$R^{13}$, —SO₂N$R^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —N$R^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH₂CO₂H, 2-(1-morpholino)ethoxy, azido, or —C($R^{14}$)═N(O$R^{14}$);
1–3 amino acids, linked together via amide bonds and linked to $R^4$ or $R^7$, $R^{20}$, or $R^{21}$ via the amine or carboxy terminus;
—($C_1$–$C_3$ alkyl)aryl substituted with 0–2 $R^{12}$;
a $C_5$–$C_{14}$ carbocyclic residue substituted with 0–3 $R^{12}$;
aryl substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–3 $R^{12}$;
$R^{12}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —CO₂H, hydroxamic acid, hydrazide, oxime, boronic acid, sulfonamide, formyl, $C_3$–$C_6$ cycloalkoxy, —O$R^{13}$, $C_1$–$C_4$ alkyl substituted with —N$R^{13}R^{14}$, —N$R^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m$R$^{13}$, —SO$_2$NR$^{13}$R$^{14}$, —NHSO$_2$R$^{14}$, —OCH$_2$CO$_2$H, 2-(1-morpholino)ethoxy; or a 5- or 6-membered heterocyclic ring containing from 1 to 4 heteroatoms independently selected from oxygen, nitrogen or sulfur;

when R$^{12}$ is attached to a saturated carbon atom, it may be carbonyl or thiocarbonyl;

or R$^{12}$ may alternatively be a 3- or 4-carbon chain attached to adjacent carbons on the ring to form a fused 5- or 6-membered ring, said 5- or 6-membered ring being optionally substituted on the aliphatic carbons with halogen, C$_1$–C$_4$ alkyl, C$_1$–C$_4$ alkoxy, hydroxy, or —NR$^{13}$R$^{14}$;

R$^{12}$, when a substituent on nitrogen, is selected from one or more of the following:

phenyl, benzyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —CH$_2$NR$^{13}$R$^{14}$, —NR$^{13}$R$^{14}$, C$_2$–C$_6$ alkoxyalkyl, C$_1$–C$_4$ haloalkyl, C$_1$–C$_4$ alkoxycarbonyl, —CO$_2$H, C$_1$–C$_4$ alkylcarbonyloxy, C$_1$–C$_4$ alkylcarbonyl, —C(R$^{14}$)=N(OR$^{14}$);

R$^{13}$ is selected from:

H;

phenyl substituted with 0–3 R$^{11A}$;

benzyl substituted with 0–3 R$^{11A}$;

C$_1$–C$_6$ alkyl substituted with 0–3 R$^{11A}$;

C$_2$–C$_4$ alkenyl substituted with 0–3 R$^{11A}$;

C$_1$–C$_6$ alkylcarbonyl substituted with 0–3 R$^{11A}$;

C$_1$–C$_6$ alkoxycarbonyl substituted with 0–3 R$^{11A}$;

C$_1$–C$_6$ alkylaminocarbonyl substituted with 0–3 R$^{11A}$;

C$_3$–C$_6$ alkoxyalkyl substituted with 0–3 R$^{11A}$;

an amine protecting group when R$^{13}$ is bonded to N;

a hydroxy protecting group when R$^{13}$ is bonded to O;

R$^{14}$ is OH, H, CF$_3$; C$_1$–C$_4$ alkyl substituted with 0–3 groups selected from OH, C$_1$–C$_4$ alkoxy, halogen, NH$_2$; C$_1$–C$_6$ alkoxy; NH$_2$; C$_2$–C$_6$ alkenyl; or benzyl; an amine protecting group when R$^{14}$ is bonded to N; a hydroxy protecting group when R$^{14}$ is bonded to O;

R$^{13}$ and R$^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

R$^{15}$ is H or CH$_3$;

m is 0, 1 or 2;

Z is O, S, or NR$^{24}$;

R$^{22}$ is independently selected from the following:

hydrogen;

C$_1$–C$_8$ alkyl substituted with 0–3 R$^{31}$;

C$_2$–C$_8$ alkenyl substituted with 0–3 R$^{31}$;

C$_2$–C$_8$ alkynyl substituted with 0–3 R$^{31}$;

a C$_3$–C$_{14}$ carbocyclic ring system substituted with 0–5 R$^{31}$ or R$^{32}$;

a 5- to 10-membered heterocyclic ring system containing 1 to 4 heteroatoms independently selected from oxygen, nitrogen or sulfur, said heterocyclic ring system being substituted with 0–2 R$^{32}$;

R$^{23}$ is independently selected from the following:

hydrogen;

C$_1$–C$_8$ alkyl substituted with 0–3 R$^{31}$;

C$_2$–C$_8$ alkenyl substituted with 0–3 R$^{31}$;

C$_2$–C$_8$ alkynyl substituted with 0–3 R$^{31}$;

a C$_3$–C$_{14}$ carbocyclic ring system substituted with 0–5 R$^{31}$ or R$^{32}$;

a 5- to 10-membered heterocyclic ring system containing 1 to 4 heteroatoms independently selected from oxygen, nitrogen or sulfur, said heterocyclic ring system being substituted with 0–2 R$^{32}$;

R$^{24}$ is selected from: hydrogen; hydroxy; amino; C$_1$–C$_4$ alkyl; C$_1$–C$_4$ alkoxy; mono- or di-(C$_1$–C$_6$ alkyl)amino; cyano; nitro; benzyloxy; —NHSO$_2$aryl, aryl being optionally substituted with (C$_1$–C$_6$)alkyl;

alternatively, R$^{22}$, R$^{25}$, or R$^{26}$, independently, can join with R$^4$ or R$^{4A}$ to form a 5- or 6-membered fused heterocyclic ring or carbocyclic ring substituted with 0–2 R$^{12}$, said heterocyclic ring containing 1–3 heteroatoms independently selected from N, S, or O; or alternatively, R$^{23}$, R$^{27}$, or R$^{28}$, independently, can join with R$^7$ to form a 5- or 6-membered fused heterocyclic ring or carbocyclic ring substituted with 0–2 R$^{12}$, said heterocyclic ring containing 1–3 heteroatoms independently selected from N, S, or O; or alternatively, R$^{22}$, R$^{23}$, R$^{27}$ or R$^{28}$ can join with R$^5$ or R$^{33}$ to form a 0- to 7-membered bridge to form a carbocyclic or heterocyclic ring, said bridge being substituted with 0–2 R$^{12}$ and said bridge containing 0–3 heteroatoms independently selected from N, S, or O (i.e., a 0-membered bridge is formed when R$^{22}$, R$^{27}$, R$^{28}$, or R$^{23}$ are taken together with R$^5$ or R$^{33}$ to form a direct bond);

R$^{31}$ is selected from one or more of the following:

keto, halogen, cyano, —CH$_2$NR$^{13}$R$^{14}$, —NR$^{13}$R$^{14}$, —CO$_2$R$^{13}$, —C(=O)R$^{11}$, —OC(=O)R$^{13}$, —OR$^{13}$, C$_2$–C$_6$ alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, C$_1$–C$_4$ alkyl, C$_2$–C$_4$ alkenyl, C$_3$–C$_{10}$ cycloalkyl, C$_3$–C$_6$ cycloalkylmethyl, benzyl, phenethyl, phenoxy, benzyloxy, nitro, C$_7$–C$_{10}$ arylalkyl, hydroxamic acid, hydrazide, oxime, boronic acid, sulfonamide, formyl, C$_3$–C$_6$ cycloalkoxy, C$_1$–C$_4$ alkyl substituted with —NR$^{13}$R$^{14}$, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —OCH$_2$CO$_2$R$^{13}$, 2-(1-morpholino)ethoxy, azido, —C(R$^{14}$)=N(OR$^{14}$); or 1–3 amino acids, linked together via amide bonds and linked to R$^{22}$, R$^{23}$, R$^{25}$, R$^{27}$, R$^4$ or R$^7$ via the amine or carboxy terminus;

a C$_5$–C$_{14}$ carbocyclic residue substituted with 0–3 R$^{32}$;

a C$_5$–C$_{14}$ carbocyclic residue substituted with 0–5 R$^{32}$; or a 5- to 10-membered heterocyclic ring system containing 1 to 4 heteroatoms independently selected from oxygen, nitrogen or sulfur, said heterocyclic ring system being substituted with 0–2 R$^{32}$;

R$^{32}$, when a substituent on carbon, is selected from one or more of the following:

phenyl, benzyl, phenethyl, phenoxy, benzyloxy, halogen, hydroxy, nitro, cyano, C$_1$–C$_4$ alkyl, C$_3$–C$_{10}$ cycloalkyl, C$_3$–C$_6$ cycloalkylmethyl, C$_7$–C$_{10}$ arylalkyl, C$_1$–C$_4$ alkoxy, —CO$_2$H, hydroxamic acid, —CONR$^{13}$NR$^{13}$R$^{14}$, hydrazide, oxime, boronic acid, sulfonamide, formyl, C$_3$–C$_6$ cycloalkoxy, —OR$^{13}$, C$_1$–C$_4$ alkyl substituted with —NR$^{13}$R$^{14}$, —NR$^{13}$R$^{14}$, C$_2$–C$_6$ alkoxyalkyl, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —S(O)$_m$ $R^{13}$, —$SO_2NR^{13}R^{14}$, —$NHSO_2R^{14}$, —$OCH_2CO_2H$,
2-(1-morpholino)ethoxy, —$C(R^{14})$=$N(OR^{14})$; $NO_2$,
—$OR^{13}$, —$NR^{40}R^{41}$, —$SO_mR^{13}$, —$SO_mNR^{13}R^{14}$,
—$C(=O)NR^{13}R^{14}$, —$OC(=O)NR^{13}R^{14}$,
—$C(=O)R^{11}$, —$OC(=O)R^{11}$, —$OCO_2R^{13}$, phenyl,
—$C(=O)NR^{13}$—$(C_1-C_4$ alkyl)-$NR^{13}R^{14}$,
—$C(=O)NR^{40}R^{41}$, $C_1-C_4$ haloalkyl, $C_1-C_4$ haloalkoxy, $C_2-C_4$ haloalkenyl, $C_1-C_4$ haloalkynyl, or
—$C(=O)NR^{13}C(R^{11})_2NR^{13}R^{14}$; —$C(=O)NR^{13}C(R^{11})_2NR^{13}NR^{14}$;
—$C(=O)NR^{13}C(R^{11})_2NR^{13}CO_2R^{13}$;
—$C(=O)NR^{13}$—$(C_1-C_4$ alkyl)-$NR^{13}CO_2R^{13}$; or
—$C(=O)C(R^{11})_2NR^{13}R^{14}$; —$C(=O)C(R^{11})_2NR^{13}NR^{14}$;
—$C(=O)C(R^{11})_2NR^{13}CO_2R^{13}$; —$C(=O)$—$(C_1-C_4$ alkyl)-$NR^{13}R^{14}$;
—$C(=O)$—$(C_1-C_4$ alkyl)-$NR^{13}CO_2R^{13}$; or
$C_1-C_4$ alkoxy substituted with 0–4 groups selected from: $R^{11}$, $C_3-C_6$ cycloalkyl, —$CO_2R^{13}$, —$C(=O)NR^{13}R^{14}$, —$NR^{13}R^{14}$ or OH;
$C_1-C_4$ alkyl substituted with 0–4 groups selected from: $R^{11}$, =$NR^{14}$, =$NNR^{13}C(=O)NR^{13}R^{14}$ or —$NR^{13}R^{14}$;
$C_2-C_4$ alkenyl substituted with 0–4 $R^{11}$;
$C_2-C_4$ alkynyl substituted with 0–4 $R^{11}$;
a 5- or 6-membered heterocyclic ring containing from 1 to 4 heteroatoms selected from oxygen, nitrogen or sulfur;
when $R^{32}$ is attached to a saturated carbon atom, it may be =O or =S;
$R^{32}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1-C_4$ alkyl, $C_1-C_4$ alkoxy, hydroxy, or —$NR^{13}R^{14}$;
$R^{32}$, when a substituent on nitrogen, is selected from one or more of the following:
phenyl, benzyl, phenethyl, hydroxy, $C_1-C_4$ hydroxyalkyl, $C_1-C_4$ alkoxy, $C_1-C_4$ alkyl, $C_3-C_6$ cycloalkyl, $C_3-C_6$ cycloalkylmethyl, —$CH_2NR^{13}R^{14}$, —$NR^{13}R^{14}$, $C_2-C_6$ alkoxyalkyl, $C_1-C_4$ haloalkyl, $C_1-C_4$ alkoxycarbonyl, —$CO_2H$, $C_1-C_4$ alkylcarbonyloxy, $C_1-C_4$ alkylcarbonyl, —$C(R^{14})$=$N(OR^{14})$;
$R^{33}$ is selected from:
H;
$C_1-C_3$ alkyl substituted at the $C_2$ or $C_3$ carbon with —$N(R^{20})_2$, —$SR^{20}$, or —$OR^{21}$;
or when taken together with $R^{33a}$, form =O, =S, or a ketal group;
$R^{33a}$ is selected from:
H;
$C_1-C_3$ alkyl substituted at the $C_2$ or $C_3$ carbon with —$N(R^{20})_2$, —$SR^{20}$, or —$OR^{21}$;
or, when taken together with $R^{33}$, form =O;
alternatively, $R^{33}$ or $R^{33a}$ can join with $R^7$ to form a fused 5- or 6-membered carbocyclic ring;
$R^{40}$ is selected from: H, $C_1-C_3$ alkyl;
$R^{41}$ is selected from:
—$C(=O)NR^{13}R^{14}$;
—$C(=O)NR^{13}NR^{14}$;
—$C(=O)C(R^{11})_2NR^{13}R^{14}$;
—$C(=O)C(R^{11})_2NR^{13}NR^{14}$;
—$C(=O)C(R^{11})_2NR^{13}CO_2R^{13}$;

—$C(=O)H$;
—$C(=O)R^{11}$;
—$C(=O)$—$(C_1-C_4$ alkyl)-$NR^{13}R^{14}$;
—$C(=O)$—$(C_1-C_4$ alkyl)-$NR^{13}CO_2R^{13}$;
1–3 amino acids linked together via amide bonds, and linked to the N atom via the carboxy terminus;
provided that:
when $R^4$ and $R^{4a}$ are hydrogen and X is N—$R^7$, at least one of the following is not hydrogen: $R^7$, $R^{22}$, $R^{27}$ or $R^{28}$;
when $R^4$ and $R^{4a}$ are hydrogen and X is S or O, at least two of the following are not hydrogen: $R^{22}$, $R^{27}$ or $R^{28}$.

[16] Preferred compounds of Formula (IIa) described above are those compounds of Formula (IIb):

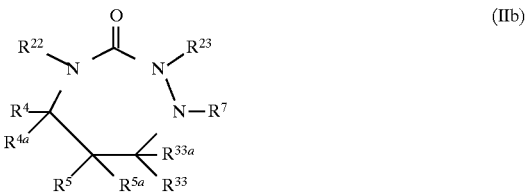

wherein:
$R^4$ and $R^7$ are independently selected from the following groups:
hydrogen;
$C_1-C_4$ alkyl substituted with 0–3 $R^{11}$;
$C_3-C_4$ alkenyl substituted with 0–3 $R^{11}$;
$R^{11}$ is selected from one or more of the following:
keto, halogen, —$CH_2NR^{13}R^{14}$, —$NR^{13}R^{14}$, —$OR^{13}$, $C_2-C_4$ alkoxyalkyl, $C_1-C_4$ alkyl, $C_2-C_4$ alkenyl, $C_3-C_6$ cycloalkyl;
aryl($C_1-C_3$ alkyl) substituted with 0–2 $R^{12}$;
aryl substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–2 $R^{12}$;
$R^{12}$, when a substituent on carbon, is selected from one or more of the following:
phenyl, benzyl, phenethyl, phenoxy, benzyloxy, halogen, $C_1-C_4$ alkyl, $C_7-C_{10}$ arylalkyl, $C_1-C_4$ alkoxy, —$CO_2H$, hydroxamic acid, hydrazide, oxime, boronic acid, sulfonamide, formyl, $C_3-C_6$ cycloalkoxy, —$OR^{13}$, $C_1-C_4$ alkyl substituted with —$NR^{13}R^{14}$, —$NR^{13}R^{14}$, methylenedioxy, $C_1-C_4$ haloalkyl, $C_1-C_4$ alkylcarbonyl, $C_1-C_4$ alkylcarbonylamino, —OH, hydroxymethyl; or
a 5- or 6-membered heterocyclic ring containing from 1 to 4 heteroatoms selected from oxygen, nitrogen or sulfur;
$R^{12}$, when a substituent on nitrogen, is benzyl or methyl;
$R^{13}$ is H, $C_1-C_4$ alkyl, or $C_3-C_6$ alkoxyalkyl, $C_2-C_4$ alkenyl, or benzyl;
$R^{14}$ is OH, H, $CF_3$, or $C_1-C_4$ alkyl, $C_1-C_4$ alkoxy, $NH_2$, $C_2-C_4$ alkenyl, or benzyl;
$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;
$R^{22}$ and $R^{23}$ are independently selected from the following:
hydrogen;
$C_1-C_8$ alkyl substituted with 0–3 $R^{31}$;
$C_2-C_6$ alkenyl substituted with 0–3 $R^{31}$;

$C_2$–$C_4$ alkynyl substituted with 0–1 $R^{31}$;

$R^{31}$ is selected from one or more of the following:
  keto, halogen, —$CH_2NR^{13}R^{14}$, —$NR^{13}R^{14}$, —$OR^{13}$, $C_2$–$C_4$ alkoxyalkyl, $C_1$–$C_4$ alkyl, $C_2$–$C_4$ alkenyl, $C_3$–$C_{10}$ cycloalkyl, —$C(R^{14})$=$N(OR^{14})$, —$CO_2R^{13}$, —$S(O)_mR^{13}$;
  aryl substituted with 0–3 $R^{32}$; or
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
  phenethyl, phenoxy, $C_3$–$C_6$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, boronic acid, sulfonamide, —CHO, $C_3$–$C_6$ cycloalkoxy, —$NR^{13}R^{14}$, —$C(R^{14})$=$N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—($C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or
  $C_1$–$C_4$ alkoxy substituted with 0–3 groups selected from: $R^{11}$, $C_3$–$C_6$ cycloalkyl, —$CO_2R^{13}$, —$C(=O)NR^{13}R^{14}$, —$NR^{13}R^{14}$ or OH;
  $C_1$–$C_4$ alkyl substituted with 0–3 groups selected from: $R^{11}$, =$NR^{14}$, =$NNR^{13}C(=O)NR^{13}R^{14}$ or —$NR^{13}R^{14}$;
  $C_2$–$C_4$ alkenyl substituted with 0–3 $R^{11}$;
  $C_2$–$C_4$ alkynyl substituted with 0–3 $R^{11}$;
  a 5- or 6-membered heterocyclic ring containing from 1 to 4 heteroatoms independently selected from oxygen, nitrogen or sulfur;

$R^{32}$, when a substituent on nitrogen, is benzyl or methyl;

$R^{33}$ is hydrogen or, when taken together with $R^{33}$, form a =O group;

provided that:
  when $R^4$ is hydrogen at least one of the following is not hydrogen: $R^7$, $R^{22}$, or $R^{27}$.

[17] Another preferred embodiment of Formula (I) are compounds of Formula (IIIa)

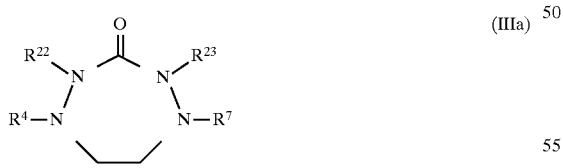

(IIIa)

or a pharmaceutically acceptable salt or prodrug form thereof, wherein:

$R^4$ and $R^7$ are independently selected from the following groups:
  hydrogen;
  $C_1$–$C_8$ alkyl substituted with 0–3 $R^{11}$;
  $C_2$–$C_8$ alkenyl substituted with 0–3 $R^{11}$;
  $C_2$–$C_8$ alkynyl substituted with 0–3 $R^{11}$;
  $C_3$–$C_8$ cycloalkyl substituted with 0–3 $R^{11}$;
  $C_6$–$C_{10}$ bicycloalkyl substituted with 0–3 $R^{11}$;
  aryl substituted with 0–3 $R^{12}$;
  a $C_6$–$C_{14}$ carbocyclic residue substituted with 0–3 $R^{12}$;
  a heterocyclic ring system substituted with 0–2 $R^{12}$, composed of 5 to 10 atoms including at least one, preferably 1–4, nitrogen, oxygen or sulfur atom;

n is 0, 1, or 2;

$R^{11}$ is selected from one or more of the following:
  keto, halogen, cyano, —$CH_2NR^{13}R^{14}$, —$NR^{13}R^{14}$, —$CO_2R^{13}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, or —$C(R^{14})$=$N(OR^{14})$;
  1–3 amino acids, linked together via amide bonds and linked to $R^4$ or $R^7$, $R^{20}$, or $R^{21}$ via the amine or carboxy terminus;
  —($C_1$–$C_3$ alkyl)aryl substituted with 0–2 $R^{12}$;
  a $C_5$–$C_{14}$ carbocyclic residue substituted with 0–3 $R^{12}$;
  aryl substituted with 0–3 $R^{12}$; or
  a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$, when a substituent on carbon, is selected from one or more of the following:
  phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy; or
  a 5- or 6-membered heterocyclic ring containing from 1 to 4 heteroatoms independently selected from oxygen, nitrogen or sulfur;
  when $R^{12}$ is attached to a saturated carbon atom, it may be carbonyl or thiocarbonyl;
  or $R^{12}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$;

$R^{12}$, when a substituent on nitrogen, is selected from one or more of the following:
  phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})$=$N(R^{14})$;

$R^{13}$ is selected from:
  H;
  phenyl substituted with 0–3 $R^{11A}$;
  benzyl substituted with 0–3 $R^{11A}$;
  $C_1$–$C_6$ alkyl substituted with 0–3 $R^{11A}$;
  $C_2$–$C_4$ alkenyl substituted with 0–3 $R^{11A}$;
  $C_1$–$C_6$ alkylcarbonyl substituted with 0–3 $R^{11A}$;
  $C_1$–$C_6$ alkoxycarbonyl substituted with 0–3 $R^{11A}$;
  $C_1$–$C_6$ alkylaminocarbonyl substituted with 0–3 $R^{11A}$;
  $C_3$–$C_6$ alkoxyalkyl substituted with 0–3 $R^{11A}$;
  an amine protecting group when $R^{13}$ is bonded to N;
  a hydroxy protecting group when $R^{13}$ is bonded to O;

$R^{14}$ is OH, H, $CF_3$; $C_1$–$C_4$ alkyl substituted with 0–3 groups selected from OH, $C_1$–$C_4$ alkoxy, halogen, $NH_2$; $C_1$–$C_6$ alkoxy; $NH_2$; $C_2$–$C_6$ alkenyl; or benzyl; an amine protecting group when $R^{14}$ is bonded to N; a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

$R^{22}$ is independently selected from the following:
  hydrogen;
  $C_1$–$C_8$ alkyl substituted with 0–3 $R^{31}$;
  $C_2$–$C_8$ alkenyl substituted with 0–3 $R^{31}$;
  $C_2$–$C_8$ alkynyl substituted with 0–3 $R^{31}$;
  a $C_3$–$C_{14}$ carbocyclic ring system substituted with 0–5 $R^{31}$ or $R^{32}$;
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{23}$ is independently selected from the following:
  hydrogen;
  $C_1$–$C_8$ alkyl substituted with 0–3 $R^{31}$;
  $C_2$–$C_8$ alkenyl substituted with 0–3 $R^{31}$;
  $C_2$–$C_8$ alkynyl substituted with 0–3 $R^{31}$;
  a $C_3$–$C_{14}$ carbocyclic ring system substituted with 0–5 $R^{31}$ or $R^{32}$;
  a 5- to 10-membered heterocyclic ring system containing 1 to 4 heteroatoms independently selected from oxygen, nitrogen or sulfur, said heterocyclic ring system being substituted with 0–2 $R^{32}$;

alternatively, $R^{22}$ can join with $R^4$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$ can join with $R^7$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$, $R^{27}$ or $R^{28}$ can join with $R^5$ or $R^{33}$ to form a 0- to 7-membered bridge to form a carbocyclic or heterocyclic ring, said bridge being substituted with 0–2 $R^{12}$ and said bridge containing 0–3 heteroatoms independently selected from N, S, or O (i.e., a 0-membered bridge is formed when $R^{22}$, $R^{27}$, or $R^{28}$ are taken together with $R^5$ or $R^{33}$ to form a direct bond);

$R^{31}$ is selected from one or more of the following:
  keto, halogen, cyano, —$CH_2NR^{13}R^{14}$, —$NR^{13}R^{14}$, —$CO_2R^{13}$, —$C(=O)R^{11}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})$=$N(OR^{14})$; or 1–3 amino acids, linked together via amide bonds and linked to $R^{22}$, $R^{23}$, $R^{25}$, $R^{27}$, $R^4$ or $R^7$ via the amine or carboxy terminus;

a $C_5$–$C_{14}$ carbocyclic residue substituted with 0–3 $R^{32}$;
  a $C_5$–$C_{14}$ carbocyclic residue substituted with 0–5 $R^{32}$; or
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
  phenyl, benzyl, phenethyl, phenoxy, benzyloxy, halogen, hydroxy, nitro, cyano, $C_1$–$C_4$ alkyl, $C_3$–$C_{10}$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, —$CONR^{13}NR^{13}R^{14}$, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_m R^{13}$, —$SO_2NR^{13}R^{14}$, —$NHSO_2R^{14}$, —$OCH_2CO_2H$, 2-(1-morpholino)ethoxy, —$C(R^{14})$=$N(OR^{14})$; $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—$(C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or
  —$C(=O)NR^{13}C(R^{11})_2NR^{13}R^{14}$; —$C(=O)NR^{13}C(R^{11})_2NR^{13}NR^{14}$;
  —$C(=O) NR^{13}C(R^{11})_2NR^{13}CO_2R^{13}$;
  —$C(=O)NR^{13}$—$(C_1$–$C_4$ alkyl)-$NR^{13}CO_2R^{13}$; or
  —$C(=O)C(R^{11})_2NR^{13}R^{14}$; —$C(=O)C(R^{11})_2NR^{13}NR^{14}$;
  —$C(=O)C(R^{11})_2NR^{13}CO_2R^{13}$; —$C(=O)$—$(C_1$–$C_4$ alkyl)-$NR^{13}R^{14}$;
  —$C(=O)$—$(C_1$–$C_4$ alkyl)-$NR^{13}CO_2R^{13}$; or
  $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or OH;
  $C_1$–$C_4$ alkyl substituted with 0–4 groups selected from: $R^{11}$, =$NR^{14}$, =$NNR^{13}C(=O)NR^{13}R^{14}$ or —$NR^{13}R^{14}$;

$C_2$–$C_4$ alkenyl substituted with 0–4 $R^{11}$;
$C_2$–$C_4$ alkynyl substituted with 0–4 $R^{11}$;
a 5- or 6-membered heterocyclic ring containing from 1 to 4 heteroatoms selected from oxygen, nitrogen or sulfur;
when $R^{32}$ is attached to a saturated carbon atom, it may be =O or =S;
$R^{32}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$;
$R^{32}$, when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;
$R^{40}$ is selected from: H, $C_1$–$C_3$ alkyl;
$R^{41}$ is selected from:
—$C(=O)NR^{13}R^{14}$;
—$C(=O)NR^{13}NR^{14}$;
—$C(=O)C(R^{11})_2NR^{13}R^{14}$;
—$C(=O)C(R^{11})_2NR^{13}NR^{14}$;
—$C(=O)C(R^{11})_2NR^{13}CO_2R^{13}$;
—$C(=O)H$;
—$C(=O)R^{11}$;
—$C(=O)$—$(C_1$–$C_4$ alkyl)-$NR^{13}R^{14}$;
—$C(=O)$—$(C_1$–$C_4$ alkyl)-$NR^{13}CO_2R^{13}$;
1–3 amino acids linked together via amide bonds, and linked to the N atom via the carboxy terminus;
provided that:
when $R^4$ is hydrogen, at least two of the following is not hydrogen: $R^7$, $R^{22}$ or $R^{23}$;

[18] Preferred compounds of formula (IIIa) are compounds described above, wherein:
$R^4$ and $R^7$ are selected from benzyl, fluorobenzyl, pyrrolylmethyl, methoxybenzyl, isobutyl, nitrobenzyl or aminobenzyl;
$R^{22}$ and $R^{23}$ are independently selected from the group consisting of:
hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime) benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, ($HONHC(=O)$)-benzyl, ($CH_3NHC(=O)$)-benzyl, N,N-dimethylaminocarbonylbenzyl, ($HOCH_2CH(OH)CH_2O$)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl) alanylaminobenzyl, phenylalanylaminobenzyl, (N-phenylmethoxycarbonyl) phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropylaminocarbonylbenzyl, N, N-di-n-propylaminocarbonylbenzyl, (hydroxypropynyl) benzyl, (imidazolyl-C(=O))-benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)-benzyl, (trifluorohydroxyethyl)benzyl, ($CF_3C(=NOH)$)-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, ($CH_3NHC(=O)O$) benzyl, ($NH_2C(=O)CH_2O$)benzyl, ($NH_2C(=NH)$) benzyl, ((N-phenylmethoxycarbonyl)glycylamino) benzyl, (imidazolylmethyl)benzyl, (($CH_3)_3C$—C(=O))benzyl, (N-methyl-N-ethylaminoethyl) aminocarbonylbenzyl, (pyrrolidinylethyl) aminocarbonylbenzyl, (piperidinylethyl) aminocarbonylbenzyl.

[19] Another embodiment of Formula (I) are compounds of Formula (IVa) or (IVb):

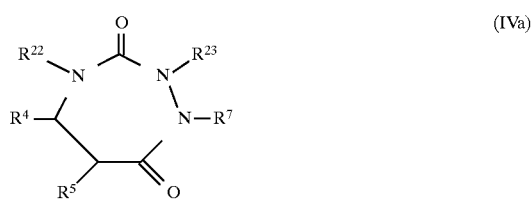

(IVa)

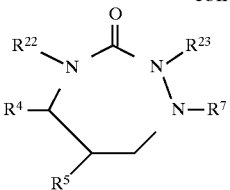

(IVb)

or a pharmaceutically acceptable salt or prodrug form thereof, wherein:

R$^4$ and R$^7$ are independently selected from the following groups:
  hydrogen;
  C$_1$–C$_8$ alkyl substituted with 0–3 R$^{11}$;
  C$_2$–C$_8$ alkenyl substituted with 0–3 R$^{11}$;
  C$_2$–C$_8$ alkynyl substituted with 0–3 R$^{11}$;
  C$_3$–C$_8$ cycloalkyl substituted with 0–3 R$^{11}$;
  C$_6$–C$_{10}$ bicycloalkyl substituted with 0–3 R$^{11}$;
  aryl substituted with 0–3 R$^{12}$;
  a C$_6$–C$_{14}$ carbocyclic residue substituted with 0–3 R$^{12}$;
  a heterocyclic ring system substituted with 0–2 R$^{12}$, composed of 5 to 10 atoms including at least one, preferably 1–4, nitrogen, oxygen or sulfur atom;

R$^5$ is selected from =O; H; halogen; C$_1$–C$_6$ alkyl substituted with 0–3 —OH; —N(R$^{20}$)$_2$; —SR$^{20}$; or —OR$^{20}$;

R$^{20}$ is selected from:
  hydrogen;
  C$_1$–C$_6$ alkyl substituted with 0–3 R$^{11}$;
  C$_3$–C$_6$ alkoxyalkyl substituted with 0–3 R$^{11}$;
  C$_1$–C$_6$ alkylcarbonyl substituted with 0–3 R$^{11}$;
  C$_1$–C$_6$ alkoxycarbonyl substituted with 0–3 R$^{11}$;
  benzoyl substituted with 0–3 R$^{12}$;
  phenoxycarbonyl substituted with 0–3 R$^{12}$;
  phenylaminocarbonyl substituted with 0–3 R$^{12}$;
  C$_1$–C$_6$ alkylsulfenyl substituted with 0–3 R$^{11}$;
  C$_1$–C$_6$ alkylsulfonyl substituted with 0–3 R$^{11}$; or
  any group that, when administered to a mammalian subject, cleaves to form a free hydroxyl, amino or sulfhydryl;

R$^{11}$ is selected from one or more of the following:
  keto, halogen, cyano, —CH$_2$NR$^{13}$R$^{14}$, —NR$^{13}$R$^{14}$, —CO$_2$R$^{13}$, —OC(=O)R$^{13}$, —OR$^{13}$, C$_2$–C$_6$ alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, C$_1$–C$_4$ alkyl, C$_2$–C$_4$ alkenyl, C$_3$–C$_{10}$ cycloalkyl, C$_3$–C$_6$ cycloalkylmethyl, benzyl, phenethyl, phenoxy, benzyloxy, nitro, C$_7$–C$_{10}$ arylalkyl, hydroxamic acid, hydrazide, boronic acid, sulfonamide, formyl, C$_3$–C$_6$ cycloalkoxy, C$_1$–C$_4$ alkyl substituted with —NR$^{13}$R$^{14}$, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —OCH$_2$CO$_2$H, 2-(1-morpholino)ethoxy, azido, or —C(R$^{14}$)=N(OR$^{14}$);
  1–3 amino acids, linked together via amide bonds and linked to R$^4$ or R$^7$, R$^{20}$, or R$^{21}$ via the amine or carboxy terminus;
  —(C$_1$–C$_3$ alkyl)aryl substituted with 0–2 R$^{12}$;
  a C$_5$–C$_{14}$ carbocyclic residue substituted with 0–3 R$^{12}$;
  aryl substituted with 0–3 R$^{12}$; or
  a 5- to 10-membered heterocyclic ring system containing 1 to 4 heteroatoms independently selected from oxygen, nitrogen or sulfur, said heterocyclic ring system being substituted with 0–3 R$^{12}$;

R$^{12}$, when a substituent on carbon, is selected from one or more of the following:
  phenyl, benzyl, phenethyl, phenoxy, benzyloxy, halogen, hydroxy, nitro, cyano, C$_1$–C$_4$ alkyl, C$_3$–C$_6$ cycloalkyl, C$_3$–C$_6$ cycloalkylmethyl, C$_7$–C$_{10}$ arylalkyl, C$_1$–C$_4$ alkoxy, —CO$_2$H, hydroxamic acid, hydrazide, oxime, boronic acid, sulfonamide, formyl, C$_3$–C$_6$ cycloalkoxy, —OR$^{13}$, C$_1$–C$_4$ alkyl substituted with —NR$^{13}$R$^{14}$, —NR$^{13}$R$^{14}$, C$_2$–C$_6$ alkoxyalkyl, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —S(O)$_m$R$^{13}$, —SO$_2$NR$^{13}$R$^{14}$, —NHSO$_2$R$^{14}$, —OCH$_2$CO$_2$H, 2-(1-morpholino)ethoxy; or
  a 5- or 6-membered heterocyclic ring containing from 1 to 4 heteroatoms independently selected from oxygen, nitrogen or sulfur;
  when R$^{12}$ is attached to a saturated carbon atom, it may be carbonyl or thiocarbonyl;
  or R$^{12}$ may alternatively be a 3- or 4-carbon chain attached to adjacent carbons on the ring to form a fused 5- or 6-membered ring, said 5- or 6-membered ring being optionally substituted on the aliphatic carbons with halogen, C$_1$–C$_4$ alkyl, C$_1$–C$_4$ alkoxy, hydroxy, or —NR$^{13}$R$^{14}$;

R$^{12}$, when a substituent on nitrogen, is selected from one or more of the following:
  phenyl, benzyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —CH$_2$NR$^{13}$R$^{14}$, —NR$^{13}$R$^{14}$, C$_2$–C$_6$ alkoxyalkyl, C$_1$–C$_4$ haloalkyl, C$_1$–C$_4$ alkoxycarbonyl, —CO$_2$H, C$_1$–C$_4$ alkylcarbonyloxy, C$_1$–C$_4$ alkylcarbonyl, —C(R$^{14}$)=N(OR$^{14}$);

R$^{13}$ is selected from:
  H;
  phenyl substituted with 0–3 R$^{11A}$;
  benzyl substituted with 0–3 R$^{11A}$;
  C$_1$–C$_6$ alkyl substituted with 0–3 R$^{11A}$;
  C$_2$–C$_4$ alkenyl substituted with 0–3 R$^{11A}$;
  C$_1$–C$_6$ alkylcarbonyl substituted with 0–3 R$^{11A}$;
  C$_1$–C$_6$ alkoxycarbonyl substituted with 0–3 R$^{11A}$;
  C$_1$–C$_6$ alkylaminocarbonyl substituted with 0–3 R$^{11A}$;
  C$_3$–C$_6$ alkoxyalkyl substituted with 0–3 R$^{11A}$;
  an amine protecting group when R$^{13}$ is bonded to N;
  a hydroxy protecting group when R$^{13}$ is bonded to O;

R$^{14}$ is OH, H, CF$_3$; C$_1$–C$_4$ alkyl substituted with 0–3 groups selected from OH, C$_1$–C$_4$ alkoxy, halogen, NH$_2$; C$_1$–C$_6$ alkoxy; NH$_2$; C$_2$–C$_6$ alkenyl; or benzyl; an amine protecting group when R$^{14}$ is bonded to N; a hydroxy protecting group when R$^{14}$ is bonded to O;

R$^{13}$ and R$^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

R$^{15}$ is H or CH$_3$;

m is 0, 1 or 2;

R$^{22}$ is independently selected from the following:
  hydrogen;
  C$_1$–C$_8$ alkyl substituted with 0–3 R$^{31}$;
  C$_2$–C$_8$ alkenyl substituted with 0–3 R$^{31}$;
  C$_2$–C$_8$ alkynyl substituted with 0–3 R$^{31}$;

a $C_3$–$C_{14}$ carbocyclic ring system substituted with 0–5 $R^{31}$ or $R^{32}$;

a 5- to 10-membered heterocyclic ring system containing 1 to 4 heteroatoms independently selected from oxygen, nitrogen or sulfur, said heterocyclic ring system being substituted with 0–2 $R^{32}$;

$R^{23}$ is independently selected from the following:

hydrogen;

$C_1$–$C_8$ alkyl substituted with 0–3 $R^{31}$;

$C_2$–$C_8$ alkenyl substituted with 0–3 $R^{31}$;

$C_2$–$C_8$ alkynyl substituted with 0–3 $R^{31}$;

a $C_3$–$C_{14}$ carbocyclic ring system substituted with 0–5 $R^{31}$ or $R^{32}$;

a 5- to 10-membered heterocyclic ring system containing 1 to 4 heteroatoms independently selected from oxygen, nitrogen or sulfur, said heterocyclic ring system being substituted with 0–2 $R^{32}$;

alternatively, $R^{22}$ can join with $R^4$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$ can join with $R^7$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$ or $R^{23}$ can join with $R^5$ to form a 0- to 7-membered bridge to form a carbocyclic or heterocyclic ring, said bridge being substituted with 0–2 $R^{12}$ and said bridge containing 0–3 heteroatoms independently selected from N, S, or ) (i.e., a 0-membered bridge is formed when $R^{22}$ or $R^{23}$ are taken together with $R^5$ to form a direct bond);

$R^{31}$ is selected from one or more of the following:

keto, halogen, cyano, —$CH_2NR^{13}R^{14}$, —$NR^{13}R^{14}$, —$CO_2R^{13}$, —$C(=O)R^{11}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, $=NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})=N(OR^{14})$; or 1–3 amino acids, linked together via amide bonds and linked to $R^{22}$, $R^{23}$, $R^4$ or $R^7$ via the amine or carboxy terminus;

a $C_5$–$C^{14}$ carbocyclic residue substituted with 0–3 $R^{32}$;

a $C_5$–$C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenyl, benzyl, phenethyl, phenoxy, benzyloxy, halogen, hydroxy, nitro, cyano, $C_1$–$C_4$ alkyl, $C_3$–$C_{10}$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, —$CONR^{13}NR^{13}R^{14}$, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy, —$C(R^{14})=N(OR^{14})$; $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—($C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or —$C(=O)NR^{13}C(R^{11})_2NR^{13}R^{14}$; —$C(=O)NR^{13}C(R^{11})_2NR^{13}NR^{14}$;

—$C(=O)NR^{13}C(R^{11})_2NR^{13}CO_2R^{13}$;

—$C(=O)NR^{13}$—($C_1$–$C_4$ alkyl)-$NR^{13}CO_2R^{13}$; or

—$C(=O)C(R^{11})_2NR^{13}R^{14}$; —$C(=O)C(R^{11})_2NR^{13}NR^{14}$;

—$C(=O)C(R^{11})_2NR^{13}CO_2R^{13}$; —$C(=O)$—($C_1$–$C_4$ alkyl)-$NR^{13}R^{14}$;

—$C(=O)$—($C_1$–$C_4$ alkyl)-$NR^{13}CO_2R^{13}$; or $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or OH;

$C_1$–$C_4$ alkyl substituted with 0–4 groups selected from: $R^{11}$, $=NR^{14}$, $=NNR^{13}C(=O)NR^{13}R^{14}$ or —$NR^{13}R^{14}$;

$C_2$–$C_4$ alkenyl substituted with 0–4 $R^{11}$;

$C_2$–$C_4$ alkynyl substituted with 0–4 $R^{11}$;

a 5- or 6-membered heterocyclic ring containing from 1 to 4 heteroatoms selected from oxygen, nitrogen or sulfur;

when $R^{32}$ is attached to a saturated carbon atom, it may be =O or =S;

$R^{32}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$;

$R^{32}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{40}$ is selected from: H, $C_1$–$C_3$ alkyl;

$R^{41}$ is selected from:

—$C(=O)$ $NR^{13}R^{14}$;

—$C(=O)NR^{13}NR^{14}$;

—$C(=O)C(R^{11})_2NR^{13}R^{14}$;

—$C(=O)C(R^{11})_2NR^{13}NR^{14}$;

—$C(=O)C(R^{11})_2NR^{13}CO_2R^{13}$;

—$C(=O)H$;

—$C(=O)R^{11}$;

—C(=O)—($C_1$–$C_4$ alkyl)-$NR^{13}R^{14}$;
—C(=O)—($C_1$–$C_4$ alkyl)-$NR^{13}CO_2R^{13}$;
1–3 amino acids linked together via amide bonds, and linked to the N atom via the carboxy terminus;

provided that:
when $R^4$ is hydrogen, at least one of the following is not hydrogen: $R^7$, $R^{22}$ or $R^{23}$;
when $R^4$ and $R^7$ are hydrogen, at least two of the following are not hydrogen: $R^{22}$ or $R^{23}$.

[20] Preferred compounds of the Formula (IVa) and Formula (IVb) as described above are those compounds wherein:

$R^4$ and $R^7$ are selected from benzyl, fluorobenzyl, pyrrolylmethyl, methoxybenzyl, isobutyl, nitrobenzyl or aminobenzyl;

$R^5$ is —OH;

$R^{22}$ and $R^{23}$ are independently selected from the group consisting of:

hydrogen, allyl, methyl, ethyl, propyl, cyclopropylmethyl, n-butyl, i-butyl, $CH_2CH$=C($CH_3$)$_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC$(=O))-benzyl, carbomethoxybenzyl, carboethoxybenzyl, tetrazolylbenzyl, and dimethylallyl, aminomethylbenzyl, (O-benzyl-formaldoxime) benzyl, (O-methyl-formaldoxime)benzyl, ($CH_3O_2CO$)-benzyl, ($HOCH_2CH_2N$=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylm-ethylboronic acid, N-hydroxylaminomethylbenzyl, (hydroxyl)ethylbenzyl, ($CH_3C$(=NOH))-benzyl, ($H_2NNHC$(=O))-benzyl, ($H_2NC$(=O)NHN=CH)-benzyl, ($CH_3ONHC$(=O))-benzyl, (HONHC(=O))-benzyl, ($CH_3NHC$(=O))-benzyl, N,N-dimethylaminocarbonylbenzyl, ($HOCH_2CH(OH)CH_2O$)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy) pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl) alanylaminobenzyl, phenylalanylaminobenzyl, (N-phenylmethoxycarbonyl) phenylalanylaminobenzyl, ($CH_3CH_2NHC$(=O))-benzyl, N,N-diethylaminocarbonylbenzyl, N-ethylaminocarbonylbenzyl, N-propylaminocarbonylbenzyl, N,N-diisopropylaminocarbonylbenzyl, N, N-di-n-propylaminocarbonylbenzyl, (hydroxypropynyl) benzyl, (imidazolyl-C(=O))-benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC$(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C$(=NOH))-benzyl, (trifluorohydroxyethyl)benzyl, ($CF_3C$(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, ($CH_3NHC$(=O)O) benzyl, ($NH_2C$(=O)$CH_2O$)benzyl, ($NH_2C$(=NH)) benzyl, ((N-phenylmethoxycarbonyl)glycylamino) benzyl, (imidazolylmethyl)benzyl, (($CH_3$)$_3$C—C (=O))benzyl, (N-methyl-N-ethylaminoethyl) aminocarbonylbenzyl, (pyrrolidinylethyl) aminocarbonylbenzyl, (piperidinylethyl) aminocarbonylbenzyl.

[21] Another embodiment of the present invention are compounds of Formula (I) having the Formula (Va):

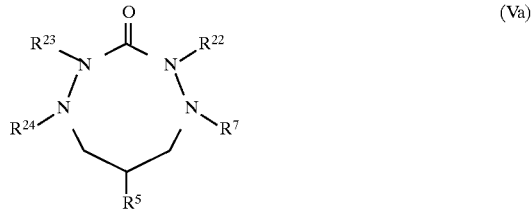

(Va)

or a pharmaceutically acceptable salt or prodrug form thereof, wherein:

$R^4$ and $R^7$ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
$C_3$–$C_8$ cycloalkyl substituted with 0–3 $R^{11}$;
$C_6$–$C_{10}$ bicycloalkyl substituted with 0–3 $R^{11}$;
aryl substituted with 0–3 $R^{12}$;
a $C_6$–$C_{14}$ carbocyclic residue substituted with 0–3 $R^{12}$;
a heterocyclic ring system substituted with 0–2 $R^{12}$, composed of 5 to 10 atoms including at least one, preferably 1–4, nitrogen, oxygen or sulfur atom;

$R^5$ is selected from =O; H; halogen; $C_1$–$C_6$ alkyl substituted with 0–3 —OH; —N($R^{20}$)$_2$; —$SR^{20}$; or —$OR^{20}$;

$R^{20}$ is selected from:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$;
$C_1$–$C_6$ alkylsulfenyl substituted with 0–3 $R^{11}$;
$C_1$–$C_6$ alkylsulfonyl substituted with 0–3 $R^{11}$; or
any group that, when administered to a mammalian subject, cleaves to form a free hydroxyl, amino or sulfhydryl;

$R^{11}$ is selected from one or more of the following:
  keto, halogen, cyano, —$CH_2NR^{13}R^{14}$, —$NR^{13}R^{14}$, —$CO_2R^{13}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, or —$C(R^{14})=N(OR^{14})$;
  1–3 amino acids, linked together via amide bonds and linked to $R^4$ or $R^7$, $R^{20}$, or $R^{21}$ via the amine or carboxy terminus;
  —$C_1$–$C_3$ alkyl)aryl substituted with 0–2 $R^{12}$;
  a $C_5$–$C_{14}$ carbocyclic residue substituted with 0–3 $R^{12}$;
  aryl substituted with 0–3 $R^{12}$; or
  a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$, when a substituent on carbon, is selected from one or more of the following:
  phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy; or
  a 5- or 6-membered heterocyclic ring containing from 1 to 4 heteroatoms independently selected from oxygen, nitrogen or sulfur;
  when $R^{12}$ is attached to a saturated carbon atom, it may be carbonyl or thiocarbonyl;
  or $R^{12}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$;

$R^{12}$, when a substituent on nitrogen is selected from one or more of the following:
  phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{13}$ is selected from:
  H;
  phenyl substituted with 0–3 $R^{11A}$;
  benzyl substituted with 0–3 $R^{11A}$;
  $C_1$–$C_6$ alkyl substituted with 0–3 $R^{11A}$;
  $C_2$–$C_4$ alkenyl substituted with 0–3 $R^{11A}$;
  $C_1$–$C_6$ alkylcarbonyl substituted with 0–3 $R^{11A}$;
  $C_1$–$C_6$ alkoxycarbonyl substituted with 0–3 $R^{11A}$;
  $C_1$–$C_6$ alkylaminocarbonyl substituted with 0–3 $R^{11A}$;
  $C_3$–$C_6$ alkoxyalkyl substituted with 0–3 $R^{11A}$;
  an amine protecting group when $R^{13}$ is bonded to N;
  a hydroxy protecting group when $R^{13}$ is bonded to O;

$R^{14}$ is OH, H, $CF_3$; $C_1$–$C_4$ alkyl substituted with 0–3 groups selected from OH, $C_1$–$C_4$ alkoxy, halogen, $NH_2$; $C_1$–$C_6$ alkoxy; $NH_2$; $C_2$–$C_6$ alkenyl; or benzyl; an amine protecting group when $R^{14}$ is bonded to N; a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

$R^{22}$ is independently selected from the following:
  hydrogen;
  $C_1$–$C_8$ alkyl substituted with 0–3 $R^{31}$;
  $C_2$–$C_8$ alkenyl substituted with 0–3 $R^{31}$;
  $C_2$–$C_8$ alkynyl substituted with 0–3 $R^{31}$;
  a $C_3$–$C_{14}$ carbocyclic ring system substituted with 0–5 $R^{31}$ or $R^{32}$;
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{23}$ is independently selected from the following:
  hydrogen;
  $C_1$–$C_8$ alkyl substituted with 0–3 $R^{31}$;
  $C_2$–$C_8$ alkenyl substituted with 0–3 $R^{31}$;
  $C_2$–$C_8$ alkynyl substituted with 0–3 $R^{31}$;
  a $C_3$–$C_{14}$ carbocyclic ring system substituted with 0–5 $R^{31}$ or $R^{32}$;
  a 5- to 10-membered heterocyclic ring system containing 1 to 4 heteroatoms independently selected from oxygen, nitrogen or sulfur, said heterocyclic ring system being substituted with 0–2 $R^{32}$;

alternatively, $R^{22}$ can join with $R^4$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$ can join with $R^7$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$, $R^{27}$ or $R^{28}$ can join with $R^5$ to form a 0- to 7-membered bridge to form a carbocyclic or heterocyclic ring, said bridge being substituted with 0–2 $R^{12}$ and said bridge containing 0–3 heteroatoms independently selected from N, S, or O (i.e., a 0-membered bridge is formed when $R^{22}$, $R^{27}$, or $R^{28}$ are taken together with $R^5$ to form a direct bond);

$R^{31}$ is selected from one or more of the following:
  keto, halogen, cyano, —$CH_2NR^{13}R^{14}$, —$NR^{13}R^{14}$, —$CO_2R^{13}$, —$C(=O)R^{11}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)$ $OR^{14}$, $-OC(=O)NR^{13}R^{14}$, $-NR^{13}C(=O)NR^{13}R^{14}$, $-NR^{14}SO_2NR^{13}R^{14}$, $-NR^{14}SO_2R^{13}$, $-SO_2NR^{13}R^{14}$, $C_1-C_4$ alkyl, $C_2-C_4$ alkenyl, $C_3-C_{10}$ cycloalkyl, $C_3-C_6$ cycloalkylmethyl, benzyl, phenethyl, phenoxy, benzyloxy, nitro, $C_7-C_{10}$ arylalkyl, hydroxamic acid, hydrazide, oxime, boronic acid, sulfonamide, formyl, $C_3-C_6$ cycloalkoxy, $C_1-C_4$ alkyl substituted with $-NR^{13}R^{14}$, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, $-OCH_2CO_2R^{13}$, 2-(1-morpholino)ethoxy, azido, $-C(R^{14})=N(OR^{14})$; or 1–3 amino acids, linked together via amide bonds and linked to $R^{22}$, $R^{23}$, $R^{25}$, $R^{27}$, $R^4$ or $R^7$ via the amine or carboxy terminus;

a $C_5-C_{14}$ carbocyclic residue substituted with 0–3 $R^{32}$;

a $C_5-C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenyl, benzyl, phenethyl, phenoxy, benzyloxy, halogen, hydroxy, nitro, cyano, $C_1-C_4$ alkyl, $C_3-C_{10}$ cycloalkyl, $C_3-C_6$ cycloalkylmethyl, $C_7-C_{10}$ arylalkyl, $C_1-C_4$ alkoxy, $-CO_2H$, hydroxamic acid, $-CONR^{13}NR^{13}R^{14}$, hydrazide, oxime, boronic acid, sulfonamide, formyl, $C_3-C_6$ cycloalkoxy, $-OR^{13}$, $C_1-C_4$ alkyl substituted with $-NR^{13}R^{14}$, $-NR^{13}R^{14}$, $C_2-C_6$ alkoxyalkyl, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, $-S(O)_mR^{13}$, $-SO_2NR^{13}R^{14}$, $-NHSO_2R^{14}$, $-OCH_2CO_2H$, 2-(1-morpholino)ethoxy, $-C(R^{14})=N(OR^{14})$; $NO_2$, $-OR^{13}$, $-NR^{40}R^{41}$, $-SO_mR^{13}$, $-SO_mNR^{13}R^{14}$, $-C(=O)NR^{13}R^{14}$, $-OC(=O)NR^{13}R^{14}$, $-C(=O)R^{11}$, $-OC(=O)R^{11}$, $-OCO_2R^{13}$, phenyl, $-C(=O)NR^{13}-(C_1-C_4$ alkyl$)-NR^{13}R^{14}$, $-C(=O)NR^{40}R^{41}$, $C_1-C_4$ haloalkyl, $C_1-C_4$ haloalkoxy, $C_2-C_4$ haloalkenyl, $C_f-C_4$ haloalkynyl, or $-C(=O)NR^{13}C(R^{11})_2NR^{13}R^{14}$; $-C(=O)NR^{13}C(R^{11})_2NR^{13}NR^{14}$;

$-C(=O)NR^{13}C(R^{11})_2NR^{13}CO_2R^{13}$;

$-C(=O)NR^{13}-(C_1-C_4$ alkyl$)-NR^{13}CO_2R^{13}$; or $-C(=O)C(R^{11})_2NR^{13}R^{14}$; $-C(=O)C(R^{11})_2NR^{13}NR^{14}$;

$-C(=O)C(R^{11})_2NR^{13}CO_2R^{13}$; $-C(=O)-(C_1-C_4$ alkyl$)-NR^{13}R^{14}$;

$-C(=O)-(C_1-C_4$ alkyl$)-NR^{13}CO_2R^{13}$; or $C_1-C_4$ alkoxy substituted with 0–4 groups selected from: $R^{11}$, $C_3-C_6$ cycloalkyl, $-CO_2R^{13}$, $-C(=O)NR^{13}R^{14}$, $-NR^{13}R^{14}$ or OH;

$C_1-C_4$ alkyl substituted with 0–4 groups selected from: $R^{11}$, $=NR^{14}$, $=NNR^{13}C(=O)NR^{13}R^{14}$ or $-NR^{13}R^{14}$;

$C_2-C_4$ alkenyl substituted with 0–4 $R^{11}$;

$C_2-C_4$ alkynyl substituted with 0–4 $R^{11}$;

a 5- or 6-membered heterocyclic ring containing from 1 to 4 heteroatoms selected from oxygen, nitrogen or sulfur;

when $R^{32}$ is attached to a saturated carbon atom, it may be $=O$ or $=S$;

$R^{32}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1-C_4$ alkyl, $C_1-C_4$ alkoxy, hydroxy, or $-NR^{13}R^{14}$;

$R^{32}$, when a substituent on nitrogen, is selected from one or more of the following:

phenyl, benzyl, phenethyl, hydroxy, $C_1-C_4$ hydroxyalkyl, $C_1-C_4$ alkoxy, $C_1-C_4$ alkyl, $C_3-C_6$ cycloalkyl, $C_3-C_6$ cycloalkylmethyl, $-CH_2NR^{13}R^{14}$, $-NR^{13}R^{14}$, $C_2-C_6$ alkoxyalkyl, $C_1-C_4$ haloalkyl, $C_1-C_4$ alkoxycarbonyl, $-CO_2H$, $C_1-C_4$ alkylcarbonyloxy, $C_1-C_4$ alkylcarbonyl, $-C(R^{14})=N(OR^{14})$;

$R^{40}$ is selected from: H, $C_1-C_3$ alkyl;

$R^{41}$ is selected from:
—$C(=O)NR^{13}R^{14}$;
—$C(=O)NR^{13}NR^{14}$;
—$C(=O)C(R^{11})_2NR^{13}R^{14}$;
—$C(=O)C(R^{11})_2NR^{13}NR^{14}$;
—$C(=O)C(R^{11})_2NR^{13}CO_2R^{13}$;
—$C(=O)H$;
—$C(=O)R^{11}$;
—$C(=O)-(C_1-C_4$ alkyl$)-NR^{13}R^{14}$;
—$C(=O)-(C_1-C_4$ alkyl$)-NR^{13}CO_2R^{13}$;

1–3 amino acids linked together via amide bonds, and linked to the N atom via the carboxy terminus;

provided that:
when $R^4$ is hydrogen, at least one of the following is not hydrogen: $R^7$, $R^{22}$ or $R^{23}$;
when $R^4$ and $R^7$ are hydrogen, at least two of the following are not hydrogen: $R^{22}$ or $R^{23}$.

[22] Preferred compounds of Formula (Va) as described above are those compounds wherein:

$R^4$ and $R^7$ are selected from benzyl, fluorobenzyl, pyrrolylmethyl, methoxybenzyl, isobutyl, nitrobenzyl or aminobenzyl;

$R^5$ is OH or $=O$;

$R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyloxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=O))$-benzyl, carbomethoxybenzyl, carboethoxybenzyl, tetrazolylbenzyl, and dimethylallyl, aminomethylbenzyl, (O-benzyl-formaldoxime)

benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, (CH$_3$C(=NOH))-benzyl, (H$_2$NNHC(=O))-benzyl, (H$_2$NC(=O)NHN=CH)-benzyl, (CH$_3$ONHC(=O))-benzyl, (HONHC(=O))-benzyl, (CH$_3$NHC(=O))-benzyl, N,N-dimethylaminocarbonylbenzyl, (HOCH$_2$CH(OH)CH$_2$O)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N, N-di-n-propylaminocarbonylbenzyl, (hydroxypropynyl)benzyl, (imidazolyl-C(=O))-benzyl, trifluoroacetylbenzyl, (pyrazolyl)benzyl, (H$_2$NSO$_2$)-benzyl, dihydroxyethylbenzyl, (MeHNC(=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))-benzyl, (trifluorohydroxyethyl)benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C—C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl.

[23] Another preferred embodiment of the present invention are those compounds of Formula (I) of the Formulae (Ie) or (If) or (Ig):

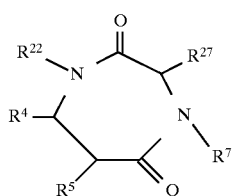

(Ie)

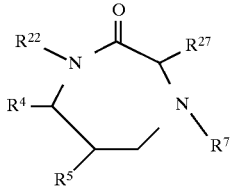

(If)

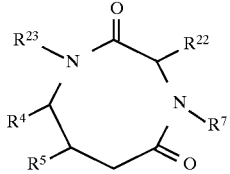

(Ig)

or a pharmaceutically acceptable salt or prodrug form thereof, wherein:

R$^4$ and R$^7$ are independently selected from the following groups:
hydrogen;
C$_1$–C$_8$ alkyl substituted with 0–3 R$^{11}$;
C$_2$–C$_8$ alkenyl substituted with 0–3 R$^{11}$;
C$_2$–C$_8$ alkynyl substituted with 0–3 R$^{11}$;
C$_3$–C$_8$ cycloalkyl substituted with 0–3 R$^{11}$;
C$_6$–C$_{10}$ bicycloalkyl substituted with 0–3 R$^{11}$;
aryl substituted with 0–3 R$^{12}$;
a C$_6$–C$_{14}$ carbocyclic residue substituted with 0–3 R$^{12}$;
a heterocyclic ring system substituted with 0–2 R$^{12}$, composed of 5 to 10 atoms including at least one, preferably 1–4, nitrogen, oxygen or sulfur atom;

R$^5$ is —OR$^{20}$;

R$^{20}$ is H or any group that, when administered to a mammalian subject, cleaves to form a free hydroxyl;

R$^{11}$ is selected from one or more of the following:
keto, halogen, cyano, —CH$_2$NR$^{13}$R$^{14}$, —NR$^{13}$R$^{14}$, —CO$_2$R$^{13}$, —OC(=O)R$^{13}$, —OR$^{13}$, C$_2$–C$_6$ alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, C$_1$–C$_4$ alkyl, C$_2$–C$_4$ alkenyl, C$_3$–C$_{10}$ cycloalkyl, C$_3$–C$_6$ cycloalkylmethyl, benzyl, phenethyl, phenoxy, benzyloxy, nitro, C$_7$–C$_{10}$ arylalkyl, hydroxamic acid, hydrazide, boronic acid, sulfonamide, formyl, C$_3$–C$_6$ cycloalkoxy, C$_1$–C$_4$ alkyl substituted with —NR$^{13}$R$^{14}$, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —OCH$_2$CO$_2$H, 2-(1-morpholino)ethoxy, azido, or —C(R$^{14}$)=N(OR$^{14}$);
1–3 amino acids, linked together via amide bonds and linked to R$^4$ or R$^7$, R$^{20}$, or R$^{21}$ via the amine or carboxy terminus;
—(C$_1$–C$_3$ alkyl)aryl substituted with 0–2 R$^{12}$;
a C$_5$–C$_{14}$ carbocyclic residue substituted with 0–3 R$^{12}$;
aryl substituted with 0–3 R$^{12}$; or
a 5- to 10-membered heterocyclic ring system containing 1 to 4 heteroatoms independently selected from oxygen, nitrogen or sulfur, said heterocyclic ring system being substituted with 0–3 R$^{12}$;

R$^{12}$, when a substituent on carbon, is selected from one or more of the following:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy; or a 5- or 6-membered heterocyclic ring containing from 1 to 4 heteroatoms independently selected from oxygen, nitrogen or sulfur;

when $R^{12}$ is attached to a saturated carbon atom, it may be carbonyl or thiocarbonyl;

or $R^{12}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$;

$R^{12}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})$=$N(OR^{14})$ $R^{13}$ is selected from:
H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_1$–$C_6$ alkylcarbonyl substituted with 0–3 $R^{11A}$;
$C_1$–$C_6$ alkoxycarbonyl substituted with 0–3 $R^{11A}$;
$C_1$–$C_6$ alkylaminocarbonyl substituted with 0–3 $R^{11A}$;
$C_3$–$C_6$ alkoxyalkyl substituted with 0–3 $R^{11A}$;
an amine protecting group when $R^{13}$ is bonded to N;
a hydroxy protecting group when $R^{13}$ is bonded to O;

$R^{14}$ is OH, H, $CF_3$; $C_1$–$C_4$ alkyl substituted with 0–3 groups selected from OH, $C_1$–$C_4$ alkoxy, halogen, $NH_2$; $C_1$–$C_6$ alkoxy; $NH_2$; $C_2$–$C_6$ alkenyl; or benzyl; an amine protecting group when $R^{14}$ is bonded to N; a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

$R^{22}$ is independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;

$R^{27}$ is independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;

alternatively, $R^{22}$ can join with $R^4$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{27}$ can join with $R^7$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$ or $R^{27}$ can join with $R^5$ to form a 0- to 7-membered bridge to form a carbocyclic or heterocyclic ring, said bridge being substituted with 0–2 $R^{12}$ and said bridge containing 0–3 heteroatoms independently selected from N, S, or O (i.e., a 0-membered bridge is formed when $R^{22}$ or $R^{27}$ are taken together with $R^5$ to form a direct bond);

$R^{31}$ is selected from one or more of the following:
keto, halogen, cyano, —$CH_2NR^{13}R^{14}$, —$NR^{13}R^{14}$, —$CO_2R^{13}$, —$C(=O)R^{11}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, $NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})$=$N(OR^{14})$; or 1–3 amino acids, linked together via amide bonds and linked to $R^{22}$, $R^{23}$, $R^{25}$, $R^{27}$, $R^4$ or $R^7$ via the amine or carboxy terminus;

a $C_5$–$C_{14}$ carbocyclic residue substituted with 0–3 $R^{32}$;
a $C_5$–$C_{14}$ carbocyclic residue substituted with 0–5 $R^{32}$; or
a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_{10}$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, —$CONR^{13}NR^{13}R^{14}$, hydrazide, oxime, boronic acid, sulfonamide, formyl, $C_3$–$C_6$ cycloalkoxy, —OR$^{13}$, C$_1$–C$_4$ alkyl substituted with —NR$^{13}$R$^{14}$, —NR$^{13}$R$^{14}$, C$_2$–C$_6$ alkoxyalkyl, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —S(O)$_m$R$^{13}$, —SO$_2$NR$^{13}$R$^{14}$, —NHSO$_2$R$^{14}$, —OCH$_2$CO$_2$H, 2-(1-morpholino)ethoxy, —C(R$^{14}$)=N(OR$^{14}$); NO$_2$, —OR$^{13}$, —NR$^{40}$R$^{41}$, —SO$_m$R$^{13}$, —SO$_m$NR$^{13}$R$^{14}$, —C(=O)NR$^{13}$R$^{14}$, —OC(=O)NR$^{13}$R$^{14}$, —C(=O)R$^{11}$, —OC(=O)R$^{11}$, —OCO$_2$R$^{13}$, phenyl, —C(=O)NR$^{13}$—(C$_1$–C$_4$ alkyl)-NR$^{13}$R$^{14}$, —C(=O)NR$^{40}$R$^{41}$, C$_1$–C$_4$ haloalkyl, C$_1$–C$_4$ haloalkoxy, C$_2$–C$_4$ haloalkenyl, C$_1$–C$_4$ haloalkynyl, or —C(=O)NR$^{13}$C(R$^{11}$)$_2$NR$^{13}$R$^{14}$; —C(=O)NR$^{13}$C(R$^{11}$)$_2$NR$^{13}$NR$^{14}$;

—C(=O)NR$^{13}$C(R$^{11}$)$_2$NR$^{13}$CO$_2$R$^{13}$;

—C(=O)NR$^{13}$—(C$_1$–C$_4$ alkyl)-NR$^{13}$CO$_2$R$^{13}$; or

—C(=O)C(R$^{11}$)$_2$NR$^{13}$R$^{14}$; —C(=O)C(R$^{11}$)$_2$NR$^{13}$NR$^{14}$;

—C(=O)C(R$^{11}$)$_2$NR$^{13}$CO$_2$R$^{13}$; —C(=O)—(C$_1$–C$_4$ alkyl)-NR$^{13}$R$^{14}$;

—C(=O)—(C$_1$–C$_4$ alkyl)-NR$^{13}$CO$_2$R$^{13}$; or

C$_1$–C$_4$ alkoxy substituted with 0–4 groups selected from: R$^{11}$, C$_3$–C$_6$ cycloalkyl, —CO$_2$R$^{13}$, —C(=O)NR$^{13}$R$^{14}$, —NR$^{13}$R$^{14}$ or OH;

C$_1$–C$_4$ alkyl substituted with 0–4 groups selected from: R$^{11}$, =NR$^{14}$, =NNR$^{13}$C(=O)NR$^{13}$R$^{14}$ or —NR$^{13}$R$^{14}$;

C$_2$–C$_4$ alkenyl substituted with 0–4 R$^{11}$;

C$_2$–C$_4$ alkynyl substituted with 0–4 R$^{11}$;

a 5- or 6-membered heterocyclic ring containing from 1 to 4 heteroatoms selected from oxygen, nitrogen or sulfur;

or R$^{32}$ may be a 3- or 4-carbon chain attached to adjacent carbons on the ring to form a fused 5- or 6-membered ring, said 5- or 6-membered ring being optionally substituted on the aliphatic carbons with halogen, C$_1$–C$_4$ alkyl, C$_1$–C$_4$ alkoxy, hydroxy, or —NR$^{13}$R$^{14}$;

or, when R$^{32}$ is attached to a saturated carbon atom, it may be =O or =S;

R$^{32}$, when a substituent on nitrogen, is selected from one or more of the following:

phenyl, benzyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —CH$_2$NR$^{13}$R$^{14}$, —NR$^{13}$R$^{14}$, C$_2$–C$_6$ alkoxyalkyl, C$_1$–C$_4$ haloalkyl, C$_1$–C$_4$ alkoxycarbonyl, —CO$_2$H, C$_1$–C$_4$ alkylcarbonyloxy, C$_1$–C$_4$ alkylcarbonyl, —C(R$^{14}$)=N(OR$^{14}$);

R$^{40}$ is selected from: H, C$_1$–C$_3$ alkyl;

R$^{41}$ is selected from:
—C(=O)NR$^{13}$R$^{14}$;
—C(=O)NR$^{13}$NR$^{14}$;
—C(=O)C(R$^{11}$)$_2$NR$^{13}$R$^{14}$;
—C(=O)C(R$^{11}$)$_2$NR$^{13}$NR$^{14}$;
—C(=O)C(R$^{11}$)$_2$NR$^{13}$CO$_2$R$^{13}$;
—C(=O)H;
—C(=O)R$^{11}$;
—C(=O)—(C$_1$–C$_4$ alkyl)-NR$^{13}$R$^{14}$;
—C(=O)—(C$_1$–C$_4$ alkyl)-NR$^{13}$CO$_2$R$^{13}$;

1–3 amino acids linked together via amide bonds, and linked to the N atom via the carboxy terminus;

provided that:
when R$^4$ is hydrogen, at least two of the following is not hydrogen: R$^7$, R$^{22}$ or R$^{27}$.

[24] Preferred compounds of formulae (Ie) or (If) or (Ig) are compounds described above, wherein:

R$^5$ is —OR$^{20}$;

R$^{20}$ is H or any group that, when administered to a mammalian subject, cleaves to form a free hydroxyl;

R$^4$ and R$^{27}$ are selected from benzyl, fluorobenzyl, pyrrolylmethyl, methoxybenzyl, isobutyl, nitrobenzyl or aminobenzyl;

R$^{22}$ and R$^7$ are independently selected from the group consisting of:

hydrogen, allyl, methyl, ethyl, propyl, cyclopropylmethyl, n-butyl, i-butyl, CH$_2$CH=C(CH$_3$)$_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, (H$_2$NC(=O))-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylm-ethylboronic acid, N-hydroxylaminomethylbenzyl, (hydroxyl)ethylbenzyl, (CH$_3$C(=NOH))-benzyl, (H$_2$NNHC(=O))-benzyl, (H$_2$NC(=O)NHN=CH)-benzyl, (CH$_3$ONHC(=O))-benzyl, (HONHC(=O))-benzyl, (CH$_3$NHC(=O))-benzyl, N,N-dimethylaminocarbonylbenzyl, (HOCH$_2$CH(OH)CH$_2$O)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, trifluoroacetylbenzyl, (pyrazolyl)benzyl, (H$_2$NSO$_2$)-benzyl, dihydroxyethylbenzyl, (MeHNC(=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))-benzyl, (trifluorohydroxyethyl)benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C—C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl.

In the present invention it has been discovered that the compounds above are useful as inhibitors of HIV protease and similar retroviral proteases, and for the treatment of HIV infection and associated diseases, and similar retrovirus infections.

The present invention also provides methods for the treatment of HIV infection and associated diseases by administering to a host infected with HIV a therapeutically effective antiviral amount of a compound of formula (I) as described above. By therapeutically effective amount, it is meant an amount of a compound of the present invention effective to inhibit HIV infection or treat the symptoms of HIV infection in a host.

Also provided by this invention are pharmaceutical compositions containing a pharmaceutically acceptable carrier and a therapeutically effective compound of formula (I) described above.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example, $R^{11}$, $R^{12}$, $R^{13}$, $R^{14}$, $R^{31}$, $R^{32}$, and m) occurs more than one time in any constituent or in formula (I) or (II), or any other formula herein, its definition on each occurrence is independent of its definition at every other occurrence. Thus, for example, if a group is shown to be substituted with 0–3 $R^{11}$, then said group may optionally be substituted with up to three $R^{11}$ and $R^{11}$ at each occurrence is selected independently from the defined list of possible $R^{11}$. Also, for example, in —N($R^{20}$)$_2$, each of the $R^{20}$ substituents may be independently selected from the list of possible $R^{20}$ groups defined. Also, combinations of substituents and/or variables are permissible only if such combinations result in stable compounds.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like. "Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" is intended to mean phenyl or naphthyl. As used herein, "carbocycle" or "carbocyclic residue" or "carbocyclic ring system" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic ring system" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, furanyl, pyranyl, isobenzofuranyl, chromenyl, xanthenyl, phenoxathiinyl, 2H-pyrrolyl, pyrrole, imidazolyl, pyrazolyl, isothiazolyl, isoxazole, pyridinyl, pyrazinyl, pyrimidinyl, pyridazinyl, indolizinyl, isoindole, 3H-indole, indole, 1H-indazole, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

The term "boronic acid" as used herein means a group of the formula —B($R^{34}$)($R^{35}$), wherein $R^{34}$ and $R^{35}$ are independently selected from: —OH; —F; —$NR^{13}R^{14}$; or $C_1$-$C_8$-alkoxy; or $R^{34}$ and $R^{35}$ can alternatively be taken together to form: a cyclic boron ester where said chain or ring contains from 2 to 20 carbon atoms and, optionally, 1–4 heteroatoms independently selected from N, S, or O; a divalent cyclic boron amide where said chain or ring contains from 2 to 20 carbon atoms and, optionally, 1–4 heteroatoms independently selected from N, S, or O; a cyclic boron amide-ester where said chain or ring contains from 2 to 20 carbon atoms and, optionally, 1–4 heteroatoms independently selected from N, S, or O. Such cyclic boron esters, boron amides, or boron amide-esters may also be optionally substituted with 1–5 groups independently selected from $R^{11}$.

Boron esters include boronic acid protecting groups, including moieties derived from diols, for example pinanediol and pinacol to form pinanediol boronic acid ester and the pinacol boronic acid, respectively. Other illustrations of diols useful for deriving boronic acid esters are perfluoropinacol, ethylene glycol, diethylene glycol, 1,2-ethanediol, 1,3-propanediol, 1,2-propanediol, 1,2-butanediol, 1,4-butanediol, 2,3-butanediol, 2,3-hexanediol, 1,2-hexanediol, catechol, 1,2-diisopropylethanediol, 5,6-decanediol, 1,2-dicyclohexylethanediol.

The term "substituted", as used herein, means that an one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

By "stable compound" or "stable structure" is meant herein a compound that is sufficiently robust to survive isolation to a useful degree of purity from a reaction mixture, and formulation into an efficacious therapeutic agent.

As used herein, the term "any group that, when administered to a mammalian subject, cleaves to form a free hydroxyl, amino or sulfhydryl" means any group bonded to an O, N, or S atom, respectively, which is cleaved from the O, N, or S atom when the compound is administered to a mammalian subject to provide a compound having a remaining free hydroxyl, amino, or sulfhydryl group, respectively. Examples of groups that, when administered to a mammalian subject, are cleaved to form a free hydroxyl, amino or sulfhydryl, include but are not limited to, $C_1$–$C_6$ alkyl substituted with 0–3 $R^{11}$, $C_3$–$C_6$ alkoxyalkyl substituted with 0–3 $R^{11}$, $C_1$–$C_6$ alkylcarbonyl substituted with 0–3 $R^11$, $C_1$–$C_6$ alkoxycarbonyl substituted with 0–3 $R^{11}$, $C_1$–$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$. Examples of group that, when administered to a mammalian subject, are cleaved to form a free hydroxyl, amino or sulfhydryl, include hydroxy, amine or sulfhydryl protecting groups, respectively.

As used herein, the term "amine protecting group" means any group known in the art of organic synthesis for the protection of amine groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenyithiocarbonyl and dithiasuccinoyl.

By a "ketal ring" or "ketal" group is meant any ketal protecting group which can be hydroyzed to form a carbonyl. Such ketal rings or ketal protecting groups are well known in the art of organic synthesis and typically include, for example, substituted or unsubstituted carbocyclic diethers, dithioethers, or mixed ethers. Such ketal protecting groups include those listed in Greene and Wuts, "Protective Groups in Organic Synthesis" John Wiley & Sons, New York (1991)

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids,such as those disclosed in, for example, Roberts and Vellaccio (1983) *The Peptides,* 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methylnorleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formula (I); and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Synthesis

Compounds of the invention can be prepared by methods described herein, or variations thereon as appreciated by those skilled in the art. Preferred methods include, but are not limited to, those described below.

Any of the compounds can be derived from the joining of two amino acids derivatives, followed by elaboration of substituents as necessary. Natural amino acids are available in abundance, and a great array of unnatural amino acids have been prepared by techniques well known to those skilled in the art of organic synthesis. D. C. Roberts and F. Vellaccio provide a comprehensive listing of unnatural amino acids, and techniques for the synthesis of many variations thereof [*The Peptides, Vol. 5: Analysis, Synthesis, Biology*, Academic Press, NY, 1983]. A more recent description of additional routes to chirally pure unnatural amino acids is found in Cintas, P. Tetrahedron, 47(32), 6079–111, 1991. Thus, one skilled in the art can synthesize the amino acid precursors used in the preparation of the compounds of the invention by a judicious selection of one or more of the methods outlined above. Each of the references cited herein are hereby incorporated by reference.

The substituent $R^4$ is chosen first, and the corresponding amino acid III with the desired stereochemistry is synthesized or purchased as necessary:

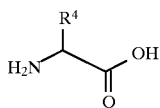

wherein $R^4$ has the meaning designated above. If substituents on $R^4$ are deemed to be sensitive to the reaction conditions employed in the following steps, then appropriate protecting groups are used, and the desired substituents are freed from protection at the end of the sequence. Extensive descriptions of the correct choice of protecting groups for various reaction conditions, and the correct method of removal, are described in T. W. Greene and P. G. M. Wuts, *Protective Groups in Organic Synthesis*, 2nd Edition, Wiley, New York, 1991.

A protecting group is also chosen for the amine terminal of amino acid III. For example, the above reference can be used to assist the choice of protecting group, or M. Bodanzky and A. Bodanzky in *The Practice of Peptide Synthesis*, Springer-Verlag, Berlin, 1984 can be consulted. A preferred amine protecting group is the N-carbobenzyloxy (CBZ) group. In the following structures, a protecting group is designated PG.

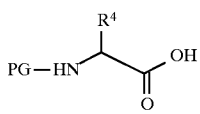

The protected amino acid is then converted to the protected amino epoxide by known techniques, such as the Wittig or Petersen olefination of a protected amino aldehyde followed by epoxidation of the olefin; or by addition of a methylene sulfur ylide to an amino aldehyde or by the following, preferred method: treatment of the protected amino acid with diazomethane to generate the diazoketone, followed by treatment with aqueous hydrochloric acid to generate the chloroketone, followed by reduction with a hydride reducing agent, preferably a metal borohydride to form the chloroalcohol. Stereochemistry of the hydroxyl group can be controlled by the choice of reducing agent; preferably a mixture can be obtained which can optionally be separated by chromatography and each diastereomer can be evaluated independently. This step is followed by base-catalyzed elimination of hydrogen chloride in an aprotic solvent, preferably potassium tert-butoxide in tetrahydrofuran, to form the protected amino epoxide V.

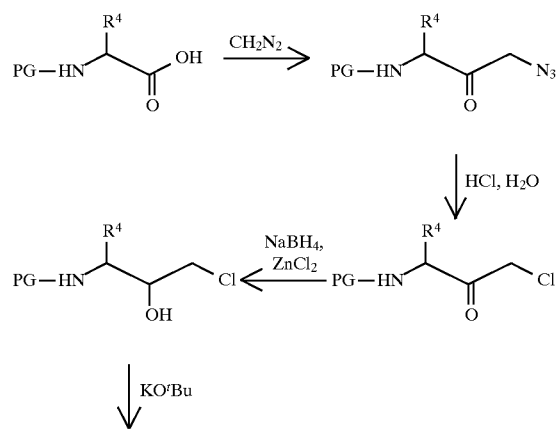

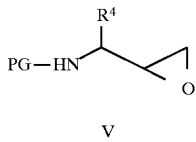

V

Next the desired $R^{27}$ substituent is chosen, with the desired stereochemistry, and the appropriate acid is synthesized or purchased. Protecting groups are added as necessary to the functionality on $R^{27}$. The acid terminus is protected, preferably with the t-butyl ester, to form compound VI:

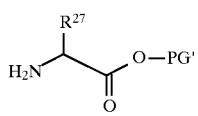

VI

V and VI are coupled in the presence of a solvent, preferably methanol, at a temperature between 0° and 100° C., to form the amino alcohol VII:

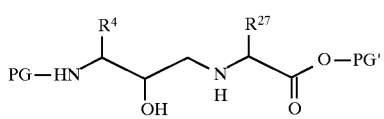

VII

The hydroxyl group of VII is protected, preferably with a silyl protecting group such as t-butyldimethylsilyl (TBDMS) chloride. The selected protective group must withstand the conditions used to remove the nitrogen and carboxy protecting groups. The wide variety of protecting groups described in the references above make the selection of the proper combination of groups straightforward to one skilled in the art.

The amine and acid protecting groups are removed to form amino acid VIII:

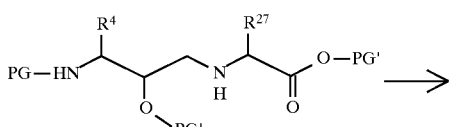

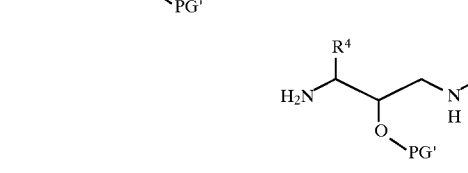

VIII which depending on cleavage conditions used may be isolated as a salt of the amines. VIII is cyclized to the lactam IX: any number of standard conditions can be used to form lactams, although the preferred procedure involves activating the carboxylate with a group such as dicylohexylcarbodiimide under conditions dilute enough to favor intramolecular condensation.

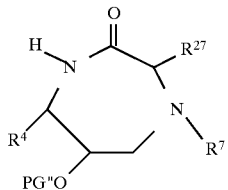

IX

Intermediate IX can be deprotected to form hydroxy lactam X. In instances where the protecting group is TBDMS, the preferred cleavage conditions are tetra-n-butylammonium fluoride in tetrahydrofuran.

When $R^4$ and $R^{27}$ are benzyl, X is Example 1. Other representative compounds of the invention are listed in Table 1.

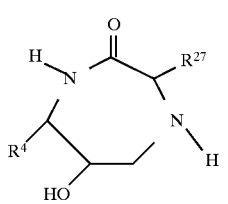

X

Alternatively, IX can be further modified to add substituents $R^7$ and $R^{22}$. Beginning with the protected alcohol, using methods known to one skilled in the art one may alkylate either the amide nitrogen or the basic nitrogen with a group $R^{22}$—LG or $R^7$—LG, respectively, where LG is a leaving group. If alkylation of the basic nitrogen is desired while keeping the amide nitrogen unsubstituted, it is advantageous to protect the amide nitrogen using one of the many protective groups discussed in the above references. A preferred protecting group is benzyl, which can be selectively removed from the basic nitrogen by hydrogenolysis.

For obtaining compounds with $R^7 \ne$ hydrogen and $R^{22}=$ hydrogen, the preferred method is to treat IX with a base, such as potassium carbonate, in a polar aprotic solvent, such as dimethylformamide, and add to the mixture between 0° and 100° C. an alkylating agent $R^7$—LG, preferably an alkyl chloride, bromide iodide, or tosylate. Preferred alkylating agents are substituted benzyl chlorides, substituted $C_1$-$C_6$ alkyl bromides, (heterocyclic)methyl chlorides and substituted (alicyclic)methyl bromides and tosylates.

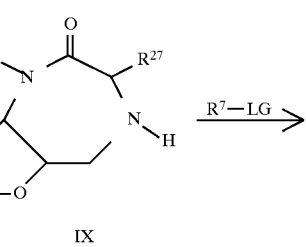

IX

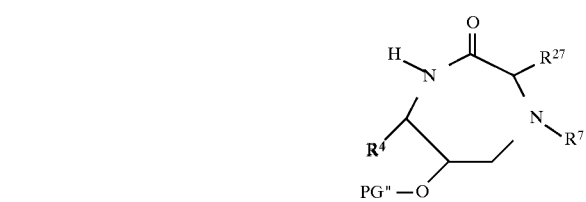

XI

If compounds wherein $R^{22}=R^7 \ne$ hydrogen are desired, the preferred method is that described in the preceding paragraph, but substituting a stronger base, preferably sodium hydride, for potassium carbonate and employing 2 equivalents alkylating agent. If $R^7 \neq R^{22}$, the product XI can be further alkylated in the same fashion to give XII, by substituting a stronger base, preferably sodium hydride, for potassium carbonate and employing 1 equivalent alkylating agent $R^{22}$—LG. Preferred alkylating agents are as described above.

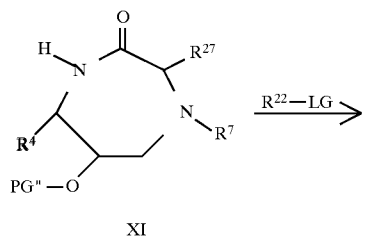

XI

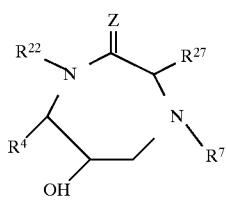

XII

For the case in which $R^{22} \neq H$ and $R^7 = H$, as exemplified in XIII, a preferred method is one in which the above procedures are followed, such that IX is first alkylated with benzyl bromide in dimethylformamide (DMF) in the presence of postassium carbonate; the material is purified and subjected to $R^{22}$—LG in the presence of sodium hydride in DMF to give XIIa; after which the N-benzyl is removed by catalytic hydrogenation or preferably by transfer hydrogenation, e.g. formic acid and palladium on carbon in methanol.

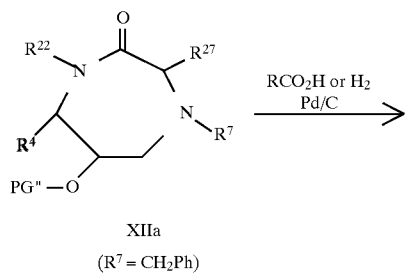

XIIa
($R^7 = CH_2Ph$)

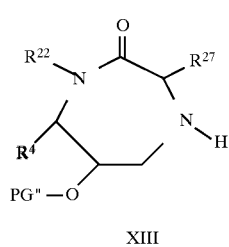

XIII

The protecting group on XI–XIII is removed to give removed structure XIV, where Z═O as described above. The representative compounds of the invention listed in Table 1 can be prepared by these methods.

XIV

By the proper manipulation and choice of protecting groups by one skilled in the art, compounds of the formula II, wherein X is S or O, can be obtained by substitution of a suitably protected form of acid VIa in the above described sequences. Further modification of these compounds are detailed above.

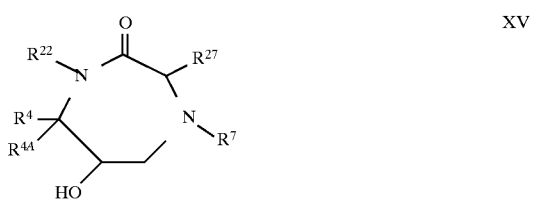

VIa

The preferred compounds are those in which Z═O; however, standard techniques can be employed to convert the carbonyl oxygen to sulfur or an amidine or substituted amidine. These techniques are described in detail in copending application U.S. patent application Ser. No. 07/883,944, filed May 15, 1992, which is incorporated by reference.

The preferred compounds are those in which $R^{4a}$ and $R^{28}$ are hydrogen. However, compounds in which $R^{4a}$ and $R^{28}$ are substituted benzyl or substituted lower alkyl can be prepared by choosing alpha, alpha'-substituted amino acids as starting materials. For example, if, in structure III, the alpha hydrogen is replaced by substituted benzyl or substituted lower alkyl, then the product derived from the synthesis described herein is XV:

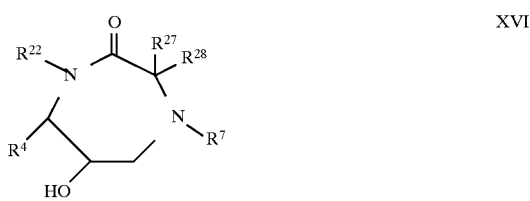

XV and if in structure VI the alpha hydrogen is replaced by substituted benzyl or substituted lower alkyl then the product of the above-described sequence is XVI. These alpha, alpha' substituted amino acids can be prepared by the means described in the references above, and by other means well known to skilled in the art of organic synthesis.

XVI

Compounds in which the side chains on the same side of the seven-membered ring are joined to form a fused ring are contemplated as part of this invention. Specifically, compound XVII can be formed by choosing amino acid VI such that $R^{27}$ is protected 4-hydroxybutyl (n=2) or protected 3-hydroxypropyl. Release of the hydroxy group, conversion to the tosylate or mesylate in dilute solution in a polar aprotic solvent at 0°–100° C. in the presence of a weak base will result in the fused ring system.

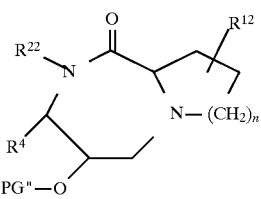

XVII

If a similar procedure is employed with $R^4$, and the resulting tosylate or mesylate is heated in dilute solution with a stronger base such as sodium hydride in a polar aprotic solvent, the fused ring system XVIII can be obtained.

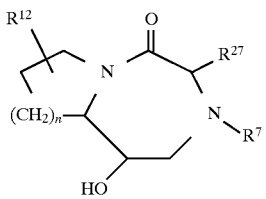

XVIII

The absolute and relative stereochemistry of the ring substituents are important for the degree of binding of these compounds to the HIV protease active site. Although a preferred diastereomer is shown in structure XIX, other diastereomers are also active and are contemplated as part of this invention. Control over stereochemistry is obtained by choice of starting materials III and VI, and by choice of reducing agent to form chloroalcohol as described above.

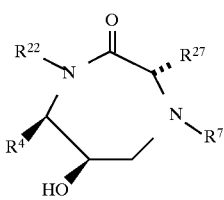

XIX

Other compounds of this invention can be prepared as outlined by the schemes below, using the methods and procedures described herein, or additionally, the methods and procedures described in U.S. patent application Ser. No. 08/023,439, filed Feb. 26, 1993.

The compounds of the general formula XX can be prepared as shown in Scheme 1. The compound of the general formula XXa and XXc can be prepared according to the method described by A. S. Dutt and J. S. Morley (*J. Chem. Soc. Perkin I*. 1712, (1975)). Treatment of XXa with 1 equivalent of ethylene oxide would provide intermediate XXb (where R=H) which can be activated to XXb (where R=mesylate or tosylate) by methods well known to the skilled in the art. The resulting intermediate then heated in solvents such as methanol, ethanol, etc. in the presence of XXc to provide XXd. The compound XXe could be obtained by treatment of XXd with acids such as trifluoroacetic acid or hydrochloric acid in a suitable solvent. The intermediate XXe can be cyclized to XXf by treatment with carbonyldiimidazole (CDI) and then alkylated with sodium hydride to give the desired XXg (where $R^{22}$=$R^{23}$).

The compounds of general formula XXI can be prepared as detailed in Scheme 2. Hydrazine XXIa (EP 521827 A) is treated with triethylsilyl chloride according to the method of Corey et al. (*J. Am. Chem. Soc.*, 1971, 93, 7319), followed by aqueous hydrolysis, to give XXIb. Carbonyl diimidazole cyclization followed by alkylation under the standard procedure gives XXId. Deprotection by HCl/MeOH yields XXIe.

As further detailed in Scheme 2 continued, XXIf is treated with KCN followed by protection, Dibal-H reduction to give XXIg, and further reaction with hydrazine to provide XXIi. XXIi could be reacted with ClC(=O)Cl (phosgene), followed by treatment with triethylamine to give XXIk which can be cyclized to XXII by heating in toluene. Following the same alkylation & deprotection procedures as described previously, the desired XXIe can be obtained.

The compounds of general formula XXIII are shown in Scheme 4. Compound XXIIIa (T. Minoto, et al. EP 0490667A2; Y. Yabe, et al. EP 0498680A; R. Herranz, et al. *J. Org. Chem.*, 1990, 55, 2232) was protected as the THP ether and the methyl ester hydrolyzed to give XXIIIb, which was coupled with O-benzyl phenylalanine using 1,3-dicyclohexylcarbodiimide (DCC). Hydrogenolysis of the O-benzyl group and phenylmethoxycarbonyl (CBZ) protecting groups would give XXIIId, which was then cyclized with DCC to give XXIIIe. Standard alkylation was performed to give XXIIIf, which was then hydrolyzed in acidic medium to give the desired XXIIIg.

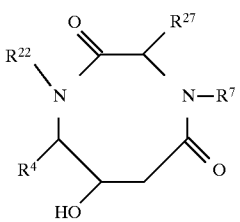

XXIV

Any of the compounds of formula XXIV described in Scheme 5 can be derived from the joining of an amino acid derivative and a hydroxy-protected statine derivative, followed by elaboration of substituents as necessary.

Natural amino acids are available in abundance, and a great array of unnatural amino acids have been prepared by techniques well known to those skilled in the art of organic synthesis. D. C. Roberts and F. Vellaccio provide a comprehensive listing of unnatural amino acids, and techniques for the synthesis of many variations thereof. [*The Peptides, Vol. 5: Analysis, Synthesis, Biology*; Academic Press, NY 1983. A more recent description of additional routes to chirally pure unnatural amino acids is in: Asymmetric synthesis of .alpha.-amino acids from carbohydrates as chiral templates; Cintas, P. *Tetrahedron*, 1991, 47(32), 6079–111. Thus one skilled in the art can synthesize the amino acid precursors used in the preparation of the compounds of the invention by a judicious selection of one or more of the methods outlined above, which articles are hereby incorporated by reference. Statine derivatives are also well known in the literature and can be prepared by methods disclosed in EP 0 401 675 A1. Other methods are described in the series cited above (*The Peptides, Vol. 5: Analysis, Synthesis, Biology*; Academic Press, NY 1983] and by Bringmann et al. in Synlett (5), 253–255 (1990); by Kessler and Schudok in Synthesis (6) 457–8 (1990); and by Nishi and Morisawa in Heterocycles 29(9), 1835–42 (1989).

The statine hydroxyl is protected if necessary; the preferred protecting group is tert-butyldimethylsilyl. The amino acid is protected at the carboxyl group, the statine derivative is protected at the amino group, and the amide bond is formed using techniques described in the references. The preferred N-protecting group is phenylmethoxycarbonyl (CBZ), the preferred carboxylic acid protecting group is tert-butyl ester, and the preferred coupling reagent is 1,3-dicyclohexylcarbodiimide.

The product XXIVC is isolated and purified if necessary, and protecting groups are removed by standard methods; if the preferred groups are employed, the CBZ protecting group is removed by treatment with 10% palladium on carbon in the presence of ethanol, tetrahydrofuran and hydrogen gas, or by the action of palladium oxide in ethanol/water in the presence of cyclohexene. The preferred t-butyl ester is removed with 25% triflouracetic acid in dichloromethane. These steps yield XXIVd.

Compound XXIVd is cyclized using standard techniques to XXIVe. Dicyclohexylcarbodiimide is the preferred cyclization reagent. The amide nitrogens are alkylated if desired; the preferred alkylating agents are benzylic or allylic bromides, or alkyl iodides or tosylates, in the presence of sodium hydride in an aprotic solvent. One or two alkyl groups can be provided depending on the stoichiometry of the alkylating agent and base.

Removal of the hydroxyl protecting group using standard conditions, preferably tetra-n-butyl ammonium flouride, yields the desired product XXIV.

Compounds of the general formula XXVI can be synthesized using Scheme 7. Norstatin, XXVIa can be hydrogenated to remove CBZ protecting group and the resulting amine can be reprotected using t-butoxycarbonyl (BOC). p-Methoxyphenylmethyl protecting groups are alkylated on both the alcohol and acid; afterwhich basic hydrolysis yields XXVIb. Condensation with t-butyl 2-benzylcarbazate (A. S. Dutta and J. S. Morley, *J. Chem. Soc. Perkin I*, 1975, 1712) was facilitated using DCC. The BOC group can be removed using acid conditons and the resulting diamine cyclized with carbonyldiimidazole to give XXVId. Alkylation as previously described, deprotection using dichlorodicyanobenzoquinone (DDQ) followed by HCl/MeOH will yield XXVIf. Sequential alkylation with different alkylating agents can also be performed.

The compounds of the present invention may be prepared using methods known in the art of organic synthesis. The compounds may be synthesized, for example, in accordance with the synthetic schemes set forth below.

Scheme 1

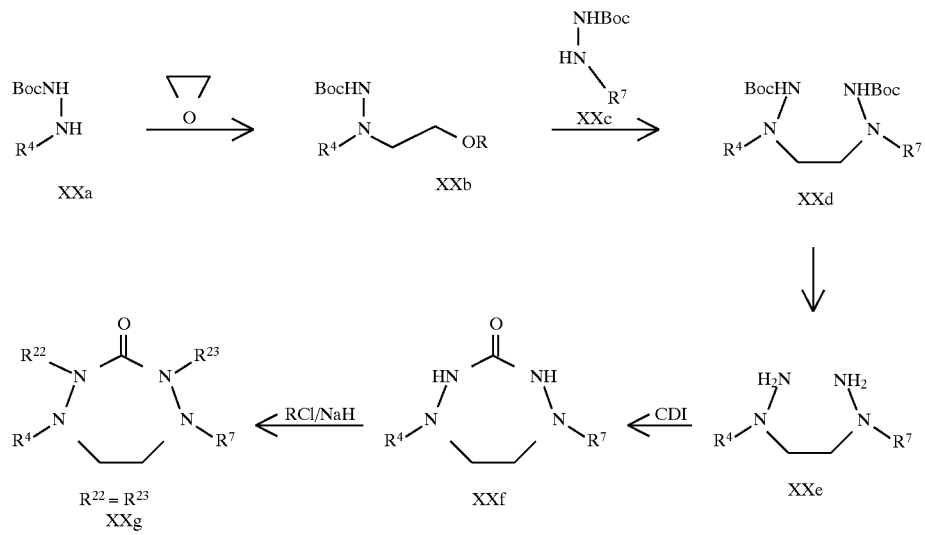

Scheme 2

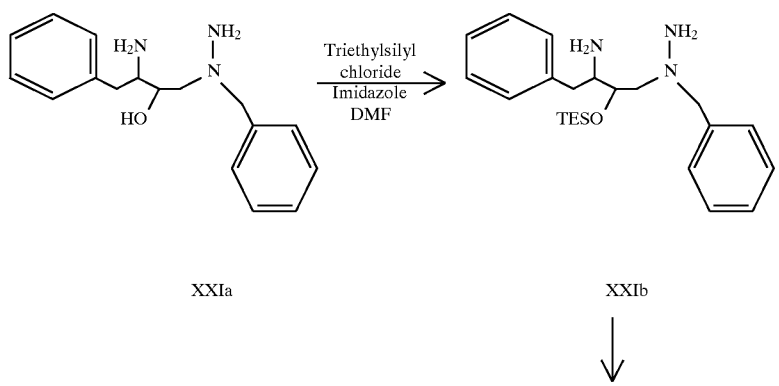

-continued
Scheme 2
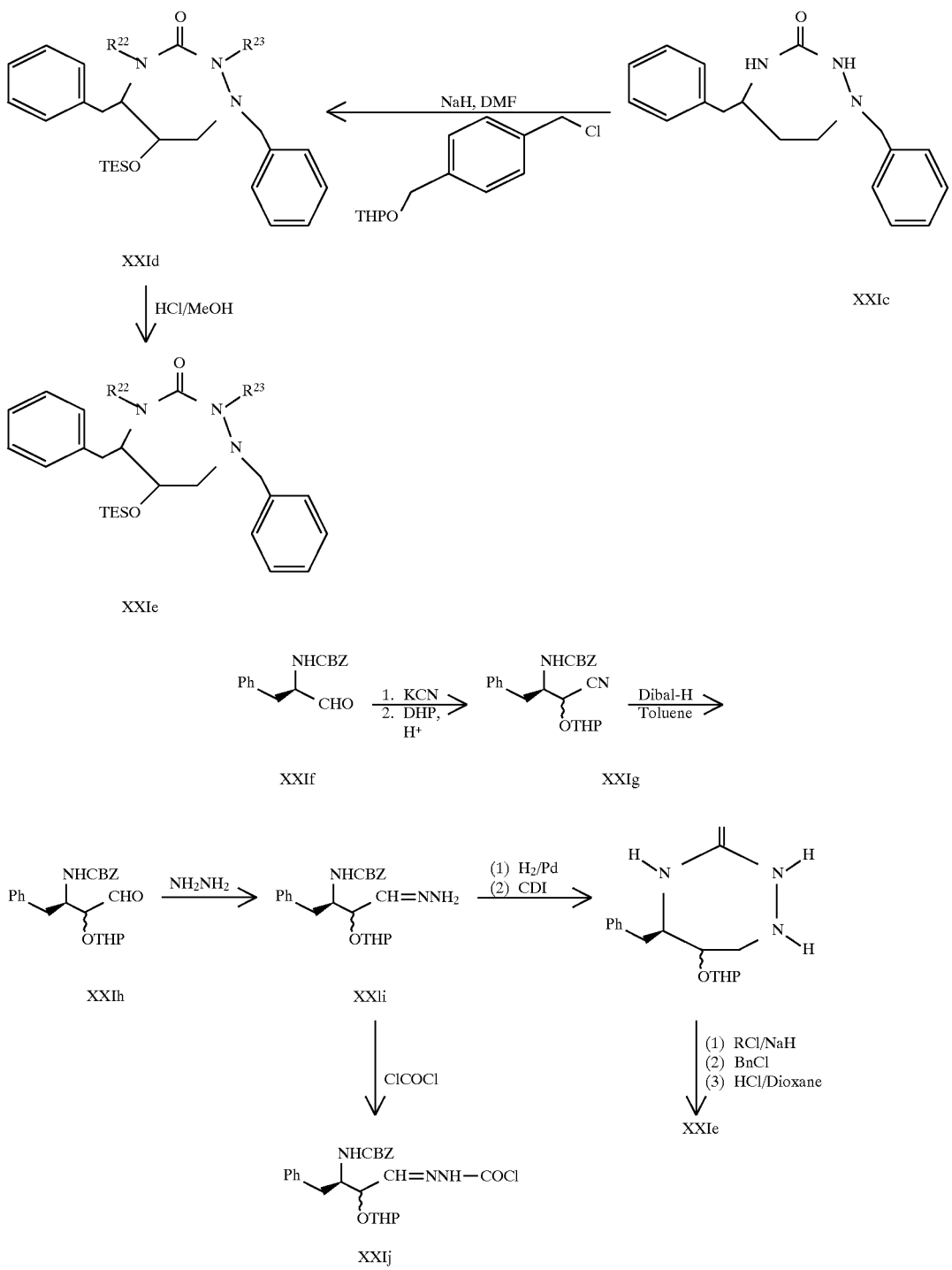

-continued
Scheme 2
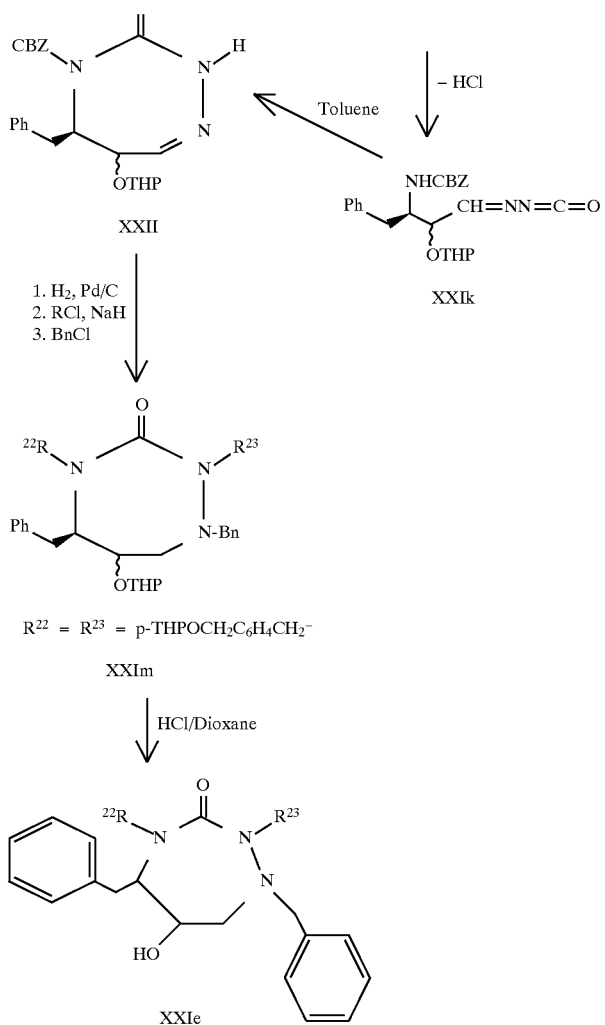
Scheme 3
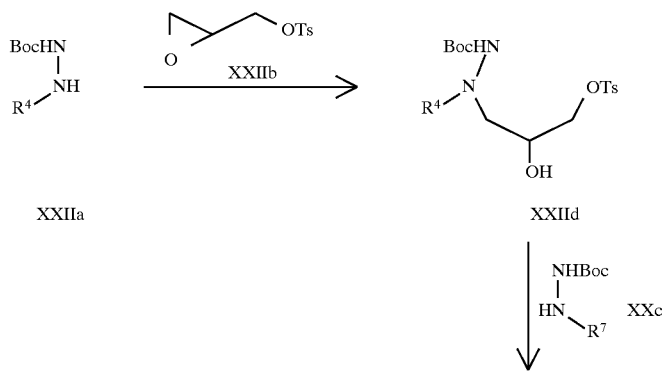

-continued
Scheme 3
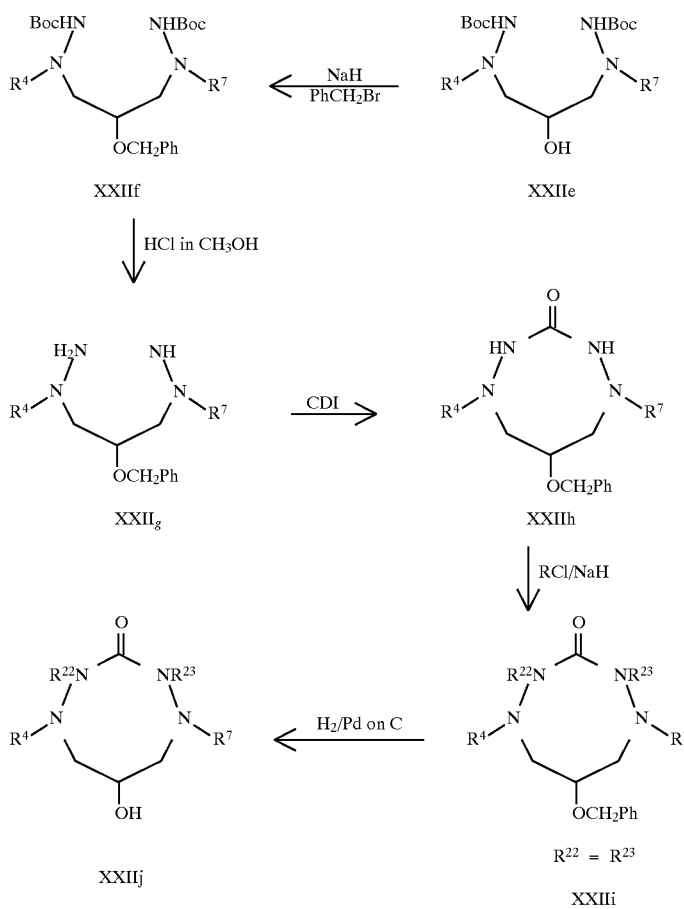
Scheme 4
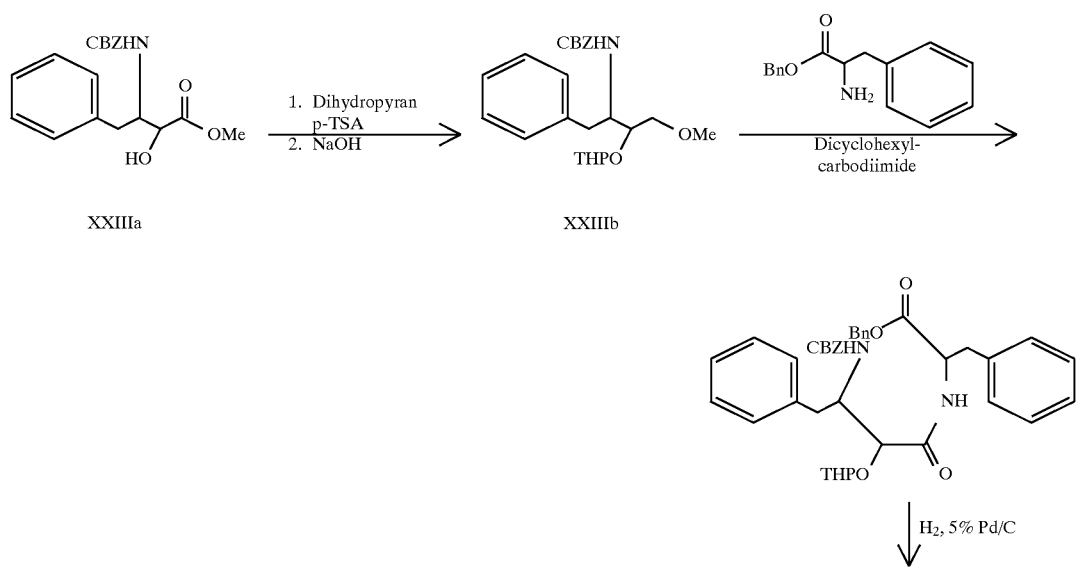

-continued
Scheme 4
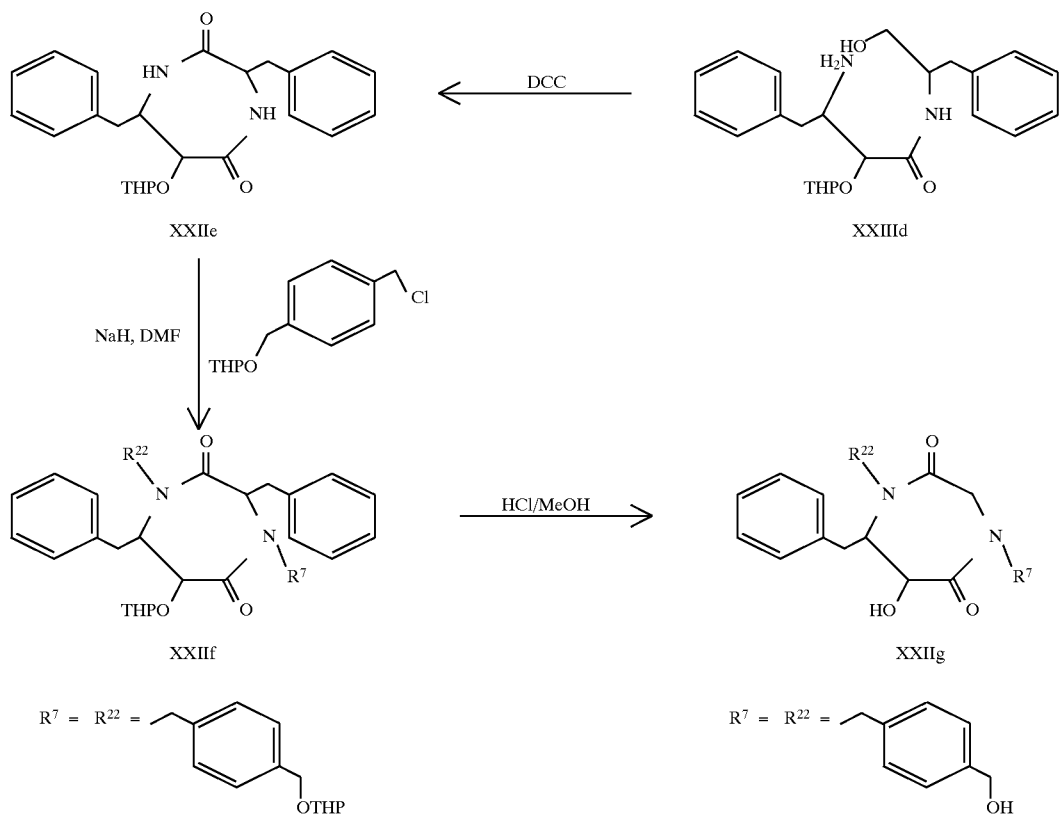
Scheme 5
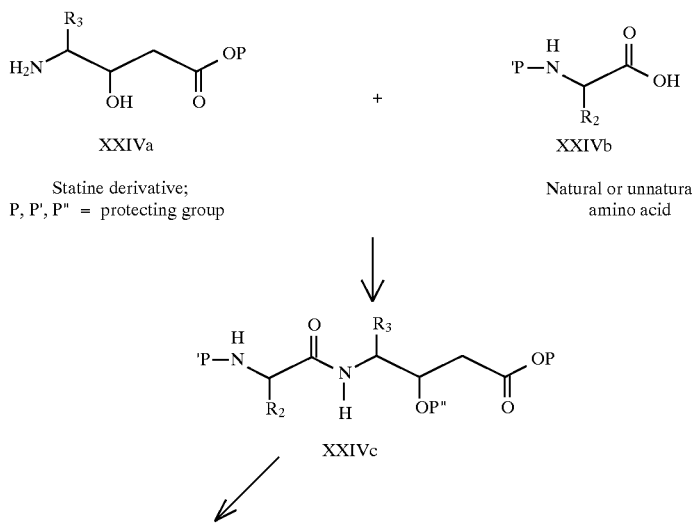

-continued
Scheme 5
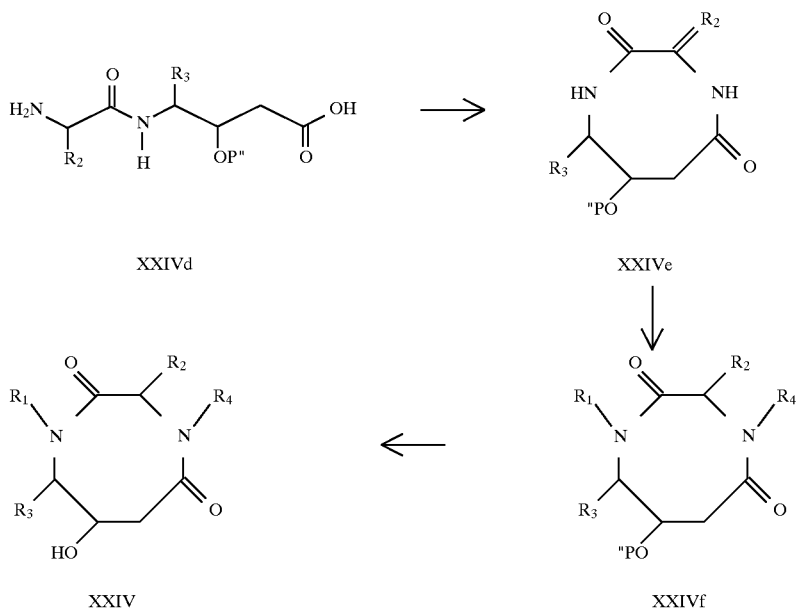
Scheme 7
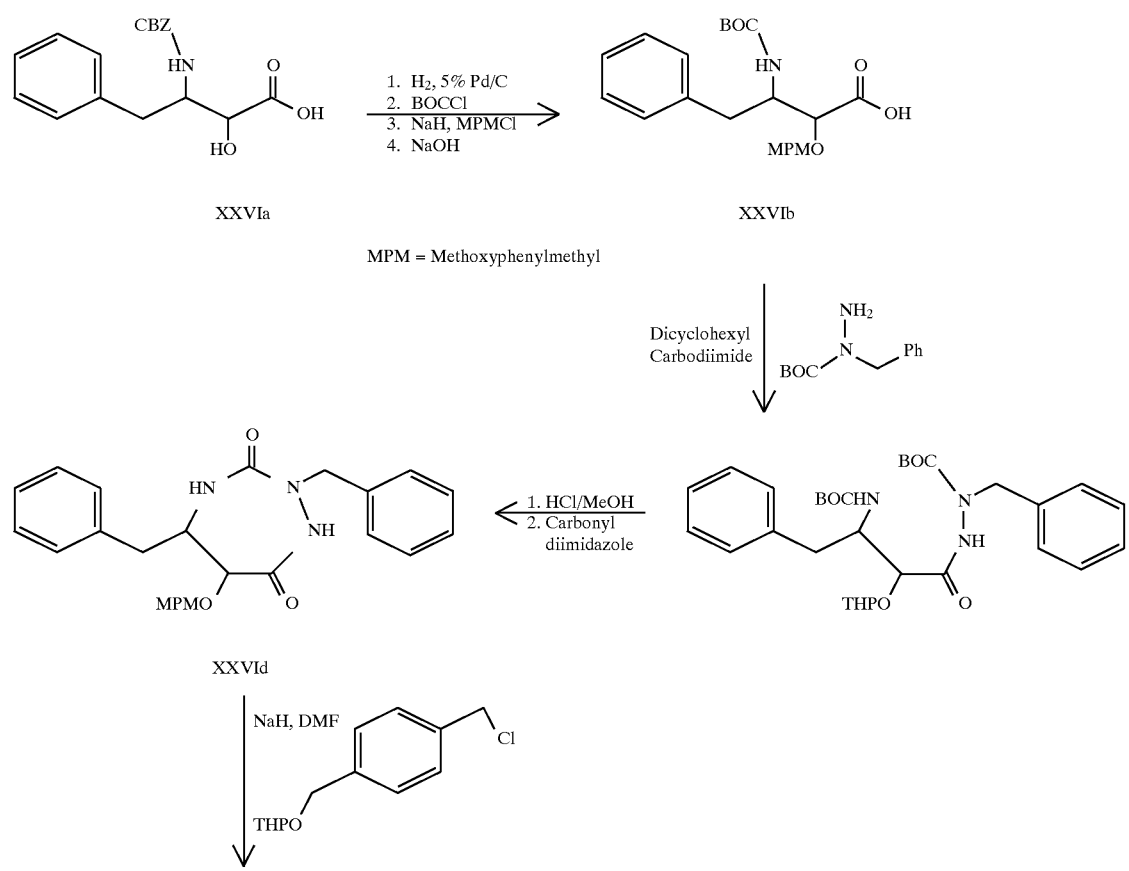
MPM = Methoxyphenylmethyl

-continued
Scheme 7

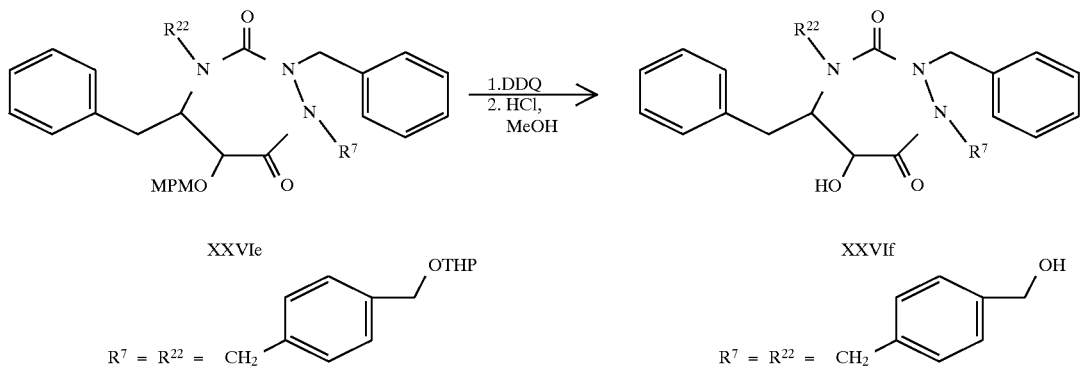

The synthesis of representative compounds of the present invention is described in further detail below.

1. Preparation of N-Carbobenzyloxy-D-Phenylalanine chloromethylketone

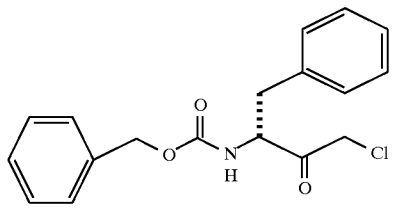

One equivalent [EQ] (15 g) of CBZ-D-phenylalanine was dissolved in tetrahydrofuran [THF, 33 ml] (1.5M). The solution was cooled to −20° C. (internal) using a dry ice/CCl₄ bath and 4-methylmorpholine (5.5 ml, 1 EQ) was added dropwise, maintaining a temperature below −15° C., followed by isobutylchloroformate (6.5 ml, 1 EQ) maintaining a temperature below −15° C. After stirring for 15 min at −15° C. the precipitate was filtered and washed with 50 ml cold THF. The combined THF solution was contained in a 1 L Erlenmeyer cooled in an ice bath and added to this an excess of diazomethane in ether (see prep below). After stirring for 25 min, the bath was removed and stirred until reaction temperature reached ~18° C. The reaction was recooled in ice bath and ~40 ml 4M HCl in dioxane was added, until bubbling ceased and solution became nearly colorless. The pH was checked to confirm acidity and concentrated invacuo. Further evaporation was carried out in high vacuum overnight to afford 18.65 g of the desired product, M.P. 88° C. NMR (CDCl₃): consistent with assigned structure.

2. Preparation of Diazomethane

A commercially available diazomethane distillation kit was charged with 2-(2-ethoxyethoxy)ethanol (84 ml), anhydrous ether (84 ml) and a solution of potassium hydroxide (15 g) in distilled water (24 ml). Upon heating to 60° C., a solution of N-methyl-N-nitroso-p-toluenesulfonamide (30 g, Diazald®) in anhydrous ether (270 ml) was added at the rate of product distillation. Once the 270 ml of expected diazomethane in ether was recovered, an additional amount of ether (100 ml) was added to the reaction vessel and 50 ml of distillate was collected. The diazomethane in ether was stored cold until ready for use.

3. CBZ-D-Phenylalanine Chloromethyl Alcohol

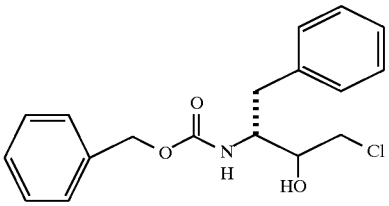

Zinc chloride in ether (1.0M, 136 ml) was added dropwise to a mechanically stirred flask containing a solution of sodium borohydride (10.30 g, 1.25 EQ) in ether (552 ml). A solution of Z—D-phenylalanine chloroketone (36 g) (from step 1 above) in tetrahydrofuran (0.27M) was added dropwise and allowed to stir at room temperature overnight. The reaction was quenched by dropwise addition of water (400 ml), followed by hydrochloric acid (1N, 200 ml) and ethyl acetate (250 ml). Upon separation of the layers, the organic layer was washed with water, saturated sodium bicarbonate and brine. Following drying over magnesium sulfate, the volatiles were removed in vacuo to recover 30.42 g of crude product. Recrystallization using ethyl acetate (100 ml) afforded 9.73 g of two isomers. These were carried through as a mixture. NMR (CDCl₃): consistent with assigned structure. Mass Spec. 334.21 (M+H).

4. CBZ-D-Phenylalanine Epoxide

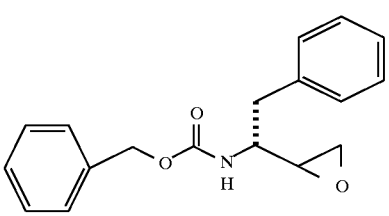

CBZ-D-phenylalanine chloroalcohol (9.73 g) from step 3 was dissolved in tetrahydrofuran (0.16M) and cooled in an ice bath. Potassium tert-butoxide (1.0M in THF, 32 ml, 1.1 EQ) was added dropwise with stirring under nitrogen. Thin Layer Chromatography (Tlc) after 30 min in 6:2:2 toluene-:ethyl acetate:hexanes indicated reaction is complete. The reaction mixture was concentrated in vacuo and partitioned between ethyl acetate and water. The organic layer was washed with brine and dried over sodium sulfate. Filtration and concentration in vacuo afforded 7.98 g of the desired product. NMR (CDCl₃): consistent with assigned structure. Mass Spec. 298 (M+H); 315.17 (M+NH₄).

5. Epoxide Condensation with L-phenylalanine tert-Butylester

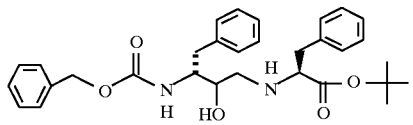

The commercially available amine (as the HCl salt) was converted to the free base by dissolution in saturated sodium bicarbonate and extraction with ethyl acetate. After drying and removal of the volatiles, free amine (2.11 g, 1 EQ) was added to a solution of above described epoxide (from step 4)(2.84 g) in methanol (0.2M) and heated until judged complete. Concentration in vacuo gave 4.95 g of the desired product. NMR (CDCl$_3$): consistent with assigned structure. Mass Spec. 519.29 (M+H).

6. tert-Butyldimethylsilyl Protection on Hydroxyl Group

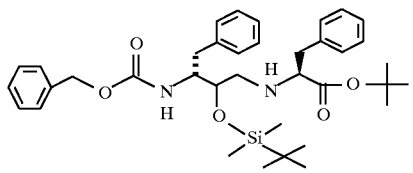

The previously described product (4.95 g) (from step 5) dissolved in anhydrous dimethylformamide (1.2M), was reacted with t-butyldimethylsilyl chloride (2.83 g, 2.2 EQ) and imidazole (1.75 g, 3 EQ) at room temperature overnight. Tlc (2% methanol in chloroform) indicated reaction was complete. The reaction was worked up by adding saturated sodium bicarbonate (100 ml) and stirring for 10 minutes. Methylene chloride was added, the organic layer was separated, washed with brine and dried over sodium sulfate. Concentration in vacuo and purification on silica gel using 6:1:3 toluene:ethyl acetate:hexanes afforded 3.24 g of the product. NMR (CDCl$_3$): consistent with assigned structure. Mass Spec 633.37 (M+H).

7. Removal of the CBZ Protecting Group

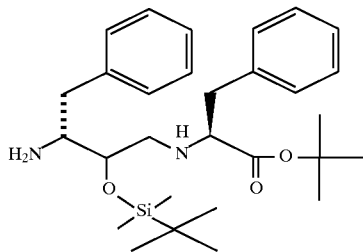

The CBZ-protected amino acid (from step 6)(3.24 g) was dissolved in tetrahydrofuran (66 ml) and glacial acetic acid (6 ml). Following a evacuation and purge sequence with nitrogen, palladium on carbon (10%, 200 mg) was added. After an evacuation and purge sequence using hydrogen, the reaction was allowed to stir until judged complete by Tlc. The catalyst was filtered off and washed with THF/HOAc. Upon concentration in vacuo and further drying on high vacuum, the recovered acetate salt was used directly in the next step. NMR (CDCl$_3$): consistent with assigned structure. Mass Spec 499.34 (M+H).

8. Acid Catalyzed Hydrolysis of the t-Butyl Ester

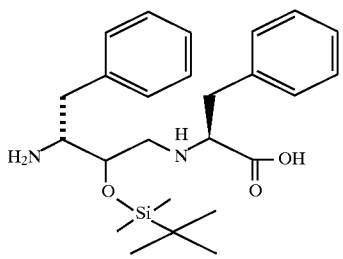

The t-butyl ester (from step 7) (100 mg) was dissolved in methylene chloride (8 ml) and trifluoroacetic acid (2.6 ml) at a concentration of 0.02M. Upon stirring under nitrogen, the reaction was judged complete by Tlc. Concentrated in vacuo while keeping cold, followed by further drying on high vacuum overnight afforded a product which was used directly in the next reaction. NMR (CDCl$_3$): consistent with assigned structure. Mass Spec. 443.27 (M+H).

9. General Procedure for Cyclization (Lactam Formation)

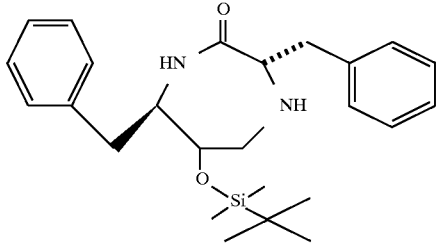

To a solution of the previously described product (from step 8) (3.08 g) in tetrahydrofuran (140 ml, 0.05M) was added 4-methylmorpholine (2.68 ml, 3.5 EQ),1-hydroxybenzotriazole hydrate (0.942 g, 1 EQ) and 1,3-dicyclohexylcarbodiimide (1.45 g, 1 EQ). After stirring at room temperature under nitrogen for 3 days, the precipitated dicyclohexylurea was filtered away and the filtrate was partitioned between methylene chloride and water. The organics were washed with saturated sodium bicarbonate and brine, dried over sodium sulfate and concentrated in vacuo. The crude material was purified by preparative thin layer chromatography (2 mm thickness silica gel plate) using toluene:ethyl acetate:methanol. NMR (CDCl$_3$): consistent with assigned structure. Mass Spec. 425.26 (M+H).

EXAMPLE 1

10. Fluoride-induced Deprotection of the t-Butyldimethylsilyl Ether

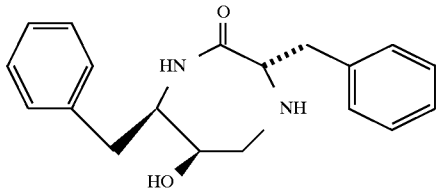

A solution of silyl ether (from step 9 above)(38 mg) dissolved in tetrabutylammonium fluoride (1M solution in tetrahydrofuran, 1.5 ml) was allowed to stir under nitrogen until judged complete by Tlc. The reaction was quenched by addition of saturated sodium bicarbonate and stirred for 10 minutes. After diluting with methylene chloride, the layers were separated and the organics were dried over sodium sulfate. Following concentration in vacuo and purification by preparative Tlc using Toluene:Ethyl Acetate:Methanol, 18 mg of the desired product was isolated. NMR (CDCl₃): consistent with assigned structure. Mass Spec. 311.18 (M+H).

11. Benzylation of Basic Amine

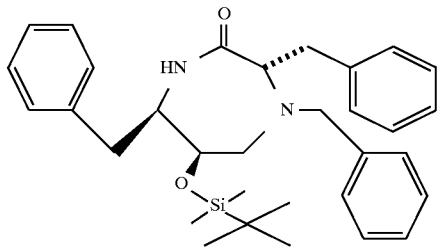

A solution of the starting lactam (from step 9) (62.5 mg) was dissolved in anhydrous N,N-dimethylformamide (0.15 ml, 1M) and allowed to stir with potassium carbonate (30.5 mg, 1.5 EQ) at room temperature under nitrogen for 10 minutes. Benzyl bromide (0.026 ml, 1.5 EQ) was added and the reaction was stirred until judged complete by Tlc. After partitioning between methylene chloride and water, the organic phase was washed with saturated sodium bicarbonate, brine and dried over sodium sulfate. Concentration in vacuo affored 50 mg of the desired product. NMR (CDCl₃): consistent with assigned structure. Mass Spec. M+H 515.31

EXAMPLE 2

12. Deprotection of Benzylated Compound

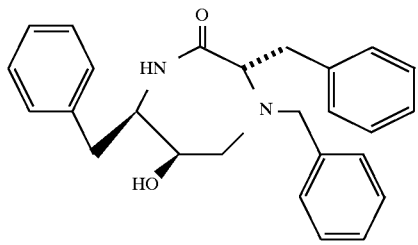

Material from step 11 (above) was treated as described above for step 10. NMR (CDCl₃): consistent with assigned structure. Mass Spec. 401 (M+H).

13. Selective Debenzylation of Cyclized N-benzylamine (Formic Acid Procedure)

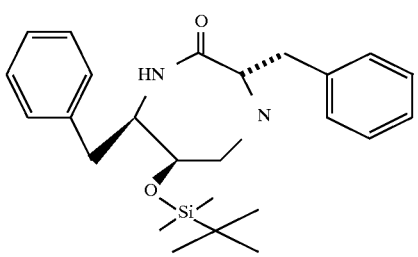

A general procedure based on that described in J. Org. Chem, 1979, 44, 3442 was used. The starting N-benzyl amine (from step 11) (30 mg) was dissolved in MeOH (0.02M) with formic acid (~5%, 3 ml). Following the addition of palladium on Carbon (10%, 30 mg), the reaction was stirred under nitrogen until judged complete by Tlc. The catalyst was removed and the filtrate was concentrated in vacuo before the silyl ether cleavage. NMR (CDCl₃): consistent with assigned structure. Mass Spec. 425.26 (M+H).

Using the above-described techniques or variations thereof appreciated by those of skill in the art of chemical synthesis, the compounds of Tables shown below can also be prepared.

TABLE 1

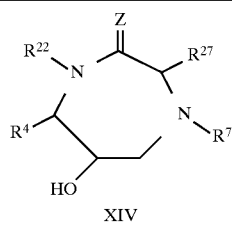

XIV

| Example | $R^4$ | $R^7$ | $R^{22}$ | $R^{27}$ | Z |
|---|---|---|---|---|---|
| 1 | benzyl | H | H | benzyl | O |
| 2 | benzyl | H | H | benzyl | S |
| 3 | benzyl | H | H | benzyl | N—CN |
| 4 | benzyl | H | H | benzyl | N—OCH₃ |
| 5 | benzyl | H | H | (p-HO—C₆H₄)CH₂ | O |
| 6 | benzyl | H | H | (m-HO—C₆H₄)CH₂ | O |
| 7 | benzyl | H | H | n-propyl | O |
| 8 | benzyl | H | H | isobutyl | O |
| 9 | benzyl | H | H | (m-CH₃NH—C₆H₄)CH₂ | O |
| 10 | benzyl | H | H | (m-CH₃O₂C—C₆H₄)CH₂ | O |
| 11 | benzyl | H | H | cyclopropyl methyl | O |

TABLE 1-continued

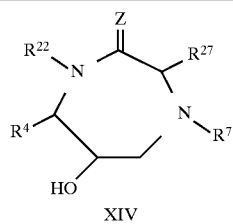

XIV

| Example | R⁴ | R⁷ | R²² | R²⁷ | Z |
|---|---|---|---|---|---|
| 12 | benzyl | H | H | (m-F—C$_6$H$_4$)CH$_2$ | O |
| 13 | benzyl | H | H | 2-naphthyl | O |
| 14 | benzyl | H | H | 4-hydroxy-n-butyl | O |
| 15 | benzyl | H | H | 3-pyridyl | O |
| 16 | n-propyl | H | H | benzyl | O |
| 17 | (p-F—C$_6$H$_4$)CH$_2$ | H | H | benzyl | O |
| 18 | n-butyl | H | H | benzyl | O |
| 19 | (m-HO—C$_6$H$_4$)CH$_2$ | H | H | benzyl | O |
| 20 | (p-H$_2$NCO—C$_6$H$_4$)CH$_2$ | H | H | benzyl | O |
| 21 | (m-CH$_3$CO$_2$—C$_6$H$_4$)CH$_2$ | H | H | benzyl | O |
| 22 | cyclopropyl methyl | H | H | benzyl | O |
| 23 | n-propyl | H | H | cyclopropyl methyl | O |
| 24 | benzyl | benzyl | H | benzyl | O |
| 25 | benzyl | benzyl | cyclopropyl methyl | benzyl | O |
| 26 | benzyl | H | benzyl | isobutyl | O |
| 27 | H | benzyl | (m-HO—C$_6$H$_4$)CH$_2$ | ethyl | O |
| 28 | benzyl | benzyl | (m-HOCH$_2$—C$_6$H$_4$)CH$_2$ | (m-HOCH$_2$—C$_6$H$_4$)CH$_2$ | O |
| 29 | benzyl | benzyl | naphthyl | naphthyl | O |
| 30 | benzyl | benzyl | cyclopropyl methyl | methyl | O |
| 31 | benzyl | benzyl | benzyl | methyl | O |
| 32 | benzyl | H | benzyl | CH$_2$—CONH$_2$ | O |
| 33 | benzyl | benzyl | cyclopropyl methyl | cyclopropyl methyl | O |
| 34 | benzyl | H | benzyl | (3,4-di-F—C$_6$H$_4$)CH$_2$ | O |
| 35 | benzyl | H | benzyl | cyclopropyl methyl | O |
| 36 | benzyl | H | (m-HO—C$_6$H$_4$)CH$_2$ | cyclopropyl methyl | O |
| 37 | benzyl | H | (m-HOCH$_2$—C$_6$H$_4$)CH$_2$ | (m-HOCH$_2$—C$_6$H$_4$)CH$_2$ | O |

Utility

The compounds of formula (I) possess retroviral protease inhibitory activity and are therefore useful as antiviral agents for the treatment of viral diseases. More particularly, the compounds of formula (I) possess HIV protease inhibitory activity and are effective as inhibitors of HIV growth. The protease inhibitory activity of the compounds of the present invention is demonstrated using standard assays of protease activity, for example, using the assay described below for assaying inhibitors of HIV protease activity. The ability of the compounds of the present invention to inhibit viral growth or infectivity is demonstrated in standard assay of viral growth or infectivity, for example, using the assays described below.

A compound is considered to be active if it has an IC$_{50}$ or Ki value of less than about 1 mM for the inhibition of HIV protease or HIV viral growth or infectivity.

HIV Protease Inhibition Assay—Spectroscopic Method
Materials

Protease: Inclusion bodies of E. coli harboring plasmid containing HIV protease under the control of an inducible T7 promoter were prepared according to Cheng et. al (1990) Gene 87: 243. Inclusion bodies were solubilized in 8M urea, 50 mM tris pH 8.0. Protease activity was recovered by dilution 20-fold into buffer containing 50 mM sodium acetate pH 5.5, 1 mM EDTA, 10% glycerol and 5% ethylene glycol. Enzyme was used at a final concentration of 1.0–10 ug/ml (ug=microgram).

Substrate: Peptide of sequence: Ala-Thr-His-Gln-Val-Tyr-Phe(NO$_2$)-Val-Arg-Lys-Ala, containing para-nitrophenylalanine (Phe(NO$_2$)), was prepared by solid phase peptide synthesis as previously described by Cheng et al. (1990) Proc. Natl. Acad. Sci. USA 87: 9660. Stock solutions of 10 mM were prepared in DMSO.

Inhibitory compounds were dissolved in sufficient DMSO to make 2.5 or 25 mM stock solutions. All further dilutions were done in DMSO.

Reactions

Compound (1–5 uL) (uL or ul=microliter) and HIV protease were mixed in buffer containing 50 mM MES, pH 6.5, 1M NaCl, 1 mM EDTA, 1 mM dithiothreitol, 10% glycerol. Reactions were initiated by the addition of peptide substrate to a final concentration of 240 uM (uM=micromolar), and absorbance at 300 nM monitored for 10 min. Values of Ki for inhibitor binding were determined from percent activity measurements in the presence and absence of known concentration of inhibitor, using a value of 0.07 mM for the Km of the substrate (Cheng et al. (1990) Proc. Natl. Acad. Sci. USA 87: 9660).

The HIV-1 protease inhibitory activity of representative compounds of the invention is shown in Table 2 (below).

HIV Protease Inhibition Assay—HPLC Method
Materials

Protease: Inclusion bodies of E. coli harboring plasmid containing plasmid T1718R with a synthetic gene coding for a single-chain tethered dimer of HIV protease were prepared as described in Cheng et al. (Proc. Natl. Acad. Sci. USA, 87, 9660–9664, 1990). Active protease was prepared as described therein by extraction with 67% acetic acid, dilution 33-fold with water, dialysis against water and then against a "refolding buffer" consisting of 20 mM MES, 1 mM dithiothreitol and 10% glycerol. Protease was stored as a stock preparation at 10 uM in refolding buffer.

Substrate: Peptide of sequence: aminobenzoyl-Ala-Thr-His-Gln-Val-Tyr-Phe($NO_2$)-Val-Arg-Lys-Ala containing p-nitrophenylalanine, was prepared by solid phase synthesis as previously described Cheng et al., op.cit. Stock solutions of 2 mM substrate were prepared in DMSO.

Inhibitory compounds were dissolved in sufficient DMSO to make 3 mM stock solutions. All further dilutions were prepared in "assay buffer": 1M NaCl, 50 mM MES, pH 5.5, 1 mM EDTA, 1 mM DTT, 20% glycerol.

Reactions

Enzyme reaction: In a 2 ml screw-cap centrifuge tube were added 50 ul protease (final concentration 0.25 nM) and 100 ul inhibitory compound (final concentration 0.1–12, 500). After 15 min preincubation at room temperature, the reaction was started with the addition of 50 ul substrate (final concentration 5 uM). Incubation was carried out at 30 C. for 1 hr. The reaction was stopped with 1 ml 0.1M ammonium hydroxide.

HPLC measurement of product formation: The product (aminobenzoyl-Ala-Thr-His-Gln-Val-Tyr) was separated from substrate on a Pharmacia MonoQ anion exchange column. The injection volume was 200 ul. The mobile phases were: A (20 mM trisHCl, pH 9.0, 0.02% sodium azide, 10% acetonitrile), B (20 mM tris HCl, pH 9.0, 0.02% sodium azide, 0.5M ammonium formate, 10% acetonitrile). The mobile phases were pumped at 1 ml/min, with a gradient from 0 to 30% B in 5 min, 100% B for 4 min to wash the column, and a re-equilibration for 4 min. The retention time of the product was 3.6 min. Detection with a Shimadzu model RF535 fluorescence monitor was at 330 nm (excitation) and 430 (emission). The Ki was calculated from the formula $Ki=I/(((Km+S-FA*S)/(FA*Km))-1)$ where I=inhibitory concentration, S=substrate concentration, FA=fractional activity=cm peak height with inhibitor/cm peak height without inhibitor, and Km=Michaelis constant=20 uM.

HIV Yield Reduction Cell Assay

Materials: MT-2, a human T-cell line, was cultured in RPMI medium supplemented with 5% (v/v) heat inactivated fetal calf serum (FCS), L-glutamine and gentamycin. Human immunodeficiency virus strains, HIV (3B) and HIV (RF) were propagated in H-9 cells in RPMI with 5% FCS. Poly-L-lysine (Sigma) coated cell culture plates were prepared according to the method of Harada et al. (1985) Science 229: 563–566. MTT, 3-(4,5-dimethyl-thiazol-2yl)-2,5-diphenyltetrazolium bromide, was obtained from Sigma.

Method: Test compounds were dissolved in dimethylsulfoxide to 5 mg/mL and serially diluted into RPMI medium to ten times the desired final concentration. MT-2 cells ($5\times10^5$/mL) in 2.3 mL were mixed with 0.3 ml of the appropriate test compound solution and allowed to sit for 30 minutes at room temperature. HIV (3B) or HIV (RF) (~5× $10^5$ plaque forming units/mL) in 0.375 ml was added to the cell and compound mixtures and incubated for one hour at 36° C. The mixtures were centrifuged at 1000 rpm for 10 minutes and the supernatants containing unattached virus were discarded. The cell pellets were suspended in fresh RPMI containing the appropriate concentrations of test compound and placed in a 36° C., 4% $CO_2$ incubator. Virus was allowed to replicate for 3 days. Cultures were centrifuged for 10 minutes at 1000 rpm and the supernatants containing cell free progeny virus were removed for plaque assay.

The virus titers of the progeny virus produced in the presence or absence of test compounds were determined by plaque assay. Progeny virus suspensions were serially diluted in RPMI and 1.0 mL of each dilution was added to 9 ml of MT-2 cells in RPMI. Cells and virus were incubated for 3 hours at 36° C. to allow for efficient attachment of the virus to cells. Aliquots of each virus and cell mixture were added equally to two wells of a six well poly-L-lysine coated culture plate and incubated overnight at 36° C., 4% $CO_2$. Liquid and unattached cells were removed prior to the addition of 1.5 mL of RPMI with 0.75% (w/v) Seaplaque agarose (FMC Corp.) and 5% FCS. Plates were incubated for 3 days and a second RPMI/agarose overlay was added. After an additional 3 days at 36° C., 4% $CO_2$, a final overlay of phosphate-buffered saline with 0.75% Seaplaque agarose and 1 mg MTT/mL was added. The plates were incubated overnight at 36° C. Clear plaques on a purple background were counted and the number of plaque forming units of virus was calculated for each sample. The antiviral activity of test compounds was determined by the percent reduction in the virus titer with respect to virus grown in the absence of any inhibitors.

HIV Low Multiplicity Assay

Materials: MT-2, a human T-cell line, was cultured in RPMI medium supplemented with 5% (v/v) heat inactivated fetal calf serum (FCS), L-glutamine and gentamycin (GIBCO). Human immunodeficiency virus strains HIV (3B) and HIV (RF) were propagated in H-9 cells in RPMI with 5% FCS. XTT, benzene-sulfonic acid, 3,3'-[1-[(phenyl-amino)carbonyl]-3,4-tetrazolium]bis(4-methoxy-6-nitro)-, sodium salt, was obtained from Starks Associates, Inc.

Method: Test compounds were dissolved in dimethylsulfoxide to 5 mg/ml and serially diluted into RPMI medium to ten times the desired final concentration. MT-2 cells ($5\times10^4$/0.1 mL) were added to each well of a 96 well culture plate and 0.02 mL of the appropriate test compound solution was added to the cells such that each compound concentration was present in two wells. The cells and compounds were allowed to sit for 30 minutes at room temperature. HIV(3B) or HIV(RF) (~$5\times10^5$ plaque forming units/mL) was diluted in medium and added to the cell and compound mixtures to give a multiplicity of infection of 0.01 plaque forming unit/cell. The mixtures were incubated for 7 days at 36° C., during which time the virus replicated and caused the death of unprotected cells. The percentage of cells protected from virus induced cell death was determined by the degree of metabolism of the tetrazolium dye, XTT. In living cells, XTT was metabolized to a colored formazan product which was quantitated spectrophotometrically at 450 nm. The amount of colored formazan was proportional to the number of cells protected from virus by the test compound. The concentration of compound protecting either 50% ($IC_{50}$) or 90% ($IC_{90}$) with respect to an uninfected cell culture was determined.

The HIV inhibitory activity of representative compounds of the present invention in the whole cell infectivity assay described above is shown in Table 2.

TABLE 2

| Example Number | $K_i$ | $IC_{90}$ |
| --- | --- | --- |
| 1 | +++ | +++ |
| 24 | ++ | +++ |

The $IC_{90}$ values in Table 2 are indicated as: +++=<10 ug/mL.

In the Tables herein the Ki values were determined using the assay conditions described above under HIV Protease Inhibition Assay-HPLC Method. The Ki values are indicated as follows: +++=<10 nM; ++=10 nM to 1 uM; +=>1 uM.

In the Tables herein the $IC_{90}$ values were determined using the assay conditions described above under HIV Low Multiplicity Assay. The $IC_{90}$ values are indicated as follows: +++=<10 ug/mL; ++=10 to 100 ug/mL; +=>100 ug/mL.

Dosage and Formulation

The antiviral compounds of this invention can be administered as treatment for viral infections by any means that produces contact of the active agent with the agent's site of action, the viral protease, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams per kilogram of body weight, with the preferred dose being 0.1 to about 30 mg/kg.

Dosage forms (compositions suitable for administration) contain from about 1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

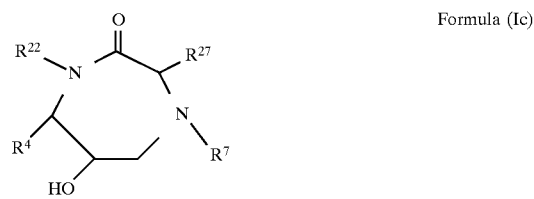

Formula (Ic)

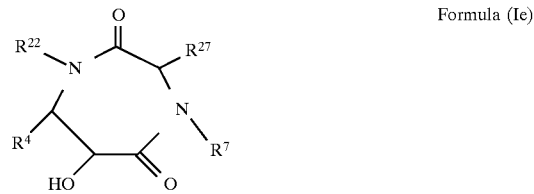

Formula (Ie)

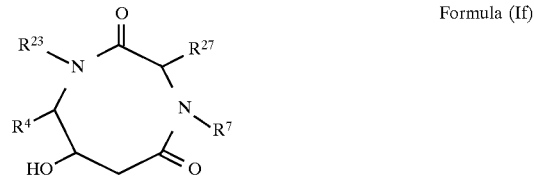

Formula (If)

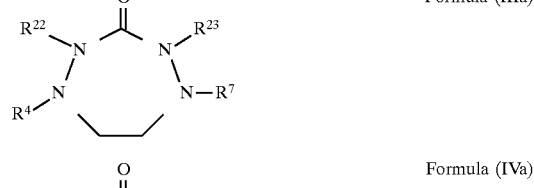

Formula (IIIa)

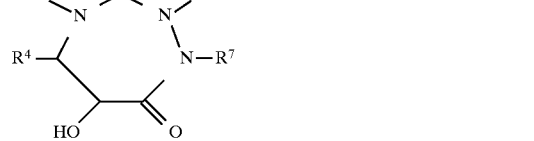

Formula (IVa)

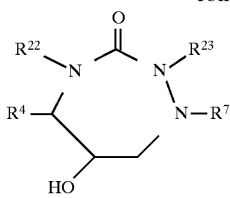

Formula (IVb)

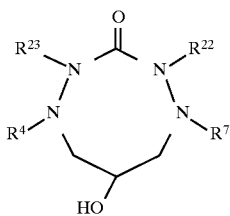

Formula (Va)

TABLE 3[a]

Formula (Ic), $R^4 = R^{27}$ = benzyl, $R^{22} = R^7$ = Table

| Ex. No | .0 | .1 | .2 |
| --- | --- | --- | --- |
| 1[a] | m-hydroxymethyl-benzyl | p-hydroxymethyl-benzyl | m-hydroxybenzyl |
| 2[a] | m-(N,N-dimethyl-amino glycyl) aminobenzyl | m-aminocarbonyl-benzyl | p-hydroxybenzyl |
| 3[a] | m-(N-methylamino) carbonylbenzyl | m-(N-methylamino) benzyl | m-formylbenzyl |
| 4[a] | m-trifluorocarbonyl benzyl | m-hydroxyamidino benzyl | m-triazolylbenzyl |
| 5[a] | m-formaldoxime-benzyl | m-acetoximebenzyl | benzyl |
| 6[a] | hydroxycarbonyl-benzyl | m-tetrazolylbenzyl | m-pyrazolylbenzyl |
| 7[a] | m-imidazolylbenzyl | p-fluorobenzyl | pyridinylmethyl |
| 8[a] | m-acetylbenzyl | m-aminosulfonyl-benzyl | m-methoxybenzyl |

TABLE 4[a]

Formula (Ic), $R^4 = R^{27}$ = fluorobenzyl, $R^{22} = R^7$ = Table

| Ex. No | .0 | .1 | .2 |
| --- | --- | --- | --- |
| 9[a] | m-hydroxymethyl-benzyl | p-hydroxymethyl-benzyl | m-hydroxybenzyl |
| 10[a] | m-(N,N-dimethyl-aminoglycyl) aminobenzyl | m-aminocarbonyl-benzyl | p-hydroxybenzyl |
| 11[a] | m-(N-methylamino) carbonylbenzyl | m-(N-methylamino) benzyl | m-formylbenzyl |
| 12[a] | m-trifluorocarbonyl benzyl | m-hydroxyamidino benzyl | m-triazolylbenzyl |
| 13[a] | m-formaldoxime-benzyl | m-acetoximebenzyl | benzyl |
| 14[a] | hydroxycarbonyl-benzyl | m-tetrazolylbenzyl | m-pyrazolylbenzyl |
| 15[a] | m-imidazolylbenzyl | p-fluorobenzyl | pyridinylmethyl |
| 16[a] | m-acetylbenzyl | m-aminosulfonyl-benzyl | m-methoxybenzyl |

TABLE 5[a]

Formula (Ic), $R^4 = R^{27}$ = pyrrolylmethyl, $R^{22} = R^7$ = Table

| Ex. No | .0 | .1 | .2 |
| --- | --- | --- | --- |
| 17[a] | m-hydroxymethyl-benzyl | p-hydroxymethyl-benzyl | m-hydroxybenzyl |
| 18[a] | m-(N,N-dimethyl-aminoglycyl) aminobenzyl | m-aminocarbonyl-benzyl | p-hydroxybenzyl |
| 19[a] | m-(N-methylamino) carbonylbenzyl | m-(N-methylamino) benzyl | m-formylbenzyl |
| 20[a] | m-trifluorocarbonyl benzyl | m-hydroxyamidino benzyl | m-triazolylbenzyl |
| 21[a] | m-formaldoxime-benzyl | m-acetoximebenzyl | benzyl |
| 22[a] | hydroxycarbonyl-benzyl | m-tetrazolylbenzyl | m-pyrazolylbenzyl |
| 23[a] | m-imidazolylbenzyl | p-fluorobenzyl | pyridinylmethyl |
| 24[a] | m-acetylbenzyl | m-aminosulfonyl-benzyl | m-methoxybenzyl |

TABLE 6[a]

Formula (Ic), $R^4 = R^{27}$ = methoxybenzyl, $R^{22} = R^7$ = Table

| Ex. No | .0 | .1 | .2 |
| --- | --- | --- | --- |
| 25[a] | m-hydroxymethyl-benzyl | p-hydroxymethyl-benzyl | m-hydroxybenzyl |
| 26[a] | m-(N,N-dimethyl-aminoglycyl) aminobenzyl | m-aminocarbonyl-benzyl | p-hydroxybenzyl |
| 27[a] | m-(N-methylamino) carbonylbenzyl | m-(N-methylamino) benzyl | m-formylbenzyl |
| 28[a] | m-trifluorocarbonyl benzyl | m-hydroxyamidino benzyl | m-triazolylbenzyl |
| 29[a] | m-formaldoxime-benzyl | m-acetoximebenzyl | benzyl |
| 30[a] | hydroxycarbonyl-benzyl | m-tetrazolylbenzyl | m-pyrazolylbenzyl |
| 31[a] | m-imidazolylbenzyl | p-fluorobenzyl | pyridinylmethyl |
| 32[a] | m-acetylbenzyl | m-aminosulfonyl-benzyl | m-methoxybenzyl |

TABLE 7[a]

Formula (Ic), $R^4 = R^{27}$ = isobutyl, $R^{22} = R^7$ = Table

| Ex. No | .0 | .1 | .2 |
| --- | --- | --- | --- |
| 33[a] | m-hydroxymethyl-benzyl | p-hydroxymethyl-benzyl | m-hydroxybenzyl |
| 34[a] | m-(N,N-dimethyl-aminoglycyl) aminobenzyl | m-aminocarbonyl-benzyl | p-hydroxybenzyl |
| 35[a] | m-(N-methylamino) carbonylbenzyl | m-(N-methylamino) benzyl | m-formylbenzyl |
| 36[a] | m-trifluorocarbonyl benzyl | m-hydroxyamidino benzyl | m-triazolylbenzyl |
| 37[a] | m-formaldoxime-benzyl | m-acetoximebenzyl | benzyl |
| 38[a] | hydroxycarbonyl-benzyl | m-tetrazolylbenzyl | m-pyrazolylbenzyl |
| 39[a] | m-imidazolylbenzyl | p-fluorobenzyl | pyridinylmethyl |
| 40[a] | m-acetylbenzyl | m-aminosulfonyl-benzyl | m-methoxybenzyl |

TABLE 8[a]

Formula (Ic), $R^4 = R^{27}$ = p-nitrobenzyl, $R^{22} = R^7$ = Table

| Ex. No | .0 | .1 | .2 |
|---|---|---|---|
| 41[a] | m-hydroxymethyl-benzyl | p-hydroxymethyl-benzyl | m-hydroxybenzyl |
| 42[a] | m-(N,N-dimethyl-aminoglycyl)aminobenzyl | m-amindcarbonyl-benzyl | p-hydroxybenzyl |
| 43[a] | m-(N-methylamino)carbonylbenzyl | m-(N-methylamino)benzyl | m-formylbenzyl |
| 44[a] | m-trifluorocarbonyl benzyl | m-hydroxyamidino benzyl | m-triazolylbenzyl |
| 45[a] | m-formaldoxime-benzyl | m-acetoximebenzyl | benzyl |
| 46[a] | hydroxycarbonyl-benzyl | m-tetrazolylbenzyl | m-pyrazolylbenzyl |
| 47[a] | m-imidazolylbenzyl | p-fluorobenzyl | pyridinylmethyl |
| 48[a] | m-acetylbenzyl | m-aminosulfonyl-benzyl | m-methoxybenzyl |

TABLE 9[a]

Formula (Ic), $R^4 = R^{27}$ = m-aminobenzyl, $R^{22} = R^7$ = Table

| Ex. No | .0 | .1 | .2 |
|---|---|---|---|
| 49[a] | m-hydroxymethyl-benzyl | p-hydroxymethyl-benzyl | m-hydroxybenzyl |
| 50[a] | m-(N,N-dimethyl-aminoglycyl)aminobenzyl | m-aminocarbonyl-benzyl | p-hydroxybenzyl |
| 51[a] | m-(N-methylamino)carbonylbenzyl | m-(N-methylamino)benzyl | m-formylbenzyl |
| 52[a] | m-trifluorocarbonyl benzyl | m-hydroxyamidino benzyl | m-triazolylbenzyl |
| 53[a] | m-formaldoxime-benzyl | m-acetoximebenzyl | benzyl |
| 54[a] | hydroxycarbonyl-benzyl | m-tetrazolylbenzyl | m-pyrazolylbenzyl |
| 55[a] | m-imidazolylbenzyl | p-fluorobenzyl | pyridinylmethyl |
| 56[a] | m-acetylbenzyl | m-aminosulfonyl-benzyl | m-methoxybenzyl |

TABLE 10[a]

Formula (Ic), $R^4 = R^{27}$ = pyridinylmethyl, $R^{22} = R^7$ = Table

| Ex. No | .0 | .1 | .2 |
|---|---|---|---|
| 57[a] | m-hydroxymethyl-benzyl | p-hydroxymethyl-benzyl | m-hydroxybenzyl |
| 58[a] | m-(N,N-dimethyl-aminoglycyl)aminobenzyl | m-aminocarbonyl-benzyl | p-hydroxybenzyl |
| 59[a] | m-(N-methylamino)carbonylbenzyl | m-(N-methylamino)benzyl | m-formylbenzyl |
| 60[a] | m-trifluorocarbonyl benzyl | m-hydroxyamidino benzyl | m-triazolylbenzyl |
| 61[a] | m-formaldoxime-benzyl | m-acetoximebenzyl | benzyl |
| 62[a] | hydroxycarbonyl-benzyl | m-tetrazolylbenzyl | m-pyrazolylbenzyl |
| 63[a] | m-imidazolylbenzyl | p-fluorobenzyl | pyridinylmethyl |
| 64[a] | m-acetylbenzyl | m-aminosulfonyl-benzyl | m-methoxybenzyl |

TABLE 11[a]

Formula (Ic), $R^4 = R^{27}$ = m-hydroxybenzyl, $R^{22} = R^7$ = Table

| Ex. No | .0 | .1 | .2 |
|---|---|---|---|
| 65[a] | m-hydroxymethyl-benzyl | p-hydroxymethyl-benzyl | m-hydroxybenzyl |
| 66[a] | m-(N,N-dimethyl-aminoglycyl)aminobenzyl | m-aminocarbonyl-benzyl | p-hydroxybenzyl |
| 67[a] | m-(N-methylamino)carbonylbenzyl | m-(N-methylamino)benzyl | m-formylbenzyl |
| 68[a] | m-trifluorocarbonyl benzyl | m-hydroxyamidino benzyl | m-triazolylbenzyl |
| 69[a] | m-formaldoxime-benzyl | m-acetoximebenzyl | benzyl |
| 70[a] | hydroxycarbonyl-benzyl | m-tetrazolylbenzyl | m-pyrazolylbenzyl |
| 71[a] | m-imidazolylbenzyl | p-fluorobenzyl | pyridinylmethyl |
| 72[a] | m-acetylbenzyl | m-aminosulfonyl-benzyl | m-methoxybenzyl |

TABLE 12[a]

Formula (Ic), $R^4 = R^{27}$ = m-hydroxybenzyl, $R^{22} = R^7$ = Table

| Ex. No | .0 | .1 | .2 |
|---|---|---|---|
| 73[a] | m-hydroxymethyl-benzyl | p-hydroxymethyl-benzyl | m-hydroxybenzyl |
| 74[a] | m-(N,N-dimethyl-aminoglycyl)aminobenzyl | m-aminocarbonyl-benzyl | p-hydroxybenzyl |
| 75[a] | m-(N-methylamino)carbonylbenzyl | m-(N-methylamino)benzyl | m-formylbenzyl |
| 76[a] | m-trifluorcarbonyl benzyl | m-hydroxyamidino benzyl | m-triazolylbenzyl |
| 77[a] | m-formaldoxime-benzyl | m-acetoximebenzyl | benzyl |
| 78[a] | hydroxycarbonyl-benzyl | m-tetrazolylbenzyl | m-pyrazolylbenzyl |
| 79[a] | m-imidazolylbenzyl | p-fluorobenzyl | pyridinylmethyl |
| 80[a] | m-acetylbenzyl | m-aminosulfonyl-benzyl | m-methoxybenzyl |

TABLE 13[a]

Formula (Ic), $R^4 = R^{27}$ = m-aminocarbonylbenzyl, $R^{22} = R^7$ = Table

| Ex. No | .0 | .1 | .2 |
|---|---|---|---|
| 79[a] | m-imidazolylbenzyl | p-fluorobenzyl | pyridinylmethyl |
| 80[a] | m-acetylbenzyl | m-aminosulfonyl-benzyl | m-methoxybenzyl |
| 81[a] | m-hydroxymethyl-benzyl | p-hydroxymethyl-benzyl | m-hydroxybenzyl |
| 82[a] | m-(N,N-dimethyl aminoglycyl)aminobenzyl | m-aminocarbonyl-benzyl | p-hydroxybenzyl |
| 83[a] | m-(N-methylamino)carbonylbenzyl | m-(N-methylamino)benzyl | m-formylbenzyl |
| 84[a] | m-trifluorcarbonyl benzyl | m-hydroxyamidino benzyl | m-triazolylbenzyl |
| 85[a] | m-formaldoxime-benzyl | m-acetoximebenzyl | benzyl |
| 86[a] | hydroxycarbonyl-benzyl | m-tetrazolylbenzyl | m-pyrazolylbenzyl |
| 87[a] | m-imidazolylbenzyl | p-fluorobenzyl | pyridinylmethyl |
| 88[a] | m-acetylbenzyl | m-aminosulfonyl-benzyl | m-methoxybenzyl |

TABLE 14[a]

Formula (Ic), $R^4 = R^{27}$ = p-hydroxymethylbenzyl, $R^{22} = R^7$ = Table

| Ex. No | .0 | .1 | .2 |
|---|---|---|---|
| 89[a] | m-hydroxymethyl-benzyl | p-hydroxymethyl-benzyl | m-hydroxybenzyl |
| 90[a] | m-(N,N-dimethyl-aminoglycyl)aminobenzyl | m-aminocarbonyl-benzyl | p-hydroxybenzyl |
| 91[a] | m-(N-methylamino)carbonylbenzyl | m-(N-methylamino)benzyl | m-formylbenzyl |
| 92[a] | m-trifluorcarbonyl benzyl | m-hydroxyamidino benzyl | m-triazolylbenzyl |
| 93[a] | m-formaldoxime-benzyl | m-acetoximebenzyl | benzyl |
| 94[a] | hydroxycarbonyl benzyl | m-tetrazolylbenzyl | m-pyrazolylbenzyl |
| 95[a] | m-imidazolylbenzyl | p-fluorobenzyl | pyridinylmethyl |
| 96[a] | m-acetylbenzyl | m-aminosulfonyl-benzyl | m-methoxybenzyl |

TABLE 15[a]

Formula (Ic), $R^4 = R^{27}$ = m-hydroxycarbonylbenzyl, $R^{22} = R^7$ = Table

| Ex. No | .0 | .1 | .2 |
|---|---|---|---|
| 97[a] | m-hydroxymethyl-benzyl | p-hydroxymethyl-benzyl | m-hydroxybenzyl |
| 98[a] | m-(N,N-dimethyl-aminoglycyl)aminobenzyl | m-aminocarbonyl-benzyl | p-hydroxybenzyl |
| 99[a] | m-(N-methylamino)carbonylbenzyl | m-(N-methylamino)benzyl | m-formylbenzyl |
| 100[a] | m-trifluorcarbonyl benzyl | m-hydroxyamidino benzyl | m-triazolylbenzyl |
| 101[a] | m-formaldoxime-benzyl | m-acetoximebenzyl | benzyl |
| 102[a] | hydroxycarbonyl benzyl | m-tetrazolylbenzyl | m-pyrazolylbenzyl |
| 103[a] | m-imidazolylbenzyl | p-fluorobenzyl | pyridinylmethyl |
| 104[a] | m-acetylbenzyl | m-aminosulfonyl-benzyl | m-methoxybenzyl |

TABLE 16[a]

Formula (Ic), $R^4 = R^{27}$ = benzyl, $R^{22}$ = m-hydroxymethylbenzyl, $R^7$ = Table

| Ex. No | .0 | .1 | .2 |
|---|---|---|---|
| 105[a] | m-hydroxymethyl-benzyl | p-hydroxymethyl-benzyl | m-hydroxybenzyl |
| 106[a] | m-(N,N-dimethyl aminoglycyl)aminobenzyl | m-aminocarbonyl-benzyl | p-hydroxybenzyl |
| 107[a] | m-(N-methylamino)carbonylbenzyl | m-(N-methylamino)benzyl | m-formylbenzyl |
| 108[a] | m-trifluorcarbonyl benzyl | m-hydroxyamidino benzyl | m-triazolylbenzyl |
| 109[a] | m-formaldoxime-benzyl | m-acetoximebenzyl | benzyl |
| 110[a] | hydroxycarbonyl benzyl | m-tetrazolylbenzyl | m-pyrazolylbenzyl |
| 111[a] | m-imidazolylbenzyl | p-fluorobenzyl | pyridinylmethyl |
| 112[a] | m-acetylbenzyl | m-aminosulfonyl-benzyl | m-methoxybenzyl |

TABLE 17[a]

Formula (Ic), $R^4 = R^{27}$ = benzyl, $R^{22}$ = p-hydroxymethylbenzyl, $R^7$ = Table

| Ex. No | .0 | .1 | .2 |
|---|---|---|---|
| 113[a] | m-hydroxymethyl-benzyl | p-hydroxymethyl-benzyl | m-hydroxybenzyl |
| 114[a] | m-(N,N-dimethyl aminoglycyl)aminobenzyl | m-aminocarbonyl-benzyl | p-hydroxybenzyl |
| 115[a] | m-(N-methylamino)carbonylbenzyl | m-(N-methylamino)benzyl | m-formylbenzyl |
| 116[a] | m-trifluorcarbonyl benzyl | m-hydroxyamidino benzyl | m-triazolylbenzyl |
| 117[a] | m-formaldoxime-benzyl | m-acetoximebenzyl | benzyl |
| 118[a] | hydroxycarbonyl-benzyl | m-tetrazolylbenzyl | m-pyrazolylbenzyl |
| 119[a] | m-imidazolylbenzyl | p-fluorobenzyl | pyridinylmethyl |
| 120[a] | m-acetylbenzyl | m-aminosulfonyl-benzyl | m-methoxybenzyl |

TABLE 18[a]

Formula (Ic), $R^4 = R^{27}$ = benzyl, $R^{22}$ = m-hydroxybenzyl, $R^7$ = Table

| Ex. No | .0 | .1 | .2 |
|---|---|---|---|
| 121[a] | m-hydroxymethyl-benzyl | p-hydroxymethyl-benzyl | m-hydroxybenzyl |
| 122[a] | m-(N,N-dimethyl-aminoglycyl)aminobenzyl | m-aminocarbonyl-benzyl | p-hydroxybenzyl |
| 123[a] | m-(N-methylamino)carbonylbenzyl | m-(N-methylamino)benzyl | m-formylbenzyl |
| 124[a] | m-trifluorcarbonyl benzyl | m-hydroxyamidino benzyl | m-triazolylbenzyl |
| 125[a] | m-formaldoxime-benzyl | m-acetoximebenzyl | benzyl |
| 126[a] | hydroxycarbonyl-benzyl | m-tetrazolylbenzyl | m-pyrazolylbenzyl |
| 127[a] | m-imidazolylbenzyl | p-fluorobenzyl | pyridinylmethyl |
| 128[a] | m-acetylbenzyl | m-aminosulfonyl-benzyl | m-methoxybenzyl |

TABLE 19[a]

Formula (Ic), $R^4 = R^{27}$ = benzyl, $R^{22}$ = m-(N,N-dimethylamino glycyl)aminobenzyl, $R^7$ = Table

| Ex. No | .0 | .1 | .2 |
|---|---|---|---|
| 129[a] | m-hydroxymethyl-benzyl | p-hydroxymethyl-benzyl | m-hydroxybenzyl |
| 130[a] | m-(N,N-dimethyl-aminoglycyl)aminobenzyl | m-aminocarbonyl-benzyl | p-hydroxybenzyl |
| 131[a] | m-(N-methylamino)carbonylbenzyl | m-(N-methylamino)benzyl | m-formylbenzyl |
| 132[a] | m-trifluorcarbonyl benzyl | m-hydroxyamidino benzyl | m-triazolylbenzyl |
| 133[a] | m-formaldoxime-benzyl | m-acetoximebenzyl | benzyl |
| 134[a] | hydroxycarbonyl-benzyl | m-tetrazolylbenzyl | m-pyrazolylbenzyl |
| 135[a] | m-imidazolylbenzyl | p-fluorobenzyl | pyridinylmethyl |
| 136[a] | m-acetylbenzyl | m-aminosulfonyl-benzyl | m-methoxybenzyl |

TABLE 20[a]

Formula (Ic), $R^4 = R^{27}$ = benzyl, $R^{22}$ = m-aminocarbonylbenzyl, $R^7$ = Table

| Ex. No | .0 | .1 | .2 |
|---|---|---|---|
| 137[a] | m-hydroxymethyl-benzyl | p-hydroxymethyl-benzyl | m-hydroxybenzyl |
| 138[a] | m-(N,N-dimethyl-aminoglycyl)aminobenzyl | m-aminocarbonyl-benzyl | p-hydroxybenzyl |
| 139[a] | m-(N-methylamino)carbonylbenzyl | m-(N-methylamino)benzyl | m-formylbenzyl |
| 140[a] | m-trifluorcarbonyl benzyl | m-hydroxyamidino benzyl | m-triazolylbenzyl |
| 141[a] | m-formaldoxime-benzyl | m-acetoximebenzyl | benzyl |
| 142[a] | hydroxycarbonyl-benzyl | m-tetrazolylbenzyl | m-pyrazolylbenzyl |
| 143[a] | m-imidazolylbenzyl | p-fluorobenzyl | pyridinylmethyl |
| 144[a] | m-acetylbenzyl | m-aminosulfonyl-benzyl | m-methoxybenzyl |

TABLE 21[a]

Formula (Ic), $R^4 = R^{27}$ = benzyl, $R^{22}$ = p-hydroxybenzyl, $R^7$ = Table

| Ex. No | .0 | .1 | .2 |
|---|---|---|---|
| 145[a] | m-hydroxymethyl-benzyl | p-hydroxymethyl-benzyl | m-hydroxybenzyl |
| 146[a] | m-(N,N-dimethyl-aminoglycyl)aminobenzyl | m-aminocarbonyl-benzyl | p-hydroxybenzyl |
| 147[a] | m-(N-methylamino)carbonylbenzyl | m-(N-methylamino)benzyl | m-formylbenzyl |
| 148[a] | m-trifluorcarbonyl benzyl | m-hydroxyamidino benzyl | m-triazolylbenzyl |
| 149[a] | m-formaldoxime-benzyl | m-acetoximebenzyl | benzyl |
| 150[a] | hydroxycarbonyl-benzyl | m-tetrazolybenzyl | m-pyrazolylbenzyl |
| 151[a] | m-imidazolybenzyl | p-fluorobenzyl | pyridinylmethyl |
| 152[a] | m-acetylbenzyl | m-aminosulfonyl-benzyl | m-methoxybenzyl |

TABLE 22[a]

Formula (Ic), $R^4 = R^{27}$ = benzyl, $R^{22}$ = m-(N-methylaminocarbonyl, benzyl, $R^7$ = Table

| Ex. No | .0 | .1 | .2 |
|---|---|---|---|
| 153[a] | m-hydroxymethyl-benzyl | p-hydroxymethyl-benzyl | m-hydroxybenzyl |
| 154[a] | m-(N,N-dimethyl-aminoglycyl)aminobenzyl | m-aminocarbonyl-benzyl | p-hydroxybenzyl |
| 155[a] | m-(N-methylamino)carbonylbenzyl | m-(N-methylamino)benzyl | m-formylbenzyl |
| 156[a] | m-trifluorcarbonyl benzyl | m-hydroxyamidino benzyl | m-triazolybenzyl |
| 157[a] | m-formaldoxime-benzyl | m-acetoximebenzyl | benzyl |
| 158[a] | hydroxycarbonyl-benzyl | m-tetrazolylbenzyl | m-pyrazolylbenzyl |
| 159[a] | m-imidazolylbenzyl | p-fluorobenzyl | pyridinylmethyl |
| 160[a] | m-acetylbenzyl | m-aminosulfonyl-benzyl | m-methoxybenzyl |

TABLE 23[a]

Formula (Ic), $R^4 = R^{27}$ = benzyl, $R^{22}$ = m-(N-methylamino)benzyl, $R^7$ = Table

| Ex. No | .0 | .1 | .2 |
|---|---|---|---|
| 161[a] | m-hydroxymethyl-benzyl | p-hydroxymethyl-benzyl | m-hydroxybenzyl |
| 162[a] | m-(N,N-dimethyl-aminoglycyl)aminobenzyl | m-aminocarbonyl-benzyl | p-hydroxybenzyl |
| 163[a] | m-(N-methylamino)carbonylbenzyl | m-(N-methylamino)benzyl | m-formylbenzyl |
| 164[a] | m-trifluorcarbonyl benzyl | m-hydroxyamidino benzyl | m-triazolylbenzyl |
| 165[a] | m-formaldoxime-benzyl | m-acetoximebenzyl | benzyl |
| 166[a] | hydroxycarbonyl-benzyl | zn-tetrazolylbenzyl | m-pyrazolylbenzyl |
| 167[a] | m-imidazolylbenzyl | p-fluorobenzyl | pyridinylmethyl |
| 168[a] | m-acetylbenzyl | m-aminosulfonyl-benzyl | m-methoxybenzyl |

TABLE 24[a]

Formula (Ic), $R^4 = R^{27}$ = benzyl, $R^{22}$ = m-formyllbenzyl, $R^7$ = Table

| Ex. No | .0 | .1 | .2 |
|---|---|---|---|
| 169[a] | m-hydroxymethyl-benzyl | p-hydroxymethyl-benzyl | m-hydroxybenzyl |
| 170[a] | m-(N,N-dimethyl-aminoglycyl)aminobenzyl | m-aminocarbonyl-benzyl | p-hydroxybenzyl |
| 171[a] | m-(N-methylamino)carbonylbenzyl | m-(N-methylamino)benzyl | m-formylbenzyl |
| 172[a] | m-trifluorcarbonyl benzyl | m-hydroxyamidino benzyl | m-triazolylbenzyl |
| 173[a] | m-formaldoxime-benzyl | m-acetoximebenzyl | benzyl |
| 174[a] | hydroxycarbonyl-benzyl | m-tetrazolylbenzyl | m-pyrazolylbenzyl |
| 175[a] | m-imidazolylbenzyl | p-fluorobenzyl | pyridinylmethyl |
| 176[a] | m-acetylbenzyl | m-aminosulfonyl-benzyl | m-methoxybenzyl |

TABLE 25[a]

Formula (Ic), $R^4 = R^{27}$ = benzyl, $R^{22}$ = m-trifluorocarbonylbenzyl, $R^7$ = Table

| Ex. No | .0 | .1 | .2 |
|---|---|---|---|
| 177[a] | m-hydroxymethyl-benzyl | p-hydroxymethyl-benzyl | m-hydroxybenzyl |
| 178[a] | m-(N,N-dimethyl-aminoglycyl)aminobenzyl | m-aminocarbonyl-benzyl | p-hydroxybenzyl |
| 179[a] | m-(N-methylamino)carbonylbenzyl | m-(N-methylamino)benzyl | m-formylbenzyl |
| 180[a] | m-trifluorcarbonyl benzyl | m-hydroxyamidino benzyl | m-triazolybenzyl |
| 181[a] | m-formaldoxime-benzyl | m-acetoximebenzyl | benzyl |
| 182[a] | hydroxycarbonyl-benzyl | m-tetrazolylbenzyl | m-pyrazolylbenzyl |
| 183[a] | m-imidazolylbenzyl | p-fluorobenzyl | pyridinylmethyl |
| 184[a] | m-acetylbenzyl | m-aminosulfonyl-benzyl | m-methoxybenzyl |

TABLE 26[a]

Formula (Ic), $R^4 = R^{27}$ = benzyl, $R^{22}$ = m-hydroxyamidinobenzyl, $R^7$ = Table

| Ex. No | .0 | .1 | .2 |
| --- | --- | --- | --- |
| 185[a] | m-hydroxymethyl-benzyl | p-hydroxymethyl-benzyl | m-hydroxybenzyl |
| 186[a] | m-(N,N-dimethyl-aminoglycyl)aminobenzyl | m-aminocarbonyl-benzyl | p-hydroxybenzyl |
| 187[a] | m-(N-methylamino)carbonylbenzyl | m-(N-methylamino)benzyl | m-formylbenzyl |
| 188[a] | m-trifluorcarbonylbenzyl | m-hydroxyarhidinobenzyl | m-triazolylbenzyl |
| 189[a] | m-formaldoxime-benzyl | m-acetoximebenzyl | benzyl |
| 190[a] | hydroxycarbonyl-benzyl | m-tetrazolylbenzyl | m-pyrazolylbenzyl |
| 191[a] | m-imidazolylbenzyl | p-fluorobenzyl | pyridinylmethyl |
| 192[a] | m-acetylbenzyl | m-aminosulfonyl-benzyl | m-methoxybenzyl |

TABLE 27[a]

Formula (Ic), $R^4 = R^{27}$ = benzyl, $R^{22}$ = m-trizaolylbenzyl, $R^7$ = Table

| Ex. No | .0 | .1 | .2 |
| --- | --- | --- | --- |
| 193[a] | m-hydroxymethyl-benzyl | p-hydroxymethyl-benzyl | m-hydroxybenzyl |
| 194[a] | m-(N,N-dimethyl-aminoglycyl)aminobenzyl | m-aminocarbonyl-benzyl | p-hydroxybenzyl |
| 195[a] | m-(N-methylamino)carbonylbenzyl | m-(N-methylamino)benzyl | m-formylbenzyl |
| 196[a] | m-trifluorcarbonylbenzyl | m-hydroxyamidinobenzyl | m-triazolylbenzyl |
| 197[a] | m-formaldoxime-benzyl | m-acetoximebenzyl | benzyl |
| 198[a] | hydroxycarbonyl-benzyl | m-tetrazolylbenzyl | m-pyrazolylbenzyl |
| 199[a] | m-imidazolylbenzyl | p-fluorobenzyl | pyridinylmethyl |
| 200[a] | m-acetylbenzyl | m-aminosulfonyl-benzyl | m-methoxybenzyl |

TABLE 28[a]

Formula (Ic), $R^4 = R^{27}$ = benzyl, $R^{22}$ = m-formaldoximebenzyl, $R^7$ = Table

| Ex. No | .0 | .1 | .2 |
| --- | --- | --- | --- |
| 201[a] | m-hydroxymethyl-benzyl | p-hydroxymethyl-benzyl | m-hydroxybenzyl |
| 202[a] | m-(N,N-dimethyl-aminoglycyl)aminobenzyl | m-aminocarbonyl-benzyl | p-hydroxybenzyl |
| 203[a] | m-(N-methylamino)carbonylbenzyl | m-(N-methylamino)benzyl | m-formylbenzyl |
| 204[a] | m-trifluorcarbonylbenzyl | m-hydroxyamidinobenzyl | m-triazolylbenzyl |
| 205[a] | m-formaldoxime-benzyl | m-acetoximebenzyl | benzyl |
| 206[a] | hydroxycarbonyl-benzyl | m-tetrazolylbenzyl | m-pyrazolylbenzyl |
| 207[a] | m-imidazolylbenzyl | p-fluorobenzyl | pyridinylmethyl |
| 208[a] | m-acetylbenzyl | m-aminosulfonyl-benzyl | m-methoxybenzyl |

TABLE 29[a]

Formula (Ic), $R^4 = R^{27}$ = benzyl, $R^{22}$ = m-acetoximebenzyl, $R^7$ = Table

| Ex. No | .0 | .1 | .2 |
| --- | --- | --- | --- |
| 209[a] | m-hydroxymethyl-benzyl | p-hydroxymethyl-benzyl | m-hydroxybenzyl |
| 210[a] | m-(N,N-dimethyl-aminoglycyl)aminobenzyl | m-aminocarbonyl-benzyl | p-hydroxybenzyl |
| 211[a] | m-(N-methylamino)carbonylbenzyl | m-(N-methylamino)benzyl | m-formylbenzyl |
| 212[a] | m-trifluorcarbonylbenzyl | m-hydroxyamidinobenzyl | m-triazolylbenzyl |
| 213[a] | m-formaldoxime-benzyl | m-acetoximebenzyl | benzyl |
| 214[a] | hydroxycarbonyl-benzyl | m-tetrazolylbenzyl | m-pyrazolylbenzyl |
| 215[a] | m-imidazolylbenzyl | p-fluorobenzyl | pyridinylmethyl |
| 216[a] | m-acetylbenzyl | m-aminosulfonyl-benzyl | m-methoxybenzyl |

TABLE 30[a]

Formula (Ic), $R^4 = R^{27}$ = benzyl, $R^{22}$ = benzyl, $R^7$ = Table

| Ex. No | .0 | .1 | .2 |
| --- | --- | --- | --- |
| 217[a] | m-hydroxymethyl-benzyl | p-hydroxymethyl-benzyl | m-hydroxybenzyl |
| 218[a] | m-(N,N-dimethyl-aminoglycyl)aminobenzyl | m-aminocarbonyl-benzyl | p-hydroxybenzyl |
| 219[a] | m-(N-methylamino)carbonylbenzyl | m-(N-methylamino)benzyl | m-formylbenzyl |
| 220[a] | m-trifluorcarbonylbenzyl | m-hydroxyamidinobenzyl | m-triazolylbenzyl |
| 221[a] | m-formaldoxime-benzyl | m-acetoximebenzyl | benzyl |
| 222[a] | hydroxycarbonyl-benzyl | m-tetrazolylbenzyl | m-pyrazolylbenzyl |
| 223[a] | m-imidazolylbenzyl | p-fluorobenzyl | pyridinylmethyl |
| 224[a] | m-acetylbenzyl | m-aminosulfonyl-benzyl | m-methoxybenzyl |

TABLE 31[a]

Formula (Ic), $R^4 = R^{27}$ = benzyl, $R^{22}$ = m-hydroxycarbonylbenzyl, $R^7$ = Table

| Ex. No | .0 | .1 | .2 |
| --- | --- | --- | --- |
| 225[a] | m-hydroxymethyl-benzyl | p-hydroxymethyl-benzyl | m-hydroxybenzyl |
| 226[a] | m-(N,N-dimethyl-aminoglycyl)aminobenzyl | m-aminocarbonyl-benzyl | p-hydroxybenzyl |
| 227[a] | m-(N-methylamino)carbonylbenzyl | m-(N-methylamino)benzyl | m-formylbenzyl |
| 228[a] | m-trifluorcarbonylbenzyl | m-hydroxyamidinobenzyl | m-triazolylbenzyl |
| 229[a] | m-formaldoxime-benzyl | m-acetoximebenzyl | benzyl |
| 230[a] | hydroxycarbonyl-benzyl | m-tetrazolylbenzyl | m-pyrazolylbenzyl |
| 231[a] | m-imidazolylbenzyl | p-fluorobenzyl | pyridinylmethyl |
| 232[a] | m-acetylbenzyl | m-aminosulfonyl-benzyl | m-methoxybenzyl |

TABLE 32[a]

Formula (Ic), $R^4 = R^{27}$ = benzyl, $R^{22}$ = m-tetrazolylbenzyl, $R^7$ = Table

| Ex. No | .0 | .1 | .2 |
|---|---|---|---|
| 233[a] | m-hydroxymethyl-benzyl | p-hydroxymethyl-benzyl | m-hydroxybenzyl |
| 234[a] | m-(N,N-dimethyl-aminoglycyl)aminobenzyl | m-aminocarbonyl-benzyl | p-hydroxybenzyl |
| 235[a] | m-(N-methylamino)carbonylbenzyl | m-(N-methylamino)benzyl | m-formylbenzyl |
| 236[a] | m-trifluorcarbonyl benzyl | m-hydroxyamidino benzyl | m-triazolylbenzyl |
| 237[a] | m-formaldoxime-benzyl | m-acetoximebenzyl | benzyl |
| 238[a] | hydroxycarbonyl-benzyl | m-tetrazolylbenzyl | m-pyrazolylbenzyl |
| 239[a] | m-imidazolylbenzyl | p-fluorobenzyl | pyridinylmethyl |
| 240[a] | m-acetylbenzyl | m-aminosulfonyl-benzyl | m-methoxybenzyl |

TABLE 33[a]

Formula (Ic), $R^4 = R^{27}$ = benzyl, $R^{22}$ = m-pyrazolylbenzyl, $R^7$ = Table

| Ex. No | .0 | .1 | .2 |
|---|---|---|---|
| 241[a] | m-hydroxymethyl-benzyl | p-hydroxymethyl-benzyl | m-hydroxybenzyl |
| 242[a] | m-(N,N-dimethyl-aminoglycyl)aminobenzyl | m-aminocarbonyl-benzyl | p-hydroxybenzyl |
| 243[a] | m-(N-methylamino)carbonylbenzyl | m-(N-methylamino)benzyb | m-formylbenzyl |
| 244[a] | m-trifluorcarbonyl benzyl | m-hydroxyamidino benzyl | m-triazolylbenzyl |
| 245[a] | m-formaldoxime-benzyl | m-acetoximebenzyl | benzyl |
| 246[a] | hydroxycarbonyl-benzyl | m-tetrazolylbenzyl | m-pyrazolylbenzyl |
| 247[a] | m-imidazolylbenzyl | p-fluorobenzyl | pyridinylmethyl |
| 248[a] | m-acetylbenzyl | m-aminosulfonyl-benzyl | m-methoxybenzyl |

TABLE 34[a]

Formula (Ic), $R^4 = R^{27}$ = benzyl, $R^{22}$ = m-imidazolylbenzyl, $R^7$ = Table

| Ex. No | .0 | .1 | .2 |
|---|---|---|---|
| 249[a] | m-hydroxymethyl-benzyl | p-hydroxymethyl-benzyl | m-hydroxybenzyl |
| 250[a] | m-(N,N-dimethyl-aminoglycyl)aminobenzyl | m-aminocarbonyl-benzyl | p-hydroxybenzyl |
| 251[a] | m-(N-methylamino)carbonylbenzyl | m-(N-methylamino)benzyl | m-formylbenzyl |
| 252[a] | m-trifluorcarbonyl benzyl | m-hydroxyamidino benzyl | m-triazolylbenzyl |
| 253[a] | m-formaldoxime-benzyl | m-acetoximebenzyl | benzyl |
| 254[a] | hydroxycarbonyl-benzyl | m-tetrazolylbenzyl | m-pyrazolylbenzyl |
| 255[a] | m-imidazolylbenzyl | p-fluorobenzyl | pyridinylmethyl |
| 256[a] | m-acetylbenzyl | m-aminosulfonyl-benzyl | m-methoxybenzyl |

TABLE 35[a]

Formula (Ic), $R^4 = R^{27}$ = benzyl, $R^{22}$ = p-fluorobenzyl, $R^7$ = Table

| Ex. No | .0 | .1 | .2 |
|---|---|---|---|
| 257[a] | m-hydroxymethyl-benzyl | p-hydroxymethyl-benzyl | m-hydroxybenzyl |
| 258[a] | m-(N,N-dimethyl-aminoglycyl)aminobenzyl | m-aminocarbonyl-benzyl | p-hydroxybenzyl |
| 259[a] | m-(N-methylamino)carbonylbenzyl | m-(N-methylamino)benzyl | m-formylbenzyl |
| 260[a] | m-trifluorcarbonyl benzyl | m-hydroxyamidino benzyl | m-triazolylbenzyl |
| 261[a] | m-formaldoxime-benzyl | m-acetoximebenzyl | benzyl |
| 262[a] | hydroxycarbonyl-benzyl | m-tetrazolylbenzyl | m-pyrazolylbenzyl |
| 263[a] | m-imidazolylbenzyl | p-fluorobenzyl | pyridinylmethyl |
| 264[a] | m-acetylbenzyl | m-aminosulfonyl-benzyl | m-methoxybenzyl |

TABLE 36[a]

Formula (Ic), $R^4 = R^{27}$ = benzyl, $R^{22}$ = pyridinylmethyl, $R^7$ = Table

| Ex. No | .0 | .1 | .2 |
|---|---|---|---|
| 265[a] | m-hydroxymethyl-benzyl | p-hydroxymethyl-benzyl | m-hydroxybenzyl |
| 266[a] | m-(N,N-dimethyl-aminoglycyl)aminobenzyl | m-aminocarbonyl-benzyl | p-hydroxybenzyl |
| 267[a] | m-(N-methylamino)carbonylbenzyl | m-(N-methylamino)benzyl | m-formylbenzyl |
| 268[a] | m-trifluorcarbonyl benzyl | m-hydroxyamidino benzyl | m-triazolylbenzyl |
| 269[a] | m-formaldoxime-benzyl | m-acetoximebenzyl | benzyl |
| 270[a] | hydroxycarbonyl-benzyl | m-tetrazolylbenzyl | m-pyrazolylbenzyl |
| 271[a] | m-imidazolylbenzyl | p-fluorobenzyl | pyridinylmethyl |
| 272[a] | m-acetylbenzyl | m-aminosulfonyl-benzyl | m-methoxybenzyl |

TABLE 37[a]

Formula (Ic), $R^4 = R^{27}$ = benzyl, $R^{22}$ = m-acetylbenzyl, $R^7$ = Table

| Ex. No | .0 | .1 | .2 |
|---|---|---|---|
| 273[a] | m-hydroxymethyl-benzyl | p-hydroxymethyl-benzyl | m-hydroxybenzyl |
| 274[a] | m-(N,N-dimethyl-aminoglycyl)aminobenzyl | m-aminocarbonyl-benzyl | p-hydroxybenzyl |
| 275[a] | m-(N-methylamino)carbonylbenzyl | m-(N-methylamino)benzyl | m-formylbenzyl |
| 276[a] | m-trifluorcarbonyl benzyl | m-hydroxyamidino benzyl | m-triazolylbenzyl |
| 277[a] | m-formaldoxime-benzyl | m-acetoximebenzyl | benzyl |
| 278[a] | hydroxycarbonyl-benzyl | m-tetrazolylbenzyl | m-pyrazolylbenzyl |
| 279[a] | m-imidazolylbenzyl | p-fluorobenzyl | pyridinylmethyl |
| 280[a] | m-acetylbenzyl | m-aminosulfonyl-benzyl | m-methoxybenzyl |

TABLE 38[a]

Formula (Ic), $R^4 = R^{27}$ = benzyl, $R^{22}$ = m-aminosulfonylbenzyl, $R^7$ = Table

| Ex. No | .0 | .1 | .2 |
|---|---|---|---|
| 281[a] | m-hydroxymethyl-benzyl | p-hydroxymethyl-benzyl | m-hydroxybenzyl |
| 282[a] | m-(N,N-dimethyl-aminoglycyl)aminobenzyl | m-aminocarbonyl-benzyl | p-hydroxybenzyl |
| 283[a] | m-(N-methylamino)carbonylbenzyl | m-(N-methylamino)benzyl | m-formylbenzyl |
| 284[a] | m-trifluorcarbonyl benzyl | m-hydraxyamidino benzyl | m-triazolylbenzyl |
| 285[a] | m-formaldoxime-benzyl | m-acetoximebenzyl | benzyl |
| 286[a] | hydroxycarbonyl-benzyl | m-tetrazolylbenzyl | m-pyrazolylbenzyl |
| 287[a] | m-imidazolylbenzyl | p-fluorobenzyl | pyridinylmethyl |
| 288[a] | m-acetylbenzyl | m-aminosulfonyl-benzyl | m-methoxybenzyl |

TABLE 39[a]

Formula (Ic), $R^4 = R^{27}$ = benzyl, $R^{22}$ = m-methoxybenzyl, $R^7$ = Table

| Ex. No | .0 | .1 | .2 |
|---|---|---|---|
| 289[a] | m-hydroxymethyl-benzyl | p-hydroxymethyl-benzyl | m-hydroxybenzyl |
| 290[a] | m-(N,N-dimethyl-aminoglycyl)aminobenzyl | m-aminocarbonyl-benzyl | p-hydroxybenzyl |
| 291[a] | m-(N-methylamino)carbonylbenzyl | m-(N-methylamino)benzyl | m-formylbenzyl |
| 292[a] | m-trifluorcarbonyl benzyl | m-hydroxyamidino benzyl | m-triazolylbenzyl |
| 293[a] | m-formaldoxime-benzyl | m-acetoximebenzyl | benzyl |
| 294[a] | hydroxycarbonyl-benzyl | m-tetrazolylbenzyl | m-pyrazolylbenzyl |
| 295[a] | m-imidazolylbenzyl | p-fluorobenzyl | pyridinylmethyl |
| 296[a] | m-acetylbenzyl | m-aminosulfonyl-benzyl | m-methoxybenzyl |

TABLE 3[b]

Formula (Ie), $R^4 = R^{27}$ = benzyl, $R^{22} = R^7$ = Table

| Ex. No | .0 | .1 | .2 |
|---|---|---|---|
| 1[b] | m-hydroxymethyl-benzyl | p-hydroxymethyl-benzyl | m-hydroxybenzyl |
| 2[b] | m-(N,N-dimethyl-aminoglycyl)aminobenzyl | m-aminocarbonyl-benzyl | p-hydroxybenzyl |
| 3[b] | m-(N-methylamino)carbonylbenzyl | m-(N-methylamino)benzyl | m-formylbenzyl |
| 4[b] | m-trifluorocarbonyl benzyl | m-hydroxyamidino benzyl | m-triazolylbenzyl |
| 5[b] | m-formaldoxime-benzyl | m-acetoximebenzyl | benzyl |
| 6[b] | hydroxycarbonyl-benzyl | m-tetrazolylbenzyl | m-pyrazolylbenzyl |
| 7[b] | m-imidazolylbenzyl | p-fluorobenzyl | pyridinylmethy1 |
| 8[b] | m-acetylbenzyl | m-aminosulfonyl-benzyl | m-methoxybenzyl |

TABLE 4[b]

Formula (Ie), $R^4 = R^{27}$ = fluorobenzyl, $R^{22} = R^7$ = Table

| Ex. No | .0 | .1 | .2 |
|---|---|---|---|
| 9[b] | m-hydroxymethyl-benzyl | p-hydroxymethyl-benzyl | m-hydroxybenzyl |
| 10[b] | m-(N,N-dimethyl-aminoglycyl)aminobenzyl | m-aminocarbonyl-benzyl | p-hydroxybenzyl |
| 11[b] | m-(N-methylamino)carbonylbenzyl | m-(N-methylamino)benzyl | m-formylbenzyl |
| 12[b] | m-trifluorocarbonyl benzyl | m-hydroxyamidino benzyl | m-triazolylbenzyl |
| 13[b] | m-formaldoxime-benzyl | m-acetoximebenzyl | benzyl |
| 14[b] | hydroxycarbonyl-benzyl | m-tetrazolylbenzyl | m-pyrazolylbenzyl |
| 15[b] | m-imidazolylbenzyl | p-fluorobenzyl | pyridinylmethyl |
| 16[b] | m-acetylbenzyl | m-aminosulfonyl-benzyl | m-methoxybenzyl |

TABLE 5[b]

Formula (Ie), $R^4 = R^{27}$ = pyrrolylmethyl, $R^{22} = R^7$ = Table

| Ex. No | .0 | .1 | .2 |
|---|---|---|---|
| 17[b] | m-hydroxymethyl-benzyl | p-hydroxymethyl-benzyl | m-hydroxybenzyl |
| 18[b] | m-(N,N-dimethyl-aminoglycyl)aminobenzyl | m-aminocarbonyl-benzyl | p-hydroxybenzyl |
| 19[b] | m-(N-methylamino)carbonylbenzyl | m-(N-methylamino)benzyl | m-formylbenzyl |
| 20[b] | m-trifluorocarbonyl benzyl | m-hydroxyamidino benzyl | m-triazolylbenzyl |
| 21[b] | m-formaldoxime-benzyl | m-acetoximebenzyl | benzyl |
| 22[b] | hydroxycarbonyl-benzyl | m-tetrazolylbenzyl | m-pyrazolylbenzyl |
| 23[b] | m-imidazolylbenzyl | p-fluorobenzyl | pyridinylmethyl |
| 24[b] | m-acetylbenzyl | m-aminosulfonyl-benzyl | m-methoxybenzyl |

TABLE 6[b]

Formula (Ie), $R^4 = R^{27}$ = methoxybenzyl, $R^{22} = R^7$ = Table

| Ex. No | .0 | .1 | .2 |
|---|---|---|---|
| 25[b] | m-hydroxymethyl-benzyl | p-hydroxymethyl-benzyl | m-hydroxybenzyl |
| 26[b] | m-(N,N-dimethyl-aminoglycyl)aminobenzyl | m-amindcarbonyl-benzyl | p-hydroxybenzyl |
| 27[b] | m-(N-methylamino)carbonylbenzyl | m-(N-methylamino)benzyl | m-formylbenzyl |
| 28[b] | m-trifluorocarbonyl benzyl | m-hydroxyamidino benzyl | m-triazolylbenzyl |
| 29[b] | m-formaldoxime-benzyl | m-acetoximebenzyl | benzy1 |
| 30[b] | hydroxycarbonyl-benzyl | m-tetrazolylbenzyl | m-pyrazolylbenzyl |
| 31[b] | m-imidazolylbenzyl | p-fluorobenzyl | pyridinylmethyl |
| 32[b] | m-acetylbenzyl | m-aminosulfonyl-benzyl | m-methoxybenzyl |

TABLE 7[b]

Formula (Ie), $R^4 = R^{27}$ = isobutyl, $R^{22} = R^7$ = Table

| Ex. No | .0 | .1 | .2 |
|---|---|---|---|
| 33[b] | m-hydroxymethyl-benzyl | p-hydroxymethyl-benzyl | m-hydroxybenzyl |
| 34 [b] | m-(N,N-dimethyl-aminoglycyl) aminobenzyl | m-aminocarbonyl-benzyl | p-hydroxybenzyl |
| 35 [b] | m-(N-methylamino) carbonylbenzyl | m-(N-methylamino) benzyl | m-formylbenzyl |
| 36[b] | m-trifluorocarbonyl benzyl | m-hydroxyamidino benzyl | m-triazolylbenzyl |
| 37[b] | m-formaldoxime-benzyl | m-acetoximebenzyl | benzyl |
| 38[b] | hydroxycarbonyl-benzyl | m-tetrazolylbenzyl | m-pyrazolylbenzyl |
| 39[b] | m-imidazolylbenzyl | p-fluorobenzyl | pyridinylmethyl |
| 40[b] | m-acetylbenzyl | m-aminosulfonyl-benzyl | m-methoxybenzyl |

TABLE 8[b]

Formula (Ie), $R^4 = R^{27}$ = p-nitrobenzyl, $R^{22} = R^7$ = Table

| Ex. No | .0 | .1 | .2 |
|---|---|---|---|
| 41[b] | m-hydroxymethyl-benzyl | p-hydroxymethyl-benzyl | m-hydroxybenzyl |
| 42[b] | m-(N,N-dimethyl-aminoglycyl) aminobenzyl | m-aminocarbonyl-benzyl | p-hydroxybenzyl |
| 43[b] | m-(N-methylamino) carbonylbenzyl | m-(N-methylamino) benzyl | m-formylbenzyl |
| 44[b] | m-trifluorocarbonyl benzyl | m-hydroxyamidino benzyl | m-triazolylbenzyl |
| 45[b] | m-formaldoxime-benzyl | m-acetoximebenzyl | benzyl |
| 46[b] | hydroxycarbonyl-benzyl | m-tetrazolylbenzyl | m-pyrazolylbenzyl |
| 47[b] | m-imidazolylbenzyl | p-fluorobenzyl | pyridinylmethyl |
| 48[b] | m-acetylbenzyl | m-aminosulfonyl-benzyl | m-methoxybenzyl |

TABLE 9[b]

Formula (Ie), $R^4 = R^{27}$ = m-aminobenzyl, $R^{22} = R^7$ = Table

| Ex. No | .0 | .1 | .2 |
|---|---|---|---|
| 49[b] | m-hydroxymethyl-benzyl | p-hydroxymethyl-benzyl | m-hydroxybenzyl |
| 50 [b] | m-(N,N-dimethyl-aminoglycyl) aminobenzyl | m-aminocarbonyl-benzyl | p-hydroxybenzyl |
| 51[b] | m-(N-methylamino) carbonylbenzyl | m-(N-methylamino) benzyl | m-formylbenzyl |
| 52 [b] | m-trifluorocarbonyl benzyl | m-hydroxyamidino benzyl | m-triazolylbenzyl |
| 53[b] | m-formaldoxime-benzyl | m-acetoximebenzyl | benzyl |
| 54[b] | hydroxycarbonyl-benzyl | m-tetrazolylbenzyl | m-pyrazolylberizyl |
| 55[b] | m-imidazolylbenzyl | p-fluorobenzyl | pyridinylmethyl |
| 56[b] | m-acetylbenzyl | m-aminosulfonyl-benzyl | m-methoxybenzyl |

TABLE 10[b]

Formula (Ie), $R^4 = R^{27}$ = pyridinylmethyl, $R^{22} = R^7$ = Table

| Ex. No | .0 | .1 | .2 |
|---|---|---|---|
| 57 [b] | m-hydroxymethyl-benzyl | p-hydroxymethyl-benzyl | m-hydroxybenzyl |
| 58[b] | m-(N,N-dimethyl-aminoglycyl) aminobenzyl | m-aminocarbonyl-benzyl | p-hydroxybenzyl |
| 59[b] | m-(N-methylamino) carbonylbenzyl | m-(N-methylamino) benzyl | m-formylbenzyl |
| 60[b] | m-trifluorocarbonyl benzyl | m-hydroxyamidino benzyl | m-triazolylbenzyl |
| 61[b] | m-formaldoxime-benzyl | m-acetoximebenzyl | benzyl |
| 62[b] | hydroxycarbonyl-benzyl | m-tetrazolylbenzyl | m-pyrazolylbenzyl |
| 63 [b] | m-imidazolylbenzyl | p-fluorobenzyl | pyridinylmethyl |
| 64[b] | m-acetylbenzyl | m-aminosulfonyl-benzyl | m-methoxybenzyl |

TABLE 11[b]

Formula (Ie), $R^4 = R^{27}$ = m-hydrobenzyl, $R^{22} = R^7$ = Table

| Ex. No | .0 | .1 | .2 |
|---|---|---|---|
| 65[b] | m-hydroxymethyl-benzyl | p-hydroxymethyl-benzyl | m-hydroxybenzyl |
| 66 [b] | m-(N,N-dimethyl-aminoglycyl) aminobenzyl | m-aminocarbonyl-benzyl | p-hydroxybenzyl |
| 67[b] | m-(N-methylamino) carbonylbenzyl | m-(N-methylamino) benzyl | m-formylbenzyl |
| 68[b] | m-trifluorocarbonyl benzyl | m-hydroxyamidino benzyl | m-triazolylbenzyl |
| 69[b] | m-formaldoxime-benzyl | m-acetoximebenzyl | benzyl |
| 70[b] | hydroxycarbonyl-benzyl | m-tetrazolylbenzyl | m-pyrazolylbenzyl |
| 71[b] | m-imidazolylbenzyl | p-fluorobenzyl | pyridinylmethyl |
| 72[b] | m-acetylbenzyl | m-aminosulfonyl-benzyl | m-methoxybenzyl |

TABLE 12[b]

Formula (Ie), $R^4 = R^{27}$ = p-hydroxybenzyl, $R^{22} = R^7$ = Table

| Ex. No | .0 | .1 | .2 |
|---|---|---|---|
| 73[b] | m-hydroxymethyl-benzyl | p-hydroxymethyl-benzyl | m-hydroxybenzyl |
| 74[b] | m-(N,N-dimethyl-aminoglycyl) aminobenzyl | m-aminocarbonyl-benzyl | p-hydroxybenzyl |
| 75[b] | m-(N-methylamino) carbonylbenzyl | m-(N-methylamino) benzyl | m-formylbenzyl |
| 76[b] | m-trifluorocarbonyl benzyl | m-hydroxyamidino benzyl | m-triazolylbenzyl |
| 77[b] | m-formaldoxime-benzyl | m-acetoximebenzyl | benzyl |
| 78[b] | hydroxycarbonyl-benzyl | m-tetrazolylbenzyl | m-pyrazolylbenzyl |
| 79[b] | m-imidazolylbenzyl | p-fluorobenzyl | pyridinylmethyl |
| 80[b] | m-acetylbenzyl | m-aminosulfonyl-benzyl | m-methoxybenzyl |

TABLE 13[b]

Formula (Ie), $R^4 = R^{27}$ = m-aminocarbonylbenzyl, $R^{22} = R^7$ = Table

| Ex. No | .0 | .1 | .2 |
|---|---|---|---|
| 81[b] | m-hydroxymethyl-benzyl | p-hydroxymethyl-benzyl | m-hydroxybenzyl |
| 82[b] | m-(N,N-dimethyl-aminoglycyl)aminobenzyl | m-aminocarbonyl-benzyl | p-hydroxybenzyl |
| 83[b] | m-(N-methylamino)carbonylbenzyl | m-(N-methylamino)benzyl | m-formylbenzyl |
| 84[b] | m-trifluorcarbonylbenzyl | m-hydroxyamidinobenzyl | m-triazolylbenzyl |
| 85[b] | m-formaldoxime-benzyl | m-acetoximebenzyl | benzyl |
| 86[b] | hydroxycarbonyl-benzyl | m-tetrazolylbenzyl | m-pyrazolylbenzyl |
| 87[b] | m-imidazolylbenzyl | p-fluorobenzyl | pyridinylmethyl |
| 88 [b] | m-acetylbenzyl | m-aminosulfonyl-benzyl | m-methoxybenzyl |

TABLE 14[b]

Formula (Ie), $R^4 = R^{27}$ = p-hydroxymethylbenzyl, $R^{22} = R^7$ = Table

| Ex. No | .0 | .1 | .2 |
|---|---|---|---|
| 89[b] | m-hydroxymethyl-benzyl | p-hydroxymethyl-benzyl | m-hydroxybenzyl |
| 90[b] | m-(N,N-dimethyl-aminoglycyl)aminobenzyl | m-aminocarbonyl-benzyl | p-hydroxybenzyl |
| 91[b] | m-(N-methylamino)carbonylbenzyl | m-(N-methylamino)benzyl | m-formylbenzyl |
| 92[b] | m-trifluorcarbonylbenzyl | m-hydroxyamidinobenzyl | m-triazolylbenzyl |
| 93[b] | m-formaldoxime-benzyl | m-acetoximebenzyl | benzyl |
| 94 [b] | hydroxycarbonyl-benzyl | m-tetrazolylbenzyl | m-pyrazolylbenzyl |
| 95[b] | m-imidazolylbenzyl | p-fluorobenzyl | pyridinylmethyl |
| 96[b] | m-acetylbenzyl | m-aminosulfonyl-benzyl | m-methoxybenzyl |

TABLE 15[b]

Formula (Ie), $R^4 = R^{27}$ = m-hydroxycarbonylbenzyl, $R^{22} = R^7$ = Table

| Ex. No | .0 | .1 | .2 |
|---|---|---|---|
| 97[b] | m-hydroxymethyl-benzyl | p-hydroxymethyl-benzyl | m-hydroxybenzyl |
| 98 [b] | m-(N,N-dimethyl-aminoglycyl)aminobenzyl | m-aminocarbonyl-benzyl | p-hydroxybenzyl |
| 99[b] | m-(N-methylamino)carbonylbenzyl | m-(N-methylamino)benzyl | m-formylbenzyl |
| 100[b] | m-trifluorcarbonylbenzyl | m-hydroxyamidinobenzyl | m-triazolylbenzyl |
| 101[b] | m-formaldoxime-benzyl | m-acetoximebenzyl | benzyl |
| 102[b] | hydroxycarbonyl-benzyl | m-tetrazolylbenzyl | m-pyrazolylbenzyl |
| 103[b] | m-imidazolylbenzyl | p-fluorobenzyl | pyridinylmethyl |
| 104[b] | m-acetylbenzyl | m-aminosulfonyl-benzyl | m-methoxybenzyl |

TABLE 16[b]

Formula (Ie), $R^4 = R^{27}$ = benzyl, $R^{22}$ = m-hydroxymethylbenzyl, $R^7$ = Table

| Ex. No | .0 | .1 | .2 |
|---|---|---|---|
| 105[b] | m-hydroxymethyl-benzyl | p-hydroxymethyl-benzyl | m-hydroxybenzyl |
| 106[b] | m-(N,N-dimethyl-aminoglycyl)aminobenzyl | m-aminocarbonyl-benzyl | p-hydroxybenzyl |
| 107[b] | m-(N-methylamino)carbonylbenzyl | m-(N-methylamino)benzyl | m-formylbenzyl |
| 108[b] | m-trifluorcarbonylbenzyl | m-hydroxyamidinobenzyl | m-triazolylbenzyl |
| 109[b] | m-formaldoxime-benzyl | m-acetoximebenzyl | benzyl |
| 110[b] | hydroxycarbonyl-benzyl | m-tetrazolylbenzyl | m-pyrazolylbenzyl |
| 111[b] | m-imidazolylbenzyl | p-fluorobenzyl | pyridinylmethyl |
| 112[b] | m-acetylbenzyl | m-aminosulfonyl-benzyl | m-methoxybenzyl |

TABLE 17[b]

Formula (Ie), $R^4 = R^{27}$ = benzyl, $R^{22}$ = p-hydroxymethylbenzyl, $R^7$ = Table

| Ex. No | .0 | .1 | .2 |
|---|---|---|---|
| 113[b] | m-hydroxymethyl-benzyl | p-hydroxymethyl-benzyl | m-hydroxybenzyl |
| 114[b] | m-(N,N-dimethyl-aminoglycyl)aminobenzyl | m-aminocarbonyl-benzyl | p-hydroxybenzyl |
| 115[b] | m-(N-methylamino)carbonylbenzyl | m-(N-methylamino)benzyl | m-formylbenzyl |
| 116[b] | m-trifluorcarbonylbenzyl | m-hydroxyamidinobenzyl | m-triazolylbenzyl |
| 117[b] | m-formaldoxime-benzyl | m-acetoximebenzyl | benzyl |
| 118[b] | hydroxycarbonyl-benzyl | m-tetrazolylbenzyl | m-pyrazolylbenzyl |
| 119[b] | m-imidazolylbenzyl | p-fluorobenzyl | pyridinylmethyl |
| 120[b] | m-acetylbenzyl | m-aminosulfonyl-benzyl | m-methoxybenzyl |

TABLE 18[b]

Formula (Ie), $R^4 = R^{27}$ = benzyl, $R^{22}$ = m-hydroxybenzyl, $R^7$ = Table

| Ex. No | .0 | .1 | .2 |
|---|---|---|---|
| 121[b] | m-hydroxymethyl-benzyl | p-hydroxymethyl-benzyl | m-hydroxybenzyl |
| 122 [b] | m-(N,N-dimethyl-aminoglycyl)aminobenzyl | m-aminocarbonyl-benzyl | p-hydroxybenzyl |
| 123 [b] | m-(N-methylamino)carbonylbenzyl | m-(N-methylamino)benzyl | m-formylbenzyl |
| 124 [b] | m-trifluorcarbonylbenzyl | m-hydroxyamidinobenzyl | m-triazolylbenzyl |
| 125 [b] | m-formaldoxime-benzyl | m-acetoximebenzyl | benzyl |
| i26[b] | hydroxycarbonyl-benzyl | m-tetrazolylbenzyl | m-pyrazolylbenzyl |
| 127[b] | m-imidazolylbenzyl | p-fluorobenzyl | pyridinylmethyl |
| 128[b] | m-acetylbenzyl | m-aminosulfonyl-benzyl | m-methoxybenzyl |

TABLE 19[b]

Formula (Ie), $R^4 = R^{27}$ = benzyl, $R^{22}$ = m-(N,N-dimethylamino glycyl)aminobenzyl, $R^7$ = Table

| Ex. No | .0 | .1 | .2 |
|---|---|---|---|
| 129[b] | m-hydroxymethyl-benzyl | p-hydroxymethyl-benzyl | m-hydroxybenzyl |
| 130[b] | m-(N,N-dimethyl-aminoglycyl) aminobenzyl | m-aminocarbonyl-benzyl | p-hydroxybenzyl |
| 131[b] | m-(N-methylamino) carbonylbenzyl | m-(N-methylamino) benzyl | m-formylbenzyl |
| 132[b] | m-trifluorcarbonyl benzyl | m-hydroxyamidino benzyl | m-triazolylbenzyl |
| 133[b] | m-formaldoxime-benzyl | m-acetoximebenzyl | benzyl |
| 134[b] | hydroxycarbonyl-benzyl | m-tetrazolylbenzyl | m-pyrazolylbenzyl |
| 135[b] | m-imidazolylbenzyl | p-fluorobenzyl | pyridinylmethyl |
| 136[b] | m-acetylbenzyl | m-aminosulfonyl-benzyl | m-methoxybenzyl |

TABLE 20[b]

Formula (Ie), $R^4 = R^{27}$ = benzyl, $R^{22}$ = m-aminocarbonylbenzyl, $R^7$ = Table

| Ex. No | .0 | .1 | .2 |
|---|---|---|---|
| 137[b] | m-hydroxymethyl-benzyl | p-hydroxymethyl-benzyl | m-hydroxybenzyl |
| 138[b] | m-(N,N-dimethyl-aminoglycyl) aminobenzyl | m-aminocarbonyl-benzyl | p-hydroxybenzyl |
| 139[b] | m-(N-methylamino) carbonylbenzyl | m-(N-methylamino) benzyl | m-formylbenzyl |
| 140[b] | m-trifluorcarbonyl benzyl | m-hydroxyamidino benzyl | m-triazolylbenzyl |
| 141[b] | m-formaldoxime-benzyl | m-acetoximebenzyl | benzyl |
| 142[b] | hydroxycarbonyl-benzyl | m-tetrazolylbenzyl | m-pyrazolylbenzyl |
| 143[b] | m-imidazolylbenzyl | p-fluorobenzyl | pyridinylmethyl |
| 144[b] | m-acetylbenzyl | m-aminosulfonyl-benzyl | m-methoxybenzyl |

TABLE 21[b]

Formula (Ie), $R^4 = R^{27}$ = benzyl, $R^{22}$ = p-hydroxybenzyl, $R^7$ = Table

| Ex. No | .0 | .1 | .2 |
|---|---|---|---|
| 145[b] | m-hydroxymethyl-benzyl | p-hydroxymethyl-benzyl | m-hydroxybenzyl |
| 146[b] | m-(N,N-dimethyl-aminoglycyl) aminobenzyl | m-aminocarbonyl-benzyl | p-hydroxybenzyl |
| 147[b] | m-(N-methylamino) carbonylbenzyl | m-(N-methylamino) benzyl | m-formylbenzyl |
| 148 [b] | m-trifluorcarbonyl benzyl | m-hydroxyamidino benzyl | m-triazolylbenzyl |
| 149 [b] | m-formaldoxime-benzyl | m-acetoximebenzyl | benzyL |
| 150 [b] | hydroxycarbonyl-benzyl | m-tetrazolylbenzyl | m-pyrazolylbenzyl |
| 151 [b] | m-imidazolylbenzyl | p-fluorobenzyl | pyridinylmethyl |
| 152[b] | m-acetylbenzyl | m-aminosulfonyl-benzyl | m-methoxybenzyl |

TABLE 22[b]

Formula (Ie), $R^4 = R^{27}$ = benzyl, $R^{22}$ = m-(N-methylaminocarbonyl benzyl, $R^7$ = Table

| Ex. No | .0 | .1 | .2 |
|---|---|---|---|
| 153[b] | m-hydroxymethyl-benzyl | p-hydroxymethyl-benzyl | m-hydroxybenzyl |
| 154 [b] | m-(N,N-dimethyl-aminoglycyl) aminobenzyl | m-aminocarbonyl-benzyl | p-hydroxybenzyl |
| 155[b] | m-(N-methylamino) carbonylbenzyl | m-(N-methylamino) benzyl | m-formylbenzyl |
| 156[b] | m-trifluorcarbonyl benzyl | m-hydroxyamidino benzyl | m-triazolylbenzyl |
| 157[b] | m-formaldoxime-benzyl | m-acetoximebenzyl | benzyl |
| 158[b] | hydroxycarbonyl-benzyl | m-tetrazolylbenzyl | m-pyrazolylbenzyl |
| 159[b] | m-imidazolylbenzyl | p-fluorobenzyl | pyridinylmethyl |
| 160[b] | m-acetylbenzyl | m-aminosulfonyl-benzyl | m-methoxybenzyl |

TABLE 23[b]

Formula (Ie), $R^4 = R^{27}$ = benzyl, $R^{22}$ = m-(N-methylamino)benzyl, $R^7$ = Table

| Ex. No | .0 | .1 | .2 |
|---|---|---|---|
| 161[b] | m-hydroxymethyl-benzyl | p-hydroxymethyl-benzyl | m-hydroxybenzyl |
| 162[b] | m-(N,N-dimethyl-aminoglycyl) aminobenzyl | m-aminocarbonyl-benzyl | p-hydroxybenzyl |
| 163[b] | m-(N-methylamino) carbonylbenzyl | m-(N-methylamino) benzyl | m-formylbenzyl |
| 164[b] | m-trifluorcarbonyl benzyl | m-hydroxyamidino benzyl | m-triazolylbenzyl |
| 165 [b] | m-formaldoxime-benzyl | m-acetoximebenzyl | benzyl |
| 166[b] | hydroxycarbonyl-benzyl | m-tetrazolylbenzyl | m-pyrazolylbenzyl |
| 167[b] | m-imidazolylbenzyl | p-fluorobenzyl | pyridinylmethyl |
| 166[b] | m-acetylbenzyl | m-aminosulfonyl-benzyl | m-methoxybenzyl |

TABLE 24[b]

Formula (Ie), $R^4 = R^{27}$ = benzyl, $R^{22}$ = m-formyllbenzyl, $R^7$ = Table

| Ex. No | .0 | .1 | .2 |
|---|---|---|---|
| 169[b] | m-hydroxymethyl-benzyl | p-hydroxymethyl-benzyl | m-hydroxybenzyl |
| 170[b] | m-(N,N-dimethyl-aminoglycyl) aminobenzyl | m-aminocarbonyl-benzyl | p-hydroxybenzyl |
| 171[b] | m-(N-methylamino) carbonylbenzyl | m-(N-methylamino) benzyl | m-formylbenzyl |
| 172[b] | m-trifluorcarbonyl benzyl | m-hydroxyamidino benzyl | m-triazolylbenzyl |
| 173[b] | m-formaldoxime-benzyl | m-acetoximebenzyl | benzyl |
| 174[b] | hydroxycarbonyl-benzyl | m-tetrazolylbenzyl | m-pyrazolylbenzyl |
| 175[b] | m-imidazolylbenzyl | p-fluorobenzyl | pyridinylmethyl |
| 176[b] | m-acetylbenzyl | m-aminosulfonyl-benzyl | m-methoxybenzyl |

TABLE 25[b]

Formula (Ie), $R^4 = R^{27}$ = benzyl, $R^{22}$ = m-trifluorocarbonylbenzyl, $R^7$ = Table

| Ex. No | .0 | .1 | .2 |
|---|---|---|---|
| 177[b] | m-hydroxymethyl-benzyl | p-hydroxymethyl-benzyl | m-hydroxybenzyl |
| 178[b] | m-(N,N-dimethyl-aminoglycyl)aminobenzyl | m-aminocarbonyl-benzyl | p-hydroxybenzyl |
| 179[b] | m-(N-methylamino)carbonylbenzyl | m-(N-methylamino)benzyl | m-formylbenzyl |
| 180[b] | m-trifluorcarbonyl benzyl | m-hydroxyamidino benzyl | m-triazolylbenzyl |
| 181[b] | m-formaldoxime-benzyl | m-acetoximebenzyl | benzyl |
| 182[b] | hydroxycarbonyl-benzyl | m-tetrazolylbenzyl | m-pyrazolylbenzyl |
| 183[b] | m-imidazolylbenzyl | p-fluorobenzyl | pyridinylmethyl |
| 184[b] | m-acetylbenzyl | m-aminosulfonyl-benzyl | m-methoxybenzyl |

TABLE 26[b]

Formula (Ie), $R^4 = R^{27}$ = benzyl, $R^{22}$ = m-hydroxyamidinobenzyl, $R^7$ = Table

| Ex. No | .0 | .1 | .2 |
|---|---|---|---|
| 185[b] | m-hydroxylmethyl-benzyl | p-hydroxymethyl-benzyl | m-hydroxybenzyl |
| 186[b] | m-(N,N-dimethyl-aminoglycyl)aminobenzyl | m-aminocarbonyl-benzyl | p-hydroxybenzyl |
| 187[b] | m-(N-methylamino)carbonylbenzyl | m-(N-methylamino)benzyl | m-formylbenzyl |
| 188[b] | m-trifluorcarbonyl benzyl | m-hydroxyamidino benzyl | m-triazolylbenzyl |
| 189[b] | m-formaldoxime-benzyl | m-acetoximebenzyl | benzyl |
| 190[b] | hydroxycarbonyl-benzyl | m-tetrazolylbenzyl | m-pyrazolylbenzyl |
| 191[b] | m-imidazolylbenzyl | p-fluorobenzyl | pyridinylmethyl |
| 192[b] | m-acetylbenzyl | m-aminosulfonyl-benzyl | m-methoxybenzyl |

TABLE 27[b]

Formula (Ie), $R^4 = R^{27}$ = benzyl, $R^{22}$ = m-triazolylbenzyl, $R^7$ = Table

| Ex. No | .0 | .1 | .2 |
|---|---|---|---|
| 193[b] | m-hydroxymethyl-benzyl | p-hydroxymethyl-benzyl | m-hydroxybenzyl |
| 194[b] | m-(N,N-dimethyl-aminoglycyl)aminobenzyl | m-aminocarbonyl-benzyl | p-hydroxybenzyl |
| 195[b] | m-(N-methylamino)carbonylbenzyl | m-(N-methylamino)benzyl | m-formylbenzyl |
| 196[b] | m-trifluorcarbonyl benzyl | m-hydroxyamidino benzyl | m-triazolylbenzyl |
| 197[b] | m-formaldoxime-benzyl | m-acetoximebenzyl | benzyl |
| 198[b] | hydroxycarbonyl-benzyl | m-tetrazolylbenzyl | m-pyrazolylbenzyl |
| 199[b] | m-imidazolylbenzyl | p-fluorobenzyl | pyridinylmethyl |
| 200[b] | m-acetylbenzyl | m-aminosulfonyl-benzyl | m-methoxybenzyl |

TABLE 28[b]

Formula (Ie), $R^4 = R^{27}$ = benzyl, $R^{22}$ = m-formaldoximebenzyl, $R^7$ = Table

| Ex. No | .0 | .1 | .2 |
|---|---|---|---|
| 201[b] | m-hydroxymethyl-benzyl | p-hydroxymethyl-benzyl | m-hydroxybenzyl |
| 202[b] | m-(N,N-dimethyl-aminoglycyl)aminobenzyl | m-aminocarbonyl-benzyl | p-hydroxybenzyl |
| 203[b] | m-(N-methylamino)carbonylbenzyl | m-(N-methylamino)benzyl | m-formylbenzyl |
| 204[b] | m-trifluorcarbonyl benzyl | m-hydroxyamidino benzyl | m-triazolylbenzyl |
| 205[b] | m-formaldoxime-benzyl | m-acetoximebenzyl | benzyl |
| 206[b] | hydroxycarbonyl-benzyl | m-tetrazolylbenzyl | m-pyrazolylbenzyl |
| 207[b] | m-imidazolylbenzyl | p-fluorobenzyl | pyridinylmethyl |
| 208[b] | m-acetylbenzyl | m-aminosulfonyl-benzyl | m-methoxybenzyl |

TABLE 29[b]

Formula (Ie), $R^4 = R^{27}$ = benzyl, $R^{22}$ = m-acetoximebenzyl, $R^7$ = Table

| Ex. No | .0 | .1 | .2 |
|---|---|---|---|
| 209[b] | m-hydroxymethyl-benzyl | p-hydroxymethyl-benzyl | m-hydroxybenzyl |
| 210[b] | m-(N,N-dimethyl-aminoglycyl)aminobenzyl | m-aminocarbonyl-benzyl | p-hydroxybenzyl |
| 211[b] | m-(N-methylamino)carbonylbenzyl | m-(N-methylamino)benzyl | m-formylbenzyl |
| 212[b] | m-trifluorcarbonyl benzyl | m-hydroxyamidino benzyl | m-triazolylbenzyl |
| 213[b] | m-formaldoxime-benzyl | m-acetoximebenzyl | benzyl |
| 214[b] | hydroxycarbonyl-benzyl | m-tetrazolylbenzyl | m-pyrazolylbenzyl |
| 215[b] | m-imidazolylbenzyl | p-fluorobenzyl | pyridinylmethyl |
| 216[b] | m-acetylbenzyl | m-aminosulfonyl-benzyl | m-methoxybenzyl |

TABLE 30[b]

Formula (Ie), $R^4 = R^{27}$ = benzyl, $R^{22}$ = benzyl, $R^7$ = Table

| Ex. No | .0 | .1 | .2 |
|---|---|---|---|
| 217[b] | m-hydroxymethyl-benzyl | p-hydroxymethyl-benzyl | m-hydroxybenzyl |
| 218[b] | m-(N,N-dimethyl-aminoglycyl)aminobenzyl | m-aminocarbonyl-benzyl | p-hydroxybenzyl |
| 219[b] | m-(N-methylamino)carbonylbenzyl | m-(N-methylamino)benzyl | m-formylbenzyl |
| 220[b] | m-trifluorcarbonyl benzyl | m-hydroxyamidino benzyl | m-triazolylbenzyl |
| 221[b] | m-formaldoxime-benzyl | m-acetoximebenzyl | benzyl |
| 222[b] | hydroxycarbonyl-benzyl | m-tetrazolylbenzyl | m-pyrazolylbenzyl |
| 223[b] | m-imidazolylbenzyl | p-fluorobenzyl | pyridinylmethyl |
| 224[b] | m-acetylbenzyl | m-aminosulfonyl-benzyl | m-methoxybenzyl |

TABLE 31[b]

Formula (Ie), $R^4 = R^{27}$ = benzyl, $R^{22}$ = m-hydroxycarbonylbenzyl, $R^7$ = Table

| Ex. No | .0 | .1 | .2 |
|---|---|---|---|
| 225[b] | m-hydroxymethyl-benzyl | p-hydroxymethyl-benzyl | m-hydroxybenzyl |
| 226[b] | m-(N,N-dimethyl-aminoglycyl)aminobenzyl | m-aminocarbonyl-benzyl | p-hydroxybenzyl |
| 227[b] | m-(N-methylamino)carbonylbenzyl | m-(N-methylamino)benzyl | m-formylbenzyl |
| 228[b] | m-trifluorcarbonyl benzyl | m-hydroxyamidino benzyl | m-triazolylbenzyl |
| 229[b] | m-formaldoxime-benzyl | m-acetoximebenzyl | benzyl |
| 230[b] | hydroxycarbonyl-benzyl | m-tetrazolylbenzyl | m-pyrazolylbenzyl |
| 231[b] | m-imidazolylbenzyl | p-fluorobenzyl | pyridinylmethyl |
| 232[b] | m-acetylbenzyl | m-aminosulfonyl-benzyl | m-methoxybenzyl |

TABLE 32[b]

Formula (Ie), $R^4 = R^{27}$ = benzyl, $R^{22}$ = m-tetrazolylbenzyl, $R^7$ = Table

| Ex. No | .0 | .1 | .2 |
|---|---|---|---|
| 233[b] | m-hydroxymethyl-benzyl | p-hydroxymethyl-benzyl | m-hydroxybenzyl |
| 234[b] | m-(N,N-dimethyl-aminoglycyl)aminobenzyl | m-aminocarbonyl-benzyl | p-hydroxybenzyl |
| 235[b] | m-(N-methylamino)carbonylbenzyl | m-(N-methylamino)benzyl | m-formylbenzyl |
| 236[b] | m-trifluorcarbonyl benzyl | m-hydroxyamidino benzyl | m-triazolylbenzyl |
| 237[b] | m-formaldoxime-benzyl | m-acetoximebenzyl | benzyl |
| 238[b] | hydroxycarbonyl-benzyl | m-tetrazolylbenzyl | m-pyrazolylbenzyl |
| 239[b] | m-imidazolylbenzyl | p-fluorobenzyl | pyridinylmethyl |
| 240[b] | m-acetylbenzyl | m-aminosulfonyl-benzyl | m-methoxybenzyl |

TABLE 33[b]

Formula (Ie), $R^4 = R^{27}$ = benzyl, $R^{22}$ = m-pyrazolylbenzyl, $R^7$ = Table

| Ex. No | .0 | .1 | .2 |
|---|---|---|---|
| 241[b] | m-hydroxymethyl-benzyl | p-hydroxymethyl-benzyl | m-hydroxybenzyl |
| 242[b] | m-(N,N-dimethyl-aminoglycyl)aminobenzyl | m-aminocarbonyl-benzyl | p-hydroxybenzyl |
| 243[b] | m-(N-methylamino)carbonylbenzyl | m-(N-methylamino)benzyl | m-formylbenzyl |
| 244[b] | m-trifluorcarbonyl benzyl | m-hydroxyamidino benzyl | m-triazolylbenzyl |
| 245[b] | m-formaldoxime-benzyl | m-acetoximebenzyl | benzyl |
| 246[b] | hydroxycarbonyl-benzyl | m-tetrazolylbenzyl | m-pyrazolylbenzyl |
| 247[b] | m-imidazolylbenzyl | p-fluorobenzyl | pyridinylmethyl |
| 248[b] | m-acetylbenzyl | m-aminosulfonyl-benzyl | m-methoxybenzyl |

TABLE 34[b]

Formula (Ie), $R^4 = R^{27}$ = benzyl, $R^{22}$ = m-imidazolylbenzyl, $R^7$ = Table

| Ex. No | .0 | .1 | .2 |
|---|---|---|---|
| 249[b] | m-hydroxymethyl-benzyl | p-hydroxymethyl-benzyl | m-hydroxybenzyl |
| 250[b] | m-(N,N-dimethyl-aminoglycyl)aminobenzyl | m-aminocarbonyl-benzyl | p-hydroxybenzyl |
| 251[b] | m-(N-methylamino)carbonylbenzyl | m-(N-methylamino)benzyl | m-formylbenzyl |
| 252[b] | m-trifluorcarbonyl benzyl | m-hydroxyamidino benzyl | m-triazolylbenzyl |
| 253[b] | m-formaldoxime-benzyl | m-acetoximebenzyl | benzyl |
| 254[b] | hydroxycarbonyl-benzyl | m-tetrazolylbenzyl | m-pyrazolylbenzyl |
| 255[b] | m-imidazolylbenzyl | p-fluorobenzyl | pyridinylmethyl |
| 256[b] | m-acetylbenzyl | m-aminosulfonyl-benzyl | m-methoxybenzyl |

TABLE 35[b]

Formula (Ie), $R^4 = R^{27}$ = benzyl, $R^{22}$ = p-fluorobenzyl, $R^7$ = Table

| Ex. No | .0 | .1 | .2 |
|---|---|---|---|
| 257[b] | m-hydroxymethyl-benzyl | p-hydroxymethyl-benzyl | m-hydroxybenzyl |
| 258[b] | m-(N,N-dimethyl-aminoglycyl)aminobenzyl | m-aminocarbonyl-benzyl | p-hydroxybenzyl |
| 259[b] | m-(N-methylamino)carbonylbenzyl | m-(N-methylamino)benzyl | m-formylbenzyl |
| 260[b] | m-trifluorcarbonyl benzyl | m-hydroxyamidino benzyl | m-triazolylbenzyl |
| 261[b] | m-formaldoxime-benzyl | m-acetoximebenzyl | benzyl |
| 262[b] | hydroxycarbonyl-benzyl | m-tetrazolylbenzyl | m-pyrazolylbenzyl |
| 263[b] | m-imidazolylbenzyl | p-fluorobenzyl | pyridinylmethyl |
| 264[b] | m-acetylbenzyl | m-aminosulfonyl-benzyl | m-methoxybenzyl |

TABLE 36[b]

Formula (Ie), $R^4 = R^{27}$ = benzyl, $R^{22}$ = pyridinylmethyl, $R^7$ = Table

| Ex. No | .0 | .1 | .2 |
|---|---|---|---|
| 265[b] | m-hydroxymethyl-benzyl | p-hydroxymethyl-benzyl | m-hydroxybenzyl |
| 266[b] | m-(N,N-dimethyl-aminoglycyl)aminobenzyl | m-aminocarbonyl-benzyl | p-hydroxybenzyl |
| 267[b] | m-(N-methylamino)carbonylbenzyl | m-(N-methylamino)benzyl | m-formylbenzyl |
| 268[b] | m-trifluorcarbonyl benzyl | m-hydroxyamidino benzyl | m-triazolylbenzyl |
| 269[b] | m-formaldoxime-benzyl | m-acetoximebenzyl | benzyl |
| 270[b] | hydroxycarbonyl-benzyl | m-tetrazolylbenzyl | m-pyrazolylbenzyl |
| 271[b] | m-imidazolylbenzyl | p-fluorobenzyl | pyridinylmethyl |
| 272[b] | m-acetylbenzyl | m-aminosulfonyl-benzyl | m-methoxybenzyl |

TABLE 37[b]

Formula (Ie), $R^4 = R^{27}$ = benzyl, $R^{22}$ = m-acetylbenzyl, $R^7$ = Table

| Ex. No | .0 | .1 | .2 |
|---|---|---|---|
| 273[b] | m-hydroxymethyl-benzyl | p-hydroxymethyl-benzyl | m-hydroxybenzyl |
| 274[b] | m-(N,N-dimethyl-aminoglycyl)aminobenzyl | m-aminocarbonyl-benzyl | p-hydroxybenzyl |
| 275[b] | m-(N-methylamino)carbonylbenzyl | m-(N-methylamino)benzyl | m-formylbenzyl |
| 276[b] | m-trifluorcarbonyl benzyl | m-hydroxyamidino benzyl | m-triazolylbenzyl |
| 277[b] | m-formaldoxime-benzyl | m-acetoximebenzyl | benzyl |
| 278[b] | hydroxycarbonyl-benzyl | m-tetrazolylbenzyl | m-pyrazolylbenzyl |
| 279[b] | m-imidazolylbenzyl | p-fluorobenzyl | pyridinylmethyl |
| 280[b] | m-acetylbenzyl | m-aminosulfonyl-benzyl | m-methoxybenzyl |

TABLE 38[b]

Formula (Ie), $R^4 = R^{27}$ = benzyl, $R^{22}$ = m-aminosulfonylbenzyl, $R^7$ = Table

| Ex. No | .0 | .1 | .2 |
|---|---|---|---|
| 281[b] | m-hydroxymethyl-benzyl | p-hydroxymethyl-benzyl | m-hydroxybenzyl |
| 282[b] | m-(N,N-dimethyl-aminoglycyl)aminobenzyl | m-aminocarbonyl-benzyl | p-hydroxybenzyl |
| 283[b] | m-(N-methylamino)carbonylbenzyl | m-(N-methylamino)benzyl | m-formylbenzyl |
| 284[b] | m-trifluorcarbonyl benzyl | m-hydroxyamidino benzyl | m-triazolylbenzyl |
| 285[b] | m-formaldoxime-benzyl | m-acetoximebenzyl | benzyl |
| 286[b] | hydroxycarbonyl-benzyl | m-tetrazolylbenzyl | m-pyrazolylbenzyl |
| 287[b] | m-imidazolylbenzyl | p-fluorobenzyl | pyridinylmethyl |
| 288[b] | m-acetylbenzyl | m-aminosulfonyl-benzyl | m-methoxybenzyl |

TABLE 39[b]

Formula (Ie), $R^4 = R^{27}$ = benzyl, $R^{22}$ = m-methoxybenzyl, $R^7$ = Table

| Ex. No | .0 | .1 | .2 |
|---|---|---|---|
| 289[b] | m-hydroxymethyl-benzyl | p-hydroxymethyl-benzyl | m-hydroxybenzyl |
| 290[b] | m-(N,N-dimethyl-aminoglycyl)aminobenzyl | m-aminocarbonyl-benzyl | p-hydroxybenzyl |
| 291[b] | m-(N-methylamino)carbonylbenzyl | m-(N-methylamino)benzyl | m-formylbenzyl |
| 292[b] | m-trifluorcarbonyl benzyl | m-hydroxyamidino benzyl | m-triazolylbenzyl |
| 293[b] | m-formaldoxime-benzyl | m-acetoximebenzyl | benzyl |
| 294[b] | hydroxycarbonyl-benzyl | m-tetrazolylbenzyl | m-pyrazolylbenzyl |
| 295[b] | m-imidazolylbenzyl | p-fluorobenzyl | pyridinylmethyl |
| 296[b] | m-acetylbenzyl | m-aminosulfonyl-benzyl | m-methoxybenzyl |

TABLE 3[c]

Formula (If), $R^4 = R^{27}$ = benzyl, $R^{22} = R^7$ = Table

| Ex. No | .0 | .1 | .2 |
|---|---|---|---|
| 1[c] | m-hydroxymethyl-benzyl | p-hydroxymethyl-benzyl | m-hydroxybenzyl |
| 2[c] | m-(N,N-dimethyl-aminoglycyl)aminobenzyl | m-aminocarbonyl-benzyl | p-hydroxybenzyl |
| 3[c] | m-(N-methylamino)carbonylbenzyl | m-(N-methylamino)benzyl | m-formylbenzyl |
| 4[c] | m-trifluorocarbonyl benzyl | m-hydroxyamidino benzyl | m-triazolylbenzyl |
| 5[c] | m-formaldoxime-benzyl | m-acetoximebenzyl | benzyl |
| 6[c] | hydroxycarbonyl-benzyl | m-tetrazolylbenzyl | m-pyrazolylbenzyl |
| 7[c] | m-imidazolylbenzyl | p-fluorobenzyl | pyridinylmethyl |
| 8[c] | m-acetylbenzyl | m-aminosulfonyl-benzyl | m-methoxybenzyl |

TABLE 4[c]

Formula (If), $R^4 = R^{27}$ = fluorobenzyl, $R^{22} = R^7$ = Table

| Ex. No | .0 | .1 | .2 |
|---|---|---|---|
| 9[c] | m-hydroxymethyl-benzyl | p-hydrroxymethyl-benzyl | m-hydroxybenzyl |
| 10[c] | m-(N,N-dimethyl-aminoglycyl)aminobenzyl | m-aminocarbonyl-benzyl | p-hydroxybenzyl |
| 11[c] | m-(N-methylamino)carbonylbenzyl | m-(N-methylamino)benzyl | m-formylbenzyl |
| 12[c] | m-trifluorocarbonyl benzyl | m-hydroxyamidino benzyl | m-triazolylbenzyl |
| 13[c] | m-formaldoxime-benzyl | m-acetoximebenzyl | benzyl |
| 14[c] | hydroxycarbonyl-benzyl | m-tetrazolylbenzyl | m-pyrazolylbenzyl |
| 15[c] | m-imidazolylbenzyl | p-fluorobenzyl | pyridinylmethyl |
| 16[c] | m-acetylbenzyl | m-aminosulfonyl-benzyl | m-methoxybenzyl |

TABLE 5[c]

Formula (If), $R^4 = R^{27}$ = pyrrolylmethyl, $R^{22} = R^7$ = Table

| Ex. No | .0 | .1 | .2 |
|---|---|---|---|
| 17[c] | m-hydroxymethyl-benzyl | p-hydroxymethyl-benzyl | m-hydroxbenzyl |
| 18[c] | m-(N,N-dimethyl-aminoglycyl)aminobenzyl | m-aminocarbonyl-benzyl | p-hydroxybenzyl |
| 19[c] | m-(N-methylamino)carbonylbenzyl | m-(N-methylamino)benzyl | m-formylbenzyl |
| 20[c] | m-trifluorocarbonyl benzyl | m-hydroxyamidino benzyl | m-triazolylbenzyl |
| 21[c] | m-formaldoxime-benzyl | m-acetoximebenzyl | benzyl |
| 22[c] | hydroxycarbonyl-benzyl | m-tetrazolylbenzyl | m-pyrazolylbenzyl |
| 23[c] | m-imidazolylbenzyl | p-fluorobenzyl | pyridinylmethyl |
| 24[c] | m-acetylbenzyl | m-aminosulfonyl-benzyl | m-methoxybenzyl |

TABLE 6[c]

Formula (If), $R^4 = R^{27}$ = methoxybenzyl, $R^{22} = R^7$ = Table

| Ex. No | .0 | .1 | .2 |
|---|---|---|---|
| 25[c] | m-hydroxymethyl-benzyl | p-hydroxymethyl-benzyl | m-hydroxybenzyl |
| 26[c] | m-(N,N-dimethyl-aminoglycyl)aminobenzyl | m-aminocarbonyl-benzyl | p-hydroxybenzyl |
| 27[c] | m-(N-methylamino)carbonylbenzyl | m-(N-methylamino)benzyl | m-formylbenzyl |
| 28[c] | m-trifluorocarbonylbenzyl | m-hydroxyamidinobenzyl | m-triazolylbenzyl |
| 29[c] | m-formaldoxime-benzyl | m-acetoximebenzyl | benzyl |
| 30[c] | hydroxycarbonyl-benzyl | m-tetrazolylbenzyl | m-pyrazolylbenzyl |
| 31[c] | m-imidazolylbenzyl | p-fluorobenzyl | pyridinylmethyl |
| 32[c] | m-acetylbenzyl | m-aminosulfonyl-benzyl | m-methoxybenzyl |

TABLE 7[c]

Formula (If), $R^4 = R^{27}$ = isobutyl, $R^{22} = R^7$ = Table

| Ex. No | .0 | .1 | .2 |
|---|---|---|---|
| 33[c] | m-hydroxymethyl-benzyl | p-hydroxymethyl-benzyl | m-hydroxybenzyl |
| 34[c] | m-(N,N-dimethyl-aminoglycyl)aminobenzyl | m-aminocarbonyl-benzyl | p-hydroxybenzyl |
| 35[c] | m-(N-methylamino)carbonylbenzyl | m-(N-methylamino)benzyl | m-formylbenzyl |
| 36[c] | m-trifluorocarbonylbenzyl | m-hydroxyamidinobenzyl | m-triazolylbenzyl |
| 37[c] | m-formaldoxime-benzyl | m-acetoximebenzyl | benzyl |
| 38[c] | hydroxycarbonyl-benzyl | m-tetrazolylbenzyl | m-pyrazolylbenzyl |
| 39[c] | m-imidazolylbenzyl | p-fluorobenzyl | pyridinylmethyl |
| 40[c] | m-acetylbenzyl | m-aminosulfonyl-benzyl | m-methoxybenzyl |

TABLE 8[c]

Formula (If), $R^4 = R^{27}$ = p-nitrobenzyl, $R^{22} = R^7$ = Table

| Ex. No | .0 | .1 | .2 |
|---|---|---|---|
| 41[c] | m-hydroxymethyl-benzyl | p-hydroxymethyl-benzyl | m-hydroxybenzyl |
| 42[c] | m-(N,N-dimethyl-aminoglycyl)aminobenzyl | m-aminocarbonyl-benzyl | p-hydroxybenzyl |
| 43[c] | m-(N-methylamino)carbonylbenzyl | m-(N-methylamino)benzyl | m-formylbenzyl |
| 44[c] | m-trifluorocarbonylbenzyl | m-hydroxyamidinobenzyl | m-triazolylbenzyl |
| 45[c] | m-formaldoxime-benzyl | m-acetoximebenzyl | benzyl |
| 46[c] | hydroxycarbonyl-benzyl | m-tetrazolylbenzyl | m-pyrazolylbenzyl |
| 47[c] | m-imidazolylbenzyl | p-fluorobenzyl | pyridinylmethyl |
| 48[c] | m-acetylbenzyl | m-aminosulfonyl-benzyl | m-methoxybenzyl |

TABLE 9[c]

Formula (If), $R^4 = R^{27}$ = m-aminobenzyl, $R^{22} = R^7$ = Table

| Ex. No | .0 | .1 | .2 |
|---|---|---|---|
| 49[c] | m-hydroxymethyl-benzyl | p-hydroxymethyl-benzyl | m-hydroxybenzyl |
| 50[c] | m-(N,N-dimethyl-aminoglycyl)aminobenzyl | m-aminocarbonyl-benzyl | p-hydroxybenzyl |
| 51[c] | m-(N-methylamino)carbonylbenzyl | m-(N-methylamino)benzyl | m-formylbenzyl |
| 52[c] | m-trifluorocarbonylbenzyl | m-hydroxyamidinobenzyl | m-triazolylbenzyl |
| 53[c] | m-formaldoxime-benzyl | m-acetoximebenzyl | benzyl |
| 54[c] | hydroxycarbonyl-benzyl | m-tetrazolylbenzyl | m-pyrazolylbenzyl |
| 55[c] | m-imidazolylbenzyl | p-fluorobenzyl | pyridinylmethyl |
| 56[c] | m-acetylbenzyl | m-aminosulfonyl-benzyl | m-methoxybenzyl |

TABLE 10[c]

Formula (If), $R^4 = R^{27}$ = pyridinylmethyl, $R^{22} = R^7$ = Table

| Ex. No | .0 | .1 | .2 |
|---|---|---|---|
| 57[c] | m-hydroxymethyl-benzyl | p-hydroxymethyl-benzyl | m-hydroxybenzyl |
| 58[c] | m-(N,N-dimethyl-aminoglycyl)aminobenzyl | m-aminocarbonyl-benzyl | p-hydroxybenzyl |
| 59[c] | m-(N-methylamino)carbonylbenzyl | m-(N-methylamino)benzyl | m-formylbenzyl |
| 60[c] | m-trifluorocarbonylbenzyl | m-hydroxyamidinobenzyl | m-triazolylbenzyl |
| 61[c] | m-formaldoxime-benzyl | m-acetoximebenzyl | benzyl |
| 62[c] | hydroxycarbonyl-benzyl | m-tetrazolylbenzyl | m-pyrazolylbenzyl |
| 63[c] | m-imidazolylbenzyl | p-fluorobenzyl | pyridinylmethyl |
| 64[c] | m-acetylbenzyl | m-aminosulfonyl-benzyl | m-methoxybenzyl |

TABLE 11[c]

Formula (If), $R^4 = R^{27}$ = m-hydroxbenzyl, $R^{22} = R^7$ = Table

| Ex. No | .0 | .1 | .2 |
|---|---|---|---|
| 65[c] | m-hydroxymethyl-benzyl | p-hydroxymethyl-benzyl | m-hydroxybenzyl |
| 66[c] | m-(N,N-dimethyl-aminoglycyl)aminobenzyl | m-aminocarbonyl-benzyl | p-hydroxybenzyl |
| 67[c] | m-(N-methylamino)carbonylbenzyl | m-(N-methylamino)benzyl | m-formylbenzyl |
| 68[c] | m-trifluorocarbonylbenzyl | m-hydroxyamidinobenzyl | m-triazolylbenzyl |
| 69[c] | m-formaldoxime-benzyl | m-acetoximebenzyl | benzyl |
| 70 [c] | hydroxycarbonyl-benzyl | m-tetrazolylbenzyl | m-pyrazolylbenzyl |
| 71 [c] | m-imidazolylbenzyl | p-fluorobenzyl | pyridinylmethyl |
| 72 [c] | m-acetylbenzyl | m-aminosulfonyl-benzyl | m-methoxybenzyl |

TABLE 12[c]

Formula (If), $R^4 = R^{27}$ = p-hydroxybenzyl, $R^{22} = R^7$ = Table

| Ex. No | .0 | .1 | .2 |
|---|---|---|---|
| 73[c] | m-hydroxymethyl-benzyl | p-hydroxymethyl-benzyl | m-hydroxybenzyl |
| 74[c] | m-(N,N-dimethyl-aminoglycyl)aminobenzyl | m-aminocarbonyl-benzyl | p-hydroxybenzyl |
| 75 [c] | m-(N-methylamino)carbonylbenzyl | m-(N-methylamino)benzyl | m-formylbenzyl |
| 76[c] | m-trifluorocarbonyl benzyl | m-hydroxyamidino benzyl | m-triazolylbenzyl |
| 77[c] | m-formaldoxime-benzyl | m-acetoximebenzyl | benzyl |
| 78[c] | hydroxycarbonyl-benzyl | m-tetrazolylbenzyl | m-pyrazolylbenzyl |
| 79[c] | m-imidazolylbenzyl | p-fluorobenzyl | pyridinylmethyl |
| 80[c] | m-acetylbenzyl | m-aminosulfonyl-benzyl | m-methoxybenzyl |

TABLE 13[c]

Formula (If), $R^4 = R^{27}$ = m-aminocarbonylbenzyl, $R^{22} = R^7$ = Table

| Ex. No | .0 | .1 | .2 |
|---|---|---|---|
| 81[c] | m-hydroxymethyl-benzyl | p-hydroxymethyl-benzyl | m-hydroxybenzyl |
| 82[c] | m-(N,N-dimethyl-aminoglycyl)aminobenzyl | m-aminocarbonyl-benzyl | p-hydroxybenzyl |
| 83[c] | m-(N-methylamino)carbonylbenzyl | m-(N-methylamino)benzyl | m-formylbenzyl |
| 84[c] | m-trifluorcarbonyl benzyl | m-hydroxyamidino benzyl | m-triazolylbenzyl |
| 85[c] | m-formaldoxime-benzyl | m-acetoximebenzyl | benzyl |
| 86[c] | hydroxycarbonyl-benzyl | m-tetrazolylbenzyl | m-pyrazolylbenzyl |
| 87[c] | m-imidazolylbenzyl | p-fluorobenzyl | pyridinylmethyl |
| 88[c] | m-acetylbenzyl | m-aminosulfonyl-benzyl | m-methoxybenzyl |

TABLE 14[c]

Formula (If), $R^4 = R^{27}$ = p-hydroxymethylbenzyl, $R^{22} = R^7$ = Table

| Ex. No | .0 | .1 | .2 |
|---|---|---|---|
| 89[c] | m-hydroxymethyl-benzyl | p-hydroxymethyl-benzyl | m-hydroxybenzyl |
| 90[c] | m-(N,N-dimethyl-aminoglycyl)aminobenzyl | m-aminocarbonyl-benzyl | p-hydroxybenzyl |
| 91[c] | m-(N-methylamino)carbonylbenzyl | m-(N-methylamino)benzyl | m-formylbenzyl |
| 92[c] | m-trifluorcarbonyl benzyl | m-hydroxyamidino benzyl | m-triazolylbenzyl |
| 93[c] | m-formaldoxime-benzyl | m-acetoximebenzyl | benzyl |
| 94 [c] | hydroxycarbonyl-benzyl | m-tetrazolylbenzyl | m-pyrazolylbenzyl |
| 95[c] | m-imidazolylbenzyl | p-fluorobenzyl | pyridinylmethyl |
| 96 [c] | m-acetylbenzyl | m-aminosulfonyl-benzyl | m-methoxybenzyl |

TABLE 15[c]

Formula (If), $R^4 = R^{27}$ = m-hydroxycarbonylbenzyl, $R^{22} = R^7$ = Table

| Ex. No | .0 | .1 | .2 |
|---|---|---|---|
| 97[c] | m-hydroxymethyl-benzyl | p-hydroxymethyl-benzyl | m-hydroxybenzyl |
| 98[c] | m-(N,N-dimethyl-aminoglycyl)aminobenzyl | m-aminocarbonyl-benzyl | p-hydroxybenzyl |
| 99[c] | m-(N-methylamino)carbonylbenzyl | m-(N-methylamino)benzyl | m-formylbenzyl |
| 100[c] | m-trifluorcarbonyl benzyl | m-hydroxyamidino benzyl | m-triazolylbenzyl |
| 101[c] | m-formaldoxime-benzyl | m-acetoximebenzyl | benzyl |
| 102[c] | hydroxycarbonyl-benzyl | m-tetrazolylbenzyl | m-pyrazolylbenzyl |
| 103[c] | m-imidazolylbenzyl | p-fluorobenzyl | pyridinylmethyl |
| 104[c] | m-acetylbenzyl | m-aminosulfonyl-benzyl | m-methoxybenzyl |

TABLE 16[c]

Formula (If), $R^4 = R^{27}$ = benzyl, $R^{22}$ = m-hydroxymethylbenzyl, $R^7$ = Table

| Ex. No | .0 | .1 | .2 |
|---|---|---|---|
| 105[c] | m-hydroxymethyl-benzyl | p-hydroxymethyl-benzyl | m-hydroxybenzyl |
| 106[c] | m-(N,N-dimethyl-aminoglycyl)aminobenzyl | m-aminocarbonyl-benzyl | p-hydroxybenzyl |
| 107[c] | m-(N-methylamino)carbonylbenzyl | m-(N-methylamino)benzyl | m-formylbenzyl |
| 108[c] | m-trifluorcarbonyl benzyl | m-hydroxyamidino benzyl | m-triazolylbenzyl |
| 109[c] | m-formaldoxime-benzyl | m-acetoximebenzyl | benzyl |
| 110[c] | hydroxycarbonyl-benzyl | m-tetrazolylbenzyl | m-pyrazolylbenzyl |
| 111[c] | m-imidazolylbenzyl | p-fluorobenzyl | pyridinylmethyl |
| 112 [c] | m-acetylbenzyl | m-aminosulfonyl-benzyl | m-methoxybenzyl |

TABLE 17[c]

Formula (If), $R^4 = R^{27}$ = benzyl, $R^{22}$ = p-hydroxymethylbenzyl, $R^7$ = Table

| Ex. No | .0 | .1 | .2 |
|---|---|---|---|
| 113[c] | m-hydroxymethyl-benzyl | p-hydroxymethyl-benzyl | m-hydroxybenzyl |
| 114[c] | m-(N,N-dimethyl-aminoglycyl)aminobenzyl | m-aminocarbonyl-benzyl | p-hydroxybenzyl |
| 115 [c] | m-(N-methylamino)carbonylbenzyl | m-(N-methylamino)benzyl | m-formylbenzyl |
| 116[c] | m-trifluorcarbonyl benzyl | m-hydroxyamidino benzyl | m-triazolylbenzyl |
| 117 [c] | m-formaldoxime-benzyl | m-acetoximebenzyl | benzyl |
| 118[c] | hydroxycarbonyl-benzyl | m-tetrazolylbenzyl | m-pyrazolylbenzyl |
| 119[c] | m-imidazolylbenzyl | p-fluorobenzyl | pyridinylmethyl |
| 120[c] | m-acetylbenzyl | m-aminosulfonyl-benzyl | m-methoxybenzyl |

TABLE 18[c]

Formula (If), $R^4 = R^{27}$ = benzyl, $R^{22}$ = m-hydroxybenzyl, $R^7$ = Table

| Ex. No | .0 | .1 | .2 |
|---|---|---|---|
| 121[c] | m-hydroxymethyl-benzyl | p-hydroxymethyl-benzyl | m-hydroxybenzyl |
| 122[c] | m-(N,N-dimethyl-aminoglycyl)aminobenzyl | m-aminocarbonyl-benzyl | p-hydroxybenzyl |
| 123[c] | m-(N-methylamino)carbonylbenzyl | m-(N-methylamino)benzyl | m-formylbenzyl |
| 124[c] | m-trifluorcarbonylbenzyl | m-hydroxyamidinobenzyl | m-triazolylbenzyl |
| 125[c] | m-formaldoxime-benzyl | m-acetoximebenzyl | benzyl |
| 126[c] | hydroxycarbonylbenzyl | m-tetrazolylbenzyl | m-pyrazolylbenzyl |
| 127[c] | m-imidazolylbenzyl | p-fluorobenzyl | pyridinylmethyl |
| 128[c] | m-acetylbenzyl | m-aminosulfonylbenzyl | m-methoxybenzyl |

TABLE 19[c]

Formula (If), $R^4 = R^{27}$ = benzyl, $R^{22}$ = m-(N,N-dimethylamino glycyl)aminobenzyl, $R^7$ = Table

| Ex. No | .0 | .1 | .2 |
|---|---|---|---|
| 129[c] | m-hydroxymethyl-benzyl | p-hydroxymethyl-benzyl | m-hydroxybenzyl |
| 130[c] | m-(N,N-dimethyl-aminoglycyl)aminobenzyl | m-aminocarbonyl-benzyl | -p-hydroxybenzyl |
| 131[c] | m-(N-methylamino)carbonylbenzyl | m-(N-methylamino)benzyl | m-formylbenzyl |
| 132[c] | m-trifluorcarbonylbenzyl | m-hydroxyamidinobenzyl | m-triazolylbenzyl |
| 133[c] | m-formaldoxime-benzyl | m-acetoximebenzyl | benzyl |
| 134[c] | hydroxycarbonylbenzyl | m-tetrazolylbenzyl | m-pyrazolylbenzyl |
| 135[c] | m-imidazolylbenzyl | p-fluorobenzyl | pyridinylmethyl |
| 136[c] | m-acetylbenzyl | m-aminosulfonylbenzyl | m-methoxybenzyl |

TABLE 20[c]

Formula (If), $R^4 = R^{27}$ = benzyl, $R^{22}$ = m-aminocarbonylbenzyl, $R^7$ = Table

| Ex. No | .0 | .1 | .2 |
|---|---|---|---|
| 137[c] | m-hydroxymethyl-benzyl | p-hydroxymethyl-benzyl | m-hydroxybenzyl |
| 138[c] | m-(N,N-dimethyl-aminoglycyl)aminobenzyl | m-aminocarbonyl-benzyl | p-hydroxybenzyl |
| 139[c] | m-(N-methylamino)carbonylbenzyl | m-(N-methylamino)benzyl | m-formylbenzyl |
| 140 [c] | m-trifluorcarbonylbenzyl | m-hydroxyamidinobenzyl | m-triazolylbenzyl |
| 141[c] | m-formaldoxime-benzyl | m-acetoximebenzyl | benzyl |
| 142[c] | hydroxycarbonylbenzyl | m-tetrazolylbenzyl | m-pyrazolylbenzyl |
| 143[c] | m-imidazolylbenzyl | p-fluorobenzyl | pyridinylmethyl |
| 144 [c] | m-acetylbenzyl | m-aminosulfonylbenzyl | m-methoxybenzyl |

TABLE 21[c]

Formula (If), $R^4 = R^{27}$ = benzyl, $R^{22}$ = p-hydroxybenzyl, $R^7$ = Table

| Ex. No | .0 | .1 | .2 |
|---|---|---|---|
| 145[c] | m-hydroxymethyl-benzyl | p-hydroxymethyl-benzyl | m-hydroxybenzyl |
| 146[c] | m-(N,N-dimethyl-aminoglycyl)aminobenzyl | m-aminocarbonyl-benzyl | p-hydroxybenzyl |
| 147[c] | m-(N-methylamino)carbonylbenzyl | m-(N-methylamino)benzyl | m-formylbenzyl |
| 148[c] | m-trifluorcarbonylbenzyl | m-hydroxyamidinobenzyl | m-triazolylbenzyl |
| 149[c] | m-formaldoxime-benzyl | m-acetoximebenzyl | benzyl |
| 150 [c] | hydroxycarbonylbenzyl | m-tetrazolylbenzyl | m-pyrazolylbenzyl |
| 151[c] | m-imidazolylbenzyl | p-fluorobenzyl | pyridinylmethyl |
| 152[c] | m-acetylbenzyl | m-aminosulfonylbenzyl | m-methoxybenzyl |

TABLE 22[c]

Formula (If), $R^4 = R^{27}$ = benzyl, $R^{22}$ = m-(N-methylaminocarbonyl benzyl, $R^7$ = Table

| Ex. No | .0 | .1 | .2 |
|---|---|---|---|
| 153[c] | m-hydroxymethyl-benzyl | p-hydroxymethyl-benzyl | m-hydroxybenzyl |
| 154[c] | m-(N,N-dimethyl-aminoglycyl)aminobenzyl | m-aminocarbonyl-benzyl | p-hydroxybenzyl |
| 155 [c] | m-(N-methylamino)carbonylbenzyl | m-(N-methylamino)benzyl | m-formylbenzyl |
| 156[c] | m-trifluorcarbonylbenzyl | m-hydroxyamidinobenzyl | m-triazolylbenzyl |
| 157[c] | m-formaldoxime-benzyl | m-acetoximebenzyl | benzyl |
| 158[c] | hydroxycarbonylbenzyl | m-tetrazolylbenzyl | m-pyrazolylbenzyl |
| 159[c] | m-imidazolylbenzyl | p-fluorobenzyl | pyridinylmethyl |
| 160[c] | m-acetylbenzyl | m-aminosulfonylbenzyl | m-methoxybenzyl |

TABLE 23[c]

Formula (If), $R^4 = R^{27}$ = benzyl, $R^{22}$ = m-(N-methylamino)benzyl, $R^7$ = Table

| Ex. No | .0 | .1 | .2 |
|---|---|---|---|
| 161[c] | m-hydroxymethyl-benzyl | p-hydroxymethyl-benzyl | m-hydroxybenzyl |
| 162 [c] | m-(N,N-dimethyl-aminoglycyl)aminobenzyl | m-aminocarbonyl-benzyl | p-hydroxybenzyl |
| 163[c] | m-(N-methylamino)carbonylbenzyl | m-(N-methylamino)benzyl | m-formylbenzyl |
| 164[c] | m-trifluorcarbonylbenzyl | m-hydroxyamidinobenzyl | m-triazolylbenzyl |
| 165 [c] | m-formaldoxime-benzyl | m-acetoximebenzyl | benzyl |
| 166 [c] | hydroxycarbonylbenzyl | m-tetrazolylbenzyl | m-pyrazolylbenzyl |
| 167[c] | m-imidazolylbenzyl | p-fluorobenzyl | pyridinylmethyl |
| 168[c] | m-acetylbenzyl | m-aminosulfonylbenzyl | m-methoxybenzyl |

TABLE 24[c]

Formula (If), $R^4 = R^{27}$ = benzyl, $R^{22}$ = m-formyllbenzyl, $R^7$ = Table

| Ex. No | .0 | .1 | .2 |
|---|---|---|---|
| 169[c] | m-hydroxymethyl-benzyl | p-hydroxymethyl-benzyl | m-hydroxybenzyl |
| 170[c] | m-(N,N-dimethyl-aminoglycyl)aminobenzyl | m-aminocarbonyl-benzyl | p-hydroxybenzyl |
| 171[c] | m-(N-methylamino)carbonylbenzyl | m-(N-methylamino)benzyl | m-formylbenzyl |
| 172[c] | m-trifluorcarbonyl benzyl | m-hydroxyamidino benzyl | m-triazolylbenzyl |
| 173[c] | m-formaldoxime-benzyl | m-acetoximebenzyl | benzyl |
| 174[c] | hydroxycarbonyl-benzyl | m-tetrazolylbenzyl | m-pyrazolylbenzyl |
| 175[c] | m-imidazolylbenzyl | p-fluorobenzyl | pyridinylmethyl |
| 176[c] | m-acetylbenzyl | m-aminosulfonyl-benzyl | m-methoxybenzyl |

TABLE 25[c]

Formula (If), $R^4 = R^{27}$ = benzyl, $R^{22}$ = m-trifluorocarbonylbenzyl, $R^7$ = Table

| Ex. No | .0 | .1 | .2 |
|---|---|---|---|
| 177[c] | m-hydroxymethyl-benzyl | p-hydroxymethyl-benzyl | m-hydroxybenzyl |
| 178[c] | m-(N,N-dimethyl-aminoglycyl)aminobenzyl | m-aminocarbonyl-benzyl | p-hydroxybenzyl |
| 179[c] | m-(N-methylamino)carbonylbenzyl | m-(N-methylamino)benzyl | m-formylbenzyl |
| 180[c] | m-trifluorcarbonyl benzyl | m-hydroxyamidino benzyl | m-triazolylbenzyl |
| 181[c] | m-formaldoxime-benzyl | m-acetoximebenzyl | benzyl |
| 182[c] | hydroxycarbonyl-benzyl | m-tetrazolylbenzyl | m-pyrazolylbenzyl |
| 183[c] | m-imidazolylbenzyl | p-fluorobenzyl | pyridinylmethyl |
| 184[c] | m-acetylbenzyl | m-aminosulfonyl-benzyl | m-methoxybenzyl |

TABLE 26[c]

Formula (If), $R^4 = R^{27}$ = benzyl, $R^{22}$ = m-hydroxyamidinobenzyl, $R^7$ = Table

| Ex. No | .0 | .1 | .2 |
|---|---|---|---|
| 185[c] | m-hydroxymethyl-benzyl | p-hydroxymethyl-benzyl | m-hydroxybenzyl |
| 186 [c] | m-(N,N-dimethyl-aminoglycyl)aminobenzyl | m-aminocarbonyl-benzyl | p-hydroxybenzyl |
| 187[c] | m-(N-methylamino)carbonylbenzyl | m-(N-methylamino)benzyl | m-formylbenzyl |
| 188[c] | m-trifluorcarbonyl benzyl | m-hydroxyamidino benzyl | m-triazolylbenzyl |
| 189 [c] | m-formaldoxime-benzyl | m-acetoximebenzy1 | benzyl |
| 190[c] | hydroxycarbonyl-benzyl | m-tetrazolylbenzyl | m-pyrazolylbenzyl |
| 191[c] | m-imidazolylbenzyl | p-fluorobenzyl | pyridinylmethyl |
| 192 [c] | m-acetylbenzyl | m-aminosulfonyl-benzyl | m-methoxybenzyl |

TABLE 27[c]

Formula (If), $R^4 = R^{27}$ = benzyl, $R^{22}$ = m-triazolylbenzyl, $R^7$ = Table

| Ex. No | .0 | .1 | .2 |
|---|---|---|---|
| 193[c] | m-hydroxymethyl-benzyl | p-hydroxymethyl-benzyl | m-hydroxybenzyl |
| 194[c] | m-(N,N-dimethyl-aminoglycyl)aminobenzyl | m-aminocarbonyl-benzyl | p-hydroxybenzyl |
| 195[c] | m-(N-methylamino)carbonylbenzyl | m-(N-methylamino)benzyl | m-formylbenzyl |
| 196[c] | m-trifluorcarbonyl benzyl | m-hydroxyamidino benzyl | m-triazolylbenzyl |
| 197[c] | m-formaldoxime-benzyl | m-acetoximebenzyl | benzyl |
| 198[c] | hydroxycarbonyl-benzyl | m-tetrazolylbenzyl | m-pyrazolylbenzyl |
| 199[c] | m-imidazolylbenzyl | p-fluorobenzyl | pyridinylmethyl |
| 200[c] | m-acetylbenzyl | m-aminosulfonyl-benzyl | m-methoxybenzyl |

TABLE 28[c]

Formula (If), $R^4 = R^{27}$ = benzyl, $R^{22}$ = m-formaldoximebenzyl, $R^7$ = Table

| Ex.No | .0 | .1 | .2 |
|---|---|---|---|
| 201[c] | m-hydroxymethyl-benzyl | p-hydroxymethyl-benzyl | m-hydroxybenzyl |
| 202[c] | m-(N,N-dimethyl-amino glycyl)-aminobenzyl | m-aminocarbonyl-benzyl | p-hydroxybenzyl |
| 203[c] | m-(N-methylamino)carbonylbenzyl | m-(N-methylamino)benzyl | m-formylbenzyl |
| 204[c] | m-trifluorcarbonyl benzyl | m-hydroxyamidino benzyl | m-triazolylbenzyl |
| 205[c] | m-formaldoxime-benzyl | m-acetoximebenzyl | benzyl |
| 206[c] | hydroxycarbonyl-benzyl | m-tetrazolylbenzyl | m-pyrazolyl-benzyl |
| 207[c] | m-imidazolylbenzyl | p-fluorobenzyl | pyridinylmethyl |
| 208[c] | m-acetylbenzyl | m-aminosulfonyl-benzyl | m-methoxybenzyl |

TABLE 29[c]

Formula (If), $R^4 = R^{27}$ = benzyl, $R^{22}$ = m-acetoximebenzyl, $R^7$ = Table

| Ex.No | .0 | .1 | .2 |
|---|---|---|---|
| 209[c] | m-hydroxymethyl-benzyl | p-hydroxymethyl-benzyl | m-hydroxybenzyl |
| 210[c] | m-(N,N-dimethyl-amino glycyl)-aminobenzyl | m-aminocarbonyl-benzyl | p-hydroxybenzyl |
| 211[c] | m-(N-methylamino)carbonylbenzyl | m-(N-methylamino)benzyl | m-formylbenzyl |
| 212[c] | m-trifluorcarbonyl benzyl | m-hydroxyamidino benzyl | m-triazolylbenzyl |
| 213[c] | m-formaldoxime-benzyl | m-acetoximebenzyl | benzyl |
| 214[c] | Hydroxycarbonyl-benzyl | m-tetrazolylbenzyl | m-pyrazolyl-benzyl |
| 215[c] | m-imidazolylbenzyl | p-fluorobenzyl | pyridinylmethyl |
| 216[c] | m-acetylbenzyl | m-aminosulfonyl-benzyl | m-methoxybenzyl |

TABLE 30[c]

Formula (If), $R^4 = R^{27}$ = benzyl, $R^{22}$ = benzyl, $R^7$ = Table

| Ex.No | .0 | .1 | .2 |
|---|---|---|---|
| 217[c] | m-hydroxymethyl-benzyl | p-hydroxymethyl-benzyl | m-hydroxybenzyl |
| 218[c] | m-(N,N-dimethyl-amino glycyl)-aminobenzyl | m-aminocarbonyl-benzyl | p-hydroxybenzyl |
| 219[c] | m-(N-methylamino)carbonylbenzyl | m-(N-methylamino)benzyl | m-formylbenzyl |
| 220[c] | m-trifluorcarbonyl benzyl | m-hydroxyamidino benzyl | m-triazolylbenzyl |
| 221[c] | m-formaldoxime-benzyl | m-acetoximebenzyl | benzyl |
| 222[c] | hydroxycarbonyl-benzyl | m-tetrazolylbenzyl | m-pyrazolyl-benzyl |
| 223[c] | m-imidazolylbenzyl | p-fluorobenzyl | pyridinylmethyl |
| 224[c] | m-acetylbenzyl | m-aminosulfonyl-benzyl | m-methoxybenzyl |

TABLE 31[c]

Formula (If), $R^4 = R^{27}$ = benzyl, $R^{22}$ = m-hydroxycarbonylbenzyl, $R^7$ = Table

| Ex.No | .0 | .1 | .2 |
|---|---|---|---|
| 225[c] | m-hydroxymethyl-benzyl | p-hydroxymethyl-benzyl | m-hydroxybenzyl |
| 226[c] | m-(N,N-dimethyl-amino glycyl)-aminobenzyl | m-aminocarbonyl-benzyl | p-hydroxybenzyl |
| 227[c] | m-(N-methylamino)carbonylbenzyl | m-(N-methylamino)benzyl | m-formylbenzyl |
| 228[c] | m-trifluorcarbonyl benzyl | m-hydroxyamidino benzyl | m-triazolylbenzyl |
| 229[c] | m-formaldoxime-benzyl | m-acetoximebenzyl | benzyl |
| 230[c] | hydroxycarbonyl-benzyl | m-tetrazolylbenzyl | m-pyrazolyl-benzyl |
| 231[c] | m-imidazolylbenzyl | p-fluorobenzyl | pyridinylmethyl |
| 232[c] | m-acetylbenzyl | m-aminosulfonyl-benzyl | m-methoxybenzyl |

TABLE 32[c]

Formula (If), $R^4 = R^{27}$ = benzyl, $R^{22}$ = m-tetrazolylbenzyl, $R^7$ = Table

| Ex.No | .0 | .1 | .2 |
|---|---|---|---|
| 233[c] | m-hydroxymethyl-benzyl | p-hydroxymethyl-benzyl | m-hydroxybenzyl |
| 234[c] | m-(N,N-dimethyl-amino glycyl)-aminobenzyl | m-aminocarbonyl-benzyl | p-hydroxybenzyl |
| 235[c] | m-(N-methylamino)carbonylbenzyl | m-(N-methylamino)benzyl | m-formylbenzyl |
| 236[c] | m-trifluorcarbonyl benzyl | m-hydroxyamidino benzyl | m-pyrazolylbenzyl |
| 237[c] | m-formaldoxime-benzyl | m-acetoximebenzyl | benzyl |
| 238[c] | hydroxycarbonyl-benzyl | m-tetrazolylbenzyl | m-pyrazolyl-benzyl |
| 239[c] | m-imidazolylbenzyl | p-fluorobenzyl | pyridinylmethyl |
| 240[c] | m-acetylbenzyl | m-aminosulfonyl-benzyl | m-methoxybenzyl |

TABLE 33[c]

Formula (If), $R^4 = R^{27}$ = benzyl, $R^{22}$ = m-pyrazolylbenzyl, $R^7$ = Table

| Ex.No | .0 | .1 | .2 |
|---|---|---|---|
| 241[c] | m-hydroxymethyl-benzyl | p-hydroxymethyl-benzyl | m-hydroxybenzyl |
| 242[c] | m-(N,N-dimethyl-amino glycyl)-aminobenzyl | m-aminocarbonyl-benzyl | p-hydroxybenzyl |
| 243[c] | m-(N-methylamino)carbonylbenzyl | m-(N-methylamino)benzyl | m-formylbenzyl |
| 244[c] | m-trifluorcarbonyl benzyl | m-hydroxyamidino benzyl | m-triazolylbenzyl |
| 245[c] | m-formaldoxime-benzyl | m-acetoximebenzyl | benzyl |
| 246[c] | hydroxycarbonyl-benzyl | m-tetrazolylbenzyl | m-pyrazolyl-benzyl |
| 247[c] | m-imidazolylbenzyl | p-fluorobenzyl | pyridinylmethyl |
| 248[c] | m-acetylbenzyl | m-aminosulfonyl-benzyl | m-methoxybenzyl |

TABLE 34[c]

Formula (If), $R^4 = R^{27}$ = benzyl, $R^{22}$ = m-imidazolylbenzyl, $R^7$ = Table

| Ex.No | .0 | .1 | .2 |
|---|---|---|---|
| 249[c] | m-hydroxymethyl-benzyl | p-hydroxymethyl-benzyl | m-hydroxybenzyl |
| 250[c] | m-(N,N-dimethyl-amino glycyl)-aminobenzyl | m-aminocarbonyl-benzyl | p-hydroxybenzyl |
| 251[c] | m-(N-methylamino)carbonylbenzyl | m-(N-methylamino)benzyl | m-formylbenzyl |
| 252[c] | m-trifluorcarbonyl benzyl | m-hydroxyamidino benzyl | m-triazolylbenzyl |
| 253[c] | m-formaldoxime-benzyl | m-acetoximebenzyl | benzyl |
| 254[c] | hydroxycarbonyl-benzyl | m-tetrazolylbenzyl | m-pyrazolylbenzyl |
| 255[c] | m-imidazolylbenzyl | p-fluorobenzyl | pyridinylmethyl |
| 256[c] | m-acetylbenzyl | m-aminosulfonyl-benzyl | m-methoxybenzyl |

TABLE 35[c]

Formula (If), $R^4 = R^{27}$ = benzyl, $R^{22}$ = p-fluorobenzyl, $R^7$ = Table

| Ex.No | .0 | .1 | .2 |
|---|---|---|---|
| 257[c] | m-hydroxymethyl-benzyl | p-hydroxymethyl-benzyl | m-hydroxybenzyl |
| 258[c] | m-(N,N-dimethyl-amino glycyl)-aminobenzyl | m-aminocarbonyl-benzyl | p-hydroxybenzyl |
| 259[c] | m-(N-methylamino)carbonylbenzyl | m-(N-methylamino)benzyl | m-formylbenzyl |
| 260[c] | m-trifluorcarbonyl benzyl | m-hydroxyamidino benzyl | m-triazolylbenzyl |
| 261[c] | m-formaldoxime-benzyl | m-acetoximebenzyl | benzyl |
| 262[c] | hydroxycarbonyl-benzyl | m-tetrazolylbenzyl | m-pyrazolyl-benzyl |
| 263[c] | m-imidazolylbenzyl | p-fluorobenzyl | pyridinylmethyl |
| 264[c] | m-acetylbenzyl | m-aminosulfonyl-benzyl | m-methoxybenzyl |

TABLE 36[c]

Formula (If), $R^4 = R^{27}$ = benzyl, $R^{22}$ = pyridinylmethyl, $R^7$ = Table

| Ex.No | .0 | .1 | .2 |
|---|---|---|---|
| 265[c] | m-hydroxymethyl-benzyl | p-hydroxymethyl-benzyl | m-hydroxybenzyl |
| 266[c] | m-(N,N-dimethyl-amino glycyl)-aminobenzyl | m-aminocarbonyl-benzyl | p-hydroxybenzyl |
| 267[c] | m-(N-methylamino)carbonylbenzyl | m-(N-methylamino)benzyl | m-formylbenzyl |
| 268[c] | m-trifluorcarbonylbenzyl | m-hydroxyamidinobenzyl | m-triazolylbenzyl |
| 269[c] | m-formaldoxime-benzyl | m-acetoximebenzyl | benzyl |
| 270[c] | hydroxycarbonyl-benzyl | m-tetrazolylbenzyl | m-pyrazolyl-benzyl |
| 271[c] | m-imidazolylbenzyl | p-fluorobenzyl | pyridinylmethyl |
| 272[c] | m-acetylbenzyl | m-aminosulfonyl-benzyl | m-methoxybenzyl |

TABLE 37[c]

Formula (If), $R^4 = R^{27}$ = benzyl, $R^{22}$ = m-acetylbenzyl, $R^7$ = Table

| Ex.No | .0 | .1 | .2 |
|---|---|---|---|
| 273[c] | m-hydroxymethyl-benzyl | p-hydroxymethyl-benzyl | m-hydroxybenzyl |
| 274[c] | m-(N,N-dimethyl-amino glycyl)-aminobenzyl | m-aminocarbonyl-benzyl | p-hydroxybenzyl |
| 275[c] | m-(N-methylamino)carbonylbenzyl | m-(N-methylamino)benzyl | m-formylbenzyl |
| 276[c] | m-trifluorcarbonylbenzyl | m-hydroxyamidinobenzyl | m-triazolylbenzyl |
| 277[c] | m-formaldoxime-benzyl | m-acetoximebenzyl | benzyl |
| 278[c] | hydroxycarbonyl-benzyl | m-tetrazolylbenzyl | m-pyrazolyl-benzyl |
| 279[c] | m-imidazolylbenzyl | p-fluorobenzyl | pyridinylmethyl |
| 280[c] | m-acetylbenzyl | m-aminosulfonyl-benzyl | m-methoxybenzyl |

TABLE 38[c]

Formula (If), $R^4 = R^{27}$ = benzyl, $R^{22}$ = m-aminosulfonylbenzyl, $R^7$ = Table

| Ex.No | .0 | .1 | .2 |
|---|---|---|---|
| 281[c] | m-hydroxymethyl-benzyl | p-hydroxymethyl-benzyl | m-hydroxybenzyl |
| 282[c] | m-(N,N-dimethyl-amino glycyl)-aminobenzyl | m-aminocarbonyl-benzyl | p-hydroxybenzyl |
| 283[c] | m-(N-methylamino)carbonylbenzyl | m-(N-methylamino)benzyl | m-formylbenzyl |
| 284[c] | m-trifluorcarbonylbenzyl | m-hydroxyamidinobenzyl | m-triazolylbenzyl |
| 285[c] | m-formaldoxime-benzyl | m-acetoximebenzyl | benzyl |
| 286[c] | hydroxycarbonyl-benzyl | m-tetrazolylbenzyl | m-pyrazolyl-benzyl |
| 287[c] | m-imidazolylbenzyl | p-fluorobenzyl | pyridinylmethyl |
| 288[c] | m-acetylbenzyl | m-aminosulfonyl-benzyl | m-methoxybenzyl |

TABLE 39[c]

Formula (If), $R^4 = R^{27}$ = benzyl, $R^{22}$ = m-methoxybenzyl, $R^7$ = Table

| Ex.No | .0 | .1 | .2 |
|---|---|---|---|
| 289[c] | m-hydroxymethyl-benzyl | p-hydroxymethyl-benzyl | m-hydroxybenzyl |
| 290[c] | m-(N,N-dimethyl-amino glycyl)-aminobenzyl | m-aminocarbonyl-benzyl | p-hydroxybenzyl |
| 291[c] | m-(N-methylamino)carbonylbenzyl | m-(N-methylamino)benzyl | m-formylbenzyl |
| 292[c] | m-trifluorcarbonylbenzyl | m-hydroxyamidinobenzyl | m-triazolylbenzyl |
| 293[c] | m-formaldoxime-benzyl | m-acetoximebenzyl | benzyl |
| 294[c] | hydroxycarbonyl-benzyl | m-tetrazolylbenzyl | m-pyrazolyl-benzyl |
| 295[c] | m-imidazolylbenzyl | p-fluorobenzyl | pyridinylmethyl |
| 296[c] | m-acetylbenzyl | m-aminosulfonyl-benzyl | m-methoxybenzyl |

TABLE 3[d]

Formula (IIIa), $R^4 = R^{23}$ = benzyl, $R^{22} = R^7$ = Table

| Ex.No | .0 | .1 | .2 |
|---|---|---|---|
| 1[d] | m-hydroxymethyl-benzyl | p-hydroxymethyl-benzyl | m-hydroxybenzyl |
| 2[d] | m-(N,N-dimethyl-amino glycyl)-aminobenzyl | m-aminocarbonyl-benzyl | p-hydroxybenzyl |
| 3[d] | m-(N-methylamino)carbonylbenzyl | m-(N-methylamino)benzyl | m-formylbenzyl |
| 4[d] | m-trifluorocarbonylbenzyl | m-hydroxyamidinobenzyl | m-triazolylbenzyl |
| 5[d] | m-formaldoxime-benzyl | m-acetoximebenzyl | benzyl |
| 6[d] | hydroxycarbonyl-benzyl | m-tetrazolylbenzyl | m-pyrazolyl-benzyl |
| 7[d] | m-imidazolylbenzyl | p-fluorobenzyl | pyridinylmethyl |
| 8[d] | m-acetylbenzyl | m-aminosulfonyl-benzyl | m-methoxybenzyl |

TABLE 4[d]

Formula (IIIa), $R^4 = R^{23}$ = fluorobenzyl, $R^{22} = R^7$ = Table

| Ex.No | .0 | .1 | .2 |
|---|---|---|---|
| 9[d] | m-hydroxymethyl-benzyl | p-hydroxymethyl-benzyl | m-hydroxybenzyl |
| 10[d] | m-(N,N-dimethyl-amino glycyl)-aminobenzyl | m-aminocarbonyl-benzyl | p-hydroxybenzyl |
| 11[d] | m-(N-methylamino)carbonylbenzyl | m-(N-methylamino)benzyl | m-formylbenzyl |
| 12[d] | m-trifluorocarbonylbenzyl | m-hydroxyamidinobenzyl | m-triazolylbenzyl |
| 13[d] | m-formaldoxime-benzyl | m-acetoximebenzyl | benzyl |
| 14[d] | hydroxycarbonyl-benzyl | m-tetrazolylbenzyl | m-pyrazolyl-benzyl |
| 15[d] | m-imidazolylbenzyl | p-fluorobenzyl | pyridinylmethyl |
| 16[d] | m-acetylbenzyl | m-aminosulfonyl-benzyl | m-methoxybenzyl |

TABLE 5[d]

Formula (IIIa), $R^4 = R^{23}$ = pyrrolylmethyl, $R^{22} = R^7$ = Table

| Ex.No | .0 | .1 | .2 |
|---|---|---|---|
| 17[d] | m-hydroxymethyl-benzyl | p-hydroxymethyl-benzyl | m-hydroxybenzyl |
| 18[d] | m-(N,N-dimethyl-amino glycyl)-aminobenzyl | m-aminocarbonyl-benzyl | p-hydroxybenzyl |
| 19[d] | m-(N-methylamino) carbonylbenzyl | m-(N-methylamino) benzyl | m-formylbenzyl |
| 20[d] | m-trifluorocarbonyl benzyl | m-hydroxyamidino benzyl | m-triazolylbenzyl |
| 21[d] | m-formaldoxime-benzyl | m-acetoximebenzyl | benzyl |
| 22[d] | hydroxycarbonyl-benzyl | m-tetrazolylbenzyl | m-pyrazolyl-benzyl |
| 23[d] | m-imidazolylbenzyl | p-fluorobenzyl | pyridinylmethyl |
| 24[d] | m-acetylbenzyl | m-aminosulfonyl-benzyl | m-methoxybenzyl |

TABLE 6[d]

Formula (IIIa), $R^4 = R^{23}$ = methoxybenzyl, $R^{22} = R^7$ = Table

| Ex.No | .0 | .1 | .2 |
|---|---|---|---|
| 25[d] | m-hydroxymethyl-benzyl | p-hydroxymethyl-benzyl | m-hydroxybenzyl. |
| 26[d] | m-(N,N-dimethyl-amino glycyl)-aminobenzyl | m-aminocarbonyl-benzyl | p-hydroxybenzyl |
| 27[d] | m-(N-methylamino) carbonylbenzyl | m-(N-methylamino) benzyl | m-formylbenzyl |
| 28[d] | m-trifluorocarbonyl benzyl | m-hydroxyamidino benzyl | m-triazolylbenzyl |
| 29[d] | m-formaldoxime-benzyl | m-acetoximebenzyl | benzyl |
| 30[d] | hydroxycarbonyl-benzyl | m-tetrazolylbenzyl | m-pyrazolylbenzyl |
| 31[d] | m-imidazolylbenzyl | p-fluorobenzyl | pyridinylmethyl |
| 32[d] | m-acetylbenzyl | m-aminosulfonyl-benzyl | m-methoxybenzyl |

TABLE 7[d]

Formula (IIIa), $R^4 = R^{23}$ = isobutyl, $R^{22} = R^7$ = Table

| Ex.No | .0 | .1 | .2 |
|---|---|---|---|
| 33[d] | m-hydroxymethyl-benzyl | p-hydroxymethyl-benzyl | m-hydroxybenzyl |
| 34[d] | m-(N,N-dimethyl-amino glycyl)-aminobenzyl | m-aminocarbonyl-benzyl | p-hydroxybenzyl |
| 35[d] | m-(N-methylamino) carbonylbenzyl | m-(N-methylamino) benzyl | m-formylbenzyl |
| 36[d] | m-trifluorocarbonyl benzyl | m-hydroxyamidino benzyl | m-triazolylbenzyl |
| 37[d] | m-formaldoxime-benzyl | m-acetoximebenzyl | benzyl |
| 38[d] | Hydroxycarbonyl-benzyl | m-tetrazolylbenzyl | m-pyrazolyl-benzyl |
| 39[d] | m-imidazolylbenzyl | p-fluorobenzyl | pyridinylmethyl |
| 40[d] | m-acetylbenzyl | m-aminosulfonyl-benzyl | m-methoxybenzyl |

TABLE 8[d]

Formula (IIIa), $R^4 = R^{23}$ = p-nitrobenzyl, $R^{22} = R^7$ = Table

| Ex.No | .0 | .1 | .2 |
|---|---|---|---|
| 41[d] | m-hydroxymethyl-benzyl | p-hydroxymethyl-benzyl | m-hydroxybenzyl |
| 42[d] | m-(N,N-dimethyl-amino glycyl)-aminobenzyl | m-aminocarbonyl-benzyl | p-hydroxybenzyl |
| 43[d] | m-(N-methylamino) carbonylbenzyl | m-(N-methylamino) benzyl | m-formylbenzyl |
| 44[d] | m-trifluorocarbonyl benzyl | m-hydroxyamidino benzyl | m-triazolylbenzyl |
| 45[d] | m-formaldoxime-benzyl | m-acetoximebenzyl | benzyl |
| 46[d] | hydroxycarbonyl-benzyl | m-tetrazolylbenzyl | m-pyrazolyl-benzyl |
| 47[d] | m-imidazolylbenzyl | p-fluorobenzyl | pyridinylmethyl |
| 48[d] | m-acetylbenzyl | m-aminosulfonyl-benzyl | m-methoxybenzyl |

TABLE 9[d]

Formula (IIIa), $R^4 = R^{23}$ = m-aminobenzyl, $R^{22} = R^7$ = Table

| Ex.No | .0 | .1 | .2 |
|---|---|---|---|
| 49[d] | m-hydroxymethyl-benzyl | p-hydroxymethyl-benzyl | m-hydroxybenzyl |
| 50[d] | m-(N,N-dimethyl-amino glycyl)-aminobenzyl | m-aminocarbonyl-benzyl | p-hydroxybenzyl |
| 51[d] | m-(N-methylamino) carbonylbenzyl | m-(N-methylamino) benzyl | m-formylbenzyl |
| 52[d] | m-trifluorocarbonyl benzyl | m-hydroxyamidino benzyl | m-triazolylbenzyl |
| 53[d] | m-formaldoxime-benzyl | m-acetoximebenzyl | benzyl |
| 54[d] | hydroxycarbonyl benzyl | m-tetrazolylbenzyl | m-pyrazolyl-benzyl |
| 55[d] | m-imidazolylbenzyl | p-fluorobenzyl | pyridinylmethyl |
| 56[d] | m-acetylbenzyl | m-aminosulfonyl-benzyl | m-methoxybenzyl |

TABLE 10[d]

Formula (IIIa), $R^4 = R^{23}$ = pyridinylmethyl, $R^{22} = R^7$ = Table

| Ex.No | .0 | .1 | .2 |
|---|---|---|---|
| 57[d] | m-hydroxymethyl-benzyl | p-hydroxymethyl-benzyl | m-hydroxybenzyl |
| 58[d] | m-(N,N-dimethyl-amino glycyl)-aminobenzyl | m-aminocarbonyl-benzyl | p-hydroxybenzyl |
| 59[d] | m-(N-methylamino) carbonylbenzyl | m-(N-methylamino) benzyl | m-formylbenzyl |
| 60[d] | m-trifluorocarbonyl benzyl | m-hydroxyamidino benzyl | m-triazolylbenzyl |
| 61[d] | m-formaldoxime-benzyl | m-acetoximebenzyl | benzyl |
| 62[d] | hydroxycarbonyl-benzyl | m-tetrazolylbenzyl | m-pyrazolyl-benzyl |
| 63[d] | m-imidazolylbenzyl | p-fluorobenzyl | pyridinylmethyl |
| 64[d] | m-acetylbenzyl | m-aminosulfonyl-benzyl | m-methoxybenzyl |

TABLE 11[d]

Formula (IIIa), $R^4 = R^{23}$ = m-hydroxybenzyl, $R^{22} = R^7$ = Table

| Ex.No | .0 | .1 | .2 |
|---|---|---|---|
| 65[d] | m-hydroxymethylbenzyl | p-hydroxymethylbenzyl | m-hydroxybenzyl |
| 66[d] | m-(N,N-dimethylamino glycyl)-aminobenzyl | m-aminocarbonylbenzyl | p-hydroxybenzyl |
| 67[d] | m-(N-methylamino)carbonylbenzyl | m-(N-methylamino)benzyl | m-formylbenzyl |
| 68[d] | m-trifluorocarbonylbenzyl | m-hydroxyamidinobenzyl | m-triazolylbenzyl |
| 69[d] | m-formaldoximebenzyl | m-acetoximebenzyl | benzyl |
| 70[d] | hydroxycarbonylbenzyl | m-tetrazolylbenzyl | m-pyrazolylbenzyl |
| 71[d] | m-imidazolylbenzyl | p-fluorobenzyl | pyridinylmethyl |
| 72[d] | m-acetylbenzyl | m-aminosulfonylbenzyl | m-methoxybenzyl |

TABLE 12[d]

Formula (IIIa), $R^4 = R^{23}$ = p-hydroxybenzyl, $R^{22} = R^7$ = Table

| Ex.No | .0 | .1 | .2 |
|---|---|---|---|
| 73[d] | m-hydroxymethylbenzyl | p-hydroxymethylbenzyl | m-hydroxybenzyl |
| 74[d] | m-(N,N-dimethylamino glycyl)-aminobenzyl | m-aminocarbonylbenzyl | p-hydroxybenzyl |
| 75[d] | m-(N-methylamino)carbonylbenzyl | m-(N-methylamino)benzyl | m-formylbenzyl |
| 76[d] | m-trifluorocarbonylbenzyl | m-hydroxyamidinobenzyl | m-triazolylbenzyl |
| 77[d] | m-formaldoximebenzyl | m-acetoximebenzyl | benzyl |
| 78[d] | hydroxycarbonylbenzyl | m-tetrazolylbenzyl | m-pyrazolylbenzyl |
| 79[d] | m-imidazolylbenzyl | p-fluorobenzyl | pyridinylmethyl |
| 80[d] | m-acetylbenzyl | m-amninosulfonylbenzyl | m-methoxybenzyl |

TABLE 13[d]

Formula (IIIa), $R^4 = R^{23}$ = m-aminocarbonybenzyl, $R^{22} = R^7$ = Table

| Ex.No | .0 | .1 | .2 |
|---|---|---|---|
| 81[d] | m-hydroxymethylbenzyl | p-hydroxymethylbenzyl | m-hydroxybenzyl |
| 82[d] | m-(N,N-dimethylamino glycyl)-aminobenzyl | m-aminocarbonylbenzyl | p-hydroxybenzyl |
| 83[d] | m-(N-methylamino)carbonylbenzyl | m-(N-methylamino)benzyl | m-formylbenzyl |
| 84[d] | m-trifluorocarbonylbenzyl | m-hydroxyamidinobenzyl | m-triazolylbenzyl |
| 85[d] | m-formaldoximebenzyl | m-acetoximebenzyl | benzyl |
| 86[d] | hydroxycarbonylbenzyl | m-tetrazolylbenzyl | m-pyrazolylbenzyl |
| 87[d] | m-imidazolylbenzyl | p-fluorobenzyl | pyridinylmethyl |
| 88[d] | m-acetylbenzyl | m-amninosulfonylbenzyl | m-methoxybenzyl |

TABLE 14[d]

Formula (IIIa), $R^4 = R^{23}$ = p-hydroxymethylbenzyl, $R^{22} = R^7$ = Table

| Ex.No | .0 | .1 | .2 |
|---|---|---|---|
| 89[d] | m-hydroxymethylbenzyl | p-hydroxymethylbenzyl | m-hydroxybenzyl |
| 90[d] | m-(N,N-dimethylamino glycyl)-aminobenzyl | m-aminocarbonylbenzyl | p-hydroxybenzyl |
| 91[d] | m-(N-methylamino)carbonylbenzyl | m-(N-methylamino)benzyl | m-formylbenzyl |
| 92[d] | m-trifluorcarbonylbenzyl | m-hydroxyamidinobenzyl | m-triazolylbenzyl |
| 93[d] | m-formaldoximebenzyl | m-acetoximebenzyl | benzyl |
| 94[d] | hydroxycarbonylbenzyl | m-tetrazolylbenzyl | m-pyrazolylbenzyl |
| 95[d] | m-imidazolylbenzyl | p-fluorobenzyl | pyridinylmethyl |
| 96[d] | m-acetylbenzyl | m-amninosulfonylbenzyl | m-methoxybenzyl |

TABLE 15[d]

Formula (IIIa), $R^4 = R^{23}$ = m-hydroxycarbonylbenzyl, $R^{22} = R^7$ = Table

| Ex.No | .0 | .1 | .2 |
|---|---|---|---|
| 97[d] | m-hydroxymethylbenzyl | p-hydroxymethylbenzyl | m-hydroxybenzyl |
| 98[d] | m-(N,N-dimethylamino glycyl)-aminobenzyl | m-aminocarbonylbenzyl | p-hydroxybenzyl |
| 99[d] | m-(N-methylamino)carbonylbenzyl | m-(N-methylamino)benzyl | m-formylbenzyl |
| 100[d] | m-trifluorcarbonylbenzyl | m-hydroxyamidinobenzyl | m-triazolylbenzyl |
| 101[d] | m-formaldoximebenzyl | m-acetoximebenzyl | benzyl |
| 102[d] | hydroxycarbonylbenzyl | m-tetrazolylbenzyl | m-pyrazolylbenzyl |
| 103[d] | m-imidazolylbenzyl | p-fluorobenzyl | pyridinylmethyl |
| 104[d] | m-acetylbenzyl | m-amninosulfonylbenzyl | m-methoxybenzyl |

TABLE 16[d]

Formula (IIIa), $R^4 = R^{23}$ = benzyl, $R^{22}$ = m-hydroxymethylbenzyl, $R^7$ = Table

| Ex.No | .0 | .1 | .2 |
|---|---|---|---|
| 105[d] | m-hydroxymethylbenzyl | p-hydroxymethylbenzyl | m-hydroxybenzyl |
| 106[d] | m-(N,N-dimethylamino glycyl)-aminobenzyl | m-aminocarbonylbenzyl | p-hydroxybenzyl |
| 107[d] | m-(N-methylamino)carbonylbenzyl | m-(N-methylamino)benzyl | m-formylbenzyl |
| 108[d] | m-trifluorcarbonylbenzyl | m-hydroxyamidinobenzyl | m-triazolylbenzyl |
| 109[d] | m-formaldoximebenzyl | m-acetoximebenzyl | benzyl |
| 110[d] | hydroxycarbonylbenzyl | m-tetrazolylbenzyl | m-pyrazolylbenzyl |
| 111[d] | m-imidazolylbenzyl | p-fluorobenzyl | pyridinylmethyl |
| 112[d] | m-acetylbenzyl | m-amninosulfonylbenzyl | m-methoxybenzyl |

TABLE 17[d]

Formula (IIIa), $R^4 = R^{23}$ = benzyl, $R^{22}$ = p-hydroxymethylbenzyl, $R^7$ = Table

| Ex.No | .0 | .1 | .2 |
|---|---|---|---|
| 113[d] | m-hydroxymethyl-benzyl | p-hydroxymethyl-benzyl | m-hydroxybenzyl |
| 114[d] | m-(N,N-dimethyl-amino glycyl)-aminobenzyl | m-aminocarbonyl-benzyl | p-hydroxybenzyl |
| 115[d] | m-(N-methylamino)carbonylbenzyl | m-(N-methylamino)benzyl | m-formylbenzyl |
| 116[d] | m-trifluorcarbonyl benzyl | m-hydroxyamidino benzyl | m-triazolylbenzyl |
| 117[d] | m-formaldoxime-benzyl | m-acetoximebenzyl | benzyl |
| 118[d] | hydroxycarbonyl-benzyl | m-tetrazolylbenzyl | m-pyrazolyl-benzyl |
| 119[d] | m-imidazolylbenzyl | p-fluorobenzyl | pyridinylmethyl |
| 120[d] | m-acetylbenzyl | m-amninosulfonyl-benzyl | m-methoxybenzyl |

TABLE 18[d]

Formula (IIIa), $R^4 = R^{23}$ = benzyl, $R^{22}$ = m-hydroxybenzyl, $R^7$ = Table

| Ex.No | .0 | .1 | .2 |
|---|---|---|---|
| 121[d] | m-hydroxymethyl-benzyl | p-hydroxymethyl-benzyl | m-hydroxybenzyl |
| 122[d] | m-(N,N-dimethyl-amino glycyl)-aminobenzyl | m-aminocarbonyl-benzyl | p-hydroxybenzyl |
| 123[d] | m-(N-methylamino)carbonylbenzyl | m-(N-methylamino)benzyl | m-formylbenzyl |
| 124[d] | m-trifluorcarbonyl benzyl | m-hydroxyamidino benzyl | m-triazolylbenzyl |
| 125[d] | m-formaldoxime-benzyl | m-acetoximebenzyl | benzyl |
| 126[d] | hydroxycarbonyl-benzyl | m-tetrazolylbenzyl | m-pyrazolyl-benzyl |
| 127[d] | m-imidazolylbenzyl | p-fluorobenzyl | pyridinylmethyl |
| 128[d] | m-acetylbenzyl | m-amninosulfonyl-benzyl | m-methoxybenzyl |

TABLE 19[d]

Formula (IIIa), $R^4 = R^{23}$ = benzyl, $R^{22}$ = m-(N,N-dimethylamino glycyl)aminobenzyl, $R^7$ = Table

| Ex.No | .0 | .1 | .2 |
|---|---|---|---|
| 129[d] | m-hydroxymethyl-benzyl | p-hydroxymethyl-benzyl | m-hydroxybenzyl |
| 130[d] | m-(N,N-dimethyl-amino glycyl)-aminobenzyl | m-aminocarbonyl-benzyl | p-hydroxybenzyl |
| 131[d] | m-(N-methylamino)carbonylbenzyl | m-(N-methylamino)benzyl | m-formylbenzyl |
| 132[d] | m-trifluorcarbonyl benzyl | m-hydroxyamidino benzyl | m-triazolylbenzyl |
| 133[d] | m-formaldoxime-benzyl | m-acetoximebenzyl | benzyl |
| 134[d] | hydroxycarbonyl-benzyl | m-tetrazolylbenzyl | m-pyrazolyl-benzyl |
| 135[d] | m-imidazolylbenzyl | p-fluorobenzyl | pyridinylmethyl |
| 136[d] | m-acetylbenzyl | m-amninosulfonyl-benzyl | m-methoxybenzyl |

TABLE 20[d]

Formula (IIIa), $R^4 = R^{23}$ = benzyl, $R^{22}$ = m-aminocarbonylbenzyl, $R^7$ = Table

| Ex.No | .0 | .1 | .2 |
|---|---|---|---|
| 137[d] | m-hydroxymethyl-benzyl | p-hydroxymethyl-benzyl | m-hydroxybenzyl |
| 138[d] | m-(N,N-dimethyl-amino glycyl)-aminobenzyl | m-aminocarbonyl-benzyl | p-hydroxybenzyl |
| 139[d] | m-(N-methylamino)carbonylbenzyl | m-(N-methylamino)benzyl | m-formylbenzyl |
| 140[d] | m-trifluorcarbonyl benzyl | m-hydroxyamidino benzyl | m-triazolylbenzyl |
| 141[d] | m-formaldoxime-benzyl | m-acetoximebenzyl | benzyl |
| 142[d] | hydroxycarbonyl-benzyl | m-tetrazolylbenzyl | m-pyrazolyl-benzyl |
| 143[d] | m-imidazolylbenzyl | p-fluorobenzyl | pyridinylmethyl |
| 144[d] | m-acetylbenzyl | m-amninosulfonyl-benzyl | m-methoxybenzyl |

TABLE 21[d]

Formula (IIIa), $R^4 = R^{23}$ = benzyl, $R^{22}$ = p-hydroxybenzyl, $R^7$ = Table

| Ex.No | .0 | .1 | .2 |
|---|---|---|---|
| 145[d] | m-hydroxymethyl-benzyl | p-hydroxymethyl-benzyl | m-hydroxybenzyl |
| 146[d] | m-(N,N-dimethyl-amino glycyl)-aminobenzyl | m-aminocarbonyl-benzyl | p-hydroxybenzyl |
| 147[d] | m-(N-methylamino)carbonylbenzyl | m-(N-methylamino)benzyl | m-formylbenzyl |
| 148[d] | m-trifluorcarbonyl benzyl | m-hydroxyamidino benzyl | m-triazolylbenzyl |
| 149[d] | m-formaldoxime-benzyl | m-acetoximebenzyl | benzyl |
| 150[d] | hydroxycarbonyl-benzyl | m-tetrazolylbenzyl | m-pyrazolyl-benzyl |
| 151[d] | m-imidazolylbenzyl | p-fluorobenzyl | pyridinylmethyl |
| 152[d] | m-acetylbenzyl | m-amninosulfonyl-benzyl | m-methoxybenzyl |

TABLE 22[d]

Formula (IIIa), $R^4 = R^{23}$ = benzyl, $R^{22}$ = m-(N-methylaminocarbonyl benzyl, $R^7$ = Table

| Ex.No | .0 | .1 | .2 |
|---|---|---|---|
| 153[d] | m-hydroxymethyl-benzyl | p-hydroxymethyl-benzyl | m-hydroxybenzyl |
| 154[d] | m-(N,N-dimethyl-amino glycyl)-aminobenzyl | m-aminocarbonyl-benzyl | p-hydroxybenzyl |
| 155[d] | m-(N-methylamino)carbonylbenzyl | m-(N-methylamino)benzyl | m-formylbenzyl |
| 156[d] | m-trifluorcarbonyl benzyl | m-hydroxyamidino benzyl | m-triazolylbenzyl |
| 157[d] | m-formaldoxime-benzyl | m-acetoximebenzyl | benzyl |
| 158[d] | hydroxycarbonyl-benzyl | m-tetrazolylbenzyl | m-pyrazolyl-benzyl |
| 159[d] | m-imidazolylbenzyl | p-fluorobenzyl | pyridinylmethyl |
| 160[d] | m-acetylbenzyl | m-amninosulfonyl-benzyl | m-methoxybenzyl |

TABLE 23[d]

Formula (IIIa), $R^4 = R^{23}$ = benzyl, $R^{22}$ = m-(N-methylamino)benzyl, $R^7$ = Table

| Ex.No | .0 | .1 | .2 |
|---|---|---|---|
| 161[d] | m-hydroxymethyl-benzyl | p-hydroxymethyl-benzyl | m-hydroxybenzyl |
| 162[d] | m-(N,N-dimethyl-amino glycyl)-aminobenzyl | m-aminocarbonyl-benzyl | p-hydroxybenzyl |
| 163[d] | m-(N-methylamino)carbonylbenzyl | m-(N-methylamino)benzyl | m-formylbenzyl |
| 164[d] | m-trifluorcarbonyl benzyl | m-hydroxyamidino benzyl | m-triazolylbenzyl |
| 165[d] | m-formaldoxime-benzyl | m-acetoximebenzyl | benzyl |
| 166[d] | hydroxycarbonyl-benzyl | m-tetrazolylbenzyl | m-pyrazolyl-benzyl |
| 167[d] | m-imidazolylbenzyl | p-fluorobenzyl | pyridinylmethyl |
| 168[d] | m-acetylbenzyl | m-amninosulfonyl-benzyl | m-methoxybenzyl |

TABLE 24[d]

Formula (IIIa), $R^4 = R^{23}$ = benzyl, $R^{22}$ = m-formyllbenzyl, $R^7$ = Table

| Ex.No | .0 | .1 | .2 |
|---|---|---|---|
| 169[d] | m-hydroxymethyl-benzyl | p-hydroxymethyl-benzyl | m-hydroxybenzyl |
| 170[d] | m-(N,N-dimethyl-amino glycyl)-aminobenzyl | m-aminocarbonyl-benzyl | p-hydroxybenzyl |
| 171[d] | m-(N-methylamino)carbonylbenzyl | m-(N-methylamino)benzyl | m-formylbenzyl |
| 172[d] | m-trifluorcarbonyl benzyl | m-hydroxyamidino benzyl | m-triazolylbenzyl |
| 173[d] | m-formaldoxime-benzyl | m-acetoximebenzyl | benzyl |
| 174[d] | hydroxycarbonyl-benzyl | m-tetrazolylbenzyl | m-pyrazolyl-benzyl |
| 175[d] | m-imidazolylbenzyl | p-fluorobenzyl | pyridinylmethyl |
| 176[d] | m-acetylbenzyl | m-amninosulfonyl-benzyl | m-methoxybenzyl |

TABLE 25[d]

Formula (IIIa), $R^4 = R^{23}$ = benzyl, $R^{22}$ = m-trifluorocarbonylbenzyl, $R^7$ = Table

| Ex.No | .0 | .1 | .2 |
|---|---|---|---|
| 177[d] | m-hydroxymethyl-benzyl | p-hydroxymethyl-benzyl | m-hydroxybenzyl |
| 178[d] | m-(N,N-dimethyl-amino glycyl)-aminobenzyl | m-aminocarbonyl-benzyl | p-hydroxybenzyl |
| 179[d] | m-(N-methylamino)carbonylbenzyl | m-(N-methylamino)benzyl | m-formylbenzyl |
| 180[d] | m-trifluorcarbonyl benzyl | m-hydroxyamidino benzyl | m-triazolylbenzyl |
| 181[d] | m-formaldoxime-benzyl | m-acetoximebenzyl | benzyl |
| 182[d] | hydroxycarbonyl-benzyl | m-tetrazolylbenzyl | m-pyrazolyl-benzyl |
| 183[d] | m-imidazolylbenzyl | p-fluorobenzyl | pyridinylmethyl |
| 184[d] | m-acetylbenzyl | m-amninosulfonyl-benzyl | m-methoxybenzyl |

TABLE 26[d]

Formula (IIIa), $R^4 = R^{23}$ = benzyl, $R^{22}$ = m-hydroxyamidinobenzyl, $R^7$ = Table

| Ex.No | .0 | .1 | .2 |
|---|---|---|---|
| 185[d] | m-hydroxymethyl-benzyl | p-hydroxymethyl-benzyl | m-hydroxybenzyl |
| 186[d] | m-(N,N-dimethyl-amino glycyl)-aminobenzyl | m-aminocarbonyl-benzyl | p-hydroxybenzyl |
| 187[d] | m-(N-methylamino)carbonylbenzyl | m-(N-methylamino)benzyl | m-formylbenzyl |
| 188[d] | m-trifluorcarbonyl benzyl | m-hydroxyamidino benzyl | m-triazolylbenzyl |
| 189[d] | m-formaldoxime-benzyl | m-acetoximebenzyl | benzyl |
| 190[d] | hydroxycarbonyl-benzyl | m-tetrazolylbenzyl | m-pyrazolyl-benzyl |
| 191[d] | m-imidazolylbenzyl | p-fluorobenzyl | pyridinylmethyl |
| 192[d] | m-acetylbenzyl | m-amninosulfonyl-benzyl | m-methoxybenzyl |

TABLE 27[d]

Formula (IIIa), $R^4 = R^{23}$ = benzyl, $R^{22}$ = m-triazolylbenzyl, $R^7$ = Table

| Ex.No | .0 | .1 | .2 |
|---|---|---|---|
| 193[d] | m-hydroxymethyl-benzyl | p-hydroxymethyl-benzyl | m-hydroxybenzyl |
| 194[d] | m-(N,N-dimethyl-amino glycyl)-aminobenzyl | m-aminocarbonyl-benzyl | p-hydroxybenzyl |
| 195[d] | m-(N-methylamino)carbonylbenzyl | m-(N-methylamino)benzyl | m-formylbenzyl |
| 196[d] | m-trifluorcarbonyl benzyl | m-hydroxyamidino benzyl | m-triazolylbenzyl |
| 197[d] | m-formaldoxime-benzyl | m-acetoximebenzyl | benzyl |
| 198[d] | hydroxycarbonyl-benzyl | m-tetrazolylbenzyl | m-pyrazolyl-benzyl |
| 199[d] | m-imidazolylbenzyl | p-fluorobenzyl | pyridinylmethyl |
| 200[d] | m-acetylbenzyl | m-amninosulfonyl-benzyl | m-methoxybenzyl |

TABLE 28[d]

Formula (IIIa), $R^4 = R^{23}$ = benzyl, $R^{22}$ = m-formaldoximebenzyl, $R^7$ = Table

| Ex.No | .0 | .1 | .2 |
|---|---|---|---|
| 201[d] | m-hydroxymethyl-benzyl | p-hydroxymethyl-benzyl | m-hydroxybenzyl |
| 202[d] | m-(N,N-dimethyl-amino glycyl)-aminobenzyl | m-aminocarbonyl-benzyl | p-hydroxybenzyl |
| 203[d] | m-(N-methylamino)carbonylbenzyl | m-(N-methylamino)benzyl | m-formylbenzyl |
| 204[d] | m-trifluorcarbonyl benzyl | m-hydroxyamidino benzyl | m-triazolylbenzyl |
| 205[d] | m-formaldoxime-benzyl | m-acetoximebenzyl | benzyl |
| 206[d] | hydroxycarbonyl-benzyl | m-tetrazolylbenzyl | m-pyrazolyl-benzyl |
| 207[d] | m-imidazolylbenzyl | p-fluorobenzyl | pyridinylmethyl |
| 208[d] | m-acetylbenzyl | m-amninosulfonyl-benzyl | m-methoxybenzyl |

TABLE 29[d]

Formula (IIIa), $R^4 = R^{23}$ = benzyl, $R^{22}$ = m-acetoximebenzyl, $R^7$ = Table

| Ex.No | .0 | .1 | .2 |
|---|---|---|---|
| 209[d] | m-hydroxymethyl-benzyl | p-hydroxymethyl-benzyl | m-hydroxybenzyl |
| 210[d] | m-(N,N-dimethyl-amino glycyl)-aminobenzyl | m-aminocarbonyl-benzyl | p-hydroxybenzyl |
| 211[d] | m-(N-methylamino)carbonylbenzyl | m-(N-methylamino)benzyl | m-formylbenzyl |
| 212[d] | m-trifluorcarbonyl benzyl | m-hydroxyamidino benzyl | m-triazolylbenzyl |
| 213[d] | m-formaldoxime-benzyl | m-acetoximebenzyl | benzyl |
| 214[d] | hydroxycarbonyl benzyl | m-tetrazolylbenzyl | m-pyrazolyl-benzyl |
| 215[d] | m-imidazolylbenzyl | p-fluorobenzyl | pyridinylmethyl |
| 216[d] | m-acetylbenzyl | m-amninosulfonyl-benzyl | m-methoxybenzyl |

TABLE 30[d]

Formula (IIIa), $R^4 = R^{23}$ = benzyl, $R^{22}$ = benzyl, $R^7$ = Table

| Ex.No | .0 | .1 | .2 |
|---|---|---|---|
| 217[d] | m-hydroxymethyl-benzyl | p-hydroxymethyl-benzyl | m-hydroxybenzyl |
| 218[d] | m-(N,N-dimethyl-amino glycyl)-aminobenzyl | m-aminocarbonyl-benzyl | p-hydroxybenzyl |
| 219[d] | m-(N-methylamino)carbonylbenzyl | m-(N-methylamino)benzyl | m-formylbenzyl |
| 220[d] | m-trifluorcarbonyl benzyl | m-hydroxyamidino benzyl | m-triazolylbenzyl |
| 221[d] | m-formaldoxime-benzyl | m-acetoximebenzyl | benzyl |
| 222[d] | hydroxycarbonyl benzyl | m-tetrazolylbenzyl | m-pyrazolyl-benzyl |
| 223[d] | m-imidazolylbenzyl | p-fluorobenzyl | pyridinylmethyl |
| 224[d] | m-acetylbenzyl | m-amninosulfonyl-benzyl | m-methoxybenzyl |

TABLE 31[d]

Formula (IIIa), $R^4 = R^{23}$ = benzyl, $R^{22}$ = m-hydroxycarbonylbenzyl, $R^7$ = Table

| Ex.No | .0 | .1 | .2 |
|---|---|---|---|
| 225[d] | m-hydroxymethyl-benzyl | p-hydroxymethyl-benzyl | m-hydroxybenzyl |
| 226[d] | m-(N,N-dimethyl-amino glycyl)-aminobenzyl | m-aminocarbonyl-benzyl | p-hydroxybenzyl |
| 227[d] | m-(N-methylamino)carbonylbenzyl | m-(N-methylamino)benzyl | m-formylbenzyl |
| 228[d] | m-trifluorcarbonyl benzyl | m-hydroxyamidino benzyl | m-triazolylbenzyl |
| 229[d] | m-formaldoxime-benzyl | m-acetoximebenzyl | benzyl |
| 230[d] | hydroxycarbonyl benzyl | m-tetrazolylbenzyl | m-pyrazolyl-benzyl |
| 231[d] | m-imidazolylbenzyl | p-fluorobenzyl | pyridinylmethyl |
| 232[d] | m-acetylbenzyl | m-amninosulfonyl-benzyl | m-methoxybenzyl |

TABLE 32[d]

Formula (IIIa), $R^4 = R^{23}$ = benzyl, $R^{22}$ = m-tetrazolylbenzyl, $R^7$ = Table

| Ex.No | .0 | .1 | .2 |
|---|---|---|---|
| 233[d] | m-hydroxymethyl-benzyl | p-hydroxymethyl-benzyl | m-hydroxybenzyl |
| 234[d] | m-(N,N-dimethyl-amino glycyl)-aminobenzyl | m-aminocarbonyl-benzyl | p-hydroxybenzyl |
| 235[d] | m-(N-methylamino)carbonylbenzyl | m-(N-methylamino)benzyl | m-formylbenzyl |
| 236[d] | m-trifluorcarbonyl benzyl | m-hydroxyamidino benzyl | m-triazolylbenzyl |
| 237[d] | m-formaldoxime-benzyl | m-acetoximebenzyl | benzyl |
| 238[d] | hydroxycarbonyl benzyl | m-tetrazolylbenzyl | m-pyrazolyl-benzyl |
| 239[d] | m-imidazolylbenzyl | p-fluorobenzyl | pyridinylmethyl |
| 240[d] | m-acetylbenzyl | m-aminosulfonyl-benzyl | m-methoxybenzyl |

TABLE 33[d]

Formula (IIIa), $R^4 = R^{23}$ = benzyl, $R^{22}$ = m-pyrazolylbenzyl, $R^7$ = Table

| Ex.No | .0 | .1 | .2 |
|---|---|---|---|
| 241[d] | m-hydroxymethyl-benzyl | p-hydroxymethyl-benzyl | m-hydroxybenzyl |
| 242[d] | m-(N,N-dimethyl-amino glycyl)-aminobenzyl | m-aminocarbonyl-benzyl | p-hydroxybenzyl |
| 243[d] | m-(N-methylamino)carbonylbenzyl | m-(N-methylamino)benzyl | m-formylbenzyl |
| 244[d] | m-trifluorcarbonyl benzyl | m-hydroxyamidino benzyl | m-triazolylbenzyl |
| 245[d] | m-formaldoxime-benzyl | m-acetoximebenzyl | benzyl |
| 246[d] | hydroxycarbonyl benzyl | m-tetrazolylbenzyl | m-pyrazolyl-benzyl |
| 247[d] | m-imidazolylbenzyl | p-fluorobenzyl | pyridinylmethyl |
| 248[d] | m-acetylbenzyl | m-aminosulfonyl-benzyl | m-methoxybenzyl |

TABLE 34[d]

Formula (IIIa), $R^4 = R^{23}$ = benzyl, $R^{22}$ = m-imidazolylbenzyl, $R^7$ = Table

| Ex.No | .0 | .1 | .2 |
|---|---|---|---|
| 249[d] | m-hydroxymethyl-benzyl | p-hydroxymethyl-benzyl | m-hydroxybenzyl |
| 250[d] | m-(N,N-dimethyl-amino glycyl)-aminobenzyl | m-aminocarbonyl-benzyl | p-hydroxybenzyl |
| 251[d] | m-(N-methylamino)carbonylbenzyl | m-(N-methylamino)benzyl | m-formylbenzyl |
| 252[d] | m-trifluorcarbonyl benzyl | m-hydroxyamidino benzyl | m-triazolylbenzyl |
| 253[d] | m-formaldoxime-benzyl | m-acetoximebenzyl | benzyl |
| 254[d] | hydroxycarbonyl benzyl | m-tetrazolylbenzyl | m-pyrazolyl-benzyl |
| 255[d] | m-imidazolylbenzyl | p-fluorobenzyl | pyridinylmethyl |
| 256[d] | m-acetylbenzyl | m-aminosulfonyl-benzyl | m-methoxybenzyl |

TABLE 35[d]

Formula (IIIa), $R^4 = R^{23}$ = benzyl, $R^{22}$ = p-fluorobenzyl, $R^7$ = Table

| Ex.No | .0 | .1 | .2 |
|---|---|---|---|
| 257[d] | m-hydroxymethyl-benzyl | p-hydroxymethyl-benzyl | m-hydroxybenzyl |
| 258[d] | m-(N,N-dimethyl-amino glycyl)-aminobenzyl | m-aminocarbonyl-benzyl | p-hydroxybenzyl |
| 259[d] | m-(N-methylamino)carbonylbenzyl | m-(N-methylamino)benzyl | m-formylbenzyl |
| 260[d] | m-trifluorcarbonyl benzyl | m-hydroxyamidino benzyl | m-triazolylbenzyl |
| 261[d] | m-formaldoxime-benzyl | m-acetoximebenzyl | benzyl |
| 262[d] | hydroxycarbonyl-benzyl | m-tetrazolylbenzyl | m-pyrazolyl-benzyl |
| 263[d] | m-imidazolylbenzyl | p-fluorobenzyl | pyridinylmethyl |
| 264[d] | m-acetylbenzyl | m-aminosulfonyl-benzyl | m-methoxybenzyl |

TABLE 36[d]

Formula (IIIa), $R^4 = R^{23}$ = benzyl, $R^{22}$ = pyridinylmethyl, $R^7$ = Table

| Ex.No | .0 | .1 | .2 |
|---|---|---|---|
| 265[d] | m-hydroxymethyl-benzyl | p-hydroxymethyl-benzyl | m-hydroxybenzyl |
| 266[d] | m-(N,N-dimethyl-amino glycyl)-aminobenzyl | m-aminocarbonyl-benzyl | p-hydroxybenzyl |
| 267[d] | m-(N-methylamino)carbonylbenzyl | m-(N-methylamino)benzyl | m-formylbenzyl |
| 268[d] | m-trifluorcarbonyl benzyl | m-hydroxyamidino benzyl | m-triazolylbenzyl |
| 269[d] | m-formaldoxime-benzyl | m-acetoximebenzyl | benzyl |
| 270[d] | hydroxycarbonyl-benzyl | m-tetrazolylbenzyl | m-pyrazolyl-benzyl |
| 271[d] | m-imidazolylbenzyl | p-fluorobenzyl | pyridinylmethyl |
| 272[d] | m-acetylbenzyl | m-aminosulfonyl-benzyl | m-methoxybenzyl |

TABLE 37[d]

Formula (IIIa), $R^4 = R^{23}$ = benzyl, $R^{22}$ = m-acetylbenzyl, $R^7$ = Table

| Ex.No | .0 | .1 | .2 |
|---|---|---|---|
| 273[d] | m-hydroxymethyl-benzyl | p-hydroxymethyl-benzyl | m-hydroxybenzyl |
| 274[d] | m-(N,N-dimethyl-amino glycyl)-aminobenzyl | m-aminocarbonyl-benzyl | p-hydroxybenzyl |
| 275[d] | m-(N-methylamino)carbonylbenzyl | m-(N-methylamino)benzyl | m-formylbenzyl |
| 276[d] | m-trifluorcarbonyl benzyl | m-hydroxyamidino benzyl | m-triazolylbenzyl |
| 277[d] | m-formaldoxime-benzyl | m-acetoximebenzyl | benzyl |
| 278[d] | hydroxycarbonyl-benzyl | m-tetrazolylbenzyl | m-pyrazolyl-benzyl |
| 279[d] | m-imidazolylbenzyl | p-fluorobenzyl | pyridinylmethyl |
| 280[d] | m-acetylbenzyl | m-aminosulfonyl-benzyl | m-methoxybenzyl |

TABLE 38[d]

Formula (IIIa), $R^4 = R^{23}$ = benzyl, $R^{22}$ = m-aminosulfonylbenzyl, $R^7$ = Table

| Ex.No | .0 | .1 | .2 |
|---|---|---|---|
| 281[d] | m-hydroxymethyl-benzyl | p-hydroxymethyl-benzyl | m-hydroxybenzyl |
| 282[d] | m-(N,N-dimethyl-amino glycyl)-aminobenzyl | m-aminocarbonyl-benzyl | p-hydroxybenzyl |
| 283[d] | m-(N-methylamino)carbonylbenzyl | m-(N-methylamino)benzyl | m-formylbenzyl |
| 284[d] | m-trifluorcarbonyl benzyl | m-hydroxyamidino benzyl | m-triazolylbenzyl |
| 285[d] | m-formaldoxime-benzyl | m-acetoximebenzyl | benzyl |
| 286[d] | hydroxycarbonyl-benzyl | m-tetrazolylbenzyl | m-pyrazolyl-benzyl |
| 287[d] | m-imidazolylbenzyl | p-fluorobenzyl | pyridinylmethyl |
| 288[d] | m-acetylbenzyl | m-aminosulfonyl-benzyl | m-methoxybenzyl |

TABLE 39[d]

Formula (IIIa), $R^4 = R^{23}$ = benzyl, $R^{22}$ = m-methoxybenzyl, $R^7$ = Table

| Ex.No | .0 | .1 | .2 |
|---|---|---|---|
| 289[d] | m-hydroxymethyl-benzyl | p-hydroxymethyl-benzyl | m-hydroxybenzyl |
| 290[d] | m-(N,N-dimethyl-amino glycyl)-aminobenzyl | m-aminocarbonyl-benzyl | p-hydroxybenzyl |
| 291[d] | m-(N-methylamino)carbonylbenzyl | m-(N-methylamino)benzyl | m-formylbenzyl |
| 292[d] | m-trifluorcarbonyl benzyl | m-hydroxyamidino benzyl | m-triazolylbenzyl |
| 293[d] | m-formaldoxime-benzyl | m-acetoximebenzyl | benzyl |
| 294[d] | hydroxycarbonyl-benzyl | m-tetrazolylbenzyl | m-pyrazolyl-benzyl |
| 295[d] | m-imidazolylbenzyl | p-fluorobenzyl | pyridinylmethyl |
| 296[d] | m-acetylbenzyl | m-aminosulfonyl-benzyl | m-methoxybenzyl |

TABLE 3[e]

Formula (IVa), $R^4 = R^{23}$ = benzyl, $R^{22} = R^7$ = Table

| Ex.No | .0 | .1 | .2 |
|---|---|---|---|
| 1[e] | m-hydroxymethyl-benzyl | p-hydroxymethyl-benzyl | m-hydroxybenzyl |
| 2[e] | m-(N,N-dimethyl-amino glycyl)-aminobenzyl | m-aminocarbonyl-benzyl | p-hydroxybenzyl |
| 3[e] | m-(N-methylamino)carbonylbenzyl | m-(N-methylamino)benzyl | m-formylbenzyl |
| 4[e] | m-trifluorocarbonyl benzyl | m-hydroxyamidino benzyl | m-triazolylbenzyl |
| 5[e] | m-formaldoxime-benzyl | m-acetoximebenzyl | benzyl |
| 6[e] | hydroxycarbonyl-benzyl | m-tetrazolylbenzyl | m-pyrazolyl-benzyl |
| 7[e] | m-imidazolylbenzyl | p-fluorobenzyl | pyridinylmethyl |
| 8[e] | m-acetylbenzyl | m-aminosulfonyl-benzyl | m-methoxybenzyl |

TABLE 4[e]

Formula (IVa), $R^4 = R^{23}$ = fluorobenzyl, $R^{22} = R^7$ = Table

| Ex.No | .0 | .1 | .2 |
|---|---|---|---|
| 9[e] | m-hydroxymethyl-benzyl | p-hydroxymethyl-benzyl | m-hydroxybenzyl |
| 10[e] | m-(N,N-dimethyl-amino glycyl)-aminobenzyl | m-aminocarbonyl-benzyl | p-hydroxybenzyl |
| 11[e] | m-(N-methylamino)carbonylbenzyl | m-(N-methylamino)benzyl | m-formylbenzyl |
| 12[e] | m-trifluorocarbonyl benzyl | m-hydroxyamidino benzyl | m-triazolylbenzyl |
| 13[e] | m-formaldoxime-benzyl | m-acetoximebenzyl | benzyl |
| 14[e] | hydroxycarbonyl-benzyl | m-tetrazolylbenzyl | m-pyrazolyl-benzyl |
| 15[e] | m-imidazolylbenzyl | p-fluorobenzyl | pyridinylmethyl |
| 16[e] | m-acetylbenzyl | m-aminosulfonyl-benzyl | m-methoxybenzyl |

TABLE 5[e]

Formula (IVa), $R^4 = R^{23}$ = pyrrolylmethyl, $R^{22} = R^7$ = Table

| Ex.No | .0 | .1 | .2 |
|---|---|---|---|
| 17[e] | m-hydroxymethyl-benzyl | p-hydroxymethyl-benzyl | m-hydroxybenzyl |
| 18[e] | m-(N,N-dimethyl-amino glycyl)-aminobenzyl | m-aminocarbonyl-benzyl | p-hydroxybenzyl |
| 19[e] | m-(N-methylamino)carbonylbenzyl | m-(N-methylamino)benzyl | m-formylbenzyl |
| 20[e] | m-trifluorocarbonyl benzyl | m-hydroxyamidino benzyl | m-triazolylbenzyl |
| 21[e] | m-formaldoxime-benzyl | m-acetoximebenzyl | benzyl |
| 22[e] | hydroxycarbonyl-benzyl | m-tetrazolylbenzyl | m-pyrazolyl-benzyl |
| 23[e] | m-imidazolylbenzyl | p-fluorobenzyl | pyridinylmethyl |
| 24[e] | m-acetylbenzyl | m-aminosulfonyl-benzyl | m-methoxybenzyl |

TABLE 6[e]

Formula (IVa), $R^4 = R^{23}$ = methoxybenzyl, $R^{22} = R^7$ = Table

| Ex.No | .0 | .1 | .2 |
|---|---|---|---|
| 25[e] | m-hydroxymethyl-benzyl | p-hydroxymethyl-benzyl | m-hydroxybenzyl |
| 26[e] | m-(N,N-dimethyl-amino glycyl)-aminobenzyl | m-aminocarbonyl-benzyl | p-hydroxybenzyl |
| 27[e] | m-(N-methylamino)carbonylbenzyl | m-(N-methylamino)benzyl | m-formylbenzyl |
| 28[e] | m-trifluorocarbonyl benzyl | m-hydroxyamidino benzyl | m-triazolylbenzyl |
| 29[e] | m-formaldoxime-benzyl | m-acetoximebenzyl | benzyl |
| 30[e] | hydroxycarbonyl-benzyl | m-tetrazolylbenzyl | m-pyrazolyl-benzyl |
| 31[e] | m-imidazolylbenzyl | p-fluorobenzyl | pyridinylmethyl |
| 32[e] | m-acetylbenzyl | m-aminosulfonyl-benzyl | m-methoxybenzyl |

TABLE 7[e]

Formula (IVa), $R^4 = R^{23}$ = isobutyl, $R^{22} = R^7$ = Table

| Ex.No | .0 | .1 | .2 |
|---|---|---|---|
| 33[e] | m-hydroxymethyl-benzyl | p-hydroxymethyl-benzyl | m-hydroxybenzyl |
| 34[e] | m-(N,N-dimethyl-amino glycyl)-aminobenzyl | m-aminocarbonyl-benzyl | p-hydroxybenzyl |
| 35[e] | m-(N-methylamino)carbonylbenzyl | m-(N-methylamino)benzyl | m-formylbenzyl |
| 36[e] | m-trifluorocarbonyl benzyl | m-hydroxyamidino benzyl | m-triazolylbenzyl |
| 37[e] | m-formaldoxime-benzyl | m-acetoximebenzyl | benzyl |
| 38[e] | hydroxycarbonyl-benzyl | m-tetrazolylbenzyl | m-pyrazolyl-benzyl |
| 39[e] | m-imidazolylbenzyl | p-fluorobenzyl | pyridinylmethyl |
| 40[e] | m-acetylbenzyl | m-aminosulfonyl-benzyl | m-methoxybenzyl |

TABLE 8[e]

Formula (IVa), $R^4 = R^{23}$ = p-nitrobenzyl, $R^{22} = R^7$ = Table

| Ex.No | .0 | .1 | .2 |
|---|---|---|---|
| 41[e] | m-hydroxymethyl-benzyl | p-hydroxymethyl-benzyl | m-hydroxybenzyl |
| 42[e] | m-(N,N-dimethyl-amino glycyl)-aminobenzyl | m-aminocarbonyl-benzyl | p-hydroxybenzyl |
| 43[e] | m-(N-methylamino)carbonylbenzyl | m-(N-methylamino)benzyl | m-formylbenzyl |
| 44[e] | m-trifluorocarbonyl benzyl | m-hydroxyamidino benzyl | m-triazolylbenzyl |
| 45[e] | m-formaldoxime-benzyl | m-acetoximebenzyl | benzyl |
| 46[e] | hydroxycarbonyl-benzyl | m-tetrazolylbenzyl | m-pyrazolyl-benzyl |
| 47[e] | m-imidazolylbenzyl | p-fluorobenzyl | pyridinylmethyl |
| 48[e] | m-acetylbenzyl | m-aminosulfonyl-benzyl | m-methoxybenzyl |

TABLE 9[e]

Formula (IVa), $R^4 = R^{23}$ = m-aminobenzyl, $R^{22} = R^7$ = Table

| Ex.No | .0 | .1 | .2 |
|---|---|---|---|
| 49[e] | m-hydroxymethyl-benzyl | p-hydroxymethyl-benzyl | m-hydroxybenzyl |
| 50[e] | m-(N,N-dimethyl-amino glycyl)-aminobenzyl | m-aminocarbonyl-benzyl | p-hydroxybenzyl |
| 51[e] | m-(N-methylamino)carbonylbenzyl | m-(N-methylamino)benzyl | m-formylbenzyl |
| 52[e] | m-trifluorocarbonyl benzyl | m-hydroxyamidino benzyl | m-triazolylbenzyl |
| 53[e] | m-formaldoxime-benzyl | m-acetoximebenzyl | benzyl |
| 54[e] | hydroxycarbonyl-benzyl | m-tetrazolylbenzyl | m-pyrazolyl-benzyl |
| 55[e] | m-imidazolylbenzyl | p-fluorobenzyl | pyridinylmethyl |
| 56[e] | m-acetylbenzyl | m-aminosulfonyl-benzyl | m-methoxybenzyl |

TABLE 10[e]

Formula (IVa), R$^4$ = R$^{23}$ = pyridinylmethyl, R$^{22}$ = R$^7$ = Table

| Ex.No | .0 | .1 | .2 |
|---|---|---|---|
| 57[e] | m-hydroxymethyl-benzyl | p-hydroxymethyl-benzyl | m-hydroxybenzyl |
| 58[e] | m-(N,N-dimethyl-amino glycyl)-aminobenzyl | m-aminocarbonyl-benzyl | p-hydroxybenzyl |
| 59[e] | m-(N-methylamino)carbonylbenzyl | m-(N-methylamino)benzyl | m-formylbenzyl |
| 60[e] | m-trifluorocarbonyl benzyl | m-hydroxyamidino benzyl | m-triazolylbenzyl |
| 61[e] | m-formaldoxime-benzyl | m-acetoximebenzyl | benzyl |
| 62[e] | hydroxycarbonyl-benzyl | m-tetrazolylbenzyl | m-pyrazolyl-benzyl |
| 63[e] | m-imidazolylbenzyl | p-fluorobenzyl | pyridinylmethyl |
| 64[e] | m-acetylbenzyl | m-aminosulfonyl-benzyl | m-methoxybenzyl |

TABLE 11[e]

Formula (IVa), R$^4$ = R$^{23}$ = m-hydroxybenzyl, R$^{22}$ = R$^7$ = Table

| Ex.No | .0 | .1 | .2 |
|---|---|---|---|
| 65[e] | m-hydroxymethyl-benzyl | p-hydroxymethyl-benzyl | m-hydroxybenzyl |
| 66[e] | m-(N,N-dimethyl-amino glycyl)-aminobenzyl | m-aminocarbonyl-benzyl | p-hydroxybenzyl |
| 67[e] | m-(N-methylamino)carbonylbenzyl | m-(N-methylamino)benzyl | m-formylbenzyl |
| 68[e] | m-trifluorocarbonyl benzyl | m-hydroxyamidino benzyl | m-triazolylbenzyl |
| 69[e] | m-formaldoxime-benzyl | m-acetoximebenzyl | benzyl |
| 70[e] | hydroxycarbonyl-benzyl | m-tetrazolylbenzyl | m-pyrazolyl-benzyl |
| 71[e] | m-imidazolylbenzyl | p-fluorobenzyl | pyridinylmethyl |
| 72[e] | m-acetylbenzyl | m-aminosulfonyl-benzyl | m-methoxybenzyl |

TABLE 12[e]

Formula (IVa), R$^4$ = R$^{23}$ = p-hydroxybenzyl, R$^{22}$ = R$^7$ = Table

| Ex.No | .0 | .1 | .2 |
|---|---|---|---|
| 73[e] | m-hydroxymethyl-benzyl | p-hydroxymethyl-benzyl | m-hydroxybenzyl |
| 74[e] | m-(N,N-dimethyl-amino glycyl)-aminobenzyl | m-aminocarbonyl-benzyl | p-hydroxybenzyl |
| 75[e] | m-(N-methylamino)carbonylbenzyl | m-(N-methylamino)benzyl | m-formylbenzyl |
| 76[e] | m-trifluorocarbonyl benzyl | m-hydroxyamidino benzyl | m-triazolylbenzyl |
| 77[e] | m-formaldoxime-benzyl | m-acetoximebenzyl | benzyl |
| 78[e] | hydroxycarbonyl-benzyl | m-tetrazolylbenzyl | m-pyrazolyl-benzyl |
| 79[e] | m-imidazolylbenzyl | p-fluorobenzyl | pyridinylmethyl |
| 80[e] | m-acetylbenzyl | m-aminosulfonyl-benzyl | m-methoxybenzyl |

TABLE 13[e]

Formula (IVa), R$^4$ = R$^{23}$ = m-aminocarbonylbenzyl, R$^{22}$ = R$^7$ = Table

| Ex.No | .0 | .1 | .2 |
|---|---|---|---|
| 81[e] | m-hydroxymethyl-benzyl | p-hydroxymethyl-benzyl | m-hydroxybenzyl |
| 82[e] | m-(N,N-dimethyl-amino glycyl)-aminobenzyl | m-aminocarbonyl-benzyl | p-hydroxybenzyl |
| 83[e] | m-(N-methylamino)carbonylbenzyl | m-(N-methylamino)benzyl | m-formylbenzyl |
| 84[e] | m-trifluorcarbonyl benzyl | m-hydroxyamidino benzyl | m-triazolylbenzyl |
| 85[e] | m-formaldoxime-benzyl | m-acetoximebenzyl | benzyl |
| 86[e] | hydroxycarbonyl-benzyl | m-tetrazolylbenzyl | m-pyrazolyl-benzyl |
| 87[e] | m-imidazolylbenzyl | p-fluorobenzyl | pyridinylmethyl |
| 88[e] | m-acetylbenzyl | m-aminosulfonyl-benzyl | m-methoxybenzyl |

TABLE 14[e]

Formula (IVa), R$^4$ = R$^{23}$ = p-hydroxymethylbenzyl, R$^{22}$ = R$^7$ = Table

| Ex.No | .0 | .1 | .2 |
|---|---|---|---|
| 89[e] | m-hydroxymethyl-benzyl | p-hydroxymethyl-benzyl | m-hydroxybenzyl |
| 90[e] | m-(N,N-dimethyl-amino glycyl)-aminobenzyl | m-aminocarbonyl-benzyl | p-hydroxybenzyl |
| 91[e] | m-(N-methylamino)carbonylbenzyl | m-(N-methylamino)benzyl | m-formylbenzyl |
| 92[e] | m-trifluorcarbonyl benzyl | m-hydroxyamidino benzyl | m-triazolylbenzyl |
| 93[e] | m-formaldoxime-benzyl | m-acetoximebenzyl | benzyl |
| 94[e] | hydroxycarbonyl-benzyl | m-tetrazolylbenzyl | m-pyrazolyl-benzyl |
| 95[e] | m-imidazolylbenzyl | p-fluorobenzyl | pyridinylmethyl |
| 96[e] | m-acetylbenzyl | m-aminosulfonyl-benzyl | m-methoxybenzyl |

TABLE 15[e]

Formula (IVa), R$^4$ = R$^{23}$ = m-hydroxycarbonylbenzyl, R$^{22}$ = R$^7$ = Table

| Ex.No | .0 | .1 | .2 |
|---|---|---|---|
| 97[e] | m-hydroxymethyl-benzyl | p-hydroxymethyl-benzyl | m-hydroxybenzyl |
| 98[e] | m-(N,N-dimethyl-amino glycyl)-aminobenzyl | m-aminocarbonyl-benzyl | p-hydroxybenzyl |
| 99[e] | m-(N-methylamino)carbonylbenzyl | m-(N-methylamino)benzyl | m-formylbenzyl |
| 100[e] | m-trifluorcarbonyl benzyl | m-hydroxyamidino benzyl | m-triazolylbenzyl |
| 101[e] | m-formaldoxime-benzyl | m-acetoximebenzyl | benzyl |
| 102[e] | hydroxycarbonyl-benzyl | m-tetrazolylbenzyl | m-pyrazolyl-benzyl |
| 103[e] | m-imidazolylbenzyl | p-fluorobenzyl | pyridinylmethyl |
| 104[e] | m-acetylbenzyl | m-aminosulfonyl-benzyl | m-methoxybenzyl |

TABLE 16[e]

Formula (IVa), $R^4 = R^{23}$ = benzyl, $R^{22}$ = m-hydroxymethylbenzyl, $R^7$ = Table

| Ex.No | .0 | .1 | .2 |
|---|---|---|---|
| 105[e] | m-hydroxymethylbenzyl | p-hydroxymethylbenzyl | m-hydroxybenzyl |
| 106[e] | m-(N,N-dimethylamino glycyl)-aminobenzyl | m-aminocarbonylbenzyl | p-hydroxybenzyl |
| 107[e] | m-(N-methylamino)carbonylbenzyl | m-(N-methylamino)benzyl | m-formylbenzyl |
| 108[e] | m-trifluorcarbonylbenzyl | m-hydroxyamidinobenzyl | m-triazolylbenzyl |
| 109[e] | m-formaldoximebenzyl | m-acetoximebenzyl | benzyl |
| 110[e] | hydroxycarbonylbenzyl | m-tetrazolylbenzyl | m-pyrazolylbenzyl |
| 111[e] | m-imidazolylbenzyl | p-fluorobenzyl | pyridinylmethyl |
| 112[e] | m-acetylbenzyl | m-aminosulfonylbenzyl | m-methoxybenzyl |

TABLE 17[e]

Formula (IVa), $R^4 = R^{23}$ = benzyl, $R^{22}$ = p-hydroxymethylbenzyl, $R^7$ = Table

| Ex.No | .0 | .1 | .2 |
|---|---|---|---|
| 113[e] | m-hydroxymethylbenzyl | p-hydroxymethylbenzyl | m-hydroxybenzyl |
| 114[e] | m-(N,N-dimethylamino glycyl)-aminobenzyl | m-aminocarbonylbenzyl | p-hydroxybenzyl |
| 115[e] | m-(N-methylamino)carbonylbenzyl | m-(N-methylamino)benzyl | m-formylbenzyl |
| 116[e] | m-trifluorcarbonylbenzyl | m-hydroxyamidinobenzyl | m-triazolylbenzyl |
| 117[e] | m-formaldoximebenzyl | m-acetoximebenzyl | benzyl |
| 118[e] | hydroxycarbonylbenzyl | m-tetrazolylbenzyl | m-pyrazolylbenzyl |
| 119[e] | m-imidazolylbenzyl | p-fluorobenzyl | pyridinylmethyl |
| 120[e] | m-acetylbenzyl | m-aminosulfonylbenzyl | m-methoxybenzyl |

TABLE 18[e]

Formula (IVa), $R^4 = R^{23}$ = benzyl, $R^{22}$ = m-hydroxybenzyl, $R^7$ = Table

| Ex.No | .0 | .1 | .2 |
|---|---|---|---|
| 121[e] | m-hydroxymethylbenzyl | p-hydroxymethylbenzyl | m-hydroxybenzyl |
| 122[e] | m-(N,N-dimethylamino glycyl)-aminobenzyl | m-aminocarbonylbenzyl | p-hydroxybenzyl |
| 123[e] | m-(N-methylamino)carbonylbenzyl | m-(N-methylamino)benzyl | m-formylbenzyl |
| 124[e] | m-trifluorcarbonylbenzyl | m-hydroxyamidinobenzyl | m-triazolylbenzyl |
| 125[e] | m-formaldoximebenzyl | m-acetoximebenzyl | benzyl |
| 126[e] | hydroxycarbonylbenzyl | m-tetrazolylbenzyl | m-pyrazolylbenzyl |
| 127[e] | m-imidazolylbenzyl | p-fluorobenzyl | pyridinylmethyl |
| 128[e] | m-acetylbenzyl | m-aminosulfonylbenzyl | m-methoxybenzyl |

TABLE 19[e]

Formula (IVa), $R^4 = R^{23}$ = benzyl, $R^{22}$ = m-(N,N-dimethylamino glycyl)aminobenzyl, $R^7$ = Table

| Ex.No | .0 | .1 | .2 |
|---|---|---|---|
| 129[e] | m-hydroxymethylbenzyl | p-hydroxymethylbenzyl | m-hydroxybenzyl |
| 130[e] | m-(N,N-dimethylamino glycyl)-aminobenzyl | m-aminocarbonylbenzyl | p-hydroxybenzyl |
| 131[e] | m-(N-methylamino)carbonylbenzyl | m-(N-methylamino)benzyl | m-formylbenzyl |
| 132[e] | m-trifluorcarbonylbenzyl | m-hydroxyamidinobenzyl | m-triazolylbenzyl |
| 133[e] | m-formaldoximebenzyl | m-acetoximebenzyl | benzyl |
| 134[e] | hydroxycarbonylbenzyl | m-tetrazolylbenzyl | m-pyrazolylbenzyl |
| 135[e] | m-imidazolylbenzyl | p-fluorobenzyl | pyridinylmethyl |
| 136[e] | m-acetylbenzyl | m-aminosulfonylbenzyl | m-methoxybenzyl |

TABLE 20[e]

Formula (IVa), $R^4 = R^{23}$ = benzyl, $R^{22}$ = m-aminocarbonylbenzyl, $R^7$ = Table

| Ex.No | .0 | .1 | .2 |
|---|---|---|---|
| 137[e] | m-hydroxymethylbenzyl | p-hydroxymethylbenzyl | m-hydroxybenzyl |
| 138[e] | m-(N,N-dimethylamino glycyl)-aminobenzyl | m-aminocarbonylbenzyl | p-hydroxybenzyl |
| 139[e] | m-(N-methylamino)carbonylbenzyl | m-(N-methylamino)benzyl | m-formylbenzyl |
| 140[e] | m-trifluorcarbonylbenzyl | m-hydroxyamidinobenzyl | m-triazolylbenzyl |
| 141[e] | m-formaldoximebenzyl | m-acetoximebenzyl | benzyl |
| 142[e] | hydroxycarbonylbenzyl | m-tetrazolylbenzyl | m-pyrazolylbenzyl |
| 143[e] | m-imidazolylbenzyl | p-fluorobenzyl | pyridinylmethyl |
| 144[e] | m-acetylbenzyl | m-aminosulfonylbenzyl | m-methoxybenzyl |

TABLE 21[e]

Formula (IVa), $R^4 = R^{23}$ = benzyl, $R^{22}$ = p-hydroxybenzyl, $R^7$ = Table

| Ex.No | .0 | .1 | .2 |
|---|---|---|---|
| 145[e] | m-hydroxymethylbenzyl | p-hydroxymethylbenzyl | m-hydroxybenzyl |
| 146[e] | m-(N,N-dimethylamino glycyl)-aminobenzyl | m-aminocarbonylbenzyl | p-hydroxybenzyl |
| 147[e] | m-(N-methylamino)carbonylbenzyl | m-(N-methylamino)benzyl | m-formylbenzyl |
| 148[e] | m-trifluorcarbonylbenzyl | m-hydroxyamidinobenzyl | m-triazolylbenzyl |
| 149[e] | m-formaldoximebenzyl | m-acetoximebenzyl | benzyl |
| 150[e] | hydroxycarbonylbenzyl | m-tetrazolylbenzyl | m-pyrazolylbenzyl |
| 151[e] | m-imidazolylbenzyl | p-fluorobenzyl | pyridinylmethyl |
| 152[e] | m-acetylbenzyl | m-aminosulfonylbenzyl | m-methoxybenzyl |

TABLE 22[e]

Formula (IVa), $R^4 = R^{23}$ = benzyl, $R^{22}$ = m-(N-methylaminocarbonyl-benzyl, $R^7$ = Table

| Ex.No | .0 | .1 | .2 |
|---|---|---|---|
| 153[e] | m-hydroxymethyl-benzyl | p-hydroxymethyl-benzyl | m-hydroxybenzyl |
| 154[e] | m-(N,N-dimethyl-amino glycyl)-aminobenzyl | m-aminocarbonyl-benzyl | p-hydroxybenzyl |
| 155[e] | m-(N-methylamino)carbonylbenzyl | m-(N-methylamino)benzyl | m-formylbenzyl |
| 156[e] | m-trifluorcarbonyl benzyl | m-hydroxyamidino benzyl | m-triazolylbenzyl |
| 157[e] | m-formaldoxime-benzyl | m-acetoximebenzyl | benzyl |
| 158[e] | hydroxycarbonyl-benzyl | m-tetrazolylbenzyl | m-pyrazolyl-benzyl |
| 159[e] | m-imidazolylbenzyl | p-fluorobenzyl | pyridinylmethyl |
| 160[e] | m-acetylbenzyl | m-aminosulfonyl-benzyl | m-methoxybenzyl |

TABLE 23[e]

Formula (IVa), $R^4 = R^{23}$ = benzyl, $R^{22}$ = m-(N-methylamino)benzyl, $R^7$ = Table

| Ex.No | .0 | .1 | .2 |
|---|---|---|---|
| 161[e] | m-hydroxymethyl-benzyl | p-hydroxymethyl-benzyl | m-hydroxybenzyl |
| 162[e] | m-(N,N-dimethyl-amino glycyl)-aminobenzyl | m-aminocarbonyl-benzyl | p-hydroxybenzyl |
| 163[e] | m-(N-methylamino)carbonylbenzyl | m-(N-methylamino)benzyl | m-formylbenzyl |
| 164[e] | m-trifluorcarbonyl benzyl | m-hydroxyamidino benzyl | m-triazolylbenzyl |
| 165[e] | m-formaldoxime-benzyl | m-acetoximebenzyl | benzyl |
| 166[e] | hydroxycarbonyl-benzyl | m-tetrazolylbenzyl | m-pyrazolyl-benzyl |
| 167[e] | m-imidazolylbenzyl | p-fluorobenzyl | pyridinylmethyl |
| 168[e] | m-acetylbenzyl | m-aminosulfonyl-benzyl | m-methoxybenzyl |

TABLE 24[e]

Formula (IVa), $R^4 = R^{23}$ = benzyl, $R^{22}$ = m-formyllbenzyl, $R^7$ = Table

| Ex.No | .0 | .1 | .2 |
|---|---|---|---|
| 169[e] | m-hydroxymethyl-benzyl | p-hydroxymethyl-benzyl | m-hydroxybenzyl |
| 170[e] | m-(N,N-dimethyl-amino glycyl)-aminobenzyl | m-aminocarbonyl-benzyl | p-hydroxybenzyl |
| 171[e] | m-(N-methylamino)carbonylbenzyl | m-(N-methylamino)benzyl | m-formylbenzyl |
| 172[e] | m-trifluorcarbonyl benzyl | m-hydroxyamidino benzyl | m-triazolylbenzyl |
| 173[e] | m-formaldoxime-benzyl | m-acetoximebenzyl | benzyl |
| 174[e] | hydroxycarbonyl-benzyl | m-tetrazolylbenzyl | m-pyrazolyl-benzyl |
| 175[e] | m-imidazolylbenzyl | p-fluorobenzyl | pyridinylmethyl |
| 176[e] | m-acetylbenzyl | m-aminosulfonyl-benzyl | m-methoxybenzyl |

TABLE 25[e]

Formula (IVa), $R^4 = R^{23}$ = benzyl, $R^{22}$ = m-trifluorocarbonyl benzyl, $R^7$ = Table

| Ex.No | .0 | .1 | .2 |
|---|---|---|---|
| 177[e] | m-hydroxymethyl-benzyl | p-hydroxymethyl-benzyl | m-hydroxybenzyl |
| 178[e] | m-(N,N-dimethyl-amino glycyl)-aminobenzyl | m-aminocarbonyl-benzyl | p-hydroxybenzyl |
| 179[e] | m-(N-methylamino)carbonylbenzyl | m-(N-methylamino)benzyl | m-formylbenzyl |
| 180[e] | m-trifluorcarbonyl-benzyl | m-hydroxyamidino benzyl | m-triazolylbenzyl |
| 181[e] | m-formaldoxime-benzyl | m-acetoximebenzyl | benzyl |
| 182[e] | hydroxycarbonyl-benzyl | m-tetrazolylbenzyl | m-pyrazolyl-benzyl |
| 183[e] | m-imidazolylbenzyl | p-fluorobenzyl | pyridinylmethyl |
| 184[e] | m-acetylbenzyl | m-aminosulfonyl-benzyl | m-methoxybenzyl |

TABLE 26[e]

Formula (IVa), $R^4 = R^{23}$ = benzyl, $R^{22}$ = m-hydroxyamidinobenzyl, $R^7$ = Table

| Ex.No | .0 | .1 | .2 |
|---|---|---|---|
| 185[e] | m-hydroxymethyl-benzyl | p-hydroxymethyl-benzyl | m-hydroxybenzyl |
| 186[e] | m-(N,N-dimethyl-amino glycyl)-aminobenzyl | m-aminocarbonyl-benzyl | p-hydroxybenzyl |
| 187[e] | m-(N-methylamino)carbonylbenzyl | m-(N-methylamino)benzyl | m-formylbenzyl |
| 188[e] | m-trifluorcarbonyl benzyl | m-hydroxyamidino benzyl | m-triazolylbenzyl |
| 189[e] | m-formaldoxime-benzyl | m-acetoximebenzyl | benzyl |
| 190[e] | hydroxycarbonyl-benzyl | m-tetrazolylbenzyl | m-pyrazolyl-benzyl |
| 191[e] | m-imidazolylbenzyl | p-fluorobenzyl | pyridinylmethyl |
| 192[e] | m-acetylbenzyl | m-aminosulfonyl-benzyl | m-methoxybenzyl |

TABLE 27[e]

Formula (IVa), $R^4 = R^{23}$ = benzyl, $R^{22}$ = m-triazolylbenzyl, $R^7$ = Table

| Ex.No | .0 | .1 | .2 |
|---|---|---|---|
| 193[e] | m-hydroxymethyl-benzyl | p-hydroxymethyl-benzyl | m-hydroxybenzyl |
| 194[e] | m-(N,N-dimethyl-amino glycyl)-aminobenzyl | m-aminocarbonyl-benzyl | p-hydroxybenzyl |
| 195[e] | m-(N-methylamino)carbonylbenzyl | m-(N-methylamino)benzyl | m-formylbenzyl |
| 196[e] | m-trifluorcarbonyl benzyl | m-hydroxyamidino benzyl | m-triazolylbenzyl |
| 197[e] | m-formaldoxime-benzyl | m-acetoximebenzyl | benzyl |
| 198[e] | hydroxycarbonyl-benzyl | m-tetrazolylbenzyl | m-pyrazolyl-benzyl |
| 199[e] | m-imidazolylbenzyl | p-fluorobenzyl | pyridinylmethyl |
| 200[e] | m-acetylbenzyl | m-aminosulfonyl-benzyl | m-methoxybenzyl |

TABLE 28[e]

Formula (IVa), $R^4 = R^{23}$ = benzyl, $R^{22}$ = m-formaldoximebenzyl, $R^7$ = Table

| Ex.No | .0 | .1 | .2 |
|---|---|---|---|
| 201[e] | m-hydroxymethyl-benzyl | p-hydroxymethyl-benzyl | m-hydroxybenzyl |
| 202[e] | m-(N,N-dimethyl-amino glycyl)-aminobenzyl | m-aminocarbonyl-benzyl | p-hydroxybenzyl |
| 203[e] | m-(N-methylamino) carbonylbenzyl | m-(N-methylamino) benzyl | m-formylbenzyl |
| 204[e] | m-trifluorcarbonyl benzyl | m-hydroxyamidino benzyl | m-triazolylbenzyl |
| 205[e] | m-formaldoxime-benzyl | m-acetoximebenzyl | benzyl |
| 206[e] | hydroxycarbonyl-benzyl | m-tetrazolylbenzyl | m-pyrazolyl-benzyl |
| 207[e] | m-imidazolylbenzyl | p-fluorobenzyl | pyridinylmethyl |
| 208[e] | m-acetylbenzyl | m-aminosulfonyl-benzyl | m-methoxybenzyl |

TABLE 29[e]

Formula (IVa), $R^4 = R^{23}$ = benzyl, $R^{22}$ = m-acetoximebenzyl, $R^7$ = Table

| Ex.No | .0 | .1 | .2 |
|---|---|---|---|
| 209[e] | m-hydroxymethyl-benzyl | p-hydroxymethyl-benzyl | m-hydroxybenzyl |
| 210[e] | m-(N,N-dimethyl-amino glycyl)-aminobenzyl | m-aminocarbonyl-benzyl | p-hydroxybenzyl |
| 211[e] | m-(N-methylamino) carbonylbenzyl | m-(N-methylamino) benzyl | m-formylbenzyl |
| 212[e] | m-trifluorcarbonyl benzyl | m-hydroxyamidino benzyl | m-triazolylbenzyl |
| 213[e] | m-formaldoxime-benzyl | m-acetoximebenzyl | benzyl |
| 214[e] | hydroxycarbonyl-benzyl | m-tetrazolylbenzyl | m-pyrazolyl-benzyl |
| 215[e] | m-imidazolylbenzyl | p-fluorobenzyl | pyridinylmethyl |
| 216[e] | m-acetylbenzyl | m-aminosulfonyl-benzyl | m-methoxybenzyl |

TABLE 30[e]

Formula (IVa), $R^4 = R^{23}$ = benzyl, $R^{22}$ = benzyl, $R^7$ = Table

| Ex.No | .0 | .1 | .2 |
|---|---|---|---|
| 217[e] | m-hydroxymethyl-benzyl | p-hydroxymethyl-benzyl | m-hydroxybenzyl |
| 218[e] | m-(N,N-dimethyl-amino glycyl)-aminobenzyl | m-aminocarbonyl-benzyl | p-hydroxybenzyl |
| 219[e] | m-(N-methylamino) carbonylbenzyl | m-(N-methylamino) benzyl | m-formylbenzyl |
| 220[e] | m-trifluorcarbonyl benzyl | m-hydroxyamidino benzyl | m-triazolylbenzyl |
| 221[e] | m-formaldoxime-benzyl | m-acetoximebenzyl | benzyl |
| 222[e] | hydroxycarbonyl-benzyl | m-tetrazolylbenzyl | m-pyrazolyl-benzyl |
| 223[e] | m-imidazolylbenzyl | p-fluorobenzyl | pyridinylmethyl |
| 224[e] | m-acetylbenzyl | m-aminosulfonyl-benzyl | m-methoxybenzyl |

TABLE 31[e]

Formula (IVa), $R^4 = R^{23}$ = benzyl, $R^{22}$ = m-hydroxycarbonylbenzyl, $R^7$ = Table

| Ex.No | .0 | .1 | .2 |
|---|---|---|---|
| 225[e] | m-hydroxymethyl-benzyl | p-hydroxymethyl-benzyl | m-hydroxybenzyl |
| 226[e] | m-(N,N-dimethyl-amino glycyl)-aminobenzyl | m-aminocarbonyl-benzyl | p-hydroxybenzyl |
| 227[e] | m-(N-methylamino) carbonylbenzyl | m-(N-methylamino) benzyl | m-formylbenzyl |
| 228[e] | m-trifluorcarbonyl benzyl | m-hydroxyamidino benzyl | m-triazolylbenzyl |
| 229[e] | m-formaldoxime-benzyl | m-acetoximebenzyl | benzyl |
| 230[e] | hydroxycarbonyl-benzyl | m-tetrazolylbenzyl | m-pyrazolyl-benzyl |
| 231[e] | m-imidazolylbenzyl | p-fluorobenzyl | pyridinylmethyl |
| 232[e] | m-acetylbenzyl | m-aminosulfonyl-benzyl | m-methoxybenzyl |

TABLE 32[e]

Formula (IVa), $R^4 = R^{23}$ = benzyl, $R^{22}$ = m-tetrazolylbenzyl, $R^7$ = Table

| Ex.No | .0 | .1 | .2 |
|---|---|---|---|
| 233[e] | m-hydroxymethyl-benzyl | p-hydroxymethyl-benzyl | m-hydroxybenzyl |
| 234[e] | m-(N,N-dimethyl-amino glycyl)-aminobenzyl | m-aminocarbonyl-benzyl | p-hydroxybenzyl |
| 235[e] | m-(N-methylamino) carbonylbenzyl | m-(N-methylamino) benzyl | m-formylbenzyl |
| 236[e] | m-trifluorcarbonyl benzyl | m-hydroxyamidino benzyl | m-triazolylbenzyl |
| 237[e] | m-formaldoxime-benzyl | m-acetoximebenzyl | benzyl |
| 238[e] | hydroxycarbonyl-benzyl | m-tetrazolylbenzyl | m-pyrazolyl-benzyl |
| 239[e] | m-imidazolylbenzyl | p-fluorobenzyl | pyridinylmethyl |
| 240[e] | m-acetylbenzyl | m-aminosulfonyl-benzyl | m-methoxybenzyl |

TABLE 33[e]

Formula (IVa), $R^4 = R^{23}$ = benzyl, $R^{22}$ = m-pyrazolylbenzyl, $R^7$ = Table

| Ex.No | .0 | .1 | .2 |
|---|---|---|---|
| 241[e] | m-hydroxymethyl-benzyl | p-hydroxymethyl-benzyl | m-hydroxybenzyl |
| 242[e] | m-(N,N-dimethyl-amino glycyl)-aminobenzyl | m-aminocarbonyl-benzyl | p-hydroxybenzyl |
| 243[e] | m-(N-methylamino) carbonylbenzyl | m-(N-methylamino) benzyl | m-formylbenzyl |
| 244[e] | m-trifluorcarbonyl benzyl | m-hydroxyamidino benzyl | m-triazolylbenzyl |
| 245[e] | m-formaldoxime-benzyl | m-acetoximebenzyl | benzyl |
| 246[e] | hydroxycarbonyl-benzyl | m-tetrazolylbenzyl | m-pyrazolyl-benzyl |
| 247[e] | m-imidazolylbenzyl | p-fluorobenzyl | pyridinylmethyl |
| 248[e] | m-acetylbenzyl | m-aminosulfonyl-benzyl | m-methoxybenzyl |

TABLE 34[e]

Formula (IVa), $R^4 = R^{23}$ = benzyl, $R^{22}$ = m-imidazolylbenzyl, $R^7$ = Table

| Ex.No | .0 | .1 | .2 |
|---|---|---|---|
| 249[e] | m-hydroxymethyl-benzyl | p-hydroxymethyl-benzyl | m-hydroxybenzyl |
| 250[e] | m-(N,N-dimethyl-amino glycyl)-aminobenzyl | m-aminocarbonyl-benzyl | p-hydroxybenzyl |
| 251[e] | m-(N-methylamino)carbonylbenzyl | m-(N-methylamino)benzyl | m-formylbenzyl |
| 252[e] | m-trifluorcarbonyl benzyl | m-hydroxyamidino benzyl | m-triazolylbenzyl |
| 253[e] | m-formaldoxime-benzyl | m-acetoximebenzyl | benzyl |
| 254[e] | hydroxycarbonyl-benzyl | m-tetrazolylbenzyl | m-pyrazolyl-benzyl |
| 255[e] | m-imidazolylbenzyl | p-fluorobenzyl | pyridinylmethyl |
| 256[e] | m-acetylbenzyl | m-aminosulfonyl-benzyl | m-methoxybenzyl |

TABLE 35[e]

Formula (IVa), $R^4 = R^{23}$ = benzyl, $R^{22}$ = p-fluorobenzyl, $R^7$ = Table

| Ex.No | .0 | .1 | .2 |
|---|---|---|---|
| 257[e] | m-hydroxymethyl-benzyl | p-hydroxymethyl-benzyl | m-hydroxybenzyl |
| 258[e] | m-(N,N-dimethyl-amino glycyl)-aminobenzyl | m-aminocarbonyl-benzyl | p-hydroxybenzyl |
| 259[e] | m-(N-methylamino)carbonylbenzyl | m-(N-methylamino)benzyl | m-formylbenzyl |
| 260[e] | m-trifluorcarbonyl benzyl | m-hydroxyamidino benzyl | m-triazolylbenzyl |
| 261[e] | m-formaldoxime-benzyl | m-acetoximebenzyl | benzyl |
| 262[e] | hydroxycarbonyl-benzyl | m-tetrazolylbenzyl | m-pyrazolyl-benzyl |
| 263[e] | m-imidazolylbenzyl | p-fluorobenzyl | pyridinylmethyl |
| 264[e] | m-acetylbenzyl | m-aminosulfonyl-benzyl | m-methoxybenzyl |

TABLE 36[e]

Formula (IVa), $R^4 = R^{23}$ = benzyl, $R^{22}$ = pyridinylmethyl, $R^7$ = Table

| Ex.No | .0 | .1 | .2 |
|---|---|---|---|
| 265[e] | m-hydroxymethyl-benzyl | p-hydroxymethyl-benzyl | m-hydroxybenzyl |
| 266[e] | m-(N,N-dimethyl-amino glycyl)-aminobenzyl | m-aminocarbonyl-benzyl | p-hydroxybenzyl |
| 267[e] | m-(N-methylamino)carbonylbenzyl | m-(N-methylamino)benzyl | m-formylbenzyl |
| 268[e] | m-trifluorcarbonyl benzyl | m-hydroxyamidino benzyl | m-triazolylbenzyl |
| 269[e] | m-formaldoxime-benzyl | m-acetoximebenzyl | benzyl |
| 270[e] | hydroxycarbonyl-benzyl | m-tetrazolylbenzyl | m-pyrazolyl-benzyl |
| 271[e] | m-imidazolylbenzyl | p-fluorobenzyl | pyridinylmethyl |
| 272[e] | m-acetylbenzyl | m-aminosulfonyl-benzyl | m-methoxybenzyl |

TABLE 37[e]

Formula (IVa), $R^4 = R^{23}$ = benzyl, $R^{22}$ = m-acetylbenzyl, $R^7$ = Table

| Ex.No | .0 | .1 | .2 |
|---|---|---|---|
| 273[e] | m-hydroxymethyl-benzyl | p-hydroxymethyl-benzyl | m-hydroxybenzyl |
| 274[e] | m-(N,N-dimethyl-amino glycyl)-aminobenzyl | m-aminocarbonyl-benzyl | p-hydroxybenzyl |
| 275[e] | m-(N-methylamino)carbonylbenzyl | m-(N-methylamino)benzyl | m-formylbenzyl |
| 276[e] | m-trifluorcarbonyl benzyl | m-hydroxyamidino benzyl | m-triazolylbenzyl |
| 277[e] | m-formaldoxime-benzyl | m-acetoximebenzyl | benzyl |
| 278[e] | hydroxycarbonyl-benzyl | m-tetrazolylbenzyl | m-pyrazolyl-benzyl |
| 279[e] | m-imidazolylbenzyl | p-fluorobenzyl | pyridinylmethyl |
| 280[e] | m-acetylbenzyl | m-aminosulfonyl-benzyl | m-methoxybenzyl |

TABLE 38[e]

Formula (IVa), $R^4 = R^{23}$ = benzyl, $R^{22}$ = m-aminosulfonylbenzyl, $R^7$ = Table

| Ex.No | .0 | .1 | .2 |
|---|---|---|---|
| 281[e] | m-hydroxymethyl-benzyl | p-hydroxymethyl-benzyl | m-hydroxybenzyl |
| 282[e] | m-(N,N-dimethyl-amino glycyl)-aminobenzyl | m-aminocarbonyl-benzyl | p-hydroxybenzyl |
| 283[e] | m-(N-methylamino)carbonylbenzyl | m-(N-methylamino)benzyl | m-formylbenzyl |
| 284[e] | m-trifluorcarbonyl benzyl | m-hydroxyamidino benzyl | m-triazolylbenzyl |
| 285[e] | m-formaldoxime-benzyl | m-acetoximebenzyl | benzyl |
| 286[e] | hydroxycarbonyl-benzyl | m-tetrazolylbenzyl | m-pyrazolyl-benzyl |
| 287[e] | m-imidazolylbenzyl | p-fluorobenzyl | pyridinylmethyl |
| 288[e] | m-acetylbenzyl | m-aminosulfonyl-benzyl | m-methoxybenzyl |

TABLE 39[e]

Formula (IVa), $R^4 = R^{23}$ = benzyl, $R^{22}$ = m-methoxybenzyl, $R^7$ = Table

| Ex.No | .0 | .1 | .2 |
|---|---|---|---|
| 289[e] | m-hydroxymethyl-benzyl | p-hydroxymethyl-benzyl | m-hydroxybenzyl |
| 290[e] | m-(N,N-dimethyl-amino glycyl)-aminobenzyl | m-aminocarbonyl-benzyl | p-hydroxybenzyl |
| 291[e] | m-(N-methylamino)carbonylbenzyl | m-(N-methylamino)benzyl | m-formylbenzyl |
| 292[e] | m-trifluorcarbonyl benzyl | m-hydroxyamidino benzyl | m-triazolylbenzyl |
| 293[e] | m-formaldoxime-benzyl | m-acetoximebenzyl | benzyl |
| 294[e] | hydroxycarbonyl-benzyl | m-tetrazolylbenzyl | m-pyrazolyl-benzyl |
| 295[e] | m-imidazolylbenzyl | p-fluorobenzyl | pyridinylmethyl |
| 296[e] | m-acetylbenzyl | m-aminosulfonyl-benzyl | m-methoxybenzyl |

TABLE 3[f]

Formula (IVb), $R^4 = R^{23}$ = benzyl, $R^{22} = R^7$ = Table

| Ex.No | .0 | .1 | .2 |
|---|---|---|---|
| 1[f] | m-hydroxymethyl-benzyl | p-hydroxymethyl-benzyl | m-hydroxybenzyl |
| 2[f] | m-(N,N-dimethyl-amino glycyl)-aminobenzyl | m-aminocarbonyl-benzyl | p-hydroxybenzyl |
| 3[f] | m-(N-methylamino)carbonylbenzyl | m-(N-methylamino)benzyl | m-formylbenzyl |
| 4[f] | m-trifluorocarbonylbenzyl | m-hydroxyamidinobenzyl | m-triazolylbenzyl |
| 5[f] | m-formaldoxime-benzyl | m-acetoximebenzyl | benzyl |
| 6[f] | hydroxycarbonyl-benzyl | m-tetrazolylbenzyl | m-pyrazolyl-benzyl |
| 7[f] | m-imidazolylbenzyl | p-fluorobenzyl | pyridinylmethyl |
| 8[f] | m-acetylbenzyl | m-aminosulfonyl-benzyl | m-methoxybenzyl |

TABLE 4[f]

Formula (IVb), $R^4 = R^{23}$ = fluorobenzyl, $R^{22} = R^7$ = Table

| Ex.No | .0 | .1 | .2 |
|---|---|---|---|
| 9[f] | m-hydroxymethyl-benzyl | p-hydroxymethyl-benzyl | m-hydroxybenzyl |
| 10[f] | m-(N,N-dimethyl-amino glycyl)-aminobenzyl | m-aminocarbonyl-benzyl | p-hydroxybenzyl |
| 11[f] | m-(N-methylamino)carbonylbenzyl | m-(N-methylamino)benzyl | m-formylbenzyl |
| 12[f] | m-trifluorocarbonylbenzyl | m-hydroxyamidinobenzyl | m-triazolylbenzyl |
| 13[f] | m-formaldoxime-benzyl | m-acetoximebenzyl | benzyl |
| 14[f] | hydroxycarbonyl-benzyl | m-tetrazolylbenzyl | m-pyrazolyl-benzyl |
| 15[f] | m-imidazolylbenzyl | p-fluorobenzyl | pyridinylmethyl |
| 16[f] | m-acetylbenzyl | m-aminosulfonyl-benzyl | m-methoxybenzyl |

TABLE 5[f]

Formula (IVb), $R^4 = R^{23}$ = pyrrolylmethyl, $R^{22} = R^7$ = Table

| Ex.No | .0 | .1 | .2 |
|---|---|---|---|
| 17[f] | m-hydroxymethyl-benzyl | p-hydroxymethyl-benzyl | m-hydroxybenzyl |
| 18[f] | m-(N,N-dimethyl-amino glycyl)-aminobenzyl | m-aminocarbonyl-benzyl | p-hydroxybenzyl |
| 19[f] | m-(N-methylamino)carbonylbenzyl | m-(N-methylamino)benzyl | m-formylbenzyl |
| 20[f] | m-trifluorocarbonylbenzyl | m-hydroxyamidinobenzyl | m-triazolylbenzyl |
| 21[f] | m-formaldoxime-benzyl | m-acetoximebenzyl | benzyl |
| 22[f] | hydroxycarbonyl-benzyl | m-tetrazolylbenzyl | m-pyrazolyl-benzyl |
| 23[f] | m-imidazolylbenzyl | p-fluorobenzyl | pyridinylmethyl |
| 24[f] | m-acetylbenzyl | m-aminosulfonyl-benzyl | m-methoxybenzyl |

TABLE 6[f]

Formula (IVb), $R^4 = R^{23}$ = methoxybenzyl, $R^{22} = R^7$ = Table

| Ex.No | .0 | .1 | .2 |
|---|---|---|---|
| 25[f] | m-hydroxymethyl-benzyl | p-hydroxymethyl-benzyl | m-hydroxybenzyl |
| 26[f] | m-(N,N-dimethyl-amino glycyl)-aminobenzyl | m-aminocarbonyl-benzyl | p-hydroxybenzyl |
| 27[f] | m-(N-methylamino)carbonylbenzyl | m-(N-methylamino)benzyl | m-formylbenzyl |
| 28[f] | m-trifluorocarbonylbenzyl | m-hydroxyamidinobenzyl | m-triazolylbenzyl |
| 29[f] | m-formaldoxime-benzyl | m-acetoximebenzyl | benzyl |
| 30[f] | hydroxycarbonyl-benzyl | m-tetrazolylbenzyl | m-pyrazolyl-benzyl |
| 31[f] | m-imidazolylbenzyl | p-fluorobenzyl | pyridinylmethyl |
| 32[f] | m-acetylbenzyl | m-aminosulfonyl-benzyl | m-methoxybenzyl |

TABLE 7[f]

Formula (IVb), $R^4 = R^{23}$ = isobutyl, $R^{22} = R^7$ = Table

| Ex.No | .0 | .1 | .2 |
|---|---|---|---|
| 33[f] | m-hydroxymethyl-benzyl | p-hydroxymethyl-benzyl | m-hydroxybenzyl |
| 34[f] | m-(N,N-dimethyl-amino glycyl)-aminobenzyl | m-aminocarbonyl-benzyl | p-hydroxybenzyl |
| 35[f] | m-(N-methylamino)carbonylbenzyl | m-(N-methylamino)benzyl | m-formylbenzyl |
| 36[f] | m-trifluorocarbonylbenzyl | m-hydroxyamidinobenzyl | m-triazolylbenzyl |
| 37[f] | m-formaldoxime-benzyl | m-acetoximebenzyl | benzyl |
| 38[f] | hydroxycarbonyl-benzyl | m-tetrazolylbenzyl | m-pyrazolyl-benzyl |
| 39[f] | m-imidazolylbenzyl | p-fluorobenzyl | pyridinylmethyl |
| 40[f] | m-acetylbenzyl | m-aminosulfonyl-benzyl | m-methoxybenzyl |

TABLE 8[f]

Formula (IVb), $R^4 = R^{23}$ = p-nitrobenzyl, $R^{22} = R^7$ = Table

| Ex.No | .0 | .1 | .2 |
|---|---|---|---|
| 41[f] | m-hydroxymethyl-benzyl | p-hydroxymethyl-benzyl | m-hydroxybenzyl |
| 42[f] | m-(N,N-dimethyl-amino glycyl)-aminobenzyl | m-aminocarbonyl-benzyl | p-hydroxybenzyl |
| 43[f] | m-(N-methylamino)carbonylbenzyl | m-(N-methylamino)benzyl | m-formylbenzyl |
| 44[f] | m-trifluorocarbonylbenzyl | m-hydroxyamidinobenzyl | m-triazolylbenzyl |
| 45[f] | m-formaldoxime-benzyl | m-acetoximebenzyl | benzyl |
| 46[f] | hydroxycarbonyl-benzyl | m-tetrazolylbenzyl | m-pyrazolyl-benzyl |
| 47[f] | m-imidazolylbenzyl | p-fluorobenzyl | pyridinylmethyl |
| 48[f] | m-acetylbenzyl | m-aminosulfonyl-benzyl | m-methoxybenzyl |

TABLE 9[f]

Formula (IVb), $R^4 = R^{23}$ = m-aminobenzyl, $R^{22} = R^7$ = Table

| Ex.No | .0 | .1 | .2 |
|---|---|---|---|
| 49[f] | m-hydroxymethyl-benzyl | p-hydroxymethyl-benzyl | m-hydroxybenzyl |
| 50[f] | m-(N,N-dimethyl-amino glycyl)-aminobenzyl | m-aminocarbonyl-benzyl | p-hydroxybenzyl |
| 51[f] | m-(N-methylamino) carbonylbenzyl | m-(N-methylamino) benzyl | m-formylbenzyl |
| 52[f] | m-trifluorocarbonyl benzyl | m-hydroxyamidino benzyl | m-triazolylbenzyl |
| 53[f] | m-formaldoxime-benzyl | m-acetoximebenzyl | benzyl |
| 54[f] | hydroxycarbonyl-benzyl | m-tetrazolylbenzyl | m-pyrazolyl-benzyl |
| 55[f] | m-imidazolylbenzyl | p-fluorobenzyl | pyridinylmethyl |
| 56[f] | m-acetylbenzyl | m-aminosulfonyl-benzyl | m-methoxybenzyl |

TABLE 10[f]

Formula (IVb), $R^4 = R^{23}$ = pyridinylmethyl, $R^{22} = R^7$ = Table

| Ex.No | .0 | .1 | .2 |
|---|---|---|---|
| 57[f] | m-hydroxymethyl-benzyl | p-hydroxymethyl-benzyl | m-hydroxybenzyl |
| 58[f] | m-(N,N-dimethyl-amino glycyl)-aminobenzyl | m-aminocarbonyl-benzyl | p-hydroxybenzyl |
| 59[f] | m-(N-methylamino) carbonylbenzyl | m-(N-methylamino) benzyl | m-formylbenzyl |
| 60[f] | m-trifluorocarbonyl benzyl | m-hydroxyamidino benzyl | m-triazolylbenzyl |
| 61[f] | m-formaldoxime-benzyl | m-acetoximebenzyl | benzyl |
| 62[f] | hydroxycarbonyl-benzyl | m-tetrazolylbenzyl | m-pyrazolyl-benzyl |
| 63[f] | m-imidazolylbenzyl | p-fluorobenzyl | pyridinylmethyl |
| 64[f] | m-acetylbenzyl | m-aminosulfonyl-benzyl | m-methoxybenzyl |

TABLE 11[f]

Formula (IVb), $R^4 = R^{23}$ = m-hydroxybenzyl, $R^{22} = R^7$ = Table

| Ex.No | .0 | .1 | .2 |
|---|---|---|---|
| 65[f] | m-hydroxymethyl-benzyl | p-hydroxymethyl-benzyl | m-hydroxybenzyl |
| 66[f] | m-(N,N-dimethyl-amino glycyl)-aminobenzyl | m-aminocarbonyl-benzyl | p-hydroxybenzyl |
| 67[f] | m-(N-methylamino) carbonylbenzyl | m-(N-methylamino) benzyl | m-formylbenzyl |
| 68[f] | m-trifluorocarbonyl benzyl | m-hydroxyamidino benzyl | m-triazolylbenzyl |
| 69[f] | m-formaldoxime-benzyl | m-acetoximebenzyl | benzyl |
| 70[f] | hydroxycarbonyl-benzyl | m-tetrazolylbenzyl | m-pyrazolyl-benzyl |
| 71[f] | m-imidazolylbenzyl | p-fluorobenzyl | pyridinylmethyl |
| 72[f] | m-acetylbenzyl | m-aminosulfonyl-benzyl | m-methoxybenzyl |

TABLE 12[f]

Formula (IVb), $R^4 = R^{23}$ = p-hydroxybenzyl, $R^{22} = R^7$ = Table

| Ex.No | .0 | .1 | .2 |
|---|---|---|---|
| 73[f] | m-hydroxymethyl-benzyl | p-hydroxymethyl-benzyl | m-hydroxybenzyl |
| 74[f] | m-(N,N-dimethyl-amino glycyl)-aminobenzyl | m-aminocarbonyl-benzyl | p-hydroxybenzyl |
| 75[f] | m-(N-methylamino) carbonylbenzyl | m-(N-methylamino) benzyl | m-formylbenzyl |
| 76[f] | m-trifluorocarbonyl benzyl | m-hydroxyamidino benzyl | m-triazolylbenzyl |
| 77[f] | m-formaldoxime-benzyl | m-acetoximebenzyl | benzyl |
| 78[f] | hydroxycarbonyl-benzyl | m-tetrazolylbenzyl | m-pyrazolyl-benzyl |
| 79[f] | m-imidazolylbenzyl | p-fluorobenzyl | pyridinylmethyl |
| 80[f] | m-acetylbenzyl | m-aminosulfonyl-benzyl | m-methoxybenzyl |

TABLE 13[f]

Formula (IVb), $R^4 = R^{23}$ = m-aminocarbonybenzyl, $R^{22} = R^7$ = Table

| Ex.No | .0 | .1 | .2 |
|---|---|---|---|
| 81[f] | m-hydroxymethyl-benzyl | p-hydroxymethyl-benzyl | m-hydroxybenzyl |
| 82[f] | m-(N,N-dimethyl-amino glycyl)-aminobenzyl | m-aminocarbonyl-benzyl | p-hydroxybenzyl |
| 83[f] | m-(N-methylamino) carbonylbenzyl | m-(N-methylamino) benzyl | m-formylbenzyl |
| 84[f] | m-trifluorcarbonyl benzyl | m-hydroxyamidino benzyl | m-triazolylbenzyl |
| 85[f] | m-formaldoxime-benzyl | m-acetoximebenzyl | benzyl |
| 86[f] | hydroxycarbonyl-benzyl | m-tetrazolylbenzyl | m-pyrazolyl-benzyl |
| 87[f] | m-imidazolylbenzyl | p-fluorobenzyl | pyridinylmethyl |
| 88[f] | m-acetylbenzyl | m-aminosulfonyl-benzyl | m-methoxybenzyl |

TABLE 14[f]

Formula (IVb), $R^4 = R^{23}$ = p-hydroxymethylbenzyl, $R^{22} = R^7$ = Table

| Ex.No | .0 | .1 | .2 |
|---|---|---|---|
| 89[f] | m-hydroxymethyl-benzyl | p-hydroxymethyl-benzyl | m-hydroxybenzyl |
| 90[f] | m-(N,N-dimethyl-amino glycyl)-aminobenzyl | m-aminocarbonyl-benzyl | p-hydroxybenzyl |
| 91[f] | m-(N-methylamino) carbonylbenzyl | m-(N-methylamino) benzyl | m-formylbenzyl |
| 92[f] | m-trifluorocarbonyl benzyl | m-hydroxyamidino benzyl | m-triazolylbenzyl |
| 93[f] | m-formaldoxime-benzyl | m-acetoximebenzyl | benzyl |
| 94[f] | hydroxycarbonyl-benzyl | m-tetrazolylbenzyl | m-pyrazolyl-benzyl |
| 95[f] | m-imidazolylbenzyl | p-fluorobenzyl | pyridinylmethyl |
| 96[f] | m-acetylbenzyl | m-aminosulfonyl-benzyl | m-methoxybenzyl |

TABLE 15[f]

Formula (IVb), $R^4 = R^{23}$ = m-hydroxycarbonylbenzyl, $R^{22} = R^7$ = Table

| Ex.No | .0 | .1 | .2 |
|---|---|---|---|
| 97[f] | m-hydroxymethyl-benzyl | p-hydroxymethyl-benzyl | m-hydroxybenzyl |
| 98[f] | m-(N,N-dimethyl-amino glycyl)-aminobenzyl | m-aminocarbonyl-benzyl | p-hydroxybenzyl |
| 99[f] | m-(N-methylamino)carbonylbenzyl | m-(N-methylamino)benzyl | m-formylbenzyl |
| 100[f] | m-trifluorcarbonyl benzyl | m-hydroxyamidino benzyl | m-triazolylbenzyl |
| 101[f] | m-formaldoxime-benzyl | m-acetoximebenzyl | benzyl |
| 102[f] | hydroxycarbonyl-benzyl | m-tetrazolylbenzyl | m-pyrazolyl-benzyl |
| 103[f] | m-imidazolylbenzyl | p-fluorobenzyl | pyridinylmethyl |
| 104[f] | m-acetylbenzyl | m-aminosulfonyl-benzyl | m-methoxybenzyl |

TABLE 16[f]

Formula (IVb), $R^4 = R^{23}$ = benzyl, $R^{22}$ = m-hydroxymethylbenzyl, $R^7$ = Table

| Ex.No | .0 | .1 | .2 |
|---|---|---|---|
| 105[f] | m-hydroxymethyl-benzyl | p-hydroxymethyl-benzyl | m-hydroxybenzyl |
| 106[f] | m-(N,N-dimethyl-amino glycyl)-aminobenzyl | m-aminocarbonyl-benzyl | p-hydroxybenzyl |
| 107[f] | m-(N-methylamino)carbonylbenzyl | m-(N-methylamino)benzyl | m-formylbenzyl |
| 108[f] | m-trifluorcarbonyl benzyl | m-hydroxyamidino benzyl | m-triazolylbenzyl |
| 109[f] | m-formaldoxime-benzyl | m-acetoximebenzyl | benzyl |
| 110[f] | hydroxycarbonyl-benzyl | m-tetrazolylbenzyl | m-pyrazolyl-benzyl |
| 111[f] | m-imidazolylbenzyl | p-fluorobenzyl | pyridinylmethyl |
| 112[f] | m-acetylbenzyl | m-aminosulfonyl-benzyl | m-methoxybenzyl |

TABLE 17[f]

Formula (IVb), $R^4 = R^{23}$ = benzyl, $R^{22}$ = p-hydroxymethylbenzyl, $R^7$ = Table

| Ex.No | .0 | .1 | .2 |
|---|---|---|---|
| 113[f] | m-hydroxymethyl-benzyl | p-hydroxymethyl-benzyl | m-hydroxybenzyl |
| 114[f] | m-(N,N-dimethyl-amino glycyl)-aminobenzyl | m-aminocarbonyl-benzyl | p-hydroxybenzyl |
| 115[f] | m-(N-methylamino)carbonylbenzyl | m-(N-methylamino)benzyl | m-formylbenzyl |
| 116[f] | m-trifluorcarbonyl benzyl | m-hydroxyamidino benzyl | m-triazolylbenzyl |
| 117[f] | m-formaldoxime-benzyl | m-acetoximebenzyl | benzyl |
| 118[f] | hydroxycarbonyl-benzyl | m-tetrazolylbenzyl | m-pyrazolyl-benzyl |
| 119[f] | m-imidazolylbenzyl | p-fluorobenzyl | pyridinylmethyl |
| 120[f] | m-acetylbenzyl | m-aminosulfonyl-benzyl | m-methoxybenzyl |

TABLE 18[f]

Formula (IVb), $R^4 = R^{23}$ = benzyl, $R^{22}$ = m-hydroxybenzyl, $R^7$ = Table

| Ex.No | .0 | .1 | .2 |
|---|---|---|---|
| 121[f] | m-hydroxymethyl-benzyl | p-hydroxymethyl-benzyl | m-hydroxybenzyl |
| 122[f] | m-(N,N-dimethyl-amino glycyl)-aminobenzyl | m-aminocarbonyl-benzyl | p-hydroxybenzyl |
| 123[f] | m-(N-methylamino)carbonylbenzyl | m-(N-methylamino)benzyl | m-formylbenzyl |
| 124[f] | m-trifluorcarbonyl benzyl | m-hydroxyamidino benzyl | m-triazolylbenzyl |
| 125[f] | m-formaldoxime-benzyl | m-acetoximebenzyl | benzyl |
| 126[f] | hydroxycarbonyl-benzyl | m-tetrazolylbenzyl | m-pyrazolyl-benzyl |
| 127[f] | m-imidazolylbenzyl | p-fluorobenzyl | pyridinylmethyl |
| 128[f] | m-acetylbenzyl | m-aminosulfonyl-benzyl | m-methoxybenzyl |

TABLE 19[f]

Formula (IVb), $R^4 = R^{23}$ = benzyl, $R^{22}$ = m-(N,N-dimethylamino glycyl)aminobenzyl, $R^7$ = Table

| Ex. No | .0 | .1 | .2 |
|---|---|---|---|
| 129[f] | m-hydroxymethyl-benzyl | p-hydroxymethyl-benzyl | m-hydroxybenzyl |
| 130[f] | m-(N,N-dimethyl-aminoglycyl)aminobenzyl | m-aminocarbonyl-benzyl | p-hydroxybenzyl |
| 131[f] | m-(N-methylamino)carbonylbenzyl | m-(N-methylamino)benzyl | m-formylbenzyl |
| 132[f] | m-trifluorcarbonyl benzyl | m-hydroxyamidino benzyl | m-triazolylbehzyl |
| 133[f] | m-formaldoxime-benzyl | m-acetoximebenzyl | benzyl |
| 134 [f] | hydroxycarbonyl-benzyl | m-tetrazolylbenzyl | m-pyrazolylbenzyl |
| 135[f] | m-imidazolylbenzyl | p-fluorobenzyl | pyridinylmethyl |
| 136[f] | m-acetylbenzyl | m-aminosulfonyl-benzyl | m-methoxybenzyl |

TABLE 20[f]

Formula (IVb), $R^4 = R^{23}$ = benzyl, $R^{22}$ = m-aminocarbonylbenzyl, $R^7$ = Table

| Ex. No | .0 | .1 | .2 |
|---|---|---|---|
| 137[f] | m-hydroxymethyl-benzyl | p-hydroxymethyl-benzyl | m-hydroxybenzyl |
| 138[f] | m-(N,N-dimethyl-aminoglycyl)aminobenzyl | m-aminocarbonyl-benzyl | p-hydroxybenzyl |
| 139[f] | m-(N-methylamino)carbonylbenzyl | m-(N-methylamino)benzyl | m-formylbenzyl |
| 140[f] | m-trifluorcarbonyl benzyl | m-hydroxyamidino benzyl | m-triazolylbenzyl |
| 141[f] | m-formaldoxime-benzyl | m-acetoximebenzyl | benzyl |
| 142[f] | hydroxycarbonyl-benzyl | m-tetrazolylbenzyl | m-pyrazolylbenzyl |
| 143 [f] | m-imidazolylbenzyl | p-fluorobenzyl | pyridinylmethyl |
| 144[f] | m-acetylbenzyl | m-aminosulfonyl-benzyl | m-methoxybenzyl |

TABLE 21[f]

Formula (IVb), $R^4 = R^{23}$ = benzyl, $R^{22}$ = p-hydroxybenzyl, $R^7$ = Table

| Ex. No | .0 | .1 | .2 |
|---|---|---|---|
| 145[f] | m-hydroxymethyl-benzyl | p-hydroxymethyl-benzyl | m-hydroxybenzyl |
| 146[f] | m-(N,N-dimethyl-aminoglycyl)aminobenzyl | m-aminocarbonyl-benzyl | p-hydroxybenzyl |
| 147[f] | m-(N-methylamino)carbonylbenzyl | m-(N-methylamino)benzyl | m-formylbenzyl |
| 148[f] | m-trifluorcarbonyl benzyl | m-hydroxyamidino benzyl | m-triazolylbenzyl |
| 149[f] | m-formaldoxime-benzyl | m-acetoximebenzyl | benzyl |
| 150[f] | hydroxycarbonyl-benzyl | m-tetrazolylbenzyl | m-pyrazolylbenzyl |
| 151[f] | m-imidazolylbenzyl | p-fluorobenzyl | pyridinylmethyl |
| 152[f] | m-acetylbenzyl | m-aminosulfonyl-benzyl | m-methoxybenzyl |

TABLE 22[f]

Formula (IVb), $R^4 = R^{23}$ = benzyl, $R^{22}$ = m-(N-methyaminocarbonyl, benzyl, $R^7$ = Table

| Ex. No | .0 | .1 | .2 |
|---|---|---|---|
| 153[f] | m-hydroxymethyl-benzyl | p-hydroxymethyl-benzyl | m-hydroxybenzyl |
| 154[f] | m-(N,N-dimethyl-aminoglycyl)aminobenzyl | m-aminocarbonyl-benzyl | p-hydroxybenzyl |
| 155[f] | m-(N-methylamino)carbonylbenzyl | m-(N-methylamino)benzyl | m-formylbenzyl |
| 156[f] | m-trifluorcarbonyl benzyl | m-hydroxyamidino benzyl | m-triazolylbenzyl |
| 157[f] | m-formaldoxime-benzyl | m-acetoximebenzyl | benzyl |
| 158[f] | hydroxycarbonyl-benzyl | m-tetrazolylbenzyl | m-pyrazolylbenzyl |
| 159[f] | m-imidazolylbenzyl | p-fluorobenzyl | pyridinylmethyl |
| 160[f] | m-acetylbenzyl | m-aminosulfonyl-benzyl | m-methoxybenzyl |

TABLE 23[f]

Formula (IVb), $R^4 = R^{23}$ = benzyl, $R^{22}$ = m-(N-methylamino)benzyl, $R^7$ = Table

| Ex. No | .0 | .1 | .2 |
|---|---|---|---|
| 161[f] | m-hydroxymethyl-benzyl | p-hydroxymethyl-benzyl | m-hydroxybenzyl |
| 162[f] | m-(N,N-dimethyl-aminoglycyl)aminobenzyl | m-aminocarbonyl-benzyl | p-hydroxybenzyl |
| 163[f] | m-(N-methylamino)carbonylbenzyl | m-(N-methylamino)benzyl | m-formylbenzyl |
| 164[f] | m-trifluorcarbonyl benzyl | m-hydroxyamidino benzyl | m-triazolylbenzyl |
| 165[f] | m-formaldoxime-benzyl | m-acetoximebenzyl | benzyl |
| 166[f] | hydroxycarbonyl-benzyl | m-tetrazolylbenzyl | m-pyrazolylbenzyl |
| 167[f] | m-imidazolylbenzyl | p-fluorobenzyl | pyridinylmethyl |
| 168[f] | m-acetylbenzyl | m-aminosulfonyl-benzyl | m-methoxybenzyl |

TABLE 24[f]

Formula (IVb), $R^4 = R^{23}$ = benzyl, $R^{22}$ = m-formyllbenzyl, $R^7$ = Table

| Ex. No | .0 | .1 | .2 |
|---|---|---|---|
| 169[f] | m-hydroxymethyl-benzyl | p-hydroxymethyl-benzyl | m-hydroxybenzyl |
| 170[f] | m-(N,N-dimethyl-aminoglycyl)aminobenzyl | m-aminocarbonyl-benzyl | p-hydroxybenzyl |
| 171[f] | m-(N-methylamino)carbonylbenzyl | m-(N-methylamino)benzyl | m-formylbenzyl |
| 172[f] | m-trifluorcarbonyl benzyl | m-hydroxyamidino benzyl | m-triazolylbenzyl |
| 173[f] | m-formaldoxime-benzyl | m-acetoximebenzyl | benzyl |
| 174[f] | hydroxycarbonyl-benzyl | m-tetrazolylbenzyl | m-pyrazolylbenzyl |
| 175[f] | m-imidazolylbenzyl | p-fluorobenzyl | pyridinylmethyl |
| 176[f] | m-acetylbenzyl | m-aminosulfonyl-benzyl | m-methoxybenzyl |

TABLE 25[f]

Formula (IVb), $R^4 = R^{23}$ = benzyl, $R^{22}$ = m-trifluorocarbonylbenzyl, $R^7$ = Table

| Ex. No | .0 | .1 | .2 |
|---|---|---|---|
| 177[f] | m-hydroxymethyl-benzyl | p-hydroxymethyl-benzyl | m-hydroxybenzyl |
| 178[f] | m-(N,N-dimethyl-aminoglycyl)aminobenzyl | m-aminocarbonyl-benzyl | p-hydroxybenzyl |
| 179[f] | m-(N-methylamino)carbonylbenzyl | m-(N-methylamino)benzyl | m-formylbenzyl |
| 180[f] | m-trifluorcarbonyl benzyl | m-hydroxyamidino benzyr | m-triazolylbenzyl |
| 181[f] | m-formaldoxime-benzyl | m-acetoximebenzyl | benzyl |
| 182[f] | hydroxycarbonyl-benzyl | m-tetrazolylbenzyl | m-pyrazolylbenzyl |
| 183[f] | m-imidazolylbenzyl | p-fluorobenzyl | pyridinylmethyl |
| 184 [f] | m-acetylbenzyl | m-aminosulfonyl-benzyl | m-methoxybenzyl |

TABLE 26[f]

Formula (IVb), $R^4 = R^{23}$ = benzyl, $R^{22}$ = m-hydroxyamidinobenzyl, $R^7$ = Table

| Ex. No | .0 | .1 | .2 |
|---|---|---|---|
| 185[f] | m-hydroxymethyl-benzyl | p-hydroxymethyl-benzyl | m-hydroxybenzyl |
| 186[f] | m-(N,N-dimethyl-aminoglycyl)aminobenzyl | m-aminocarbonyl-benzyl | p-hydroxybenzyl |
| 187[f] | m-(N-methylamino)carbonylbenzyl | m-(N-methylamino)benzyl | m-formylbenzyl |
| 188[f] | m-trifluorcarbonyl benzyl | m-hydroxyamidino benzyl | m-triazolylbenzyl |
| 189[f] | m-formaldoxime-benzyl | m-acetoximebenzyl | benzyl |
| 190[f] | hydroxycarbonyl-benzyl | m-tetrazolylbenzyl | m-pyrazolylbenzyl |
| 191[f] | m-imidazolylbenzyl | p-fluorobenzyl | pyridinylmethyl |
| 192 [f] | m-acetylbenzyl | m-aminosulfonyl-benzyl | m-methoxybenzyl |

TABLE 27[f]

Formula (IVb), $R^4 = R^{23}$ = benzyl, $R^{22}$ = m-triazolybenzyl, $R^7$ = Table

| Ex. No | .0 | .1 | .2 |
| --- | --- | --- | --- |
| 193[f] | m-hydroxymethyl-benzyl | p-hydroxymethyl-benzyl | m-hydroxybenzyl |
| 194[f] | m-(N,N-dimethyl-aminoglycyl)aminobenzyl | m-aminocarbonyl-benzyl | p-hydroxybenzyl |
| 195[f] | m-(N-methylamino)carbonylbenzyl | m-(N-methylamino)benzyl | m-formylbenzyl |
| 196[f] | m-trifluorcarbonylbenzyl | m-hydroxyamidinobenzyl | m-triazolylbenzyl |
| 197[f] | m-formaldoxime-benzyl | m-acetoximebenzyl | benzyl |
| 198[f] | hydroxycarbonylbenzyl | m-tetrazolylbenzyl | m-pyrazolylbenzyl |
| 199[f] | m-imidazolylbenzyl | p-fluorobenzyl | pyridinylmethyl |
| 200[f] | m-acetylbenzyl | m-aminosulfonyl-benzyl | m-methoxybenzyl |

TABLE 28[f]

Formula (IVb), $R^4 = R^{23}$ = benzyl, $R^{22}$ = m-formaldoximebenzyl, $R^7$ = Table

| Ex. No | .0 | .1 | .2 |
| --- | --- | --- | --- |
| 201[f] | m-hydroxymethyl-benzyl | p-hydroxymethyl-benzyl | m-hydroxybenzyl |
| 202[f] | m-(N,N-dimethyl-aminoglycyl)aminobenzyl | m-aminocarbonyl-benzyl | p-hydroxybenzyl |
| 203[f] | m-(N-methylamino)carbonylbenzyl | m-(N-methylamino)benzyl | m-formylbenzyl |
| 204[f] | m-trifluorcarbonylbenzyl | m-hydroxyamidinobenzyl | m-triazolylbenzyl |
| 205[f] | m-formaldoxime-benzyl | m-acetoximebenzyl | benzyl |
| 206[f] | hydroxycarbonylbenzyl | m-tetrazolylbenzyl | m-pyrazolylbenzyl |
| 207[f] | m-imidazolylbenzyl | p-fluorobenzyl | pyridinylmethyl |
| 208[f] | m-acetylbenzyl | m-aminosulfonyl-benzyl | m-methoxybenzyl |

TABLE 29[f]

Formula (IVb), $R^4 = R^{23}$ = benzyl, $R^{22}$ = m-acetoximebenzyl, $R^7$ = Table

| Ex. No | .0 | .1 | .2 |
| --- | --- | --- | --- |
| 209[f] | m-hydroxymethyl-benzyl | p-hydroxymethyl-benzyl | m-hydroxybenzyl |
| 210[f] | m-(N,N-dimethyl-aminoglycyl)aminobenzyl | m-aminocarbonyl-benzyl | p-hydroxybenzyl |
| 211[f] | m-(N-methylamino)carbonylbenzyl | m-(N-methylamino)benzyl | m-formylbenzyl |
| 212[f] | m-trifluorcarbonylbenzyl | m-hydroxyamidinobenzyl | m-triazolylbenzyl |
| 213[f] | m-formaldoxime-benzyl | m-acetoximebenzyl | benzyl |
| 214[f] | hydroxycarbonylbenzyl | m-tetrazolylbenzyl | m-pyrazolylbenzyl |
| 215[f] | m-imidazolylbenzyl | p-fluorobenzyl | pyridinylmethyl |
| 216[f] | m-acetylbenzyl | m-aminosulfonyl-benzyl | m-methoxybenzyl |

TABLE 30[f]

Formula (IVb), $R^4 = R^{23}$ = benzyl, $R^{22}$ = benzyl, $R^7$ = Table

| Ex. No | .0 | .1 | .2 |
| --- | --- | --- | --- |
| 217[f] | m-hydroxymethyl-benzyl | p-hydroxymethyl-benzyl | m-hydroxybenzyl |
| 218[f] | m-(N,N-dimethyl-aminoglycyl)aminobenzyl | m-aminocarbonyl-benzyl | p-hydroxybenzyl |
| 219[f] | m-(N-methylamino)carbonylbenzyl | m-(N-methylamino)benzyl | m-formylbenzyl |
| 220[f] | m-trifluorcarbonylbenzyl | m-hydroxyamidinobenzyl | m-triazolylbenzyl |
| 221[f] | m-formaldoxime-benzyl | m-acetoximebenzyl | benzyl |
| 222[f] | hydroxycarbonylbenzyl | m-tetrazolylbenzyl | m-pyrazolylbenzyl |
| 223[f] | m-imidazolylbenzyl | p-fluorobenzyl | pyridinylmethyl |
| 224[f] | m-acetylbenzyl | m-aminosulfonyl-benzyl | m-methoxybenzyl |

TABLE 31[f]

Formula (IVb), $R^4 = R^{23}$ = benzyl, $R^{22}$ = m-hydroxycarbonylbenzyl, $R^7$ = Table

| Ex. No | .0 | .1 | .2 |
| --- | --- | --- | --- |
| 225[f] | m-hydroxymethyl-benzyl | p-hydroxymethyl-benzyl | m-hydroxybenzyl |
| 226[f] | m-(N,N-dimethyl-aminoglycyl)aminobenzyl | m-aminocarbonyl-benzyl | p-hydroxybenzyl |
| 227[f] | m-(N-methylamino)carbonylbenzyl | m-(N-methylamino)benzyl | m-formylbenzyl |
| 228[f] | m-trifluorcarbonylbenzyl | m-hydroxyamidinobenzyl | m-triazolylbenzyl |
| 229[f] | m-formaldoxime-benzyl | m-acetoximebenzyl | benzyl |
| 230[f] | hydroxycarbonylbenzyl | m-tetrazolylbenzyl | m-pyrazolylbenzyl |
| 231[f] | m-imidazolylbenzyl | p-fluorobenzyl | pyridinylmethyl |
| 232[f] | m-acetylbenzyl | m-aminosulfonyl-benzyl | m-methoxybenzyl |

TABLE 32[f]

Formula (IVb), $R^4 = R^{23}$ = benzyl, $R^{22}$ = m-tetrazolylbenzyl, $R^7$ = Table

| Ex. No | .0 | .1 | .2 |
| --- | --- | --- | --- |
| 233[f] | m-hydroxymethyl-benzyl | p-hydroxymethyl-benzyl | m-hydroxybenzyl |
| 234[f] | m-(N,N-dimethyl-aminoglycyl)aminobenzyl | m-aminocarbonyl-benzyl | p-hydroxybenzyl |
| 235[f] | m-(N-methylamino)carbonylbenzyl | m-(N-methylamino)benzyl | m-formylbenzyl |
| 236[f] | m-trifluorcarbonylbenzyl | m-hydroxyamidinobenzyl | m-triazolylbenzyl |
| 237[f] | m-formaldoxime-benzyl | m-acetoximebenzyl | benzyl |
| 238[f] | hydroxycarbonylbenzyl | m-tetrazolylbenzyl | m-pyrazolylbenzyl |
| 239[f] | m-imidazolylbenzyl | p-fluorobenzyl | pyridinylmethyl |
| 240[f] | m-acetylbenzyl | m-aminosulfonyl-benzyl | m-methoxybenzyl |

TABLE 33[f]

Formula (IVb), $R^4 = R^{23}$ = benzyl, $R^{22}$ = m-pyrazolylbenzyl, $R^7$ = Table

| Ex. No | .0 | .1 | .2 |
|---|---|---|---|
| 241[f] | m-hydroxymethyl-benzyl | p-hydroxymethyl-benzyl | m-hydroxybenzyl |
| 242[f] | m-(N,N-dimethyl-aminoglycyl)aminobenzyl | m-aminocarbonyl-benzyl | p-hydroxybenzyl |
| 243[f] | m-(N-methylamino)carbonylbenzyl | m-(N-methylamino)benzyl | m-formylbenzyl |
| 244[f] | m-trifluorcarbonylbenzyl | m-hydroxyamidinobenzyl | m-triazolylbenzyl |
| 245[f] | m-formaldoxime-benzyl | m-acetoximebenzyl | benzyl |
| 246[f] | hydroxycarbonyl-benzyl | m-tetrazolylbenzyl | m-pyrazolylbenzyl |
| 247[f] | m-imidazolylbenzyl | p-fluorobenzyl | pyridinylmethyl |
| 248[f] | m-acetylbenzyl | m-aminosulfonyl-benzyl | m-methoxybenzyl |

TABLE 34[f]

Formula (IVb), $R^4 = R^{23}$ = benzyl, $R^{22}$ = m-imidazolylbenzyl, $R^7$ = Table

| Ex. No | .0 | .1 | .2 |
|---|---|---|---|
| 249[f] | m-hydroxymethyl-benzyl | p-hydroxymethyl-benzyl | m-hydroxybenzyl |
| 250[f] | m-(N,N-dimethyl-aminoglycyl)aminobenzyl | m-aminocarbonyl-benzyl | p-hydroxybenzyl |
| 251[f] | m-(N-methylamino)carbonylbenzyl | m-(N-methylamino)benzyl | m-formylbenzyl |
| 252[f] | m-trifluorcarbonylbenzyl | m-hydroxyamidinobenzyl | m-triazolylbenzyl |
| 253[f] | m-formaldoxime-benzyl | m-acetoximebenzyl | benzyl |
| 254[f] | hydroxycarbonyl-benzyl | m-tetrazolylbenzyl | m-pyrazolylbenzyl |
| 255[f] | m-imidazolylbenzyl | p-fluorobenzyl | pyridinylmethyl |
| 256[f] | m-acetylbenzyl | m-aminosulfonyl-benzyl | m-methoxybenzyl |

TABLE 35[f]

Formula (IVb), $R^4 = R^{23}$ = benzyl, $R^{22}$ = p-fluorobenzyl, $R^7$ = Table

| Ex. No | .0 | .1 | .2 |
|---|---|---|---|
| 257[f] | m-hydroxymethyl-benzyl | p-hydroxymethyl-benzyl | m-hydroxybenzyl |
| 258[f] | m-(N,N-dimethyl-aminoglycyl)aminobenzyl | m-aminocarbonyl-benzyl | p-hydroxybenzyl |
| 259[f] | m-(N-methylamino)carbonylbenzyl | m-(N-methylamino)benzyl | m-formylbenzyl |
| 260[f] | m-trifluorcarbonylbenzyl | m-hydroxyamidinobenzyl | m-triazolylbenzyl |
| 261[f] | m-formaldoxime-benzyl | m-acetoximebenzyl | benzyl |
| 262[f] | hydroxycarbonyl-benzyl | m-tetrazolylbenzyl | m-pyrazolylbenzyl |
| 263[f] | m-imidazolylbenzyl | p-fluorobenzyl | pyridinylmethyl |
| 264[f] | m-acetylbenzyl | m-aminosulfonyl-benzyl | m-methoxybenzyl |

TABLE 36[f]

Formula (IVb), $R^4 = R^{23}$ = benzyl, $R^{22}$ = pyridinylmethyl, $R^7$ = Table

| Ex. No | .0 | .1 | .2 |
|---|---|---|---|
| 265[f] | m-hydroxymethyl-benzyl | p-hydroxymethyl-benzyl | m-hydroxybenzyl |
| 266[f] | m-(N,N-dimethyl-aminoglycyl)aminobenzyl | m-aminocarbonyl-benzyl | p-hydroxybenzyl |
| 267[f] | m-(N-methylamino)carbonylbenzyl | m-(N-methylamino)benzyl | m-formylbenzyl |
| 268[f] | m-trifluorcarbonylbenzyl | m-hydroxyamidinobenzyl | m-triazolylbenzyl |
| 269[f] | m-formaldoxime-benzyl | m-acetoximebenzyl | benzyl |
| 270[f] | hydroxycarbonyl-benzyl | m-tetrazolylbenzyl | m-pyrazolylbenzyl |
| 271[f] | m-imidazolylbenzyl | p-fluorobenzyl | pyridinylmethyl |
| 272[f] | m-acetylbenzyl | m-aminosulfonyl-benzyl | m-methoxybenzyl |

TABLE 37[f]

Formula (IVb), $R^4 = R^{23}$ = benzyl, $R^{22}$ = m-acetylbenzyl, $R^7$ = Table

| Ex. No | .0 | .1 | .2 |
|---|---|---|---|
| 273[f] | m-hydroxymethyl-benzyl | p-hydroxymethyl-benzyl | m-hydroxybenzyl |
| 274[f] | m-(N,N-dimethyl-aminoglycyl)aminobenzyl | m-aminocarbonyl-benzyl | p-hydroxybenzyl |
| 275[f] | m-(N-methylamino)carbonylbenzyl | m-(N-methylamino)benzyl | m-formylbenzyl |
| 276[f] | m-trifluorcarbonylbenzyl | m-hydroxyamidinobenzyl | m-triazolylbenzyl |
| 277[f] | m-formaldoxime-benzyl | m-acetoximebenzyl | benzyl |
| 278[f] | hydroxycarbonyl-benzyl | m-tetrazolylbenzyl | m-pyrazolylbenzyl |
| 279[f] | m-imidazolylbenzyl | p-fluorobenzyl | pyridinylmethyl |
| 280[f] | m-acetylbenzyl | m-aminosulfonyl-benzyl | m-methoxybenzyl |

TABLE 38[f]

Formula (IVb), $R^4 = R^{23}$ = benzyl, $R^{22}$ = m-aminosulfonylbenzyl, $R^7$ = Table

| Ex. No | .0 | .1 | .2 |
|---|---|---|---|
| 281[f] | m-hydroxymethyl-benzyl | p-hydroxymethyl-benzyl | m-hydroxybenzyl |
| 282[f] | m-(N,N-dimethyl-aminoglycyl)aminobenzyl | m-aminocarbonyl-benzyl | p-hydroxybenzyl |
| 283[f] | m-(N-methylamino)carbonylbenzyl | m-(N-methylamino)benzyl | m-formylbenzyl |
| 284[f] | m-trifluorcarbonylbenzyl | m-hydroxyamidinobenzyl | m-triazolylbenzyl |
| 285[f] | m-formaldoxime-benzyl | m-acetoximebenzyl | benzyl |
| 286[f] | hydroxycarbonyl-benzyl | m-tetrazolylbenzyl | m-pyrazolylbenzyl |
| 287[f] | m-imidazolylbenzyl | p-fluorobenzyl | pyridinylmethyl |
| 288[f] | m-acetylbenzyl | m-aminosulfonyl-benzyl | m-methoxybenzyl |

TABLE 39[f]

Formula (IVb), $R^4 = R^{23}$ = benzyl, $R^{22}$ = m-methoxybenzyl, $R^7$ = Table

| Ex. No | .0 | .1 | .2 |
|---|---|---|---|
| 289[f] | m-hydroxymethyl-benzyl | p-hydroxymethyl-benzyl | m-hydroxybenzyl |
| 290[f] | m-(N,N-dimethyl-aminoglycyl)aminobenzyl | m-aminocarbonyl-benzyl | p-hydroxybenzyl |
| 291[f] | m-(N-methylamino)carbonylbenzyl | m-(N-methylamino)benzyl | m-formylbenzyl |
| 292[f] | m-trifluorcarbonylbenzyl | m-hydroxyamidinobenzyl | m-triazolylbenzyl |
| 293[f] | m-formaldoxime-benzyl | m-acetoximebenzyl | benzyl |
| 294[f] | hydroxycarbonylbenzyl | m-tetrazolylbenzyl | m-pyrazolylbenzyl |
| 295[f] | m-imidazolylbenzyl | p-fluorobenzyl | pyridinylmethyl |
| 296[f] | m-acetylbenzyl | m-aminosulfonyl-benzyl | m-methoxybenzyl |

TABLE 3[g]

Formula (Va), $R^4 = R^{23}$ = benzyl, $R^{22} = R^7$ = Table

| Ex. No | .0 | .1 | .2 |
|---|---|---|---|
| 1[g] | m-hydroxymethyl-benzyl | p-hydroxymethyl-benzyl | m-hydroxybenzyl |
| 2[g] | m-(N,N-dimethyl-aminoglycyl)aminobenzyl | m-aminocarbonyl-benzyl | p-hydroxybenzyl |
| 3[g] | m-(N-methylamino)carbonylbenzyl | m-(N-methylamino)benzyl | m-formylbenzyl |
| 4[g] | m-trifluorocarbonylbenzyl | m-hydroxyamidinobenzyl | m-triazolylbenzyl |
| 5[g] | m-formaldoxime-benzyl | m-acetoximebenzyl | benzyl |
| 6[g] | hydroxycarbonylbenzyl | m-tetrazolylbenzyl | m-pyrazolylbenzyl |
| 7[g] | m-imidazolylbenzyl | p-fluorobenzyl | pyridinylmethyl |
| 8[g] | m-acetylbenzyl | m-aminosulfonyl-benzyl | m-methoxybenzyl |

TABLE 4[g]

Formula (Va), $R^4 = R^{23}$ = fluorobenzyl, $R^{22} = R^7$ = Table

| Ex. No | .0 | .1 | .2 |
|---|---|---|---|
| 9[g] | m-hydroxymethyl-benzyl | p-hydroxymethyl-benzyl | m-hydroxybenzyl |
| 10[g] | m-(N,N-dimethyl-aminoglycyl)aminobenzyl | m-aminocarbonyl-benzyl | p-hydroxybenzyl |
| 11[g] | m-(N-methylamino)carbonylbenzyl | m-(N-methylamino)benzyl | m-formylbenzyl |
| 12[g] | m-trifluorocarbopylbenzyl | m-hydroxyamidinobenzyl | m-triazolylbenzyl |
| 13[g] | m-formaldoxime-benzyl | m-acetoximebenzyl | benzyl |
| 14[g] | hydroxycarbonylbenzyl | m-tetrazolylbenzyl | m-pyrazolylbenzyl |
| 15[g] | m-imidazolylbenzyl | p-fluorobenzyl | pyridinylmethyl |
| 16[g] | m-acetylbenzyl | m-aminosulfonyl-benzyl | m-methoxybenzyl |

TABLE 5[g]

Formula (Va), $R^4 = R^{23}$ = pyrrolylmethyl, $R^{22} = R^7$ = Table

| Ex. No | .0 | .1 | .2 |
|---|---|---|---|
| 17[g] | m-hydroxymethyl-benzyl | p-hydroxymethyl-benzyl | m-hydroxybenzyl |
| 18[g] | m-(N,N-dimethyl-aminoglycyl)aminobenzyl | m-aminocarbonyl-benzyl | p-hydroxybenzyl |
| 19[g] | m-(N-methylamino)carbonylbenzyl | m-(N-methylamino)benzyl | m-formylbenzyl |
| 20[g] | m-trifluorocarbonylbenzyl | m-hydroxyamidinobenzyl | m-triazolylbenzyl |
| 21[g] | m-formaldoxime-benzyl | m-acetoximebenzyl | benzyl |
| 22[g] | hydroxycarbonylbenzyl | m-tetrazolylbenzyl | m-pyrazolylbenzyl |
| 23[g] | m-imidazolylbenzyl | p-fluorobenzyl | pyridinylmethyl |
| 24[g] | m-acetylbenzyl | m-aminosulfonyl-benzyl | m-methoxybenzyl |

TABLE 6[g]

Formula (Va), $R^4 = R^{23}$ = methoxybenzyl, $R^{22} = R^7$ = Table

| Ex. No | .0 | .1 | .2 |
|---|---|---|---|
| 25[g] | m-hydroxymethyl-benzyl | p-hydroxymethyl-benzyl | m-hydroxybenzyl |
| 26[g] | m-(N,N-dimethyl-aminoglycyl)aminobenzyl | m-aminocarbonyl-benzyl | p-hydroxybenzyl |
| 27[g] | m-(N-methylamino)carbonylbenzyl | m-(N-methylamino)benzyl | m-formylbenzyl |
| 28[g] | m-trifluorocarbonylbenzyl | m-hydroxyamidinobenzyl | m-triazolylbenzyl |
| 29[g] | m-formaldoxime-benzyl | m-acetoximebenzyl | benzyl |
| 30[g] | hydroxycarbonylbenzyl | m-tetrazolylbenzyl | m-pyrazolylbenzyl |
| 31[g] | m-imidazolylbenzyl | p-fluorobenzyl | pyridinylmethyl |
| 32[g] | m-acetylbenzyl | m-aminosulfonyl-benzyl | m-methoxybenzyl |

TABLE 7[g]

Formula (Va), $R^4 = R^{23}$ = isobutyl, $R^{22} = R^7$ = Table

| Ex. No | .0 | .1 | .2 |
|---|---|---|---|
| 33[g] | m-hydroxymethyl-benzyl | p-hydroxymethyl-benzyl | m-hydroxybenzyl |
| 34[g] | m-(N,N-dimethy-aminoglycyl)aminobenzyl | m-aminocarbonyl-benzyl | p-hydroxybenzyl |
| 35[g] | m-(N-methylamino)carbonylbenzyl | m-(N-methylamino)benzyl | m-formylbenzyl |
| 36[g] | m-trifluorocarbonylbenzyl | m-hydroxyamidinobenzyl | m-triazolylbenzyl |
| 37[g] | m-formaldoxime-benzyl | m-acetoximebenzyl | benzyl |
| 38[g] | hydroxycarbonylbenzyl | m-tetrazolylbenzyl | m-pyrazolylbenzyl |
| 39[g] | m-imidazolylbenzyl | p-fluorobenzyl | pyridinylmethyl |
| 40[g] | m-acetylbenzyl | m-aminosulfonyl-benzyl | m-methoxybenzyl |

TABLE 8[g]

Formula (Va), $R^4 = R^{23}$ = p-nitrobenzyl, $R^{22} = R^7$ = Table

| Ex. No | .0 | .1 | .2 |
|---|---|---|---|
| 41[g] | m-hydroxymethyl-benzyl | p-hydroxymethyl-benzyl | m-hydroxybenzyl |
| 42[g] | m-(N,N-dimethyl-aminoglycyl)aminobenzyl | m-aminocarbonyl-benzyl | p-hydroxybenzyl |
| 43[g] | m-(N-methylamino)carbonylbenzyl | m-(N-methylamino)benzyl | m-formylbenzyl |
| 44[g] | m-trifluorocarbonyl benzyl | m-hydroxyamidino benzyl | m-triazolylbenzyl |
| 45[g] | m-formaldoxime-benzyl | m-acetoximebenzyl | benzyl |
| 46[g] | hydroxycarbonyl-benzyl | m-tetrazolylbenzyl | m-pyrazolylbenzyl |
| 47[g] | m-imidazolylbenzyl | p-fluorobenzyl | pyridinylmethyl |
| 48[g] | m-acetylbenzyl | m-aminosulfonyl-benzyl | m-methoxybenzyl |

TABLE 9[g]

Formula (Va), $R^4 = R^{23}$ = m-aminobenzyl, $R^{22} = R^7$ = Table

| Ex. No | .0 | .1 | .2 |
|---|---|---|---|
| 49[g] | m-hydroxymethyl-benzyl | p-hydroxylmethyl-benzyl | m-hydroxybenzyl |
| 50[g] | m-(N,N-dimethyl-aminoglycyl)aminobenzyl | m-aminocarbonyl-benzyl | p-hydroxybenzyl |
| 51[g] | m-(N-methylamino)carbonylbenzyl | m-(N-methylamino)benzyl | m-formylbenzyl |
| 52[g] | m-trifluorocarbonyl benzyl | m-hydroxyamidino benzyl | m-triazolylbenzyl |
| 53[g] | m-formaldoxime-benzyl | m-acetoximebenzyl | benzyl |
| 54[g] | hydroxycarbonyl-benzyl | m-tetrazolylbenzyl | m-pyrazolylbenzyl |
| 55[g] | m-imidazolylbenzyl | p-fluorobenzyl | pyridinylmethyl |
| 56[g] | m-acetylbenzyl | m-aminosulfonyl-benzyl | m-methoxybenzyl |

TABLE 10[g]

Formula (Va), $R^4 = R^{23}$ = pyrdinylmethyl, $R^{22} = R^7$ = Table

| Ex. No | .0 | .1 | .2 |
|---|---|---|---|
| 57[g] | m-hydroxymethyl-benzyl | p-hydroxymethyl-benzyl | m-hydroxybenzyl |
| 58[g] | m-(N,N-dimethyl-aminoglycyl)aminobenzyl | m-aminocarbonyl-benzyl | p-hydroxybenzyl |
| 59[g] | m-(N-methylamino)carbonylbenzyl | m-(N-methylamino)benzyl | m-formylbenzyl |
| 60[g] | m-trifluorcarbonyl benzyl | m-hydroxyamidino benzyl | m-triazolylbenzyl |
| 61[g] | m-formaldoxime-benzyl | m-acetoximebenzyl | benzyl |
| 62[g] | hydroxycarbonyl-benzyl | m-tetrazolylbenzyl | m-pyrazolylbenzyl |
| 63[g] | m-imidazolylbenzyl | p-fluorobenzyl | pyridinylmethyl |
| 64[g] | m-acetylbenzyl | m-aminosulfonyl-benzyl | m-methoxybenzyl |

TABLE 11[g]

Formula (Va), $R^4 = R^{23}$ = m-hydroxybenzyl, $R^{22} = R^7$ = Table

| Ex. No | .0 | .1 | .2 |
|---|---|---|---|
| 65[g] | m-hydroxymethyl-benzyl | p-hydroxymethyl-benzyl | m-hydroxybenzyl |
| 66[g] | m-(N,N-dimethyl-aminoglycyl)aminobenzyl | m-aminocarbonyl-benzyl | p-hydroxybenzyl |
| 67[g] | m-(N-methylamino)carbonylbenzyl | m-(N-methylamino)benzyl | m-formylbenzyl |
| 68[g] | m-trifluorocarbonyl benzyl | m-hydroxyamidino benzyl | m-triazolylbenzyl |
| 69[g] | m-formaldoxime-benzyl | m-acetoximebenzyl | benzyl |
| 70[g] | hydroxycarbonyl-benzyl | m-tetrazolylbenzyl | m-pyrazolylbenzyl |
| 71[g] | m-imidazolylbenzyl | p-fluorobenzyl | pyridinylmethyl |
| 72[g] | m-acetylbenzyl | m-aminosulfonyl-benzyl | m-methoxybenzyl |

TABLE 12[g]

Formula (Va), $R^4 = R^{23}$ = p-hydroxybenzyl, $R^{22} = R^7$ = Table

| Ex. No | .0 | .1 | .2 |
|---|---|---|---|
| 73[g] | m-hydroxymethyl-benzyl | p-hydroxymethyl-benzyl | m-hydroxybenzyl |
| 74[g] | m-(N,N-dimethyl-aminoglycyl)aminobenzyl | m-aminocarbonyl-benzyl | p-hydroxybenzyl |
| 75[g] | m-(N-methylamino)carbonylbenzyl | m-(N-methylamino)benzyl | m-formylbenzyl |
| 76[g] | m-trifluorocarbonyl benzyl | m-hydroxyamidino benzyl | m-triazolylbenzyl |
| 77[g] | m-formaldoxime-benzyl | m-acetoximebenzyl | benzyl |
| 76[g] | hydroxycarbonyl-benzyl | m-tetrazolylbenzyl | m-pyrazolylbenzyl |
| 79[g] | m-imidazolylbenzyl | p-fluorobenzyl | pyridinylmethyl |
| 80[g] | m-acetylbenzyl | m-aminosulfonyl-benzyl | m-methoxybenzyl |

TABLE 13[g]

Formula (Va), $R^4 = R^{23}$ = m-aminocarbonylbenzyl, $R^{22} = R^7$ = Table

| Ex. No | .0 | .1 | .2 |
|---|---|---|---|
| 81[g] | m-hydroxymethyl-benzyl | p-hydroxymethyl-benzyl | m-hydroxybenzyl |
| 82[g] | m-(N,N-dimethyl-aminoglycyl)aminobenzyl | m-aminocarbonyl-benzyl | p-hydroxybenzyl |
| 83[g] | m-(N-methylamino)carbonylbenzyl | m-(N-methylamino)benzyl | m-formylbenzyl |
| 84[g] | m-trifluorcarbonyl benzyl | m-hydroxyamidino benzyl | m-triazolylbenzyl |
| 85[g] | m-formaldoxime-benzyl | m-acetoximebenzyl | benzyl |
| 86[g] | hydroxycarbonyl-benzyl | m-tetrazolylbenzyl | m-pyrazolylbenzyl |
| 87[g] | m-imidazolylbenzyl | p-fluorobenzyl | pyridinylmethyl |
| 88[g] | m-acetylbenzyl | m-aminosulfonyl-benzyl | m-methoxybenzyl |

TABLE 14[g]

Formula (Va), $R^4 = R^{23}$ = p-hydroxymethylbenzyl, $R^{22} = R^7$ = Table

| Ex. No | .0 | .1 | .2 |
|---|---|---|---|
| 89[g] | m-hydroxymethyl-benzyl | p-hydroxymethyl-benzyl | m-hydroxybenzyl |
| 90[g] | m-(N,N-dimethyl-aminoglycyl)aminobenzyl | m-aminocarbonyl-benzyl | p-hydroxybenzyl |
| 91[g] | m-(N-methylamino)carbonylbenzyl | m-(N-methylamino)benzyl | m-formylbenzyl |
| 92[g] | m-trifluorcarbonyl benzyl | m-hydroxyamidino benzyl | m-triazolylbenzyl |
| 93[g] | m-formaldoxime-benzyl | m-acetoximebenzyl | benzyl |
| 94[g] | hydroxycarbonyl-benzyl | m-tetrazolylbenzyl | m-pyrazolylbenzyl |
| 95[g] | m-imidazolylbenzyl | p-fluorobenzyl | pyridinylmethyl |
| 96[g] | m-acetylbenzyl | m-aminosulfonyl-benzyl | m-methoxybenzyl |

TABLE 15[g]

Formula (Va), $R^4 = R^{23}$ = m-hydroxycarbonylbenzyl, $R^{22} = R^7$ = Table

| Ex. No | .0 | .1 | .2 |
|---|---|---|---|
| 97[g] | m-hydroxymethyl-benzyl | p-hydroxymethyl-benzyl | m-hydroxybenzyl |
| 98[g] | m-(N,N-dimethyl-aminoglycyl)aminobenzyl | m-aminocarbonyl-benzyl | p-hydroxybenzyl |
| 99[g] | m-(N-methylamino)carbonylbenzyl | m-(N-methylamino)benzyl | m-formylbenzyl |
| 100[g] | m-trifluorcarbonyl benzyl | m-hydroxyamidino benzyl | m-triazolylbenzyl |
| 101[g] | m-formaldoxime-benzyl | m-acetoximebenzyl | benzyl |
| 102[g] | hydroxycarbonyl-benzyl | m-tetrazolylbenzyl | m-pyrazolylbenzyl |
| 103[g] | m-imidazolylbenzyl | p-fluorobenzyl | pyridinylmethyl |
| 104[g] | m-acetylbenzyl | m-aminosulfonyl-benzyl | m-methoxybenzyl |

TABLE 16[g]

Formula (Va), $R^4 = R^{23}$ = benzyl, $R^{22}$ = m-hydroxymethylbenzyl, $R^7$ = Table

| Ex. No | .0 | .1 | .2 |
|---|---|---|---|
| 105[g] | m-hydroxymethyl-benzyl | p-hydroxymethyl-benzyl | m-hydroxybenzyl |
| 106[g] | m-(N,N-dimethyl-aminoglycyl)aminobenzyl | m-aminocarbonyl-benzyl | p-hydroxybenzyl |
| 107[g] | m-(N-methylamino)carbonylbenzyl | m-(N-methylamino)benzyl | m-formylbenzyl |
| 108[g] | m-trifluorcarbonyl benzyl | m-hydroxyamidino benzyl | m-triazolylbenzyl |
| 109[g] | m-formaldoxime-benzyl | m-acetoximebenzyl | benzyl |
| 110[g] | hydroxycarbonyl-benzyl | m-tetrazolylbenzyl | m-pyrazolylbenzyl |
| 111[g] | m-imidazolylbenzyl | p-fluorobenzyl | pyridinylmethyl |
| 112[g] | m-acetylbenzyl | m-aminosulfonyl-benzyl | m-methoxybenzyl |

TABLE 17[g]

Formula (Va), $R^4 = R^{23}$ = benzyl, $R^{22}$ = p-hydroxymethylbenzyl, $R^7$ = Table

| Ex. No | .0 | .1 | .2 |
|---|---|---|---|
| 113[g] | m-hydroxymethyl-benzyl | p-hydroxymethyl-benzyl | m-hydroxybenzyl |
| 114[g] | m-(N,N-dimethyl-aminoglycyl)aminobenzyl | m-aminocarbonyl-benzyl | p-hydroxybenzyl |
| 115[g] | m-(N-methylamino)carbonylbenzyl | m-(N-methylamino)benzyl | m-formylbenzyl |
| 116[g] | m-trifluorcarbonyl benzyl | m-hydroxyamidino benzyl | m-triazolylbenzyl |
| 117[g] | m-formaldoxime-benzyl | m-acetoximebenzyl | benzyl |
| 118[g] | hydroxycarbonyl-benzyl | m-tetrazolylbenzyl | m-pyrazolylbenzyl |
| 119[g] | m-imidazolylbenzyl | p-fluorobenzyl | pyridinylmethyl |
| 120[g] | m-acetylbenzyl | m-aminosulfonyl-benzyl | m-methoxybenzyl |

TABLE 18[g]

Formula (Va), $R^4 = R^{23}$ = benzyl, $R^{22}$ = m-hydroxybenzyl, $R^7$ = Table

| Ex. No | .0 | .1 | .2 |
|---|---|---|---|
| 121[g] | m-hydroxymethyl-benzyl | p-hydroxymethyl-benzyl | m-hydroxybenzyl |
| 122[g] | m-(N,N-dimethyl-aminoglycyl)aminobenzyl | m-aminocarbonyl-benzyl | p-hydroxybenzyl |
| 123[g] | m-(N-methylamino)carbonylbenzyl | m-(N-methylamino)benzyl | m-formylbenzyl |
| 124[g] | m-trifluorcarbonyl benzyl | m-hydroxyamidino benzyl | m-triazolylbenzyl |
| 125[g] | m-formaldoxime-benzyl | m-acetoximebenzyl | benzyl |
| 126[g] | hydroxycarbonyl-benzyl | m-tetrazolylbenzyl | m-pyrazolylbenzyl |
| 127[g] | m-imidazolylbenzyl | p-fluorobenzyl | pyridinylmethyl |
| 128[g] | m-acetylbenzyl | m-aminosulfonyl-benzyl | m-methoxybenzyl |

TABLE 19[g]

Formula (Va), $R^4 = R^{23}$ = benzyl, $R^{22}$ = m-(N,N-dimethylamino glycyl)aminobenzyl, $R^7$ = Table

| Ex. No | .0 | .1 | .2 |
|---|---|---|---|
| 129[g] | m-hydroxymethyl-benzyl | p-hydroxymethyl-benzyl | m-hydroxybenzyl |
| 130[g] | m-(N,N-dimethyl-aminoglycyl)aminobenzyl | m-aminocarbonyl-benzyl | p-hydroxybenzyl |
| 131[g] | m-(N-methylamino)carbonylbenzyl | m-(N-methylamino)benzyl | m-formylbenzyl |
| 132[g] | m-trifluorcarbonyl benzyl | m-hydroxyamidino benzyl | m-triazolylbenzyl |
| 133[g] | m-formaldoxime-benzyl | m-acetoximebenzyl | benzyl |
| 134[g] | hydroxycarbonyl-benzyl | m-tetrazolylbenzyl | m-pyrazolylbenzyl |
| 135[g] | m-imidazolylbenzyl | p-fluorobenzyl | pyridinylmethyl |
| 136[g] | m-acetylbenzyl | m-aminosulfonyl-benzyl | m-methoxybenzyl |

TABLE 20[g]

Formula (Va), $R^4 = R^{23}$ = benzyl, $R^{22}$ = m-aminocarbonylbenzyl, $R^7$ = Table

| Ex. No | .0 | .1 | .2 |
|---|---|---|---|
| 137[g] | m-hydroxymethyl-benzyl | p-hydroxymethyl-benzyl | m-hydroxybenzyl |
| 138[g] | m-(N,N-dimethyl-aminoglycyl)aminobenzyl | m-aminocarbonyl-benzyl | p-hydroxybenzyl |
| 139[g] | m-(N-methylamino)carbonylbenzyl | m-(N-methylamino)benzyl | m-formylbenzyl |
| 140[g] | m-trifluorcarbonylbenzyl | m-hydroxyamidinobenzyl | m-triazolylbenzyl |
| 141[g] | m-formaldoxime-benzyl | m-acetoximebenzyl | benzyl |
| 142[g] | hydroxycarbonyl-benzyl | m-tetrazolylbenzyl | m-pyrazolylbenzyl |
| 143[g] | m-imidazolylbenzyl | p-fluorobenzyl | pyridinylmethyl |
| 144[g] | m-acetylbenzyl | m-aminosulfonylbenzyl | m-methoxybenzyl |

TABLE 21[g]

Formula (Va), $R^4 = R^{23}$ = benzyl, $R^{22}$ = p-hydroxybenzyl, $R^7$ = Table

| Ex. No | .0 | .1 | .2 |
|---|---|---|---|
| 145[g] | m-hydroxymethyl-benzyl | p-hydroxymethyl-benzyl | m-hydroxybenzyl |
| 146[g] | m-(N,N-dimethyl-aminoglycyl)aminobenzyl | m-aminocarbonyl-benzyl | p-hydroxybenzyl |
| 147[g] | m-(N-methylamino)carbonylbenzyl | m-(N-methylamino)benzyl | m-formylbenzyl |
| 148[g] | m-trifluorcarbonylbenzyl | m-hydroxyamidinobenzyl | m-triazolylbenzyl |
| 149[g] | m-formaldoxime-benzyl | m-acetoximebenzyl | benzyl |
| 150[g] | hydroxycarbonyl-benzyl | m-tetrazolylbenzyl | m-pyrazolylbenzyl |
| 151[g] | m-imidazolylbenzyl | p-fluorobenzyl | pyridinylmethyl |
| 152[g] | m-acetylbenzyl | m-aminosulfonylbenzyl | m-methoxybenzyl |

TABLE 22[g]

Formula (Va), $R^4 = R^{23}$ = benzyl, $R^{22}$ = m-(N-methylaminocarbonyl)benzyl, $R^7$ = Table

| Ex. No | .0 | .1 | .2 |
|---|---|---|---|
| 153[g] | m-hydroxymethyl-benzyl | p-hydroxymethyl-benzyl | m-hydroxybenzyl |
| 154[g] | m-(N,N-dimethyl-aminoglycyl)aminobenzyl | m-aminocarbonyl-benzyl | p-hydroxybenzyl |
| 155[g] | m-(N-methylamino)carbonylbenzyl | m-(N-methylamino)benzyl | m-formylbenzyl |
| 156[g] | m-trifluorcarbonylbenzyl | m-hydroxyamidinobenzyl | m-triazolylbenzyl |
| 157[g] | m-formaldoxime-benzyl | m-acetoximebenzyl | benzyl |
| 158[g] | hydroxycarbonyl-benzyl | m-tetrazolylbenzyl | m-pyrazolylbenzyl |
| 159[g] | m-imidazolylbenzyl | p-fluorobenzyl | pyridinylmethyl |
| 160[g] | m-acetylbenzyl | m-aminosulfonylbenzyl | m-methoxybenzyl |

TABLE 23[g]

Formula (Va), $R^4 = R^{23}$ = benzyl, $R^{22}$ = m-(N-methylamino)benzyl, $R^7$ = Table

| Ex.No | .0 | .1 | .2 |
|---|---|---|---|
| 161[g] | m-hydroxymethyl-benzyl | p-hydroxymethyl-benzyl | m-hydroxybenzyl |
| 162[g] | m-(N,N-dimethyl-amino glycyl)-aminobenzyl | m-aminocarbonyl-benzyl | p-hydroxybenzyl |
| 163[g] | m-(N-methylamino)carbonylbenzyl | m-(N-methylamino)benzyl | m-formylbenzyl |
| 164[g] | m-trifluorcarbonylbenzyl | m-hydroxyamidinobenzyl | m-triazolylbenzyl |
| 165[g] | m-formaldoxime-benzyl | m-acetoximebenzyl | benzyl |
| 166[g] | hydroxycarbonyl-benzyl | m-tetrazolylbenzyl | m-pyrazolylbenzyl |
| 167[g] | m-imidazolylbenzyl | p-fluorobenzyl | pyridinylmethyl |
| 168[g] | m-acetylbenzyl | m-aminosulfonylbenzyl | m-methoxybenzyl |

TABLE 24[g]

Formula (Va), $R^4 = R^{23}$ = benzyl, $R^{22}$ = m-formyllbenzyl, $R^7$ = Table

| Ex.No | .0 | .1 | .2 |
|---|---|---|---|
| 169[g] | m-hydroxymethyl-benzyl | p-hydroxymethyl-benzyl | m-hydroxybenzyl |
| 170[g] | m-(N,N-dimethyl-amino glycyl)-aminobenzyl | m-aminocarbonyl-benzyl | p-hydroxybenzyl |
| 171[g] | m-(N-methylamino)carbonylbenzyl | m-(N-methylamino)benzyl | m-formylbenzyl |
| 172[g] | m-trifluorcarbonylbenzyl | m-hydroxyamidinobenzyl | m-triazolylbenzyl |
| 173[g] | m-formaldoxime-benzyl | m-acetoximebenzyl | benzyl |
| 174[g] | hydroxycarbonyl-benzyl | m-tetrazolylbenzyl | m-pyrazolylbenzyl |
| 175[g] | m-imidazolylbenzyl | p-fluorobenzyl | pyridinylmethyl |
| 176[g] | m-acetylbenzyl | m-aminosulfonylbenzyl | m-methoxybenzyl |

TABLE 25[g]

Formula (Va), $R^4 = R^{23}$ = benzyl, $R^{22}$ = m-trifluorocarbonylbenzyl, $R^7$ = Table

| Ex.No | .0 | .1 | .2 |
|---|---|---|---|
| 177[g] | m-hydroxymethyl-benzyl | p-hydroxymethyl-benzyl | m-hydroxybenzyl |
| 178[g] | m-(N,N-dimethyl-amino glycyl)-aminobenzyl | m-aminocarbonyl-benzyl | p-hydroxybenzyl |
| 179[g] | m-(N-methylamino)carbonylbenzyl | m-(N-methylamino)benzyl | m-formylbenzyl |
| 180[g] | m-trifluorcarbonylbenzyl | m-hydroxyamidinobenzyl | m-triazolylbenzyl |
| 181[g] | m-formaldoxime-benzyl | m-acetoximebenzyl | benzyl |
| 182[g] | hydroxycarbonyl-benzyl | m-tetrazolylbenzyl | m-pyrazolylbenzyl |
| 183[g] | m-imidazolylbenzyl | p-fluorobenzyl | pyridinylmethyl |
| 184[g] | m-acetylbenzyl | m-aminosulfonylbenzyl | m-methoxybenzyl |

TABLE 26[g]

Formula (Va), $R^4 = R^{23}$ = benzyl, $R^{22}$ = m-hydroxyamidinobenzyl, $R^7$ = Table

| Ex.No | .0 | .1 | .2 |
| --- | --- | --- | --- |
| 185[g] | m-hydroxymethyl-benzyl | p-hydroxymethyl-benzyl | m-hydroxybenzyl |
| 186[g] | m-(N,N-dimethyl-amino glycyl)-aminobenzyl | m-aminocarbonyl-benzyl | p-hydroxybenzyl |
| 187[g] | m-(N-methylamino)carbonylbenzyl | m-(N-methylamino)benzyl | m-formylbenzyl |
| 188[g] | m-trifluorcarbonylbenzyl | m-hydroxyamidinobenzyl | m-triazolylbenzyl |
| 189[g] | m-formaldoxime-benzyl | m-acetoximebenzyl | benzyl |
| 190[g] | hydroxycarbonyl-benzyl | m-tetrazolylbenzyl | m-pyrazolyl-benzyl |
| 191[g] | m-imidazolylbenzyl | p-fluorobenzyl | pyridinylmethyl |
| 192[g] | m-acetylbenzyl | m-aminosulfonylbenzyl | m-methoxybenzyl |

TABLE 27[g]

Formula (Va), $R^4 = R^{23}$ = benzyl, $R^{22}$ = m-triazolylbenzyl, $R^7$ = Table

| Ex.No | .0 | .1 | .2 |
| --- | --- | --- | --- |
| 193[g] | m-hydroxymethyl-benzyl | p-hydroxymethyl-benzyl | m-hydroxybenzyl |
| 194[g] | m-(N,N-dimethyl-amino glycyl)-aminobenzyl | m-aminocarbonyl-benzyl | p-hydroxybenzyl |
| 195[g] | m-(N-methylamino)carbonylbenzyl | m-(N-methylamino)benzyl | m-formylbenzyl |
| 196[g] | m-trifluorcarbonylbenzyl | m-hydroxyamidinobenzyl | m-triazolylbenzyl |
| 197[g] | m-formaldoxime-benzyl | m-acetoximebenzyl | benzyl |
| 198[g] | hydroxycarbonyl-benzyl | m-tetrazolylbenzyl | m-pyrazolyl-benzyl |
| 199[g] | m-imidazolylbenzyl | p-fluorobenzyl | pyridinylmethyl |
| 200[g] | m-acetylbenzyl | m-aminosulfonylbenzyl | m-methoxybenzyl |

TABLE 28[g]

Formula (Va), $R^4 = R^{23}$ = benzyl, $R^{22}$ = m-formaldoximebenzyl, $R^7$ = Table

| Ex.No | .0 | .1 | .2 |
| --- | --- | --- | --- |
| 201[g] | m-hydroxymethyl-benzyl | p-hydroxymethyl-benzyl | m-hydroxybenzyl |
| 202[g] | m-(N,N-dimethyl-amino glycyl)-aminobenzyl | m-aminocarbonyl-benzyl | p-hydroxybenzyl |
| 203[g] | m-(N-methylamino)carbonylbenzyl | m-(N-methylamino)benzyl | m-formylbenzyl |
| 204[g] | m-trifluorcarbonylbenzyl | m-hydroxyamidinobenzyl | m-triazolylbenzyl |
| 205[g] | m-formaldoxime-benzyl | m-acetoximebenzyl | benzyl |
| 206[g] | hydroxycarbonyl-benzyl | m-tetrazolylbenzyl | m-pyrazolyl-benzyl |
| 207[g] | m-imidazolylbenzyl | p-fluorobenzyl | pyridinylmethyl |
| 208[g] | m-acetylbenzyl | m-aminosulfonylbenzyl | m-methoxybenzyl |

TABLE 29[g]

Formula (Va), $R^4 = R^{23}$ = benzyl, $R^{22}$ = m-acetoximebenzyl, $R^7$ = Table

| Ex.No | .0 | .1 | .2 |
| --- | --- | --- | --- |
| 209[g] | m-hydroxymethyl-benzyl | p-hydroxymethyl-benzyl | m-hydroxybenzyl |
| 210[g] | m-(N,N-dimethyl-amino glycyl)-aminobenzyl | m-aminocarbonyl-benzyl | p-hydroxybenzyl |
| 211[g] | m-(N-methylamino)carbonylbenzyl | m-(N-methylamino)benzyl | m-formylbenzyl |
| 212[g] | m-trifluorcarbonylbenzyl | m-hydroxyamidinobenzyl | m-triazolylbenzyl |
| 213[g] | m-formaldoxime-benzyl | m-acetoximebenzyl | benzyl |
| 214[g] | hydroxycarbonyl-benzyl | m-tetrazolylbenzyl | m-pyrazolyl-benzyl |
| 215[g] | m-imidazolylbenzyl | p-fluorobenzyl | pyridinylmethyl |
| 216[g] | m-acetylbenzyl | m-aminosulfonylbenzyl | m-methoxybenzyl |

TABLE 30[g]

Formula (Va), $R^4 = R^{23}$ = benzyl, $R^{22}$ = benzyl, $R^7$ = Table

| Ex.No | .0 | .1 | .2 |
| --- | --- | --- | --- |
| 217[g] | m-hydroxymethyl-benzyl | p-hydroxymethyl-benzyl | m-hydroxybenzyl |
| 218[g] | m-(N,N-dimethyl-amino glycyl)-aminobenzyl | m-aminocarbonyl-benzyl | p-hydroxybenzyl |
| 219[g] | m-(N-methylamino)carbonylbenzyl | m-(N-methylamino)benzyl | m-formylbenzyl |
| 220[g] | m-trifluorcarbonylbenzyl | m-hydroxyamidinobenzyl | m-triazolylbenzyl |
| 221[g] | m-formaldoxime-benzyl | m-acetoximebenzyl | benzyl |
| 222[g] | hydroxycarbonyl-benzyl | m-tetrazolylbenzyl | m-pyrazolyl-benzyl |
| 223[g] | m-imidazolylbenzyl | p-fluorobenzyl | pyridinylmethyl |
| 224[g] | m-acetylbenzyl | m-aminosulfonylbenzyl | m-methoxybenzyl |

TABLE 31[g]

Formula (Va), $R^4 = R^{23}$ = benzyl, $R^{22}$ = m-hydroxycarbonylbenzyl, $R^7$ = Table

| Ex.No | .0 | .1 | .2 |
| --- | --- | --- | --- |
| 225[g] | m-hydroxymethyl-benzyl | p-hydroxymethyl-benzyl | m-hydroxybenzyl |
| 226[g] | m-(N,N-dimethyl-amino glycyl)-aminobenzyl | m-aminocarbonyl-benzyl | p-hydroxybenzyl |
| 227[g] | m-(N-methylamino)carbonylbenzyl | m-(N-methylamino)benzyl | m-formylbenzyl |
| 228[g] | m-trifluorcarbonylbenzyl | m-hydroxyamidinobenzyl | m-triazolylbenzyl |
| 229[g] | m-formaldoxime-benzyl | m-acetoximebenzyl | benzyl |
| 230[g] | hydroxycarbonyl-benzyl | m-tetrazolylbenzyl | m-pyrazolyl-benzyl |
| 231[g] | m-imidazolylbenzyl | p-fluorobenzyl | pyridinylmethyl |
| 232[g] | m-acetylbenzyl | m-aminosulfonylbenzyl | m-methoxybenzyl |

TABLE 32[g]

Formula (Va), $R^4 = R^{23}$ = benzyl, $R^{22}$ = m-tetrazolylbenzyl, $R^7$ = Table

| Ex.No | .0 | .1 | .2 |
|---|---|---|---|
| 233[g] | m-hydroxymethyl-benzyl | p-hydroxymethyl-benzyl | m-hydroxybenzyl |
| 234[g] | m-(N,N-dimethyl-amino glycyl)-aminobenzyl | m-aminocarbonyl-benzyl | p-hydroxybenzyl |
| 235[g] | m-(N-methylamino)carbonylbenzyl | m-(N-methylamino)benzyl | m-formylbenzyl |
| 236[g] | m-trifluorcarbonyl benzyl | m-hydroxyamidino benzyl | m-triazolylbenzyl |
| 237[g] | m-formaldoxime-benzyl | m-acetoximebenzyl | benzyl |
| 238[g] | hydroxycarbonyl-benzyl | m-tetrazolylbenzyl | m-pyrazolyl-benzyl |
| 239[g] | m-imidazolylbenzyl | p-fluorobenzyl | pyridinylmethyl |
| 240[g] | m-acetylbenzyl | m-aminosulfonyl-benzyl | m-methoxybenzyl |

TABLE 33[g]

Formula (Va), $R^4 = R^{23}$ = benzyl, $R^{22}$ = m-pyrazolylbenzyl, $R^7$ = Table

| Ex.No | .0 | .1 | .2 |
|---|---|---|---|
| 241[g] | m-hydroxymethyl-benzyl | p-hydroxymethyl-benzyl | m-hydroxybenzyl |
| 242[g] | m-(N,N-dimethyl-amino glycyl)-aminobenzyl | m-aminocarbonyl-benzyl | p-hydroxybenzyl |
| 243[g] | m-(N-methylamino)carbonylbenzyl | m-(N-methylamino)benzyl | m-formylbenzyl |
| 244[g] | m-trifluorcarbonyl benzyl | m-hydroxyamidino benzyl | m-triazolylbenzyl |
| 245[g] | m-formaldoxime-benzyl | m-acetoximebenzyl | benzyl |
| 246[g] | hydroxycarbonyl-benzyl | m-tetrazolylbenzyl | m-pyrazolyl-benzyl |
| 247[g] | m-imidazolylbenzyl | p-fluorobenzyl | pyridinylmethyl |
| 248[g] | m-acetylbenzyl | m-aminosulfonyl-benzyl | m-methoxybenzyl |

TABLE 34[g]

Formula (Va), $R^4 = R^{23}$ = benzyl, $R^{22}$ = m-imidazolylbenzyl, $R^7$ = Table

| Ex.No | .0 | .1 | .2 |
|---|---|---|---|
| 249[g] | m-hydroxymethyl-benzyl | p-hydroxymethyl-benzyl | m-hydroxybenzyl |
| 250[g] | m-(N,N-dimethyl-amino glycyl)-aminobenzyl | m-aminocarbonyl-benzyl | p-hydroxybenzyl |
| 251[g] | m-(N-methylamino)carbonylbenzyl | m-(N-methylamino)benzyl | m-formylbenzyl |
| 252[g] | m-trifluorcarbonyl benzyl | m-hydroxyamidino benzyl | m-triazolylbenzyl |
| 253[g] | m-formaldoxime-benzyl | m-acetoximebenzyl | benzyl |
| 254[g] | hydroxycarbonyl-benzyl | m-tetrazolylbenzyl | m-pyrazolyl-benzyl |
| 255[g] | m-imidazolylbenzyl | p-fluorobenzyl | pyridinylmethyl |
| 256[g] | m-acetylbenzyl | m-aminosulfonyl-benzyl | m-methoxybenzyl |

TABLE 35[g]

Formula (Va), $R^4 = R^{23}$ = benzyl, $R^{22}$ = p-fluorobenzyl, $R^7$ = Table

| Ex.No | .0 | .1 | .2 |
|---|---|---|---|
| 257[g] | m-hydroxymethyl-benzyl | p-hydroxymethyl-benzyl | m-hydroxybenzyl |
| 258[g] | m-(N,N-dimethyl-amino glycyl)-aminobenzyl | m-aminocarbonyl-benzyl | p-hydroxybenzyl |
| 259[g] | m-(N-methylamino)carbonylbenzyl | m-(N-methylamino)benzyl | m-formylbenzyl |
| 260[g] | m-trifluorcarbonyl benzyl | m-hydroxyamidino benzyl | m-triazolylbenzyl |
| 261[g] | m-formaldoxime-benzyl | m-acetoximebenzyl | benzyl |
| 262[g] | hydroxycarbonyl-benzyl | m-tetrazolylbenzyl | m-pyrazolyl-benzyl |
| 263[g] | m-imidazolylbenzyl | p-fluorobenzyl | pyridinylmethyl |
| 264[g] | m-acetylbenzyl | m-aminosulfonyl-benzyl | m-methoxybenzyl |

TABLE 36[g]

Formula (Va), $R^4 = R^{23}$ = benzyl, $R^{22}$ = pyridinylmethyl, $R^7$ = Table

| Ex.No | .0 | .1 | .2 |
|---|---|---|---|
| 265[g] | m-hydroxymethyl-benzyl | p-hydroxymethyl-benzyl | m-hydroxybenzyl |
| 266[g] | m-(N,N-dimethyl-amino glycyl)-aminobenzyl | m-aminocarbonyl-benzyl | p-hydroxybenzyl |
| 267[g] | m-(N-methylamino)carbonylbenzyl | m-(N-methylamino)benzyl | m-formylbenzyl |
| 268[g] | m-trifluorcarbonyl benzyl | m-hydroxyamidino benzyl | m-triazolylbenzyl |
| 269[g] | m-formaldoxime-benzyl | m-acetoximebenzyl | benzyl |
| 270[g] | hydroxycarbonyl-benzyl | m-tetrazolylbenzyl | m-pyrazolyl-benzyl |
| 271[g] | m-imidazolylbenzyl | p-fluorobenzyl | pyridinylmethyl |
| 272[g] | m-acetylbenzyl | m-aminosulfonyl-benzyl | m-methoxybenzyl |

TABLE 37[g]

Formula (Va), $R^4 = R^{23}$ = benzyl, $R^{22}$ = m-acetylbenzyl, $R^7$ = Table

| Ex.No | .0 | .1 | .2 |
|---|---|---|---|
| 273[g] | m-hydroxymethyl-benzyl | p-hydroxymethyl-benzyl | m-hydroxybenzyl |
| 274[g] | m-(N,N-dimethyl-amino glycyl)-aminobenzyl | m-aminocarbonyl-benzyl | p-hydroxybenzyl |
| 275[g] | m-(N-methylamino)carbonylbenzyl | m-(N-methylamino)benzyl | m-formylbenzyl |
| 276[g] | m-trifluorcarbonyl benzyl | m-hydroxyamidino benzyl | m-triazolylbenzyl |
| 277[g] | m-formaldoxime-benzyl | m-acetoximebenzyl | benzyl |
| 278[g] | hydroxycarbonyl-benzyl | m-tetrazolylbenzyl | m-pyrazolyl-benzyl |
| 279[g] | m-imidazolylbenzyl | p-fluorobenzyl | pyridinylmethyl |
| 280[g] | m-acetylbenzyl | m-aminosulfonyl-benzyl | m-methoxybenzyl |

TABLE 38[g]

Formula (Va), R⁴ = R²³ = benzyl, R²² = m-aminosulfonylbenzyl, R⁷ = Table

| Ex.No | .0 | .1 | .2 |
|---|---|---|---|
| 281[g] | m-hydroxymethyl-benzyl | p-hydroxymethyl-benzyl | m-hydroxybenzyl |
| 282[g] | m-(N,N-dimethyl-amino glycyl)-aminobenzyl | m-aminocarbonyl-benzyl | p-hydroxybenzyl |
| 283[g] | m-(N-methylamino) carbonylbenzyl | m-(N-methylamino) benzyl | m-formylbenzyl |
| 284[g] | m-trifluorcarbonyl benzyl | m-hydroxyamidino benzyl | m-triazolylbenzyl |
| 285[g] | m-formaldoxime-benzyl | m-acetoximebenzyl | benzyl |
| 286[g] | hydroxycarbonyl-benzyl | m-tetrazolylbenzyl | m-pyrazolyl-benzyl |
| 287[g] | m-imidazolylbenzyl | p-fluorobenzyl | pyridinylmethyl |
| 288[g] | m-acetylbenzyl | m-aminosulfonyl-benzyl | m-methoxybenzyl |

TABLE 39[g]

Formula (Va), R⁴ = R²³ = benzyl, R²² = m-methoxybenzyl, R⁷ = Table

| Ex.No | .0 | .1 | .2 |
|---|---|---|---|
| 289[g] | m-hydroxymethyl-benzyl | p-hydroxymethyl-benzyl | m-hydroxybenzyl |
| 290[g] | m-(N,N-dimethyl-amino glycyl)-aminobenzyl | m-aminocarbonyl-benzyl | p-hydroxybenzyl |
| 291[g] | m-(N-methylamino) carbonylbenzyl | m-(N-methylamino) benzyl | m-formylbenzyl |
| 292[g] | m-trifluorcarbonyl benzyl | m-hydroxyamidino benzyl | m-triazolylbenzyl |
| 293[g] | m-formaldoxime-benzyl | m-acetoximebenzyl | benzyl |
| 294[g] | hydroxycarbonyl-benzyl | m-tetrazolylbenzyl | m-pyrazolyl-benzyl |
| 295[g] | m-imidazolylbenzyl | p-fluorobenzyl | pyridinylmethyl |
| 296[g] | m-acetylbenzyl | m-aminosulfonyl-benzyl | m-methoxybenzyl |

What is claimed is:
1. A compound of the formula (I):

or a pharmaceutically acceptable salt form thereof wherein:
X is N—$R^7$;
$X^1$ is $C(R^4)(R^{4a})$;
$R^4$ and $R^7$ are independently selected from the following groups:
  hydrogen;
  $C_1$–$C_8$ alkyl substituted with 0–3 $R^{11}$;
  $C_2$–$C_8$ alkenyl substituted with 0–3 $R^{11}$;
  $C_2$–$C_8$ alkynyl substituted with 0–3 $R^{11}$;
  $C_3$–$C_8$ cycloalkyl substituted with 0–3 $R^{11}$;
  $C_6$–$C_{10}$ bicycloalkyl substituted with 0–3 $R^{11}$;
  aryl substituted with 0–3 $R^{12}$;
  a $C_6$–$C_{14}$ carbocyclic ring system substituted with 0–3 $R^{12}$;
  a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–3 $R^{12}$;

$R^{4a}$ is selected from the following groups:
  hydrogen;
  $C_1$–$C_4$ alkyl substituted with 1–4 groups selected independently from: halogen or $C_1$–$C_2$ alkoxy;
  benzyl substituted with 1–4 groups selected independently from: halogen or $C_1$–$C_2$ alkoxy;
  —$OR^{20}$;
  $SR^{20}$;

$R^4$ and $R^{4a}$ can alternatively join to form a 5–7 membered carbocyclic ring substituted with 0–2 $R^{12}$;

n is 0, 1

$R^5$ is selected from H; halogen; —$N(R^{20})_2$; —$SR^{20}$; —$OR^{20}$; or $C_1$–$C_6$ alkyl substituted with 0–3 —$N(R^{20})_2$, —$SR^{20}$, or —$OR^{20}$;

$R^{5a}$ is selected from H, halogen, $C_1$–$C_6$ alkyl, —$N(R^{20})_2$, —$SR^{20}$, or —$OR^{20}$;

$R^5$ and $R^{5a}$ can alternatively join to form =O, =S, or a ketal ring;

$R^{20}$ and $R^{21}$ are independently selected from:
  hydrogen;
  $C_1$–$C_6$ alkyl substituted with 0–3 $R^{11}$;
  $C_3$–$C_6$ alkoxyalkyl substituted with 0–3 $R^{11}$;
  $C_1$–$C_6$ alkylcarbonyl substituted with 0–3 $R^{11}$;
  $C_1$–$C_6$ alkoxycarbonyl substituted with 0–3 $R^{11}$;
  benzoyl substituted with 0–3 $R^{12}$;
  phenoxycarbonyl substituted with 0–3 $R^{12}$;
  phenylaminocarbonyl substituted with 0–3 $R^{12}$;
  $C_1$–$C_6$ alkylsulfenyl substituted with 0–3 $R^{11}$;
  $C_1$–$C_6$ alkylsulfonyl substituted with 0–3 $R^{11}$; or
  any group that, when administered to a mammalian subject, cleaves to form a free hydroxyl, amino or sulfhydryl;

$R^{11}$ is selected from one or more of the following:
  keto, halogen, cyano, —$CH_2NR^{13}R^{14}$, —$NR^{13}R^{14}$, —$CO_2R^{13}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, or —$C(R^{14})=N(OR^{14})$;

$C_1$–$C_4$ alkyl substituted with 0–2 $R^{12}$,
1–3 amino acids, linked together via amide bonds and linked to $R^4$ or $R^7$, $R^{20}$, or $R^{21}$ via the amine or carboxy terminus;
—($C_1$–$C_3$ alkyl)aryl substituted with 0–2 $R^{12}$;
a $C_3$–$C_{14}$ carbocyclic residue substituted with 0–3 $R^{12}$;
aryl substituted with 0–3 $R^{12}$; or
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–3 $R^{12}$;

$R^{12}$, when a substituent on carbon, is selected from one or more of the following:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy; or a 5- or 6-membered heterocyclic ring containing from 1 to 4 heteroatoms independently selected from oxygen, nitrogen or sulfur;

when $R^{12}$ is attached to a saturated carbon atom, it may be carbonyl or thiocarbonyl;

or $R^{12}$ may alternatively be a 3- or 4- carbon chain attached to adjacent carbons on the ring to form a fused 5- or 6- membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$;

$R^{12}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})$=$N(OR^{14})$;

$R^{13}$ is selected from:

H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_1$–$C_6$ alkylcarbonyl substituted with 0–3 $R^{11A}$;
$C_1$–$C_6$ alkoxycarbonyl substituted with 0–3 $R^{11A}$;
$C_1$–$C_6$ alkylaminocarbonyl substituted with 0–3 $R^{11A}$;
$C_3$–$C_6$ alkoxyalkyl substituted with 0–3 $R^{11A}$;
an amine protecting group when $R^{13}$ is bonded to N;
a hydroxy protecting group when $R^{13}$ is bonded to O;

$R_{14}$ is OH; H; $CF_3$; $C_1$–$C_4$ alkyl substituted with 0–3 groups selected from OH, $C_1$–$C_4$ alkoxy, halogen, $NH_2$; $C_1$–$C_6$ alkoxy; $NH_2$; $C_2$–$C_6$ alkenyl; benzyl; an amine protecting group when $R^{14}$ is bonded to N; a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

W is selected from:
—$N(R^{22})C(=Z)N(R^{23})$—;

Z is O, S, or $NR^{24}$;

$R^{22}$ is independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$;
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 $R^{32}$;

$R^{23}$ is independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$;
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 $R^{32}$;

$R^{24}$ is selected from: hydrogen; hydroxy; amino; $C_1$–$C_4$ alkyl; $C_1$–$C_4$ alkoxy; mono- or di-($C_1$–$C_6$ alkyl)amino; cyano; nitro; benzyloxy; —$NHSO_2$aryl, aryl being optionally substituted with ($C_1$–$C_6$)alkyl;

alternatively, $R^{22}$ can join with $R^4$ or $R^{4A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$ can join with $R^7$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$ or $R^{23}$ can join with $R^5$ or $R^6$ to form a 0- to 7-membered bridge to form a carbocyclic or heterocyclic ring, said bridge being substituted with 0–2 $R^{12}$ and said bridge containing 0–3 heteroatoms independently selected from N, S, or O (i.e., a 0-membered bridge is formed when $R^{22}$, or $R^{23}$, are taken together with $R^5$ or $R^6$ to form a direct bond);

$R^{31}$ is selected from one or more of the following:
keto, halogen, cyano, —$CH_2NR^{13}R^{14}$, —$NR^{13}R^{14}$, —$CO_2R^{13}$, —$C(=O)R^{11}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})$=$N(OR^{14})$; or 1–3 amino acids, linked together via amide bonds and linked to $R^{22}$, $R^{23}$, $R^4$ or $R^7$ via the amine or carboxy terminus;

a $C_3$–$C_{14}$ carbocyclic residue substituted with 0–5 $R^{32}$; or a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 $R^{32}$;

$R^{32}$, when a substituent on carbon, is selected from one or more of the following:

phenyl, benzyl, phenethyl, phenoxy, benzyloxy, halogen, hydroxy, nitro, cyano, $C_1$–$C_4$ alkyl, $C_3$–$C_{10}$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, —$CONR^{13}NR^{13}R^{14}$, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_m$ $R^{13}$, —$SO_2NR^{13}R^{14}$, —$NHSO_2R^{14}$, —$OCH_2CO_2H$, 2-(1-morpholino)ethoxy, —$C(R^{14})$=$N(OR^{14})$; $NO_2$, —$OR^{13}$, —$NR^{40}R^{41}$, —$SO_mNR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—$(C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or —$C(=O)NR^{13}C(R^{11})_2NR^{13}R^{14}$; —$C(=O)NR^{13}C(R^{11})_2NR^{13}NR^{14}$;

—$C(=O)NR^{13}C(R^{11})_2NR^{13}CO_2R^{13}$;

—$C(=O)NR^{13}$—$(C_1$–$C_4$ alkyl)-$NR^{13}CO_2R^{13}$; or

—$C(=O)C(R^{11})_2NR^{13}R^{14}$; —$C(=O)C(R^{11})_2NR^{13}NR^{14}$;

—$C(=O)C(R^{11})_2NR^{13}CO_2R^{13}$; —$C(=O)$—$(C_1$–$C_4$ alkyl)-$NR^{13}R^{14}$; —$C(=O)$—$(C_1$–$C_4$ alkyl)-$NR^{13}CO_2R^{13}$; or $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or OH;

$C_1$–$C_4$ alkyl substituted with 0–4 groups selected from: $R^{11}$, =$NR^{14}$, =$NNR^{13}C(=O)NR^{13}R^{14}$ or —$NR^{13}R^{14}$;

$C_2$–$C_4$ alkenyl substituted with 0–4 $R^{11}$;

$C_2$–$C_4$ alkynyl substituted with 0–4 $R^{11}$;

a 5- or 6-membered heterocyclic ring containing from 1 to 4 heteroatoms selected from oxygen, nitrogen or sulfur;

when $R^{32}$ is attached to a saturated carbon atom, it may be =O or =S;

$R^{32}$ may alternatively be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$;

$R^{32}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})$=$N(OR^{14})$;

$R^{33}$ is selected from:
H;
$C_1$–$C_3$ alkyl substituted at the $C_2$ or $C_3$ carbon with —$N(R^{20})_2$, —$SR^{20}$, or —$OR^{21}$;
or when taken together with $R^{33a}$, form =O, =S, or a ketal group;

$R^{33a}$ is selected from:
H;
$C_1$–$C_3$ alkyl substituted at the $C_2$ or $C_3$ carbon with —$N(R^{20})_2$, —$SR^{20}$, or —$OR^{21}$;
or, when taken together with $R^{33}$, form =O;
alternatively, $R^{33}$ or $R^{33a}$ can join with $R^7$ to form a fused 5- or 6- membered carbocyclic ring;

$R^{40}$ is selected from: H, $C_1$–$C_3$ alkyl;

$R^{41}$ is selected from:
—$C(=O)NR^{13}R^{14}$;
—$C(=O)NR^{13}NR^{14}$;
—$C(=O)C(R^{11})_2NR^{13}R^{14}$;
—$C(=O)C(R^{11})_2NR^{13}NR^{14}$;
—$C(=O)C(R^{11})_2NR^{13}CO_2R^{13}$;
—$C(=O)H$;
—$C(=O)R^{11}$;
—$C(=O)$—$(C_1$–$C_4$ alkyl)-$NR^{13}R^{14}$;
—$C(=O)$—$(C_1$–$C_4$ alkyl)-$NR^{13}CO_2R^{13}$;
1–3 amino acids linked together via amide bonds, and linked to the N atom via the carboxy terminus;

provided that:
when $R^4$ and $R^{4a}$ are hydrogen and X is N—$R^7$, at least one of the following is not hydrogen: $R^7$, $R^{22}$.

2. A compound of claim 1, or a pharmaceutically acceptable salt thereof, of the formula (IIa):

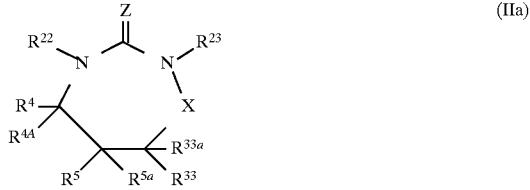

(IIa)

or a pharmaceutically acceptable salt form thereof, wherein:
X is N—$R^7$;
$R^4$ and $R^7$ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
$C_3$–$C_8$ cycloalkyl substituted with 0–3 $R^{11}$;
$C_6$–$C_{10}$ bicycloalkyl substituted with 0–3 $R^{11}$;
aryl substituted with 0–3 $R^{12}$;
a $C_6$–$C_{14}$ carbocyclic residue substituted with 0–3 $R^{12}$;
a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system substituted with 0–2 $R^{12}$ $R^{4a}$ is selected from the following groups:
hydrogen;
$C_1$–$C_4$ alkyl substituted with halogen or $C_1$–$C_2$ alkoxy;
benzyl substituted with halogen or $C_1$–$C_2$ alkoxy;
—$OR^{20}$; or $SR^{20}$;
$R^4$ and $R^{4a}$ can alternatively join to form a 5–7 membered carbocyclic ring substituted with 0–2 $R^{12}$;
$R^5$ is selected from =O; H; halogen; $C_1$–$C_6$ alkyl substituted with 0–3 —OH; —$N(R^{20})_2$; —$SR^{20}$; or —$OR^{20}$;

$R^{5a}$ is selected from hydrogen, halogen, $C_1-C_6$ alkyl, —N($R^{20}$)$_2$, —S$R^{20}$, or —O$R^{20}$;

$R^5$ and $R^{5a}$ can alternatively join to form =O, =S, or a ketal ring;

$R^{20}$ and $R^{21}$ are independently selected from:
hydrogen;
$C_1-C_6$ alkyl substituted with 0–3 $R^{11}$;
$C_3-C_6$ alkoxyalkyl substituted with 0–3 $R^{11}$;
$C_1-C_6$ alkylcarbonyl substituted with 0–3 $R^{11}$;
$C_1-C_6$ alkoxycarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$;
$C_1-C_6$ alkylsulfenyl substituted with 0–3 $R^{11}$;
$C_1-C_6$ alkylsulfonyl substituted with 0–3 $R^{11}$; or
any group that, when administered to a mammalian subject, cleaves to form a free hydroxyl, amino or sulfhydryl;

$R^{11}$ is selected from one or more of the following:
keto, halogen, cyano, —CH$_2$N$R^{13}R^{14}$, —N$R^{13}R^{14}$, —CO$_2R^{13}$, —OC(=O)$R^{13}$, —O$R^{13}$, $C_2-C_6$ alkoxyalkyl, —S(O)$_m R^{13}$, —NHC(=NH)NH$R^{13}$, —C(=NH)NH$R^{13}$, —C(=O)N$R^{13}R^{14}$, —N$R^{14}$C(=O)$R^{13}$, =NO$R^{14}$, —N$R^{14}$C(=O)O$R^{14}$, —OC(=O)N$R^{13}R^{14}$, —N$R^{13}$C(=O)N$R^{13}R^{14}$, —N$R^{14}$SO$_2$N$R^{13}R^{14}$, —N$R^{14}$SO$_2R^{13}$, —SO$_2$N$R^{13}R^{14}$, $C_1-C_4$ alkyl, $C_2-C_4$ alkenyl, $C_3-C_{10}$ cycloalkyl, $C_3-C_6$ cycloalkylmethyl, benzyl, phenethyl, phenoxy, benzyloxy, nitro, $C_7-C_{10}$ arylalkyl, hydroxamic acid, hydrazide, boronic acid, sulfonamide, formyl, $C_3-C_6$ cycloalkoxy, $C_1-C_4$ alkyl substituted with —N$R^{13}R^{14}$, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, —OCH$_2$CO$_2$H, 2-(1-morpholino)ethoxy, azido, or —C($R^{14}$)=N(O$R^{14}$);
1–3 amino acids, linked together via amide bonds and linked to $R^4$ or $R^7$, $R^{20}$, or $R^{21}$ via the amine or carboxy terminus;
—($C_1-C_3$ alkyl)aryl substituted with 0–2 $R^{12}$;
a $C_5-C_{14}$ carbocyclic residue substituted with 0–3 $R^{12}$;
aryl substituted with 0–3 $R^{12}$; or
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–3 $R^{12}$;

$R^{12}$, when a substituent on carbon, is selected from one or more of the following:
phenyl, benzyl, phenethyl, phenoxy, benzyloxy, halogen, hydroxy, nitro, cyano, $C_1-C_4$ alkyl, $C_3-C_6$ cycloalkyl, $C_3-C_6$ cycloalkylmethyl, $C_7-C_{10}$ arylalkyl, $C_1-C_4$ alkoxy, —CO$_2$H, hydroxamic acid, hydrazide, oxime, boronic acid, sulfonamide, formyl, $C_3-C_6$ cycloalkoxy, —O$R^{13}$, $C_1-C_4$ alkyl substituted with —N$R^{13}R^{14}$, —N$R^{13}R^{14}$, $C_2-C_6$ alkoxyalkyl, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, —S(O)$_m R^{13}$, —SO$_2$N$R^{13}R^{14}$, —NHSO$_2R^{14}$, —OCH$_2$CO$_2$H, 2-(1-morpholino)ethoxy; or
a 5- or 6-membered heterocyclic ring containing from 1 to 4 heteroatoms independently selected from oxygen, nitrogen or sulfur;

when $R^{12}$ is attached to a saturated carbon atom, it may be carbonyl or thiocarbonyl;
or $R^{12}$ may alternatively be a 3- or 4- carbon chain attached to adjacent carbons on the ring to form a fused 5- or 6- membered ring, said 5- or 6- membered ring being optionally substituted on the aliphatic carbons with halogen, $C_1-C_4$ alkyl, $C_1-C_4$ alkoxy, hydroxy, or —N$R^{13}R^{14}$;

$R^{12}$, when a substituent on nitrogen, is selected from one or more of the following:
phenyl, benzyl, phenethyl, hydroxy, $C_1-C_4$ hydroxyalkyl, $C_1-C_4$ alkoxy, $C_1-C_4$ alkyl, $C_3-C_6$ cycloalkyl, $C_3-C_6$ cycloalkylmethyl, —CH$_2$N$R^{13}R^{14}$, —N$R^{13}R^{14}$, $C_2-C_6$ alkoxyalkyl, $C_1-C_4$ haloalkyl, $C_1-C_4$ alkoxycarbonyl, —CO$_2$H, $C_1-C_4$ alkylcarbonyloxy, $C_1-C_4$ alkylcarbonyl, —C($R^{14}$)=N(O$R^{14}$);

$R^{13}$ is selected from:
H;
phenyl substituted with 0–3 $R^{11A}$;
benzyl substituted with 0–3 $R^{11A}$;
$C_1-C_6$ alkyl substituted with 0–3 $R^{11A}$;
$C_2-C_4$ alkenyl substituted with 0–3 $R^{11A}$;
$C_1-C_6$ alkylcarbonyl substituted with 0–3 $R^{11A}$;
$C_1-C_6$ alkoxycarbonyl substituted with 0–3 $R^{11A}$;
$C_1-C_6$ alkylaminocarbonyl substituted with 0–3 $R^{11A}$;
$C_3-C_6$ alkoxyalkyl substituted with 0–3 $R^{11A}$;
an amine protecting group when $R^{13}$ is bonded to N;
a hydroxy protecting group when $R^{13}$ is bonded to O;

$R^{14}$ is OH, H, CF$_3$; $C_1-C_4$ alkyl substituted with 0–3 groups selected from OH, $C_1-C_4$ alkoxy, halogen, NH$_2$; $C_1-C_6$ alkoxy; NH$_2$; $C_2-C_6$ alkenyl; or benzyl; an amine protecting group when $R^{14}$ is bonded to N; a hydroxy protecting group when $R^{14}$ is bonded to O;

$R^{13}$ and $R^{14}$ can alternatively join to form —(CH$_2$)$_4$—, —(CH$_2$)$_5$—, —CH$_2$CH$_2$N($R^{15}$)CH$_2$CH$_2$—, or —CH$_2$CH$_2$OCH$_2$CH$_2$—;

$R^{15}$ is H or CH$_3$;
m is 0, 1 or 2;
Z is O, S, or N$R^{24}$;

$R^{22}$ is independently selected from the following:
hydrogen;
$C_1-C_8$ alkyl substituted with 0–3 $R^{31}$;
$C_2-C_8$ alkenyl substituted with 0–3 $R^{31}$;
$C_2-C_8$ alkynyl substituted with 0–3 $R^{31}$;
a $C_3-C_{14}$ carbocyclic ring system substituted with 0–5 $R^{31}$ or $R^{32}$;
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 $R^{32}$;

$R^{23}$ is independently selected from the following:
hydrogen;
$C_1-C_8$ alkyl substituted with 0–3 $R^{31}$;
$C_2-C_8$ alkenyl substituted with 0–3 $R^{31}$;
$C_2-C_8$ alkynyl substituted with 0–3 $R^{31}$;
a $C_3-C_{14}$ carbocyclic ring system substituted with 0–5 $R^{31}$ or $R^{32}$;
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 $R^{32}$;

$R^{24}$ is selected from: hydrogen; hydroxy; amino; $C_1$–$C_4$ alkyl; $C_1$–$C_4$ alkoxy; mono- or di-($C_1$–$C_6$ alkyl)amino; cyano; nitro; benzyloxy; —NHSO$_2$aryl, aryl being optionally substituted with ($C_1$–$C_6$)alkyl;

alternatively, $R^{22}$ can join with $R^4$ or $R^{4A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$ can join with $R^7$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$, or $R^{23}$ can join with $R^5$ or $R^{33}$ to form a 0- to 7-membered bridge to form a carbocyclic or heterocyclic ring, said bridge being substituted with 0–2 $R^{12}$ and said bridge containing 0–3 heteroatoms independently selected from N, S, or O;

$R^{31}$ is selected from one or more of the following:
keto, halogen, cyano, —CH$_2$NR$^{13}$R$^{14}$, —NR$^{13}$R$^{14}$, —CO$_2$R$^{13}$, —C(=O)R$^{11}$, —OC(=O)R$^{13}$, —OR$^{13}$, $C_2$–$C_6$ alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —NR$^{13}$R$^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2$R$^{13}$, 2-(1-morpholino)ethoxy, azido, —C(R$^{14}$)=N(OR$^{14}$); or 1–3 amino acids, linked together via amide bonds and linked to $R^{22}$, $R^{23}$, $R^4$ or $R^7$ via the amine or carboxy terminus;

a $C_5$–$C_{14}$ carbocyclic residue substituted with 0–3 $R^{32}$;
a $C_5$–$C_{14}$ carbocyclic residue substituted with 0–5 $R^{32}$; or a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 $R^{32}$;

$R^{32}$, when a substituent on carbon, is selected from one or more of the following:

phenyl, benzyl, phenethyl, phenoxy, benzyloxy, halogen, hydroxy, nitro, cyano, $C_1$–$C_4$ alkyl, $C_3$–$C_{10}$ cycloalkyl, $C_3$–$C_6$ cycloalkylmethyl, $C_7$–$C_{10}$ arylalkyl, $C_1$–$C_4$ alkoxy, —CO$_2$H, hydroxamic acid, —CONR$^{13}$NR$^{13}$R$^{14}$, hydrazide, oxime, boronic acid, sulfonamide, formyl, $C_3$–$C_6$ cycloalkoxy, —OR$^{13}$, $C_1$–$C_4$ alkyl substituted with —NR$^{13}$R$^{14}$, —NR$^{13}$R$^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m$R$^{13}$, —SO$_2$NR$^{13}$R$^{14}$, —NHSO$_2$R$^{14}$, —OCH$_2$CO$_2$H, 2-(1-morpholino)ethoxy, —C(R$^{14}$)=N(OR$^{14}$); NO$_2$, —OR$^{13}$, —NR$^{40}$R$^{41}$, —SO$_m$R$^{13}$, —SO$_m$NR$^{13}$R$^{14}$, —C(=O)NR$^{13}$R$^{14}$, —OC(=O)NR$^{13}$R$^{14}$, —C(=O)R$^{11}$, —OC(=O)R$^{11}$, —OCO$_2$R$^{13}$, phenyl, —C(=O)NR$^{13}$—($C_1$–$C_4$ alkyl)-NR$^{13}$R$^{14}$, —C(=O)NR$^{40}$R$^{41}$, $C_1$–$C_4$ haloalkyl, $C_1$–$C_4$ haloalkoxy, $C_2$–$C_4$ haloalkenyl, $C_1$–$C_4$ haloalkynyl, or —C(=O)NR$^{13}$C(R$^{11}$)$_2$NR$^{13}$R$^{14}$; —C(=O)NR$^{13}$C(R$^{11}$)$_2$NR$^{13}$NR$^{14}$;
—C(=O)NR$^{13}$C(R$^{11}$)$_2$NR$^{13}$CO$_2$R$^{13}$;
—C(=O)NR$^{13}$—($C_1$–$C_4$ alkyl)-NR$^{13}$CO$_2$R$^{13}$; or
—C(=O)C(R$^{11}$)$_2$NR$^{13}$R$^{14}$; —C(=O)C(R$^{11}$)$_2$NR$^{13}$NR$^{14}$;
—C(=O)C(R$^{11}$)$_2$NR$^{13}$CO$_2$R$^{13}$; —C(=O)—($C_1$–$C_4$ alkyl)-NR$^{13}$R$^{14}$; —C(=O)—($C_1$–$C_4$ alkyl)-NR$^{13}$CO$_2$R$^{13}$; or $C_1$–$C_4$ alkoxy substituted with 0–4 groups selected from: R$^{11}$, $C_3$–$C_6$ cycloalkyl, —CO$_2$R$^{13}$, —C(=O)NR$^{13}$R$^{14}$, —NR$^{13}$R$^{14}$ or OH;

$C_1$–$C_4$ alkyl substituted with 0–4 groups selected from: R$^{11}$, =NR$^{14}$, =NNR$^{13}$C(=O)NR$^{13}$R$^{14}$ or —NR$^{13}$R$^{14}$;

$C_2$–$C_4$ alkenyl substituted with 0–4 R$^{11}$;
$C_2$–$C_4$ alkynyl substituted with 0–4 R$^{11}$;

a 5- or 6-membered heterocyclic ring containing from 1 to 4 heteroatoms selected from oxygen, nitrogen or sulfur;

when $R^{32}$ is attached to a saturated carbon atom, it may be =O or =S;

$R^{32}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —NR$^{13}$R$^{14}$;

$R^{32}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$NR$^{13}$R$^{14}$, —NR$^{13}$R$^{14}$, $C_2$–$C_6$ alkoxyalkyl, $C_1$–$C_4$ haloalkyl, $C_1$–$C_4$ alkoxycarbonyl, —CO$_2$H, $C_1$–$C_4$ alkylcarbonyloxy, $C_1$–$C_4$ alkylcarbonyl, —C(R$^{14}$)=N(OR$^{14}$);

$R^{33}$ is selected from:
H;
$C_1$–$C_3$ alkyl substituted at the $C_2$ or $C_3$ carbon with —N(R$^{20}$)$_2$, —SR$^{20}$, or —OR$^{21}$;
or when taken together with $R^{33a}$, form =O, =S, or a ketal group;

$R^{33a}$ is selected from:
H;
$C_1$–$C_3$ alkyl substituted at the $C_2$ or $C_3$ carbon with —N(R$^{20}$)$_2$, —SR$^{20}$, or —OR$^{21}$;
or, when taken together with $R^{33}$, form =O;

alternatively, $R^{33}$ or $R^{33a}$ can join with $R^7$ to form a fused 5- or 6-membered carbocyclic ring;

$R^{40}$ is selected from: H, $C_1$–$C_3$ alkyl;
$R^{41}$ is selected from:
—C(=O)NR$^{13}$R$^{14}$;
—C(=O)NR$^{13}$NR$^{14}$;
—C(=O)C(R$^{11}$)$_2$NR$^{13}$R$^{14}$;
—C(=O)C(R$^{11}$)$_2$NR$^{13}$NR$^{14}$;
—C(=O)C(R$^{11}$)$_2$NR$^{13}$CO$_2$R$^{13}$;
—C(=O)H;

—C(=O)R$^{11}$;
—C(=O)—(C$_1$-C$_4$ alkyl)-NR$^{13}$R$^{14}$;
—C(=O)—(C$_1$-C$_4$ alkyl)-NR$^{13}$CO$_2$R$^{13}$;
1–3 amino acids linked together via amide bonds, and linked to the N atom via the carboxy terminus;
provided that:
when R$^4$ and R$^{4a}$ are hydrogen and X is N—R$^7$, at least one of the following is not hydrogen: R$^7$, R$^{22}$.

3. A compound of claim 2, or a pharmaceutically acceptable salt thereof, of formula (IIb):

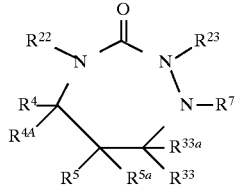

wherein:
R$^4$ and R$^7$ are independently selected from the following groups:
hydrogen;
C$_1$-C$_4$ alkyl substituted with 0–3 R$^{11}$;
C$_3$-C$_4$ alkenyl substituted with 0–3 R$^{11}$;
R$^{11}$ is selected from one or more of the following:
keto, halogen, —CH$_2$NR$^{13}$R$^{14}$, —NR$^{13}$R$^{14}$, —OR$^{13}$, C$_2$-C$_4$ alkoxyalkyl, C$_1$-C$_4$ alkyl, C$_2$-C$_4$ alkenyl, C$_3$-C$_6$ cycloalkyl;
aryl(C$_1$-C$_3$ alkyl) substituted with 0–2 R$^{12}$;
aryl substituted with 0–3 R$^{12}$; or
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 R$^{12}$;
R$^{12}$, when a substituent on carbon, is selected from one or more of the following:
phenyl, benzyl, phenethyl, phenoxy, benzyloxy, halogen, C$_1$-C$_4$ alkyl, C$_7$-C$_{10}$ arylalkyl, C$_1$-C$_4$ alkoxy, —CO$_2$H, hydroxamic acid, hydrazide, oxime, boronic acid, sulfonamide, formyl, C$_3$-C$_6$ cycloalkoxy, —OR$^{13}$, C$_1$-C$_4$ alkyl substituted with —NR$^{13}$R$^{14}$, —NR$^{13}$R$^{14}$, methylenedioxy, C$_1$-C$_4$ haloalkyl, C$_1$-C$_4$ alkylcarbonyl, C$_1$-C$_4$ alkylcarbonylamino, —OH, hydroxymethyl; or
a 5- or 6-membered heterocyclic ring containing from 1 to 4 heteroatoms selected from oxygen, nitrogen or sulfur;
R$^{12}$, when a substituent on nitrogen, is benzyl or methyl;
R$^{13}$ is H, C$_1$-C$_4$ alkyl, or C$_3$-C$_6$ alkoxyalkyl, C$_2$-C$_4$ alkenyl, or benzyl;
R$^{14}$ is OH, H, CF$_3$, or C$_1$-C$_4$ alkyl, C$_1$-C$_4$ alkoxy, NH$_2$, C$_2$-C$_4$ alkenyl, or benzyl;
R$^{13}$ and R$^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;
R$^{22}$ and R$^{23}$ are independently selected from the following:
hydrogen;
C$_1$-C$_8$ alkyl substituted with 0–3 R$^{31}$;
C$_2$-C$_6$ alkenyl substituted with 0–3 R$^{31}$;
C$_2$-C$_4$ alkynyl substituted with 0–1 R$^{31}$;
R$^{31}$ is selected from one or more of the following:
keto, halogen, —CH$_2$NR$^{13}$R$^{14}$, —NR$^{13}$R$^{14}$, —OR$^{13}$, C$_2$-C$_4$ alkoxyalkyl, C$_1$-C$_4$ alkyl, C$_2$-C$_4$ alkenyl, C$_3$-C$_{10}$ cycloalkyl, —C(R$^{14}$)=N(OR$^{14}$), —CO$_2$R$^{13}$, —S(O)$_m$R$^{13}$;
aryl substituted with 0–3 R$^{32}$; or
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 R$^{32}$;
R$^{32}$, when a substituent on carbon, is selected from one or more of the following:
phenethyl, phenoxy, C$_3$-C$_6$ cycloalkyl, C$_3$-C$_6$ cycloalkylmethyl, C$_7$-C$_{10}$ arylalkyl, hydrazide, oxime, boronic acid, C$_2$-C$_6$ alkoxyalkyl, methylenedioxy, ethylenedioxy, C$_1$-C$_4$ alkylcarbonyloxy, —NHSO$_2$R$^{14}$, benzyloxy, halogen, 2-(1-morpholino)ethoxy, —CO$_2$R$^{13}$, hydroxamic acid, —CONR$^{13}$NR$^{13}$R$^{14}$, cyano, boronic acid, sulfonamide, —CHO, C$_3$-C$_6$ cycloalkoxy, —NR$^{13}$R$^{14}$, —C(R$^{14}$)=N(OR$^{14}$), NO$_2$, —OR$^{13}$, —NR$^{40}$R$^{41}$, —SO$_m$R$^{13}$, —SO$_m$NR$^{13}$R$^{14}$, —C(=O)NR$^{13}$R$^{14}$, —OC(=O) NR$^{13}$R$^{14}$, —C(=O)R$^{11}$, —OC(=O)R$^{11}$, —OCO$_2$R$^{13}$, phenyl, —C(=O)NR$^{13}$—(C$_1$-C$_4$ alkyl)-NR$^{13}$R$^{14}$, —C(=O)NR$^{40}$R$^{41}$, C$_1$-C$_4$ haloalkyl, C$_1$-C$_4$ haloalkoxy, C$_2$-C$_4$ haloalkenyl, C$_1$-C$_4$ haloalkynyl, or
C$_1$-C$_4$ alkoxy substituted with 0–3 groups selected from: R$^{11}$, C$_3$-C$_6$ cycloalkyl, —CO$_2$R$^{13}$, —C(=O) NR$^{13}$R$^{14}$, —NR$^{13}$R$^{14}$ or OH;
C$_1$-C$_4$ alkyl substituted with 0–3 groups selected from: R$^{11}$, =NR$^{14}$, =NNR$^{13}$C(=O)NR$^{13}$R$^{14}$ or —NR$^{13}$R$^{14}$;
C$_2$-C$_4$ alkenyl substituted with 0–3 R$^{11}$;
C$_2$-C$_4$ alkynyl substituted with 0–3 R$^{11}$;
a 5- or 6-membered heterocyclic ring containing from 1 to 4 heteroatoms independently selected from oxygen, nitrogen or sulfur;
R$^{32}$, when a substituent on nitrogen, is benzyl or methyl;
R$^{33}$ is hydrogen or, when taken together with R$^{33}$, form a =O group;
provided that:
when R$^4$ is hydrogen at least one of the following is not hydrogen: R$^7$, or R$^{22}$.

4. A compound of claim 1 of the formula (IVa) or the formula (IVb):

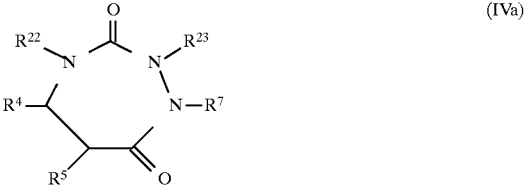

(IVa)

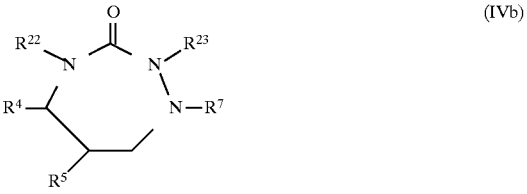

(IVb)

or a pharmaceutically acceptable salt form thereof, wherein:
R$^4$ and R$^7$ are independently selected from the following groups:

hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
$C_3$–$C_8$ cycloalkyl substituted with 0–3 $R^{11}$;
$C_6$–$C_{10}$ bicycloalkyl substituted with 0–3 $R^{11}$;
aryl substituted with 0–3 $R^{12}$;
a $C_6$–$C_{14}$ carbocyclic residue substituted with 0–3 $R^{12}$;
a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system substituted with 0–2 $R^{12}$;

$R^5$ is selected from =O; H; halogen; $C_1$–$C_6$ alkyl substituted with 0–3 —OH; —N$(R^{20})_2$; —S$R^{20}$; or —O$R^{20}$;

$R^{20}$ is selected from:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$;
$C_1$–$C_6$ alkylsulfenyl substituted with 0–3 $R^{11}$;
$C_1$–$C_6$ alkylsulfonyl substituted with 0–3 $R^{11}$; or
any group that, when administered to a mammalian subject, cleaves to form a free hydroxyl, amino or sulfhydryl;

$R^{11}$ is selected from one or more of the following:
keto, halogen, cyano, —CH$_2$NR$^{13}$R$^{14}$, —NR$^{13}$R$^{14}$, —CO$_2$R$^{13}$, —OC(=O)R$^{13}$, —OR$^{13}$, $C_2$–$C_6$ alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —NR$^{13}$R$^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, azido, or —C(R$^{14}$)=N(OR$^{14}$);
1–3 amino acids, linked together via amide bonds and linked to $R^4$ or $R^7$, $R^{20}$, or $R^{21}$ via the amine or carboxy terminus;
—(C$_1$–C$_3$ alkyl)aryl substituted with 0–2 $R^{12}$;
a $C_5$–$C_{14}$ carbocyclic residue substituted with 0–3 $R^{12}$;
aryl substituted with 0–3 $R^{12}$; or
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–3 $R^{12}$;

$R^{12}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —CO$_2$H, hydroxamic acid, hydrazide, oxime, boronic acid, sulfonamide, formyl, $C_3$–$C_6$ cycloalkoxy, —OR$^{13}$, $C_1$–$C_4$ alkyl substituted with —NR$^{13}$R$^{14}$, —NR$^{13}$R$^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m$R$^{13}$, —SO$_2$NR$^{13}$R$^{14}$, —NHSO$_2$R$^{14}$, —OCH$_2$CO$_2$H, 2-(1-morpholino)ethoxy; or
a 5- or 6-membered heterocyclic ring containing from 1 to 4 heteroatoms independently selected from oxygen, nitrogen or sulfur;
when $R^{12}$ is attached to a saturated carbon atom, it may be carbonyl or thiocarbonyl;
or $R^{12}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —NR$^{13}$R$^{14}$;

$R^{12}$, when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$NR$^{13}$R$^{14}$, —NR$^{13}$R$^{14}$, $C_2$–$C_6$ alkoxyalkyl, $C_1$–$C_4$ haloalkyl, $C_1$–$C_4$ alkoxycarbonyl, —CO$_2$H, $C_1$–$C_4$ alkylcarbonyloxy, $C_1$–$C_4$ alkylcarbonyl, —C(R$^{14}$)=N(OR$^{14}$);

$R^{13}$ is selected from:
H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_1$–$C_6$ alkylcarbonyl substituted with 0–3 $R^{11A}$;
$C_1$–$C_6$ alkoxycarbonyl substituted with 0–3 $R^{11A}$;
$C_1$–$C_6$ alkylaminocarbonyl substituted with 0–3 $R^{11A}$;
$C_3$–$C_6$ alkoxyalkyl substituted with 0–3 $R^{11A}$;
an amine protecting group when $R^{13}$ is bonded to N;
a hydroxy protecting group when $R^{13}$ is bonded to O;

$R^{14}$ is OH, H, CF$_3$; $C_1$–$C_4$ alkyl substituted with 0–3 groups selected from OH, $C_1$–$C_4$ alkoxy, halogen, NH$_2$; $C_1$–$C_6$ alkoxy; NH$_2$; $C_2$–$C_6$ alkenyl; or benzyl; an amine protecting group when $R^{14}$ is bonded to N; a hydroxy protecting group when $R^{14}$ is bonded to O;

$R^{13}$ and $R^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

$R^{15}$ is H or CH$_3$;

m is 0, 1 or 2;

$R^{22}$ is independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$;
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 $R^{32}$;

$R^{23}$ is independently selected from the following:
hydrogen;
$C_1-C_8$ alkyl substituted with 0–3 $R^{31}$;
$C_2-C_8$ alkenyl substituted with 0–3 $R^{31}$;
$C_2-C_8$ alkynyl substituted with 0–3 $R^{31}$;
a $C_3-C_{14}$ carbocyclic ring system substituted with 0–5 $R^{31}$ or $R^{32}$;
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 $R^{32}$;

alternatively, $R^{22}$ can join with $R^4$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$ can join with $R^7$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$ or $R^{23}$ can join with $R^5$ to form a 0- to 7-membered bridge to form a carbocyclic or heterocyclic ring, said bridge being substituted with 0–2 $R^{12}$ and said bridge containing 0–3 heteroatoms independently selected from N, S, or O (i.e., a 0-membered bridge is formed when $R^{22}$ or $R^{23}$ are taken together with $R^5$ to form a direct bond);

$R^{31}$ is selected from one or more of the following:
keto, halogen, cyano, $—CH_2NR^{13}R^{14}$, $—NR^{13}R^{14}$, $—CO_2R^{13}$, $—C(=O)R^{11}$, $—OC(=O)R^{13}$, $—OR^{13}$, $C_2-C_6$ alkoxyalkyl, $—S(O)_mR^{13}$, $—NHC(=NH)NHR^{13}$, $—C(=NH)NHR^{13}$, $—C(=O)NR^{13}R^{14}$, $—NR^{14}C(=O)R^{13}$, $=NOR^{14}$, $—NR^{14}C(=O)OR^{14}$, $—OC(=O)NR^{13}R^{14}$, $—NR^{13}C(=O)NR^{13}R^{14}$, $—NR^{14}SO_2NR^{13}R^{14}$, $—NR^{14}SO_2R^{13}$, $—SO_2NR^{13}R^{14}$, $C_1-C_4$ alkyl, $C_2-C_4$ alkenyl, $C_3-C_{10}$ cycloalkyl, $C_3-C_6$ cycloalkylmethyl, benzyl, phenethyl, phenoxy, benzyloxy, nitro, $C_7-C_{10}$ arylalkyl, hydroxamic acid, hydrazide, oxime, boronic acid, sulfonamide, formyl, $C_3-C_6$ cycloalkoxy, $C_1-C_4$ alkyl substituted with $—NR^{13}R^{14}$, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, $—OCH_2CO_2R^{13}$, 2-(1-morpholino)ethoxy, azido, $—C(R^{14})=N(OR^{14})$; or 1–3 amino acids, linked together via amide bonds and linked to $R^{22}$, $R^{23}$, $R^4$ or $R^7$ via the amine or carboxy terminus;
a $C_5-C_{14}$ carbocyclic residue substituted with 0–3 $R^{32}$;
a $C_5-C_{14}$ carbocyclic residue substituted with 0–5 $R^{32}$; or
a 5- to 10-membered heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, and oxazolidinyl, said heterocyclic ring system being substituted with 0–2 $R^{32}$;

$R^{32}$, when a substituent on carbon, is selected from one or more of the following:
phenyl, benzyl, phenethyl, phenoxy, benzyloxy, halogen, hydroxy, nitro, cyano, $C_1-C_4$ alkyl, $C_3-C_{10}$ cycloalkyl, $C_3-C_6$ cycloalkylmethyl, $C_7-C_{10}$ arylalkyl, $C_1-C_4$ alkoxy, $—CO_2H$, hydroxamic acid, $—CONR^{13}NR^{13}R^{14}$, hydrazide, oxime, boronic acid, sulfonamide, formyl, $C_3-C_6$ cycloalkoxy, $—OR^{13}$, $C_1-C_4$ alkyl substituted with $—NR^{13}R^{14}$, $—NR^{13}R^{14}$, $C_2-C_6$ alkoxyalkyl, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, $—S(O)_mR^{13}$, $—SO_2NR^{13}R^{14}$, $—NHSO_2R^{14}$, $—OCH_2CO_2H$, 2-(1-morpholino)ethoxy, $—C(R^{14})=N(OR^{14})$; $NO_2$, $—OR^{13}$, $—NR^{40}R^{41}$, $—SO_mR^{13}$, $—SO_mNR^{13}R^{14}$, $—C(=O)NR^{13}R^{14}$, $—OC(=O)NR^{13}R^{14}$, $—C(=O)R^{11}$, $—OC(=O)R^{11}$, $—OCO_2R^{13}$, phenyl, $—C(=O)NR^{13}—(C_1-C_4 \text{ alkyl})-NR^{13}R^{14}$, $—C(=O)NR^{40}R^{41}$, $C_1-C_4$ haloalkyl, $C_1-C_4$ haloalkoxy, $C_2-C_4$ haloalkenyl, $C_1-C_4$ haloalkynyl, or
$—C(=O)NR^{13}C(R^{11})_2NR^{13}R^{14}$; $—C(=O)NR^{13}C(R^{11})_2NR^{13}NR^{14}$;
$—C(=O)NR^{13}C(R^{11})_2NR^{13}CO_2R^{13}$;
$—C(=O)NR^{13}—(C_1-C_4 \text{ alkyl})-NR^{13}CO_2R^{13}$; or
$—C(=O)C(R^{11})_2NR^{13}R^{14}$; $—C(=O)C(R^{11})_2NR^{13}NR^{14}$;
$—C(=O)C(R^{11})_2NR^{13}CO_2R^{13}$; $—C(=O)—(C_1-C_4 \text{ alkyl})-NR^{13}R^{14}$; $—C(=O)—(C_1-C_4 \text{ alkyl})-NR^{13}CO_2R^{13}$; or
$C_1-C_4$ alkoxy substituted with 0–4 groups selected from: $R^{11}$, $C_3-C_6$ cycloalkyl, $—CO_2R^{13}$, $—C(=O)NR^{13}R^{14}$, $—NR^{13}R^{14}$ or OH;
$C_1-C_4$ alkyl substituted with 0–4 groups selected from: $R^{11}$, $=NR^{14}$, $=NNR^{13}C(=O)NR^{13}R^{14}$ or $—NR^{13}R^{14}$;
$C_2-C_4$ alkenyl substituted with 0–4 $R^{11}$;
$C_2-C_4$ alkynyl substituted with 0–4 $R^{11}$;
a 5- or 6-membered heterocyclic ring containing from 1 to 4 heteroatoms selected from oxygen, nitrogen or sulfur;
when $R^{32}$ is attached to a saturated carbon atom, it may be =O or =S;
$R^{32}$ may alternatively be a 3- or 4-carbon chain attached to adjacent carbons on the ring to form a fused 5- or 6-membered ring, said 5- or 6-membered ring being optionally substituted on the aliphatic carbons with halogen, $C_1-C_4$ alkyl, $C_1-C_4$ alkoxy, hydroxy, or $—NR^{13}R^{14}$;

$R^{32}$, when a substituent on nitrogen, is selected from one or more of the following:
phenyl, benzyl, phenethyl, hydroxy, $C_1-C_4$ hydroxyalkyl, $C_1-C_4$ alkoxy, $C_1-C_4$ alkyl, $C_3-C_6$ cycloalkyl, $C_3-C_6$ cycloalkylmethyl, $—CH_2NR^{13}R^{14}$, $—NR^{13}R^{14}$, $C_2-C_6$ alkoxyalkyl, $C_1-C_4$ haloalkyl, $C_1-C_4$ alkoxycarbonyl, $—CO_2H$, $C_1-C_4$ alkylcarbonyloxy, $C_1-C_4$ alkylcarbonyl, $—C(R^{14})=N(OR^{14})$;

$R^{40}$ is selected from: H, $C_1-C_3$ alkyl;
$R^{41}$ is selected from:
$—C(=O)NR^{13}R^{14}$;
$—C(=O)NR^{13}NR^{14}$;
$—C(=O)C(R^{11})_2NR^{13}R^{14}$;
$—C(=O)C(R^{11})_2NR^{13}NR^{14}$;
$—C(=O)C(R^{11})_2NR^{13}CO_2R^{13}$;
$—C(=O)H$;
$—C(=O)R^{11}$;
$—C(=O)—(C_1-C_4 \text{ alkyl})-NR^{13}R^{14}$;
$—C(=O)—(C_1-C_4 \text{ alkyl})-NR^{13}CO_2R^{13}$;

1–3 amino acids linked together via amide bonds, and linked to the N atom via the carboxy terminus;
provided that:
  when $R^4$ is hydrogen, at least one of the following is not hydrogen: $R^7$, $R^{22}$ or $R^{23}$;
  when $R^4$ and $R^7$ are hydrogen, at least two of the following are not hydrogen: $R^{22}$ or $R^{23}$.

5. A compound of claim 4, or a pharmaceutically acceptable salt thereof, wherein:
  $R^4$ and $R^7$ are selected from benzyl, fluorobenzyl, pyrrolylmethyl, methoxybenzyl, isobutyl, nitrobenzyl or aminobenzyl;
  $R^5$ is —OH;
  $R^{22}$ and $R^{23}$ are independently selected from the group consisting of:
    hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyloxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=O))$-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, $(CH_3O_2CO)$-benzyl, $(HOCH_2CH_2N=CH)$-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, $(CH_3NHC(=O))$-benzyl, N,N-dimethylaminocarbonylbenzyl, $(HOCH_2CH(OH)CH_2O)$-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, $(CH_3CH_2NHC(=O))$-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-$C(=O)$)-benzyl, trifluoroacetylbenzyl, (pyrazolyl)benzyl, $(H_2NSO_2)$-benzyl, dihydroxyethylbenzyl, $(MeHNC(=O)NH)$-benzyl, $(H_2NC(=O)NH)$-benzyl, $(HC(=O)NH)$-benzyl, methanesulfonylpentyl, methoxypentyl, N-formyl-N-methylaminobenzyl, acetylaminobenzyl, propionylbenzyl, butyrylbenzyl, $(CH_3CH_2C(=NOH))$-benzyl, (trifluorohydroxyethyl)benzyl, $(CF_3C(=NOH))$-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, $(benzyl-NHC(=O)O)$benzyl, $(CH_3NHC(=O)O)$benzyl, $(NH_2C(=O)CH_2O)$benzyl, $(NH_2C(=NH))$benzyl, ((N-phenylmethoxycarbonyl)glycylamino)benzyl, (imidazolylmethyl)benzyl, $((CH_3)_3C—C(=O))$benzyl, (N-methyl-N-ethylaminoethyl)aminocarbonylbenzyl, (pyrrolidinylethyl)aminocarbonylbenzyl, (piperidinylethyl)aminocarbonylbenzyl.

6. A compound of claim 3, or a pharmaceutically acceptable salt thereof, wherein:
  $R^4$ and $R^7$ are benzyl;
  $R^{4a}$, $R^{5a}$, $R^{33}$, and $R^{33a}$ are hydrogen;
  $R^5$ is —OH;
  $R^{22}$ and $R^{23}$ are independently selected from the group consisting of: hydrogen, allyl, methyl, ethyl, propyl, n-butyl, i-butyl, $CH_2CH=C(CH_3)_2$, methallyl, n-pentyl, i-pentyl, hexyl, isoprenyl, propargyl, picolinyl, methoxyethyl, dimethyl-butyl, vinyloxyethyl, ethoxyethyl, dimethylallyl, (hydroxyl)hexyl, hexenyl, (hydroxy)octyl, (hydroxyl)pentyl, (carboxy)pentyl, (carbomethoxy)pentyl, methoxypentyl, methanesulfonylpentyl, adamantylethyl, cyclopropylmethyl, cyclobutylmethyl, cyclopentylmethyl, cyclohexylmethyl, pyridinylmethyl, methyloxazolinylmethyl, naphthylmethyl, aminonaphthylmethyl, thienylmethyl, chlorothienyl, quinolinylmethyl, aminoquinolinylmethyl, indazolylmethyl, 3-aminoindazolylmethyl, 3-methyl-indazolylmethyl, 3-carboxymethyl-indazolylmethyl, 3-hydroxymethyl-indazolylmethyl, 3-phenoxymethyl-indazolylmethyl, benzimidazolylmethyl, benzyl, carboxybenzyl, phenylbenzyl, methylbenzyl, cyclopropylmethoxybenzyl, methoxybenzyl, ethoxybenzyl, hydroxybenzyl, hydroxymethylbenzyl, aminobenzyl, formylbenzyl, cyanobenzyl, cinnamyl, benzyloxybenzyl, allyloxybenzyl, fluorobenzyl, difluorobenzyl, pentafluorobenzyl, chlorobenzyl, chloromethylbenzyl, fluoromethylbenzyl, iodobenzyl, bromobenzyl, formaldoximebenzyl, nitrobenzyl, $(H_2NC(=O))$-benzyl, carbomethoxybenzyl, carboethoxybenzyl, tetrazolylbenzyl, aminomethylbenzyl, (O-benzyl-formaldoxime)benzyl, (O-methyl-formaldoxime)benzyl, $(CH_3O_2CO)$-benzyl, $(HOCH_2CH_2N=CH)$-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl)ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, (CH₃NHC(=O))-benzyl, N,N-dimethylaminocarbonylbenzyl, (HOCH₂CH(OH)CH₂O)-benzyl, hydroxyethoxybenzyl (oxazolidinyl)benzyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, (N-phenylmethoxycarbonyl)alanylaminobenzyl, alanylaminobenzyl, phenylalanylaminobenzyl, (N-phenylmethoxycarbonyl), phenylalanylaminobenzyl, (N-methylglycyl)aminobenzyl, (CH₃CH₂NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, trifluoroacetylbenzyl, (pyrazolyl)benzyl, (H₂NSO₂)-benzyl, dihydroxyethylbenzyl, (MeHNC(=O)NH)-benzyl, (H₂NC(=O)NH)-benzyl, (HC(=O)NH)-benzyl, N-formyl-N-methylaminobenzyl, acetylaminobenzyl, propionylbenzyl, butyrylbenzyl, (CH₃CH₂C(=NOH))-benzyl, (trifluorohydroxyethyl)benzyl, (CF₃C(=NOH))-benzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH₃NHC(=O)O)benzyl, (NH₂C(=O)CH₂O)benzyl, (NH₂C(=NH))benzyl, ((N-phenylmethoxycarbonyl)glycylamino)benzyl, (imidazolylmethyl)benzyl, ((CH₃)₃C—C(=O))benzyl, (N-methyl-N-ethylaminoethyl)aminocarbonylbenzyl, (pyrrolidinylethyl)aminocarbonylbenzyl, and (piperidinylethyl)aminocarbonylbenzyl.

7. A method for the treatment of HIV infections which comprises administering to a host in need of such treatment a therapeutically effective amount of a compound of claim 1.

8. A method for the treatment of HIV infections which comprises administering to a host in need of such treatment a therapeutically effective amount of a compound of claim 2.

9. A method for the treatment of HIV infections which comprises administering to a host in need of such treatment a therapeutically effective amount of a compound of claim 3.

10. A method for the treatment of HIV infections which comprises administering to a host in need of such treatment a therapeutically effective amount of a compound of claim 4.

11. A method for the treatment of HIV infections which comprises administering to a host in need of such treatment a therapeutically effective amount of a compound of claim 5.

12. A method for the treatment of HIV infections which comprises administering to a host in need of such treatment a therapeutically effective amount of a compound of claim 6.

13. A pharmaceutical composition comprising a compound of claim 1 and a pharmaceutically acceptable carrier.

14. A pharmaceutical composition comprising a compound of claim 2 and a pharmaceutically acceptable carrier.

15. A pharmaceutical composition comprising a compound of claim 3 and a pharmaceutically acceptable carrier.

16. A pharmaceutical composition comprising a compound of claim 4 and a pharmaceutically acceptable carrier.

17. A pharmaceutical composition comprising a compound of claim 5 and a pharmaceutically acceptable carrier.

18. A pharmaceutical composition comprising a compound of claim 6 and a pharmaceutically acceptable carrier.

* * * * *